(12) United States Patent
Karschnik et al.

(10) Patent No.: US 11,684,167 B2
(45) Date of Patent: Jun. 27, 2023

(54) BED AIR CONTROL SYSTEM

(71) Applicant: Sleep Number Corporation, Minneapolis, MN (US)

(72) Inventors: Kody Lee Karschnik, Plymouth, MN (US); Chee Nong Yang, Fridley, MN (US); Eric Rose, Piedmont, SC (US); Wade Daniel Palashewski, Andover, MN (US)

(73) Assignee: Sleep Number Corporation, Minneapolis, MN (US)

( * ) Notice: Subject to any disclaimer, the term of this patent is extended or adjusted under 35 U.S.C. 154(b) by 179 days.

(21) Appl. No.: 17/139,683

(22) Filed: Dec. 31, 2020

(65) Prior Publication Data

US 2021/0204720 A1 Jul. 8, 2021

Related U.S. Application Data

(60) Provisional application No. 62/957,103, filed on Jan. 3, 2020.

(51) Int. Cl.
*A47C 21/04* (2006.01)
*A47C 27/14* (2006.01)
(Continued)

(52) U.S. Cl.
CPC .......... *A47C 21/048* (2013.01); *A47C 19/027* (2013.01); *A47C 20/041* (2013.01);
(Continued)

(58) Field of Classification Search
CPC ..... A47C 27/082; A47C 27/148; A47C 27/15; A47C 27/001; A47C 27/05; A47C 27/056;
(Continued)

(56) References Cited

U.S. PATENT DOCUMENTS 679,656 A 7/1901 Whiting
2,807,809 A 10/1957 Kottemann
(Continued)

FOREIGN PATENT DOCUMENTS

CN 108784122 A 11/2018
EP 3569948 11/2019

OTHER PUBLICATIONS

"Fasten." Merriam-Webster, Merriam-Webster, www.merriam-webster.com/dictionary/fasten.*
(Continued)

*Primary Examiner* — David R Hare
*Assistant Examiner* — Madison Emanski
(74) *Attorney, Agent, or Firm* — Fish & Richardson P.C.

(57) ABSTRACT

A bed system includes microclimate control capabilities for providing quality sleep experience. The bed system can include a microclimate control subsystem configured to supply conditioned air (e.g., heated or cooled air) to a mattress, or draw ambient air from the mattress, to achieve a desired temperature at the top of the mattress. Utilizing supply of conditioned air to provide air at desired temperature to the mattress system, or utilizing air suction to drain heat away from the mattress system, can provide precise microclimate control at the mattress, thereby permitting conformable sleep.

17 Claims, 72 Drawing Sheets

(51) Int. Cl.
    *A47C 27/08*     (2006.01)
    *A47C 27/10*     (2006.01)
    *A47C 27/18*     (2006.01)
    *A47C 31/00*     (2006.01)
    *A47C 27/15*     (2006.01)
    *G05B 19/4155*   (2006.01)
    *A47C 20/04*     (2006.01)
    *G05B 19/042*    (2006.01)
    *A47C 19/02*     (2006.01)

(52) U.S. Cl.
    CPC .......... *A47C 21/044* (2013.01); *A47C 27/081* (2013.01); *A47C 27/082* (2013.01); *A47C 27/083* (2013.01); *A47C 27/10* (2013.01); *A47C 27/14* (2013.01); *A47C 27/18* (2013.01); *A47C 31/001* (2013.01); *A47C 31/005* (2013.01); *A47C 31/007* (2013.01); *G05B 19/0426* (2013.01); *G05B 19/4155* (2013.01); *A47C 20/04* (2013.01); *A47C 27/15* (2013.01); *A47C 31/008* (2013.01); *G05B 2219/2614* (2013.01); *G05B 2219/2638* (2013.01); *G05B 2219/37371* (2013.01); *G05B 2219/50333* (2013.01)

(58) Field of Classification Search
    CPC ..... A47C 27/066; A47C 27/088; A47C 27/10; A47C 21/044; A47C 21/048; A47C 27/18; A47C 7/74
    See application file for complete search history.

(56) References Cited

U.S. PATENT DOCUMENTS

| | | |
|---|---|---|
| 3,230,556 A | 1/1966 | Shippee |
| 3,681,797 A | 8/1972 | Messner |
| 4,391,009 A | 7/1983 | Schild et al. |
| 4,766,628 A | 8/1988 | Greer et al. |
| 4,788,729 A | 12/1988 | Greer et al. |
| D300,194 S | 3/1989 | Walker |
| 4,829,616 A | 5/1989 | Walker |
| 4,867,230 A | 9/1989 | Voss |
| 4,890,344 A | 1/1990 | Walker |
| 4,897,890 A | 2/1990 | Walker |
| 4,901,383 A | 2/1990 | Yang et al. |
| 4,908,895 A | 3/1990 | Walker |
| D313,973 S | 1/1991 | Walker |
| 4,991,244 A | 2/1991 | Walker |
| 5,144,706 A | 9/1992 | Walker et al. |
| 5,170,522 A | 12/1992 | Walker |
| 5,184,612 A | 2/1993 | Augustine |
| 5,473,783 A | 12/1995 | Allen |
| D368,475 S | 4/1996 | Scott |
| 5,509,154 A | 4/1996 | Shafer et al. |
| 5,557,813 A | 9/1996 | Steed et al. |
| 5,564,140 A | 10/1996 | Shoenhair et al. |
| 5,564,141 A | 10/1996 | Anderson |
| 5,566,409 A | 10/1996 | Klearman |
| 5,642,546 A | 6/1997 | Shoenhair |
| 5,652,484 A | 7/1997 | Shafer et al. |
| 5,704,085 A | 1/1998 | Sabalaskey |
| 5,713,137 A | 2/1998 | Fujita |
| 5,765,246 A | 6/1998 | Shoenhair |
| 5,794,289 A | 8/1998 | Wortman et al. |
| 5,815,861 A | 10/1998 | LaGrange et al. |
| 5,903,941 A | 5/1999 | Shafer et al. |
| 5,904,172 A | 5/1999 | Gifft et al. |
| 5,960,493 A | 10/1999 | Rhey et al. |
| 5,960,496 A | 10/1999 | Boyd |
| 5,987,666 A | 11/1999 | Zigmont |
| 6,037,723 A | 3/2000 | Shafer et al. |
| 6,085,369 A | 7/2000 | Feher |
| 6,108,844 A | 8/2000 | Kraft et al. |
| 6,161,231 A | 12/2000 | Kraft et al. |
| 6,202,239 B1 | 3/2001 | Ward et al. |
| 6,243,894 B1 | 6/2001 | Kosumsuppamala et al. |
| 6,249,924 B1 | 6/2001 | Kluft |
| 6,256,821 B1 | 7/2001 | Boyd |
| 6,397,419 B1 | 6/2002 | Mechache |
| 6,430,763 B2 | 8/2002 | Kosumsuppamala et al. |
| 6,483,264 B1 | 11/2002 | Shafer et al. |
| 6,511,501 B1 | 1/2003 | Augustine et al. |
| 6,546,576 B1 | 4/2003 | Lin |
| 6,686,711 B2 | 2/2004 | Rose et al. |
| 6,708,357 B2 | 3/2004 | Gaboury et al. |
| 6,763,541 B2 | 7/2004 | Mahoney et al. |
| 6,804,848 B1 | 10/2004 | Rose |
| 6,832,397 B2 | 12/2004 | Gaboury |
| D502,929 S | 3/2005 | Copeland et al. |
| 6,883,191 B2 | 5/2005 | Gaboury et al. |
| 6,971,132 B2 | 12/2005 | Feinsod |
| 7,036,163 B2 | 5/2006 | Schmid |
| 7,165,281 B2 | 1/2007 | Larssson et al. |
| 7,165,282 B2 | 1/2007 | Watson |
| 7,237,285 B2 | 7/2007 | Brewin et al. |
| 7,389,554 B1 | 6/2008 | Rose |
| 7,865,988 B2 | 1/2011 | Koughan et al. |
| 7,914,611 B2 | 3/2011 | Vrzalik et al. |
| 7,975,331 B2 | 7/2011 | Flocard et al. |
| 8,118,920 B2 | 2/2012 | Vrzalik et al. |
| 8,191,187 B2 | 6/2012 | Brykalski et al. |
| 8,332,975 B2 | 12/2012 | Brykalski et al. |
| 8,336,369 B2 | 12/2012 | Mahoney |
| 8,359,684 B2 | 1/2013 | Hoo |
| 8,372,182 B2 | 2/2013 | Vrzalik et al. |
| 8,444,558 B2 | 5/2013 | Young et al. |
| 8,539,628 B2 | 9/2013 | Lee |
| D691,118 S | 10/2013 | Ingham et al. |
| D697,874 S | 1/2014 | Stusynski et al. |
| D698,338 S | 1/2014 | Ingham |
| 8,621,687 B2 | 1/2014 | Brykalski et al. |
| D701,536 S | 3/2014 | Shakal |
| 8,672,853 B2 | 3/2014 | Young |
| 8,769,747 B2 | 7/2014 | Mahoney et al. |
| 8,893,339 B2 | 11/2014 | Fleury |
| 8,931,329 B2 | 1/2015 | Mahoney et al. |
| 8,966,689 B2 | 3/2015 | McGuire et al. |
| 8,973,183 B1 | 3/2015 | Palashewski et al. |
| 8,984,687 B2 | 3/2015 | Stusynski et al. |
| 9,057,746 B1 | 6/2015 | Houlette et al. |
| D737,250 S | 8/2015 | Ingham et al. |
| 9,131,780 B2 | 9/2015 | Lachenbruch et al. |
| 9,131,781 B2 | 9/2015 | Zaiss et al. |
| 9,198,796 B2 | 12/2015 | Pierre et al. |
| 9,254,231 B2 | 2/2016 | Vrzalik et al. |
| 9,370,457 B2 | 6/2016 | Nunn et al. |
| 9,392,879 B2 | 7/2016 | Nunn et al. |
| 9,510,688 B2 | 12/2016 | Nunn et al. |
| 9,603,459 B2 | 3/2017 | Brykalski et al. |
| 9,635,953 B2 | 5/2017 | Nunn et al. |
| 9,730,524 B2 | 8/2017 | Chen et al. |
| 9,737,154 B2 | 8/2017 | Mahoney et al. |
| 9,770,114 B2 | 9/2017 | Brosnan et al. |
| 9,814,641 B2 | 11/2017 | Brykalski et al. |
| 9,835,344 B2 | 12/2017 | Vrzalik et al. |
| 9,844,277 B2 | 12/2017 | Parish et al. |
| 9,877,591 B2 | 1/2018 | Morgan et al. |
| D809,843 S | 2/2018 | Keeley et al. |
| 9,888,782 B1 | 2/2018 | Jannke |
| D812,393 S | 3/2018 | Karschnik et al. |
| 9,907,407 B2 | 3/2018 | Aramli |
| 9,924,813 B1 | 3/2018 | Basten et al. |
| 9,943,172 B2 | 4/2018 | Lachenbruch et al. |
| 10,051,973 B2 | 8/2018 | Morgan et al. |
| 10,058,467 B2 | 8/2018 | Stusynski et al. |
| 10,092,242 B2 | 10/2018 | Nunn et al. |
| 10,143,312 B2 | 12/2018 | Brosnan et al. |
| 10,149,549 B2 | 12/2018 | Erko et al. |
| 10,182,661 B2 | 1/2019 | Nunn et al. |
| 10,194,752 B2 | 2/2019 | Zaiss et al. |
| 10,194,753 B2 | 2/2019 | Fleury et al. |
| 10,201,234 B2 | 2/2019 | Nunn et al. |
| 10,251,490 B2 | 4/2019 | Nunn et al. |

(56) References Cited

U.S. PATENT DOCUMENTS

| | | | |
|---|---|---|---|
| 10,314,407 B1 | 6/2019 | Main et al. | |
| 10,342,358 B1 | 7/2019 | Palashewski et al. | |
| 10,681,991 B1 | 6/2020 | Edgar et al. | |
| 10,729,253 B1 | 8/2020 | Gaunt | |
| 11,036,189 B2 | 6/2021 | Gupta et al. | |
| 11,103,081 B2 | 8/2021 | Sherman et al. | |
| 11,134,789 B2 | 10/2021 | DeFranks et al. | |
| 11,160,386 B2 * | 11/2021 | Jansen ................. | A47C 27/144 |
| 2004/0128774 A1 | 7/2004 | Chen | |
| 2005/0278863 A1 | 12/2005 | Bahash et al. | |
| 2006/0031995 A1 | 2/2006 | Barkhouse | |
| 2006/0137099 A1 | 6/2006 | Feher | |
| 2006/0198617 A1 | 9/2006 | Sirkis | |
| 2007/0261548 A1 | 11/2007 | Vrzalik et al. | |
| 2008/0005843 A1 | 1/2008 | Lokhorst et al. | |
| 2008/0077020 A1 | 3/2008 | Young et al. | |
| 2008/0148481 A1 | 6/2008 | Brykalski et al. | |
| 2009/0064411 A1 | 3/2009 | Marquette et al. | |
| 2010/0011502 A1 | 1/2010 | Brykalski et al. | |
| 2010/0275379 A1 | 11/2010 | Streightiff | |
| 2011/0049327 A1 | 3/2011 | Young et al. | |
| 2011/0115635 A1 | 5/2011 | Petrovski et al. | |
| 2011/0144455 A1 | 6/2011 | Young et al. | |
| 2013/0097776 A1 | 4/2013 | Brykalski et al. | |
| 2013/0205506 A1 | 8/2013 | Lachenbruch et al. | |
| 2013/0263380 A1 | 10/2013 | Page et al. | |
| 2014/0250597 A1 | 9/2014 | Chen et al. | |
| 2014/0259418 A1 | 9/2014 | Nunn et al. | |
| 2014/0277822 A1 | 9/2014 | Nunn et al. | |
| 2015/0007393 A1 | 1/2015 | Palashewski | |
| 2015/0012147 A1 | 1/2015 | Haghighat-Kashani et al. | |
| 2015/0025327 A1 | 1/2015 | Young et al. | |
| 2015/0048178 A1 | 2/2015 | Edwards et al. | |
| 2015/0121621 A1 | 5/2015 | Aramli | |
| 2015/0182397 A1 | 7/2015 | Palashewski et al. | |
| 2015/0182399 A1 | 7/2015 | Palashewski et al. | |
| 2015/0182418 A1 | 7/2015 | Zaiss | |
| 2015/0208814 A1 | 7/2015 | Alletto et al. | |
| 2015/0289666 A1 | 10/2015 | Chandler et al. | |
| 2015/0296992 A1 | 10/2015 | Ghanei et al. | |
| 2015/0359347 A1 | 12/2015 | Loomis | |
| 2016/0100696 A1 | 4/2016 | Palashewski et al. | |
| 2016/0136385 A1 | 5/2016 | Scorcioni | |
| 2016/0235210 A1 | 8/2016 | Lachenbruch et al. | |
| 2016/0242562 A1 | 8/2016 | Karschnik et al. | |
| 2016/0338871 A1 | 11/2016 | Nunn et al. | |
| 2016/0367039 A1 | 12/2016 | Young et al. | |
| 2017/0003666 A1 | 1/2017 | Nunn et al. | |
| 2017/0049242 A1 | 2/2017 | Franken | |
| 2017/0049243 A1 | 2/2017 | Nunn et al. | |
| 2017/0191516 A1 | 7/2017 | Griffith et al. | |
| 2017/0202362 A1 | 7/2017 | Reynolds | |
| 2017/0239131 A1 | 8/2017 | Brzenchek et al. | |
| 2017/0303697 A1 | 10/2017 | Chen et al. | |
| 2017/0318980 A1 | 11/2017 | Mahoney et al. | |
| 2017/0354268 A1 | 12/2017 | Brosnan et al. | |
| 2017/0360212 A1 | 12/2017 | Rawls-Meehan | |
| 2018/0027981 A1 | 2/2018 | Sherman et al. | |
| 2018/0027988 A1 | 2/2018 | Poodeh et al. | |
| 2018/0098637 A1 | 4/2018 | Griese et al. | |
| 2018/0110960 A1 | 4/2018 | Youngblood et al. | |
| 2018/0116415 A1 | 5/2018 | Karschnik et al. | |
| 2018/0116418 A1 | 5/2018 | Shakal et al. | |
| 2018/0116419 A1 | 5/2018 | Shakal et al. | |
| 2018/0116420 A1 | 5/2018 | Shakal | |
| 2018/0119686 A1 | 5/2018 | Shakal et al. | |
| 2018/0125259 A1 | 5/2018 | Peterson et al. | |
| 2018/0125260 A1 | 5/2018 | Peterson et al. | |
| 2018/0242753 A1 | 8/2018 | Ghanei et al. | |
| 2018/0338857 A1 | 11/2018 | Diller et al. | |
| 2019/0029597 A1 | 1/2019 | Nunn et al. | |
| 2019/0059603 A1 | 2/2019 | Griffith et al. | |
| 2019/0082855 A1 | 3/2019 | Brosnan et al. | |
| 2019/0104858 A1 | 4/2019 | Erko et al. | |
| 2019/0125095 A1 | 5/2019 | Nunn et al. | |
| 2019/0125097 A1 | 5/2019 | Nunn et al. | |
| 2019/0126000 A1 | 5/2019 | Main et al. | |
| 2019/0200777 A1 | 7/2019 | Demirli et al. | |
| 2019/0201265 A1 | 7/2019 | Sayadi et al. | |
| 2019/0201266 A1 | 7/2019 | Sayadi et al. | |
| 2019/0201267 A1 | 7/2019 | Demirli et al. | |
| 2019/0201268 A1 | 7/2019 | Sayadi et al. | |
| 2019/0201269 A1 | 7/2019 | Sayadi et al. | |
| 2019/0201270 A1 | 7/2019 | Sayadi et al. | |
| 2019/0201271 A1 | 7/2019 | Grey et al. | |
| 2019/0206416 A1 | 7/2019 | Demirli et al. | |
| 2019/0208918 A1 | 7/2019 | DeFranks et al. | |
| 2019/0209405 A1 | 7/2019 | Sayadi et al. | |
| 2019/0279745 A1 | 9/2019 | Sayadi et al. | |
| 2019/0293319 A1 | 9/2019 | Okeya et al. | |
| 2019/0320808 A1 | 10/2019 | Chapin et al. | |
| 2019/0328146 A1 | 10/2019 | Palashewski et al. | |
| 2019/0335913 A1 | 11/2019 | Tsern et al. | |
| 2019/0336721 A1 | 11/2019 | Tsern et al. | |
| 2020/0071079 A1 | 3/2020 | Shutes et al. | |
| 2020/0237108 A1 | 7/2020 | Alletto | |
| 2020/0380619 A1 | 12/2020 | Torpy et al. | |
| 2021/0186224 A1 | 6/2021 | Chapin et al. | |
| 2021/0219737 A1 | 7/2021 | Youngblood et al. | |
| 2021/0368994 A1 | 12/2021 | De La Haye et al. | |

OTHER PUBLICATIONS

PCT International Search Report and Written Opinion in International Appln. No. PCT/US2020/067614, dated Jul. 1, 2021, 25 pages.
U.S. Appl. No. 16/682,675, filed Nov. 13, 2019, Demirli et al.
U.S. Appl. No. 16/714,312, filed Dec. 13, 2019, Demirli et al.
U.S. Appl. No. 16/714,349, filed Dec. 13, 2019, Sayadi et al.
U.S. Appl. No. 16/730,464, filed Dec. 30, 2019, Sayadi et al.
U.S. Appl. No. 16/731,577, filed Dec. 31, 2019, Negus et al.
U.S. Appl. No. 16/731,986, filed Dec. 31, 2019, Holmvik et al.
U.S. Appl. No. 16/891,773, filed Jun. 3, 2020, Brosnan et al.
U.S. Appl. No. 16/936,540, filed Jul. 23, 2020, Sayadi et al.
U.S. Appl. No. 17/001,081, filed Aug. 24, 2020, Palashewski et al.
U.S. Appl. No. 17/006,388, filed Aug. 28, 2020, Stusynski et al.
U.S. Appl. No. 17/018,578, filed Sep. 11, 2020, Griffith et al.
U.S. Appl. No. 29/583,852, filed Nov. 9, 2016, Keeley.
U.S. Appl. No. 29/676,117, filed Jan. 8, 2019, Stusynski et al.
U.S. Appl. No. 29/690,492, filed May 8, 2019, Stusynski et al.
U.S. Appl. No. 29/719,090, filed Dec. 31, 2019, Negus et al.
[No Author Listed] [online], "Tempur-Pedic Active Breeze," Retrieved from the Internet on Dec. 31, 2019, <http://tempurpedicactivebreeze.com/>, 19 pages [Video Submission].
www.qshion.com, "Qshion Mattress Revolution," retrieved on Dec. 30, 2020, dated Jan. 7, 2021, 19 pages.
International Preliminary Report on Patentability in International Appln. No. PCT/US2020/067614, dated Jul. 14, 2022, 17 pages.
PCT Invitation to Pay Additional Fees in International Appln. No. PCT/US2020/067614, dated May 10, 2021, 17 pages.

* cited by examiner

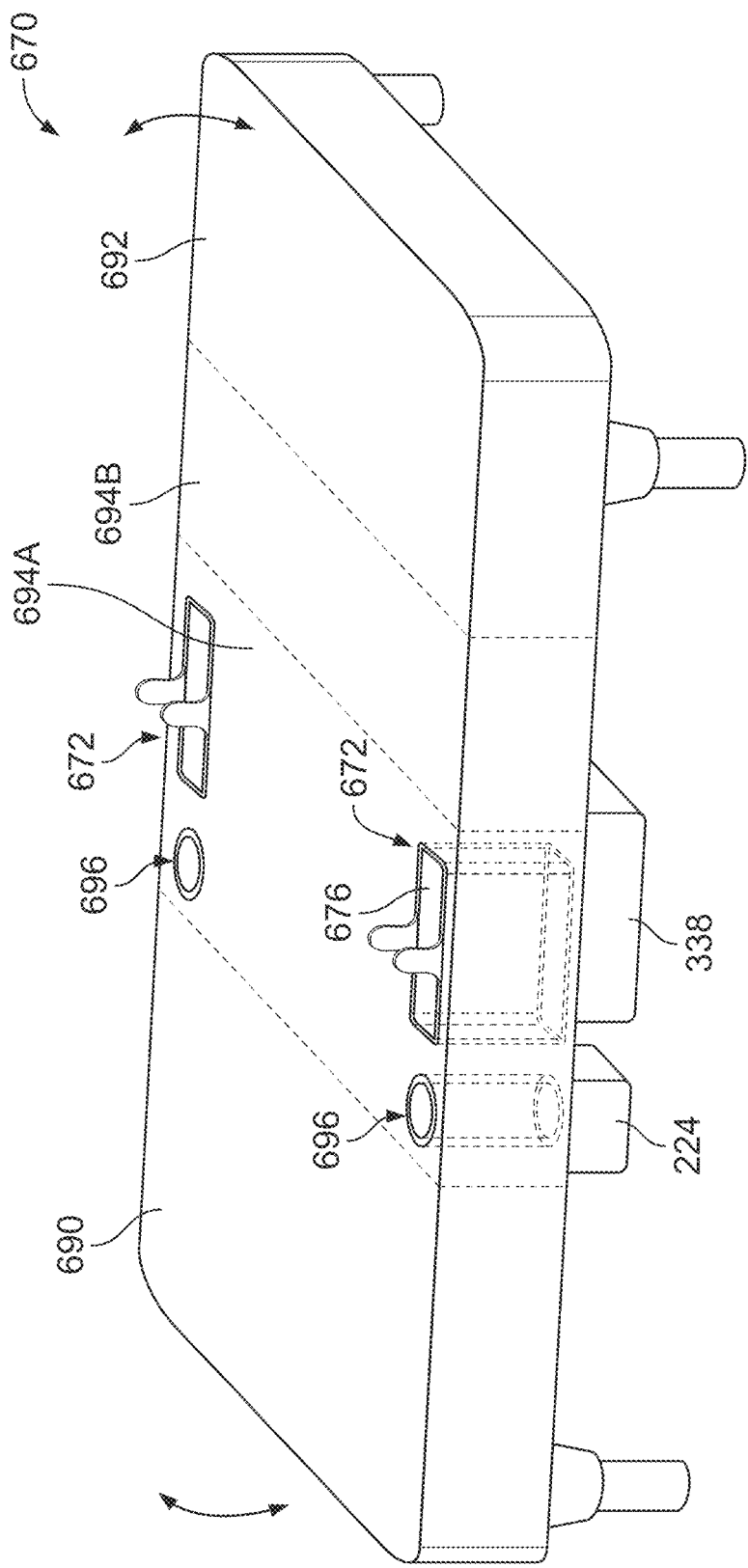

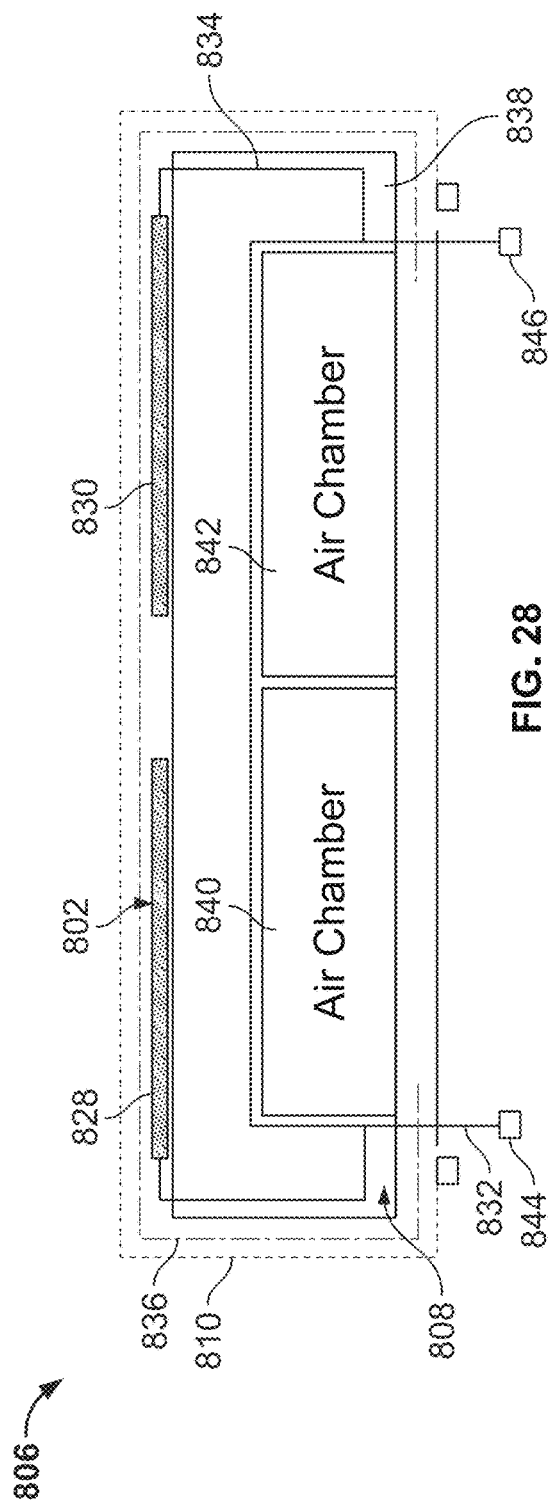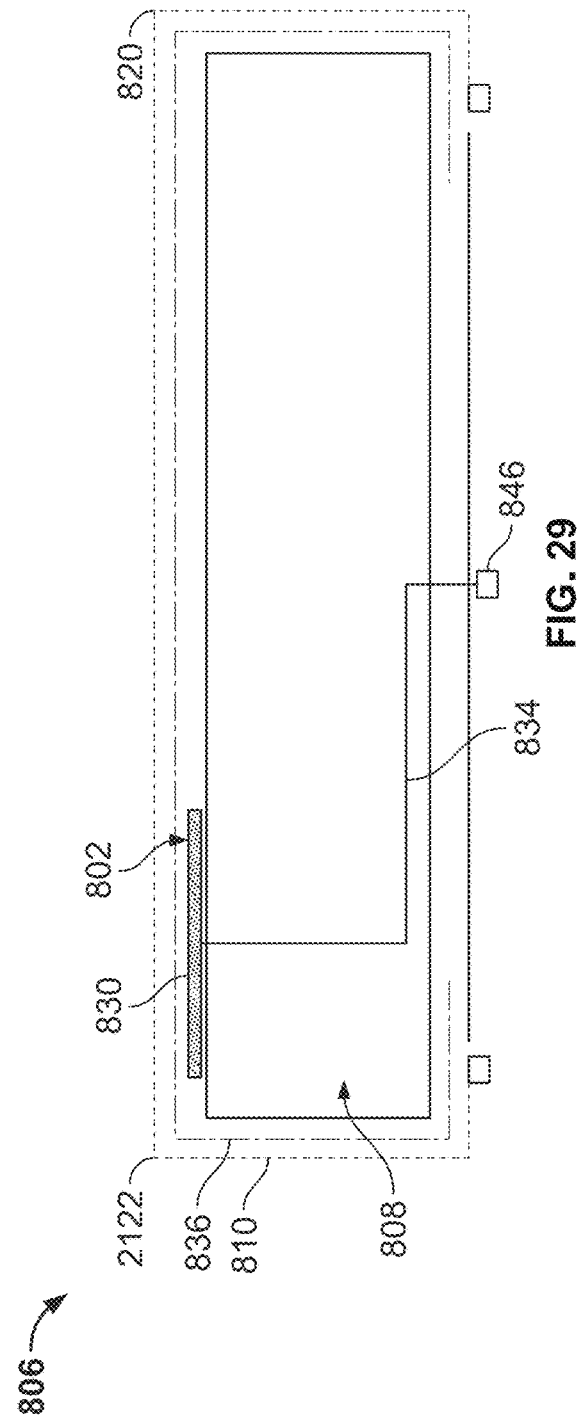

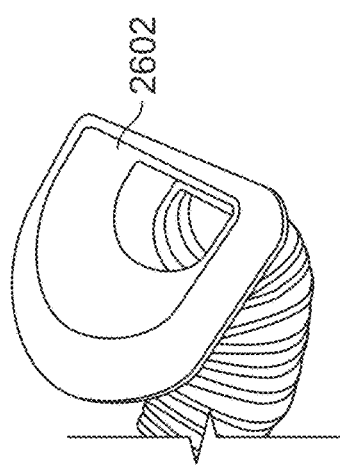
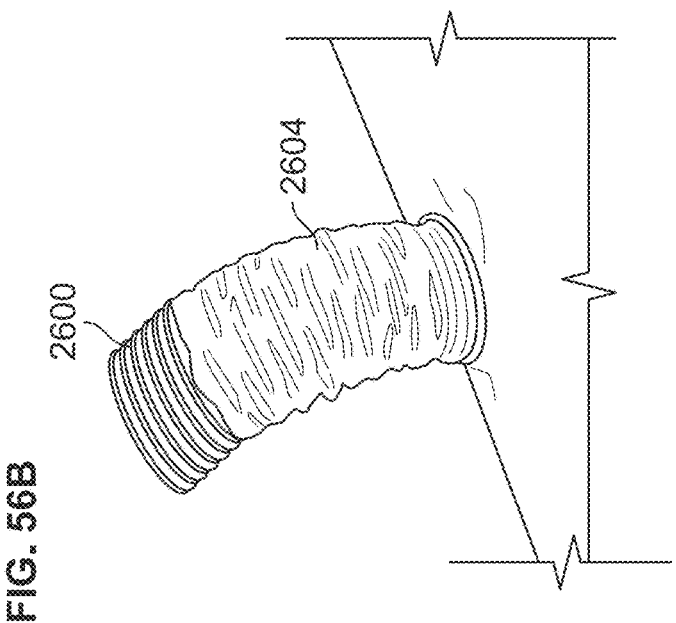
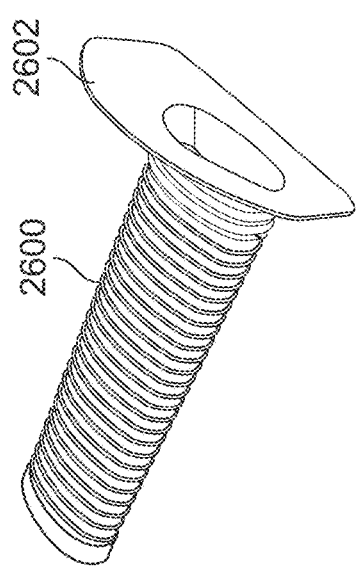
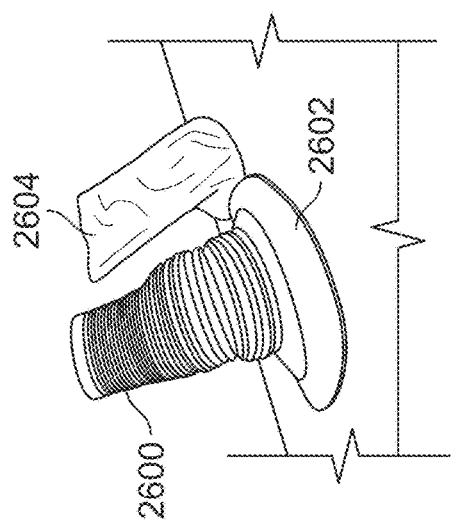

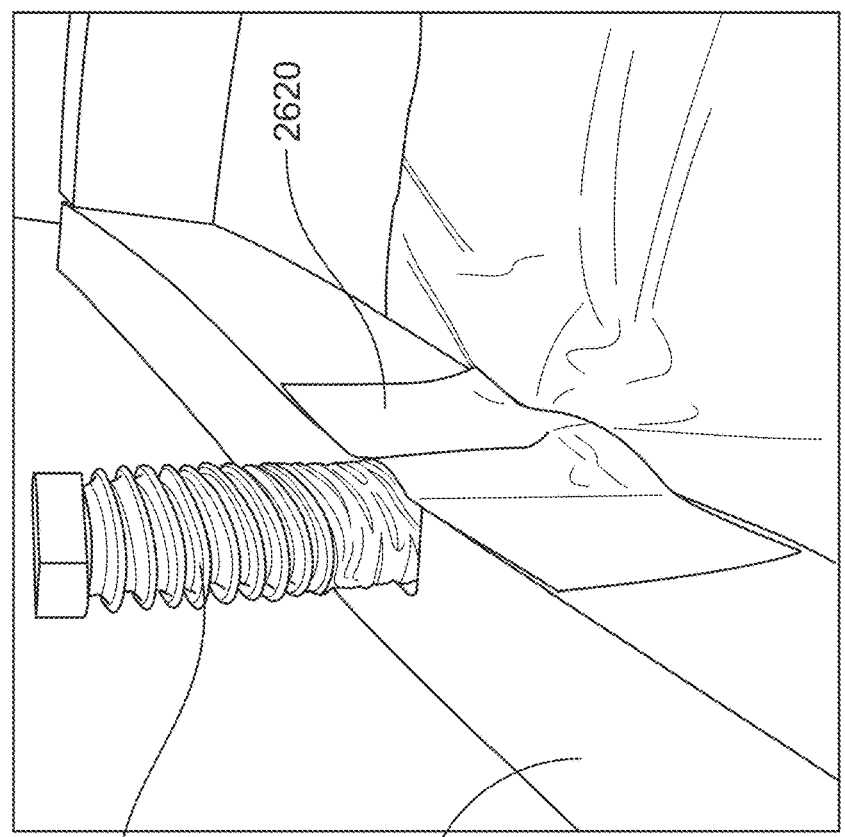
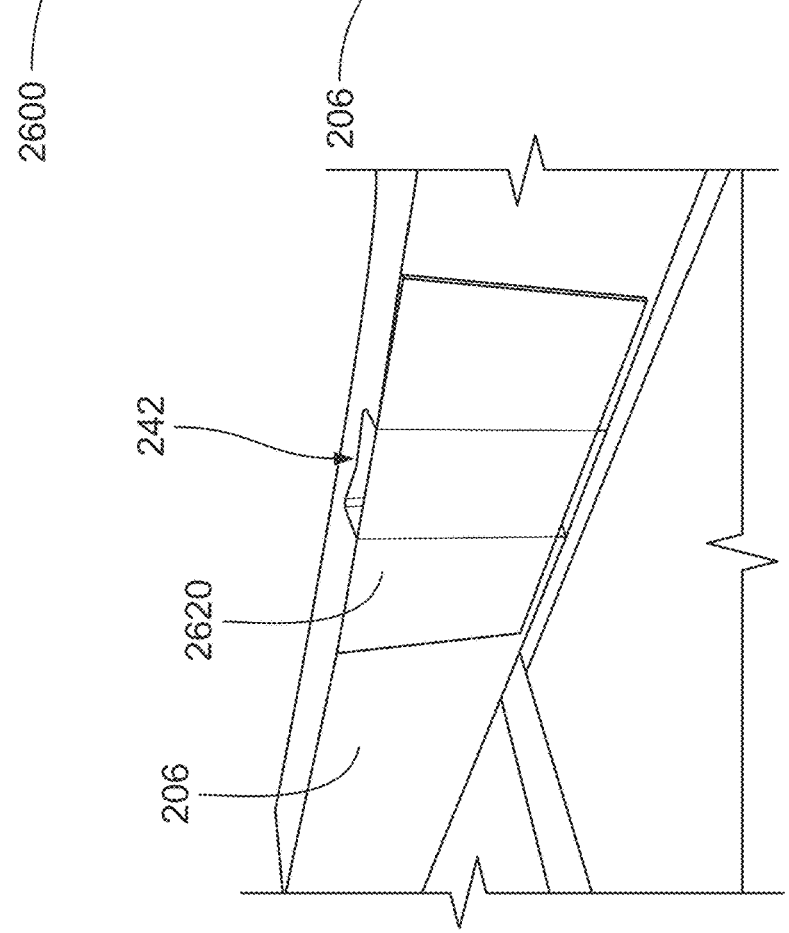
FIG. 57B
FIG. 57A

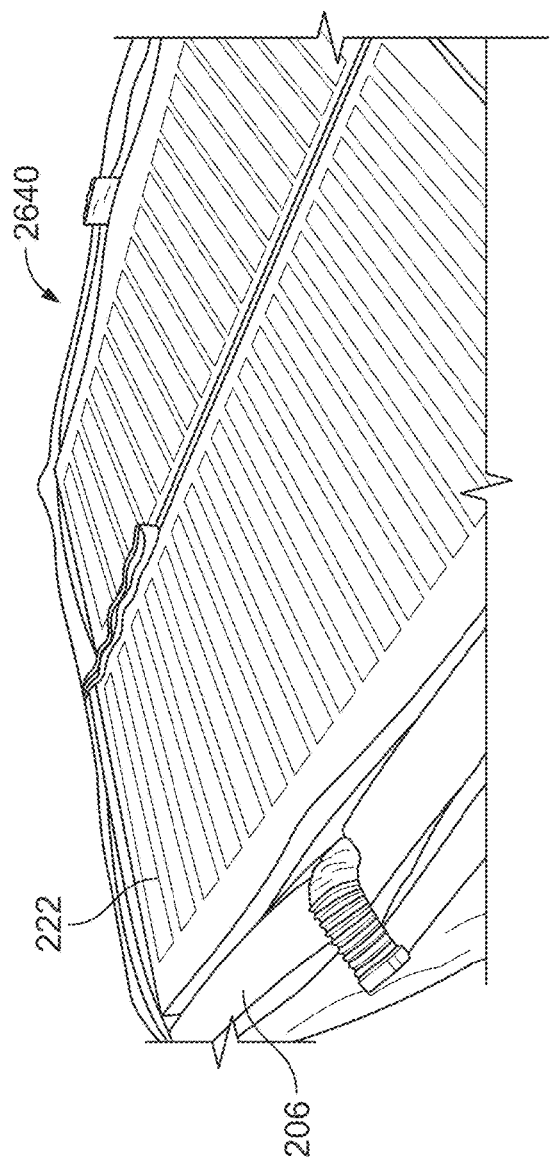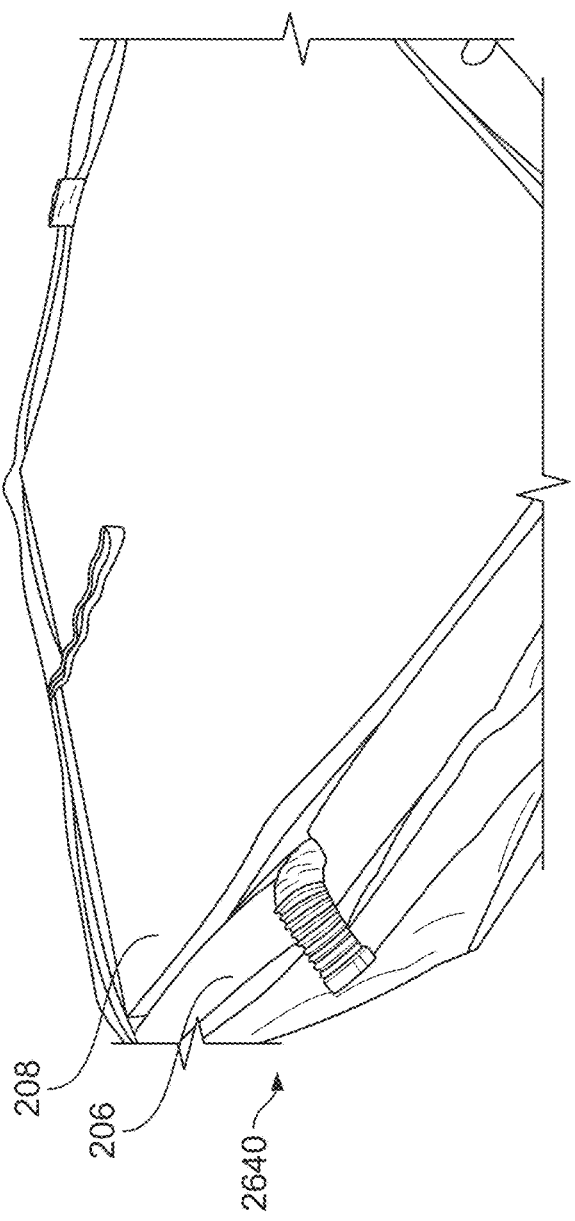

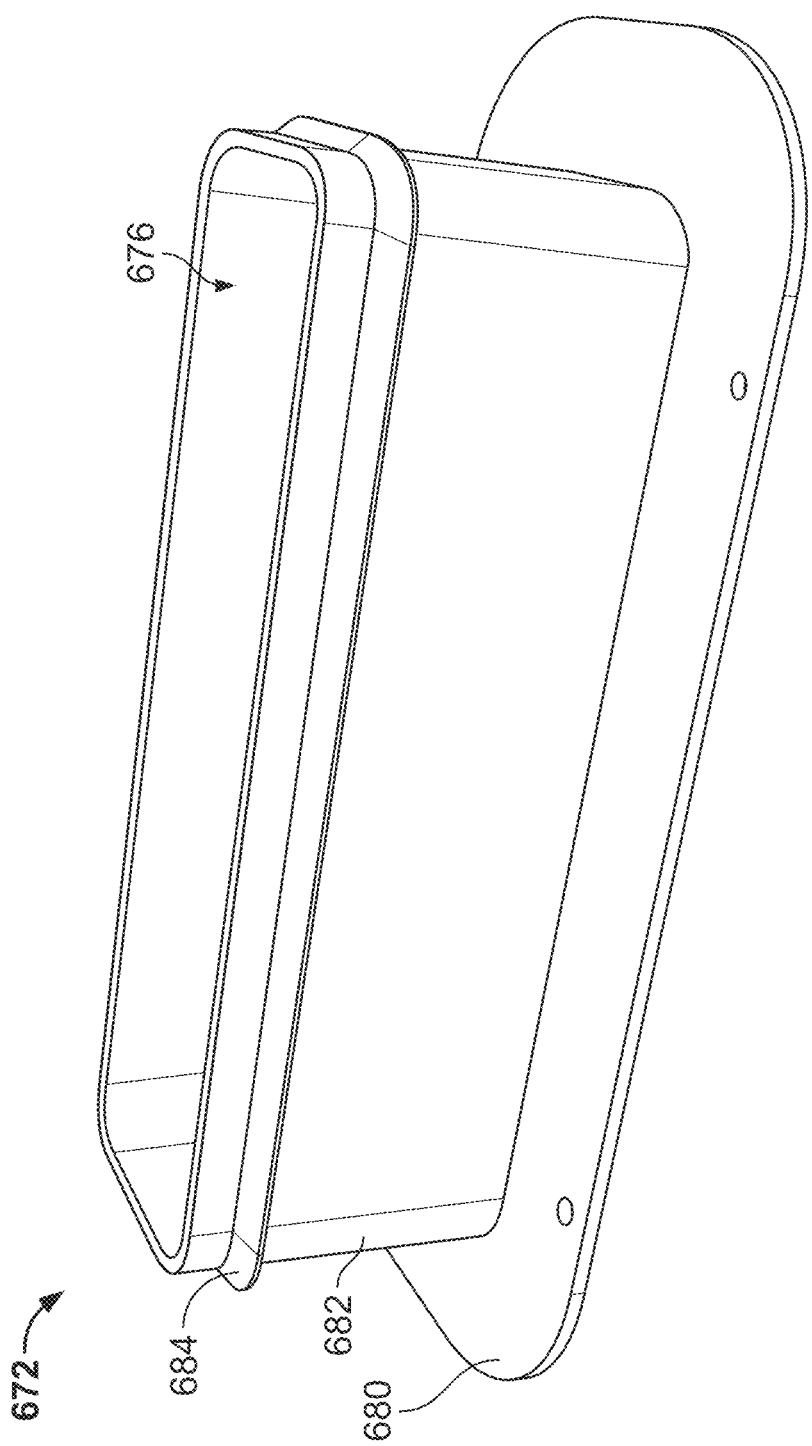

BED AIR CONTROL SYSTEM

CROSS-REFERENCE TO RELATED APPLICATIONS

This application claims the benefit of U.S. Provisional Application Ser. No. 62/957,103, filed Jan. 3, 2020. The disclosure of the prior application is considered part of (and is incorporated by reference in) the disclosure of this application.

TECHNICAL FIELD

This document relates to bed systems, and more particularly to devices, systems, and methods for controlling air flow and temperature of a bed.

BACKGROUND

In general, a bed is a piece of furniture used as a location to sleep or relax. Many modern beds include a soft mattress on a bed frame. The mattress may include springs, foam material, and/or an air chamber to support the weight of one or more occupants. Various features and systems have been used in conjunction with beds, including heating and cooling systems for heating and cooling a user of a bed.

SUMMARY

Some embodiments described herein include a bed system with microclimate control capabilities for providing quality sleep experience. The bed system can include a microclimate control subsystem configured to supply conditioned air (e.g., heated or cooled air) to a mattress to achieve a desired temperature at the top of the mattress. In some implementations, conditioned air can be supplied to one or more airflow pads arranged under the mattress top, so that the conditioned air is distributed to the mattress top through the airflow pads. Alternatively, the microclimate control subsystem can draw ambient air from the mattress, thereby conditioning the temperature at the top of the mattress. For example, air is forced to be drawn from the airflow pads so that air at the mattress top is suctioned into the mattress and permits for the air to be circulated and refreshed at the mattress top. Utilizing supply of conditioned air to provide air at desired temperature to the mattress system, or utilizing air suction to drain heat away from the mattress system, can provide precise microclimate control at the mattress, thereby permitting conformable sleep.

In some implementations, the bed system can include an integrated high airflow zone or layer, which can be implemented by one or more airflow pads, located below a top layer (e.g., topper foam layer) of a mattress. For example, the airflow pads can be arranged (e.g., inserted) to replace at least part of a support foam layer below the top foam layer. The airflow zone enables directed air suctioning from, or supplying to, the mattress, in particular the mattress top. The material used for the airflow zone can be configured to permit for air to move freely throughout. In one example, the material can include three-dimensional structures with elastic polyolefin fibers, such as Qshion™ material. Other example materials can include a spacer monofilament, reticulated form, and channeling.

In some implementations, the airflow layer can be at least partially wrapped and/or sealed with a membrane to allow for directed suction of air therethrough. The wrapping material can be configured to be air impermeable or restrictive. For example, the wrapping can be made of a PU, PVC, fabric with backing, or other materials for helping direct air to be pulled through the membrane of the layer, not the wrapping. Another example of the wrapping material includes a laminated material. The wrapping can be made as a jacket that can be pulled up around the edges of the airflow layer material. In some implementations, a pull cord can be used to tighten or sewn together with a zipper.

In some implementations, the top surface of the airflow layer can be open with no restriction. Alternatively, the top surface of the airflow layer can be configured using a partially impermeable material to optimize a location where larger portions of air can be pulled from. For example, the top surface of the airflow layer can be configured to be more permeable near the middle of the mattress—furthest away from a fan suction—to create an even surface. Alternatively, the top surface of the airflow layer can be configured using an air restrictive material with a zone of holes or punches to help direct flow of air. Hole punching can be selective to help direct air in desired ways.

The airflow zone or layer can be configured and arranged such that a large or substantial amount of air can be pulled from the areas of the mattress, or supplied to the areas of the mattress, that the most amount of heat is built up. For example, the middle section of the mattress (e.g., an area between the head and foot sections) may build up most of heat when sleepers rest on the mattress. Therefore, the airflow zone can be arranged in the middle section of the mattress.

The airflow zone or layer can be configured in various thickness. For example, the airflow layers can be provided with different thickness options, such as 0.5 inches, 2 inches, etc., and selectively used for desired purposes and outcomes. The airflow zone can have different sizes in a mattress. For example, the airflow zone can be formed from an edge to a middle of the bed to cover each sleeper, and from the shoulder down to the knee area. This configuration can permit for the head/neck and feet to be zoned differently. In alternative examples, the airflow zone can be increased or decreased to help optimize effectivity. In some implementations, the airflow layer can be inserted so as to be recessed (e.g., 2 inches) from the edge or perimeter of the mattress. This configuration can allow the topper layer and the rail form to be laminated together and maintain a clean edge to the mattress. Further, this configuration can create a finite cavity for the airflow layer to rest within.

The bed system can provide an air duct system that is coupled to the airflow layer and permit for air to flow (e.g., supply or draw) from/into the airflow layer. For example, the air duct system is configured to draw air from the airflow layer down and out of the bottom of the mattress and foundation. The bed system can further include a fan assembly configured to push or pull air into/from the airflow layer. The fan assembly can be mounted below the mattress foundation, while the air duct system is fluidly connected to the fan assembly and routed through the foundation and partially the mattress up to an inlet of the airflow layer. In some implementations, the air duct system can be routed through a carved-out section of the rail foam that surrounds the bed, thereby avoiding interference with the air chamber and its parts (e.g., air hoses, wiring, etc.). Alternatively, the fan assembly and the air duct system can be configured to be mounted and/or routed outside the foundation. This configuration may be advantageous where the fan assembly and the air duct system are to be provided separately from the bed system and assembled with the bed system afterwards.

The bed system with the airflow layer can operate to pull away and remove the heat that normally builds up within comfort layers (e.g., the topper layer), thereby effectively conditioning the microclimate of the mattress system. Further, the bed system with the airflow layer can operate to pull room ambient air into and take place of warmer air at the top of the mattress, and thus create calming refresh within the microclimate and comfort materials in the mattress. In addition, the bed system with the airflow layer can provide humidity control, which is another factor of comfort sleep. The airflow layer is configured and disposed in the mattress so that comfort and durability of the mattress are not affected by the airflow layer.

In some implementations, the fan assembly can provide temperature control functionalities. For example, the fan assembly can include temperature sensors (e.g., thermocouples) configured to directly monitor the heat being pulled from the mattress. The monitored temperature can be a direct reflection of the microclimate and mattress system temperature. The temperature sensors can be arranged in different locations, such as in the air duct system. The fan assembly can have a variable CFM to control how much heat is removed from the bed system. In some implementations, the bed system can be operated in a closed loop control. For example, thermal events can be monitored for a predetermined period of time (e.g., throughout the night) by, for example, turning on the airflow system for a short period of time to collect thermal data from the sleep environment. Such collected thermal data can be fed into the system for adjustment to the control.

In some implementations, the fan assembly can be configured as a thermal module for heating, cooling, and air movement. For example, the thermal module can include one or more fans, an electronic circuit board for on-board control, and a heating element. The thermal module can further include guards or screens on openings (e.g., air inlet opening and air outlet opening) to provide safe operation and prevent foreign objects (e.g., dusts, particles, etc.) from entering a housing of the thermal module. In some implementations, the thermal module can include one or more reversible electric fans, one or more unidirectional axial fans, one or more radial fans, or any combination thereof, to move air into and out of the mattress. The heating element can be disposed in or near air stream to supply warmed air to the mattress. The heating element may be sized smaller than the total air passage area to allow increased airflow with the system in the air suction mode, but still supply adequate airflow and temperature increase in the heating mode. The cooling element can be placed in or near air stream to supply cooed air to the mattress.

In some implementations, the thermal module can include one or more measures of sound and/or vibration reduction mechanisms. In some examples, such sound and/or vibration reduction mechanisms can include adhesive foam placed on the interior of the housing, and/or adhesive mass tape (e.g., butyl tape) placed on the interior or the exterior of the housing. In addition or alternatively, the sound and/or vibration reduction mechanisms can include a mass and foam assembly that can be placed on the interior or outside of the housing, and/or can be partially or fully installed in the air stream. In addition or alternatively, the sound and/or vibration reduction mechanisms can include stiffening ribs placed in the housing to minimize the drumming effect of air pulsations. Such ribs can be tuned to stiffen the housing and ensure the natural frequency of the housing does not overlap or come near to forced vibration frequencies supplied by the fan.

The fan(s) in the thermal module can be isolated from the housing of the thermal module and/or the mattress foundation to which the thermal module is mounted. Various methods can be used for such isolation. In some examples, adhesive foam strip can be used to provide a compressive or friction fit between the housing and the fan. In addition or alternatively, molded foam strip can be provided to engage ribs in the housing and the ribs/mounting features of the fan to couple the two together mechanically, but still isolate vibration caused by the fan. In addition or alternatively, molded elastomer strip can be provided to engage ribs in the housing and the ribs/mounting features of the fan to couple the two together mechanically, but still isolate vibration caused by the fan.

The thermal module can include a thermal protective circuit that can be inherent to the heating element and configured to keep the unit from becoming hotter than the designed maximum temperature. In some implementations, the thermal module can include two thermostats installed in series in the circuit that powers the heating element. The heating circuitry can be either DC or AC power in desired voltage. The thermostats can be placed directly on the heating element, wedged between the heating element fins, and/or installed near the heating element. The heating element can be operated in a closed loop control, by for example measuring outlet temperature and adjusting (e.g., reducing or increasing) heating power to achieve a desired outlet temperature.

The thermal module can include two temperature sensors (e.g., thermocouples) within the housing. For example, the sensors can be arranged on opposite sides of the heating element. The temperature sensors can be used to verify the fan function, heating element function, heating element output, and/or airflow direction. The sensors can be used to verify these functions during normal operation, at end of line testing during manufacturing, and/or during troubleshooting or diagnostic activities.

The thermal module can include one or more integrated thermocouples that measure an extracted temperature of the microclimate of the mattress, and compare it against the ambient temperature to measure and react to the amount of heat being extracted from the microclimate of the mattress.

The microclimate of the bed system can be controlled in closed loop. Multiple methods may be employed to provide closed loop microclimate control. In general, this involves measuring the temperature of the microclimate and increasing or decreasing heating or cooling to obtain the desired microclimate temperature or energy addition/extraction. For example, when in the heating mode, warm air is pushed through the mattress and into the microclimate, and the fan can be periodically reversed to pull air from the microclimate to "sample the temperature" and react (e.g., increase or decrease heating/cooling) accordingly. Alternatively or in addition, an additional fan can be periodically or continuously activated to pull a small amount (less than what is being delivered to the microclimate) of air for measurement and react (e.g., increase or decrease heating/cooling) accordingly. When in the cooling mode, microclimate air is extracted from the mattress, and one or more thermocouples in the thermal module are used to measure the temperature as discussed above, thereby providing a partial level of "closed loop microclimate" control.

In some implementations, the bed system can include air supply and air return. The air supply and air return can be used to introduce ambient or conditioned air at a specific point or area in the mattress and return air from another point or area of the mattress. This configuration can provide nearly fully control of the airflow across the sleeper's body on the mattress, and increase cooling and/or heating performance. Further, the air supply and return at different locations can provide ability to wash warm air, or suction air, across the extremities of the user's body as opposed to just a local zone. Moreover, this configuration can provide ability to wash externally cooled air across the extremities of the user's body as opposed to ambient air circulation. This may be a way to increase the feeling of cold air and further increase cooling performance without increasing airflow/noise/disruption. The bed system with air supply and return at different locations can provide nearly 100% closed loop control because it can control both supply and return air, and measure true microclimate temperature change. For example, air changes its temperature as it washes across the body between the air supply and the air return, thereby creating the feeling of "zones" with the most extreme zone happening where the air enters the mattress and a less extreme zone being where it exits the mattress.

In some implementations, the bed system can provide various configurations for keeping the air duct secured and maintaining the structural integrity of the mattress rail. For example, a piece of material can be attached to the inside of the rail to keep the air duct securely in place. In addition or alternatively, a channel cut can be provided through the rail foam for the air duct to travel through, thereby keeping the duct from being pulled outside of the rail.

The fan in the bed system can be reversible. When air is being inserted into the sleep system, an energy source can be used to heat the air that is being moved. This would allow the same system to effectively heat or cool without requiring specialized plumbing or additional systems.

In some implementations, the plenum (e.g., the air duct) that draws air from the insert can be optimized to draw the largest amount of air with minimum restriction. For example, the plenum can be configured in a "funnel" design to provide optimal air suction and/or supply results.

In some implementations, a sleeve can be provided to be connected to the airflow pad and extends therefrom to surround the air duct coupled to the airflow pad. The sleeve can help reduce air leakage with this connection and also hold the ducting in place.

In some implementations, the airflow pads can be separated into different zones in the mattress and sized differently within the mattress to control where the thermal performance is directed. The airflow pads can be attached to the mating assembly to ensure it remains in place. This can be done through adhesive, tape, or another type of attachment method. A hose routing for air chambers in an air mattress can have a "jog" or offset created to avoid interference with the air duct routing from the airflow pads.

In some implementations, the bed system can provide various configurations to minimize the dB level of the system. For example, the fan and ductwork can be placed within the foundation to help block noise. In addition or alternatively, a jacket or insulated wrap can be placed around the fan and ductwork. In addition or alternatively, a muffler can be incorporated to minimize the exhaust noise of the air. In addition or alternatively, specialized foam can be used near the air intake to help dampen the air flow noise.

The airflow zone or layer can be used with a separate foot warming layer in a mattress. For example, the foot warming layer can be constructed with one or more heating elements arranged or attached to the foot section of the mattress, and independently controlled. The airflow zone can be provided in the other section of the mattress, such as the middle section, so that the microclimate control can be provided in both the airflow zone and the foot section independently. Further, the airflow zone can be operated selectively in multiple modes of operations. For example, the airflow zone can be selectively operated in a cooling mode, a heating mode, a cleaning mode, a refresh mode, and a preparation mode.

The bed system described herein can be configured to control the microclimate of the mattress to limit deviation of an internal pressure of an air mattress, thereby providing consistent comfort while the mattress is operated in heating or cooling mode. For example, when an air mattress is actively controlled in a heating or cooling operation, the pressure inside the mattress air chamber changes, which may cause a deviation from the air pressure set point. The bed system can limit the amount of air pressure change caused by such active heating or cooling operation. For example, the bed system can limit the amount of energy inputted into the system or removed from the system, thereby reducing or eliminating a deviation from the air pressure set point.

In addition or alternatively, the bed system can control the microclimate of the mattress to compensate thermal effects of a user resting on the mattress. For example, a sleeper generates a body heat, and such thermal outputs can heat up an air chamber of the mattress, thereby causing an increase in pressure of the air chamber. The pressure change in the air chamber causes a deviation from a pressure set point that was selected by the sleeper or automatically determined based on one or more factors to provide personal comfort. For example, the pressure inside the mattress air chamber can be deviated from a set point due to the thermal output from the user's body. The bed system can offset the thermal input to the bed from active heating or cooling systems by the amount of the thermal effect of the user's body resting on the bed, thereby minimizing a deviation from the set point of air pressure inside the mattress air chamber, and thus ensuring to provide consistent comfort with the bed.

Particular embodiments described herein include a mattress system including a mattress cover, a first layer, heating unit, an airflow insert pad, and an air controller. The first layer has a top surface and an opposite bottom surface. The top surface may be covered by the mattress cover. The first layer may be configured to permit a first airflow rate. The heating unit may be arranged above the top surface of the first layer and under the mattress cover. The heating unit may be electrically controlled to increase temperature. The airflow insert pad may be arranged under the bottom surface of the first layer, and configured to permit a second airflow rate being higher than the first airflow. The air controller may be configured to move air through the airflow insert pad and through the first layer to decrease a temperature at the top surface of the first layer.

In some implementations, the system can optionally include one or more of the following features. The heating unit may include a foot warming envelop positioned at a foot of the mattress system, and the airflow insert pad may be positioned closer to a head of the mattress system than the foot warming envelop. The first layer may be configured as a foam layer. The air controller may be configured to draw air from the airflow insert pad. The air controller may be configured to supply conditioned air to the air insert pad. The conditioned air may include heated air. The conditioned air may include cooled air. The airflow insert pad may include a pad cover and an airflow material enclosed in the pad cover. The pad cover may include a vent, and the airflow insert pad may be arranged for the vent to face the bottom surface of the first layer. The pad cover may be made of an air restrictive material, and the vent is covered by a meshed material. The vent may include a window provided in the pad cover. The vent may have edges spaced inward of a perimeter of the airflow insert pad to form a border around the vent. The mattress system may include an air duct fluidly connected to the airflow insert pad. The air duct may include an opening that is connected to a portion of the airflow insert pad that corresponds to the border around the vent. The airflow insert pad may be free of holes. The airflow insert pad may be made of Qshion™ material. The airflow insert pad may be made of one of a spacer monofilament material and a reticulated foam. The mattress system may include an inflatable chamber positioned below the first layer. The mattress system may include a foam rail structure including top, bottom, and opposite side form rails extending between the top and bottom foam rails, and configured to surround the inflatable chamber. The rails may be attached to the periphery of the first foam layer on the bottom surface. The mattress system may include a second foam layer (i.e., support foam layer) attached to the bottom surface and including a cutout section configured to receive the airflow insert pad. The airflow insert pad may be enclosed in the cutout section and surrounded by the second foam layer such that the airflow insert pad is not laterally exposed. The airflow insert pad may be attached to the bottom surface of the first foam layer through the cutout section of the second foam layer. The foam rail structure may be attached to the second form layer. The mattress system may include an air duct extending between the airflow insert pad and the air controller. At least one of the rails may have a notch configured to at least partially receive the air duct. The mattress system may include one or more reinforcement straps attached to the side rails and extending between the side rails. The mattress system may include an air chamber at least partially surrounded by the rails, and an air hose extending from the air chamber. The air hose may extend at least partially along the duct. The mattress system may include a foundation including a duct opening configured to mate with an end of the air duct. The mattress system may include a sleeve at least partially disposed around the air duct. The heating unit may include a layer positioned at a foot of the mattress system above the first layer and under the mattress cover that is configured to generate heat in response to an electric current. The air controller may include an air controller housing defining a housing inlet and a housing outlet, a fan positioned in the air controller housing, and an air passage connecting at least one of the housing inlet and the housing outlet of the air controller housing to the airflow insert pad. The air controller may include a heater positioned in the air controller housing between the housing inlet and the housing outlet. The air passage may connect the housing inlet to the airflow insert pad. The air controller may be configured to draw air from the airflow insert pad into the air controller housing.

Particular embodiments described herein include a method of operating the mattress system described herein. The method may include heating via the heating unit, and cooling via the air controller.

In some implementations, the system can optionally include one or more of the following features. The method may include heating a foot portion of the mattress system via the heating unit while cooling a second portion of the mattress system via the air controller. The method may include heating a foot portion of the mattress system via the heating unit before a user enters the mattress system, stopping heating the foot portion of the mattress system via the heating unit either before or when a user is sensed entering the mattress system, and cooling a second portion of the mattress system via the air controller after a user is sensed entering the mattress system.

Particular embodiments described herein include a mattress system including a mattress cover, a first foam layer, a foot warming envelop, an airflow insert pad, and an air controller. The first foam layer has a top surface and an opposite bottom surface. The top surface may be covered by the mattress cover. The first foam layer may be configured to permit a first airflow rate. The foot warming envelop may enclose a heating unit and arranged under the mattress cover. The heating unit may be electrically controlled. The airflow insert pad may be arranged under the bottom surface of the first foam layer, and configured to permit a second airflow rate being higher than the first airflow. The air controller may be configured to draw air from the airflow insert pad to increase distribution of air through the first foam layer and decrease a temperature at the top surface of the first foam layer.

Particular embodiments described herein include a mattress system including a first foam layer, an airflow pad, and an air controller. The first foam layer may be configured to permit a first airflow rate. The airflow pad may be arranged under the first foam layer and configured to permit a second airflow rate being higher than the first airflow. The air controller may be configured to move air through the airflow pad to and through the first foam layer to decrease a temperature at a top surface of the first foam layer. The airflow pad may be made of a water-resistant, breathable, resilient, and supportive airflow material that is different than the first foam layer.

In some implementations, the system can optionally include one or more of the following features. The airflow material may have three-dimensional structures with elastic polyolefin fibers. The airflow material may be made of 100% polyolefin. The airflow material may include Qshion™ material. The airflow material may have a resilience rate of thickness no less than 95% after 80,000 times of repeated compressions. The airflow pad may include a pad cover to enclose the airflow material. The pad cover may include a vent, and the airflow pad may be arranged for the vent to face a bottom surface of the first foam layer. The pad cover may be made of an air restrictive material, and the vent may be covered by a meshed material. The airflow pad may be free of holes.

Particular embodiments described herein include a mattress system including a first foam layer, an airflow pad, an air hose, and a mattress core. The first foam layer may be positioned proximate a mattress top. The airflow pad may be positioned under the first foam layer. The airflow pad includes a core of Qshion™ material and a plenum chamber. The plenum chamber may substantially surround the core of Qshion™ material via a cover material that limits airflow. The cover material may be positioned on at least part of a top, a bottom, and sides of the core of Qshion™ material. The plenum chamber may define a top opening. A mesh material may cover the top opening such that air can flow through the top opening. The air hose may be connected to the plenum chamber. The mattress core may be configured to support a user positioned under the airflow pad.

Particular embodiments described herein include a mattress including a first layer, a first side rail, a second side rail, a core, and a first strap. The first layer has a first layer top and a first layer bottom and extends from a first layer edge to a second layer edge. The first side rail may be attached to the first layer bottom proximate the first layer edge. The second side rail may be attached to the first layer bottom proximate the second layer edge. The core may be positioned under the first layer bottom between the first side rail and the second side rail. The first strap may be connected to the first side rail and the second side rail at a connection locations such that the first strap extends under the core from a bottom of the first side rail to a bottom of the second side rail.

In some implementations, the system can optionally include one or more of the following features. The mattress may include a mattress cover enclosing the first layer, the first side rail, the second side rail, the core, and the first strap. The mattress may include a second strap connected to the first side rail and the second side rail such that the second strap extends under the core from the first rail bottom to the second rail bottom. The first strap and the second strap may be both positioned in a longitudinal middle section of the mattress with the second strap spaced from the first strap. The mattress may include a second strap connected to the first side rail and the second side rail such that the second strap extends under the core from the first rail bottom to the second rail bottom. The first strap may cross the second strap such that the strap is connected to the first side rail between a head of the mattress and the second strap. The first strap may be connected to the second side rail between a foot of the mattress and the second strap. The mattress may include a second strap connected to the first side rail and the second side rail such that the second strap extends under the core from the first rail bottom to the second rail bottom. The first side rail may define a first cutout and the second side rail defines a second cutout such that the first and second side rails are structurally weakened at the first and second cutouts, and wherein the first and second straps connect to the first and second side rails on opposite sides of the first and second cutouts. The first side rail may define a first cutout and the second side rail defines a second cutout such that the first and second side rails are structurally weakened at the first and second cutouts. The first strap may be connected to the first and second side rails proximate the first and second cutouts. The first layer, the first side rail, and the second side rail may include one or more foam materials. The core may include an inflatable air chamber. The first layer, the first side rail, and the second side rail may be part of an upside-down foam tub. The upside-down foam tub may include a foot rail and a head rail. The mattress may include a second strap, a first air hose, and a second air hose. The second strap may be connected to the first side rail and the second side rail such that the second strap extends under the core from the first rail bottom to the second rail bottom. The first air hose may extend through the first side rail between the first strap and the second strap. The second air hose may extend through the second side rail between the first strap and the second strap.

Particular embodiments described herein include a bed including a mattress and a plurality of straps. The mattress may include a first foam layer having a top surface and an opposite bottom surface, an inflatable chamber arranged opposite to the top surface of the first foam layer, and a foam rail structure including top, bottom, and opposite side form rails extending between the top and bottom foam rails. The foam rail structure may extend from a periphery of the first foam layer and configured to surround the inflatable chamber. The plurality of straps may each have opposite ends attached to the opposite side foam rails, respectively, and extend across the inflatable chamber between the opposite side foam rails.

In some implementations, the system can optionally include one or more of the following features. The plurality of straps may be arranged to extend between a bottom of the mattress. The bed may include a foundation configured to support the mattress. The plurality of straps are disposed between a bottom of the mattress and a top of the foundation. The mattress system may include a plurality of fastening elements configured to attach the plurality of straps onto the opposite side foam rails. The plurality of fastening elements may include adhesive tapes applied between the foam rail structure and the ends of the straps. The foam rail structure may include a notch, and at least one of the plurality of straps may be attached to the foam rail structure adjacent the notch.

Particular embodiments described herein include a bed including a mattress and a foundation. The mattress has a mattress top and a mattress bottom defining a mattress interior between the mattress top and the mattress bottom. The mattress may include a first connection portion and an air hose. The first connection portion may be positioned on the mattress bottom. The first connection portion may be in fluid communication with a first air hole located within the mattress interior and configured to allow air flow therethrough. The air hose may extend from the first air hole and out from the mattress bottom through the first connection portion. The foundation may be sized and configured to be positioned under the mattress bottom to support the mattress. The foundation may include a support surface and a second connection portion. The second connection portion may be positioned on the support surface. The second connection portion may define a second air hole configured to allow air flow through the second connection portion. The second connection portion may be positioned on the foundation at a location configured to align with and connect to the first connection portion when the mattress is positioned on the foundation. The first air hole may be fluidly connected with the second air hole such that air can flow between the foundation and the mattress through the first and second air holes when the first connection portion is connected to the second connection portion.

In some implementations, the system can optionally include one or more of the following features. The mattress may include a mattress cover. The first connection portion may include a first part positioned on an inside of the mattress cover that connects to a second part positioned on an outside of the mattress cover. The mattress may include an inflatable air chamber, an air distribution layer, and a second air hose. Both the air hose and the second air hoses may extend through the first air hole such that the air hose extends to the air distribution layer and the second air hose extends to the inflatable air chamber. The first connection portion may connect to the second connection portion via a snap connection. The foundation may be an adjustable foundation configured to selectively raise and lower a head of the mattress and a foot of the mattress. The foundation may include a head panel configured to raise the head of the mattress, a foot panel configured to raise the foot of the mattress, and a middle panel positioned between the head panel and the foot panel. The second connection portion may be positioned on the middle panel. The middle panel may remain substantially stationary when the head panel and the foot panel are articulated. The bed may include a third connection portion positioned on the mattress bottom defining a third air hole and a fourth connection portion positioned on the support surface defining a fourth hole. The fourth connection portion may be positioned on the foundation at a location configured to align with and connect to the third connection portion when the mattress is positioned on the foundation. The third air hole may be aligned with the fourth air hole such that air can flow between the foundation and the mattress through the third and fourth air holes when the third connection portion is connected to the fourth connection portion. The first, second, third, and fourth connection portions may be connected with sufficient strength to hold the mattress to the foundation without any additional connectors between the mattress and the foundation when the foundation raises the head and the foot of the mattress. The air hose may extend through the first air hole and connects to the second connection portion. The second connection portion may include a hose support portion sized and shaped to extend upward into the first hole and into a first end of the air hose to provide structural rigidity to the air hose when the first connection portion is connected to the second connection portion.

Particular embodiments described herein include a bed including a mattress and a foundation. The mattress has a mattress top and a mattress bottom defining a mattress interior between the mattress top and the mattress bottom. The mattress may include a first connection portion defining a first air hole positioned at or proximate the mattress bottom. The foundation may be sized and configured to be positioned under the mattress bottom to support the mattress. The foundation may include a support surface and a second connection portion. The second connection portion may be positioned on the support surface. The second connection portion may define a second air hole configured to allow air flow through the second connection portion. The second connection portion may be positioned on the foundation at a location configured to align with and connect to the first connection portion when the mattress is positioned on the foundation. The first connection portion may be fluidly connected with the second connection portion such that air can flow between the foundation and the mattress through the first and second air holes when the first connection portion is connected to the second connection portion. The second connection portion may include a rib extending into the first connection portion to support the first connection portion.

In some implementations, the system can optionally include one or more of the following features. The rib may include first and second sidewalls extending upward from the second connection portion on opposite sides of the second air hole. The rib may include a cross wall extending across the second air hole.

Particular embodiments described herein include a bed including a mattress, a foundation, a duct connector, and an air controller. The mattress may include a foam layer configured to permit a first airflow rate, an airflow insert pad arranged under the foam layer and configured to permit a second airflow rate being higher than the first airflow, and an air duct having first and second ends, the first end being fluidly connected to the airflow insert pad. The foundation may support the mattress and including a duct opening. The duct connector may be attached around the duct opening of the foundation and configured to fit the second end of the air duct. The air controller may be fluidly connected to the duct opening and configured to draw air from the airflow insert pad through the air duct to increase distribution of air through the foam layer and decrease a temperature at a top surface of the foam layer.

In some implementations, the system can optionally include one or more of the following features. The duct connector may be arranged adjacent a periphery of the foundation. The duct connector may include a base fixed to a top surface of the foundation, and a rib extending from the base away from the top surface of the foundation. The rib may be configured to inserted into the air duct and maintain a width of at least the second end of the air duct when the second end of the air duct is connected to the duct connector. The duct connector may include a first sub-connector fixed to a top surface of the foundation, and a second sub-connector fixed to a bottom surface of the mattress. The second sub-connector may be configured to snap to the first sub-connector to position the mattress relative to the foundation. The second sub-connector may be configured to slide relative to the first sub-connector to lock the position of the mattress relative to the foundation.

Particular embodiments described herein include a mattress system including a foam layer, an airflow insert pad, and an air controller. The foam layer may be configured to permit a first airflow rate. The airflow insert pad may be arranged under the foam layer and configured to permit a second airflow rate being higher than the first airflow. The air controller may be configured to draw air from the airflow insert pad and supply heated air to the airflow insert pad. The air controller may include a housing having a connection-side opening and an ambient-side opening, a reversible fan mounted in the housing, a heating element mounted in the housing, and a control unit configured to control the air controller in a cooling mode in which the reversible fan operates to cause airflow from the connection-side opening to the ambient-side opening through the housing, and further configured to control the air controller in a heating mode in which the heating element is heated and the reversible fan operates to cause air to flow from the ambient-side opening to the connection-side opening, passing through the heating element.

In some implementations, the system can optionally include one or more of the following features. The air controller may include a first temperature sensor configured to detect a heating element temperature, and a second temperature sensor configured to detect an outlet temperature of air exiting the housing. The control unit may receive signals from the first and second temperature sensors and control the heating element based on the signals to achieve a predetermined outlet temperature. The air controller may include a third temperature sensor configured to detect a temperature of the air drawn from the airflow insert pad, and a fourth temperature sensor configured to detect an ambient temperature. The control unit may receive signals from the third and fourth temperature sensors, and control the reversible fan based on the signals. The control unit may calculate an amount of heat extracted from the airflow insert pad based on the signals. The air controller may include one or more humidity sensors. The control unit may receive signals from the humidity sensors and controls the reversible fan and the heating element based on the signals. The housing may include a curved conduit between the connection-side opening and the ambient-side opening, and the heating element may be arranged at the curved conduit. The heating element may be sized to be smaller than a cross section of the curved conduit. The heating element may be arranged closer to an outer corner of the curved conduit than an inner corner of the curved conduit. The reversible fan may be arranged at the ambient-side opening of the housing. The housing may include ribs extending from an inner surface of the housing and configured to engage the reversible fan to secure the reversible fan at the ambient-side opening of the housing. The air controller may include a foam material disposed between the ribs and the reversible fan. The air controller may include a first screen arranged at the connection-side opening of the housing, and a second screen arranged at the ambient-side opening of the housing. The housing may include opposite spacers extending from an inner surface of the housing and configured to interference-fit the heating element therebetween.

Particular embodiments described herein include an air controller configured to be used with a mattress. The air controller may include a housing having a mattress-side opening and an ambient-side opening, a reversible fan mounted in the housing, and a heating element that includes a plurality of fins that allow air flow in between the fins to be heated by the heating element. The heating element may be mounted in the housing in a location that is at least partially spaced from an inner wall of the housing so as to define a bypass flow path that allows air to flow around the heating element while air simultaneously flows through the heating element when air flows from the ambient-side opening toward the mattress-side opening and when air flows from the mattress-side opening to the ambient-side opening.

In some implementations, the system can optionally include one or more of the following features. The air controller may include a printed circuit board positioned in the housing between the ambient-side opening and the heating element. The reversible fan may be positioned in the housing between the ambient-side opening and the heating element. The printed circuit board may be electrically connected to both the reversible fan and the heating element to control operation of the reversible fan and the heating element.

Particular embodiments described herein include a method for controlling a microclimate of a mattress. The method may include activating a heating element to heat air; activating a reversible fan in a direction to supply the heated air to a top of the mattress; controlling the reversible fan in an opposite direction to draw an amount of air from the top of the mattress for a predetermined period time; detecting a temperature of the amount of air drawn from the top of the mattress; and activating the heating element and the reversible fan again whereby activation of at least one of the heating element and the reversible fan is adjusted based on the temperature detected.

Particular embodiments described herein include a method for controlling a microclimate of a mattress. The method may include activating a heating element to heat air; activating a first fan to supply the heated air to an air layer; controlling a second fan to draw an amount of air from the air layer for a predetermined period time; detecting a temperature of the amount of air drawn from the air layer; and adjusting activation of at least one of the heating element and the first fan based on the temperature.

Particular embodiments described herein include a method for controlling a microclimate of a mattress. The method may include activating a fan to draw air from an air insert pad, detecting a temperature of the air drawn from the air insert pad, and adjusting activation of the fan based on the temperature. The air insert pad may be arranged under a top foam layer and configured to permit an airflow rate being higher than an airflow rate of the top foam layer.

Particular embodiments described herein include a method for controlling a microclimate of a mattress. The method may include activating an air conditioner to condition air; supplying the conditioned air to an inlet of an air insert pad, detecting supply characteristics of air entering the inlet of the air insert pad, detecting return characteristics of air exiting an outlet of the air inset pad, and adjusting activation of the air conditioner based on the supply characteristics and the return characteristics. The air insert pad may be arranged under a top foam layer and configured to permit an airflow rate being higher than an airflow rate of the top foam layer.

In some implementations, the system can optionally include one or more of the following features. Supplying the conditioned air may include activating a fan to supply the conditioned air. The method may include adjusting activation of the fan based on the supply characteristics and the return characteristics. The supply characteristics and the return characteristics may include at least one of temperature and humidity.

Particular embodiments described herein include a method including first, supplying air to a mattress over a first extended period to control a microclimate at a top of the mattress; second, sampling air temperature at the microclimate over a brief sampling period by reversing airflow to draw air from the mattress to a temperature sensor; and third, supplying air to the mattress again over a second extended period whereby air is supplied in a manner different than during the first extended period as a function of the air temperature sampled while airflow was reversed.

In some implementations, the system can optionally include one or more of the following features. The first and second extended periods may be between 5 and 300 minutes long and wherein the brief sampling period is between 5 and 300 seconds long.

Particular embodiments described herein include a bed system including a mattress, a fan assembly configured to cause air to flow from or to the mattress, a temperature sensor configured to sense a temperature of the air that flows from or to the mattress, and a controller configured to activate the fan assembly to supply air to the mattress over a first extended period to control a microclimate at a top of the mattress; activate the fan assembly to reverse airflow to draw air from the mattress for a sampling period of time; sample air temperature based on a signal from the temperature sensor, the signal representative of a temperature of the air detected by the temperature sensor; and activate the fan assembly to supply air to the mattress again over a second extended period whereby air is supplied in a manner different than during the first extended period as a function of the air temperature sampled while airflow was reversed.

In some implementations, the system can optionally include one or more of the following features. The temperature sensor may be arranged adjacent the fan assembly. The temperature sensor may be arranged outside of the mattress. The temperature sensor may be arranged in an airflow path between the fan assembly and the mattress. The bed system may include a humidity sensor configured to detect humidity of the air that flows from or to the mattress. The humidity of the air may be usable to control an operation of the fan assembly.

Particular embodiments described herein include a method of operating a mattress air controller. The method may include flowing air through a housing of the mattress air controller in a first direction from a housing inlet to a housing outlet during a first operation mode configured to condition air at a top of a mattress; and reversing flow of air through the housing in a second direction from the housing outlet to the housing inlet during a filter cleaning mode in order to blow particles out of a filter positioned at the housing inlet. The filter cleaning mode may have a substantially shorter duration than the first operation mode.

In some implementations, the system can optionally include one or more of the following features. The method may include sensing user presence on the mattress; determining that a user exited the mattress; and operating the filter cleaning mode after determining that the user exited the mattress. The filter cleaning mode may be operated daily when a user is not on the mattress.

Particular embodiments described herein include a method of controlling an air controller configured to draw air from an airflow insert pad for a mattress and supply conditioned air to the airflow insert pad. The method may include providing the air controller that includes a housing, a reversible fan, a heating element, and a filtering unit. The housing has a connection-side opening and an ambient-side opening. The connection-side opening may be in fluid communication with the airflow insert pad, and the ambient-side opening exposed to a surrounding. The reversible fan may be mounted in the housing. The heating element may be mounted in the housing. The filtering unit may be arranged at the ambient-side opening of the housing. The method may further include controlling the air controller in a cooling mode by operating the reversible fan to cause airflow from the connection-side opening to the ambient-side opening through the housing; and controlling the air controller in a cleaning mode by operating the reversible fan to blow air out through the filtering unit at the ambient-side opening of the housing for a predetermined period of time, thereby cleaning the filtering unit.

In some implementations, the system can optionally include one or more of the following features. The air controller may be configured to perform the cleaning mode periodically. The air control may include a second filtering unit arranged at the connection-side opening of the housing. The method may include controlling the air controller in a heating mode in which the heating element is heated and the reversible fan operates to cause air to flow from the ambient-side opening to the connection-side opening, passing through the heating element.

Particular embodiments described herein include a method of controlling an air controller configured to draw air from an air distribution layer for a mattress and supply conditioned air to the air distribution layer. The method may include providing the air controller that includes a reversible fan and a heating element. The method may further include controlling the air controller in a cooling mode by operating the reversible fan to draw air from the air distribution layer; and controlling the air controller in a refresh mode by operating the reversible fan to cause air to circulate through the air distribution layer for a predetermined period of time.

In some implementations, the system can optionally include one or more of the following features. The air controller may be controlled in the refresh mode for a predetermined period of time. The predetermined period of time may range from 30 minutes to 60 minutes. The method may include sensing user presence on the mattress; and determining that a user is not present on the mattress prior to controlling the air controller in the refresh mode. The method may include detecting a humidity level in the air in the refresh mode; and operating the air controller in the refresh mode until the humidity level reaches a predetermined value. Controlling the air controller in a refresh mode may include controlling the reversible fan to draw air from the air distribution layer for the predetermined period of time. Controlling the air controller in a refresh mode may include controlling the reversible fan to supply air to the air distribution layer for the predetermined period of time. The method may include flowing air through a HEPA filter during the refresh mode. The method may include applying aromatherapy to circulated air during the refresh mode. The method may include applying essential oils to air circulated into the mattress during the refresh mode. The mattress may include no materials treated with antimicrobial chemicals and the refresh mode may be automatically operated regularly at intervals configured to reduce microbial growth.

Particular embodiments described herein include a method of operating a mattress air controller. The method may include determining that a user is in bed; operating the mattress air controller to heat or cool the user while the user is determined to be in bed; determining that the user is not in bed; and operating the mattress air controller in a refresh mode to refresh air in the mattress while the user is determined to be not in bed.

Particular embodiments described herein include a bed system including a mattress and a mattress air controller. The mattress air controller may include a fan, one or more processors, and a computer-readable storage medium coupled to the one or more processors and having instructions stored thereon which, when executed by the one or more processors, cause the one or more processors to perform operations including: operating the mattress air controller in a conditioning mode whereby the fan is operated to move air at a top of the mattress to heat or cool the user; and operating the mattress air controller in a refresh mode whereby the fan is operated to move air at the top of the mattress to refresh the mattress.

In some implementations, the system can optionally include one or more of the following features. The operations may include determining that the user is in bed. The mattress air controller may be operated in the conditioning mode while the user is determined to be in bed; and determining that the user is not in bed. The mattress air controller may be operated in the refresh mode while the user is determined to be not in bed. The mattress air controller may include a heater. The heater may be operated in the conditioning mode and the heater is not operated in the refresh mode.

Particular embodiments described herein include a method of controlling a microclimate of a mattress. The method may include determining a sleep cycle of a subject on the mattress; determining a mode from a plurality of modes based on the sleep cycle; and controlling the air controller in the determined mode. The plurality of modes may include a cooling mode in which an air controller is operated to cause ambient air to flow from an airflow insert pad of the mattress, and a heating mode in which the air controller is operated to cause heated air to flow to the airflow insert pad of the mattress.

In some implementations, the system can optionally include one or more of the following features. The air controller may operate in a first mode in response to one or more processors determining that a user is in stage N1. The air controller may operate in a second mode in response to the one or more processors determining that the user is in stage N2. The air controller may operate in a third mode in response to the one or more processors determining that the user is in stage N3. The air controller may operate in a fourth mode in response to the one or more processors determining that the user is in REM sleep.

Particular embodiments described herein include a method of controlling a microclimate of a mattress. The method may include determining a sleep cycle of a subject on the mattress; determining a mode from a plurality of modes based on the sleep cycle; and controlling the air controller in the determined mode. The plurality of modes may include a cooling mode in which an air controller is operated to draw air from a top of the mattress, and a heating mode in which the air controller is operated to blow heated air to a top of the mattress.

In some implementations, the system can optionally include one or more of the following features. The air controller may operate in a first mode in response to one or more processors determining that a user is in stage N1. The air controller may operate in a second mode in response to the one or more processors determining that the user is in stage N2. The air controller may operate in a third mode in response to the one or more processors determining that the user is in stage N3. The air controller may operate in a fourth mode in response to the one or more processors determining that the user is in REM sleep. The air controller may be configured to draw air from the top of the mattress during a first determined sleep stage and the air controller may be configured to blow air to the top of the mattress during a second determined sleep stage.

Particular embodiments described herein include a method of controlling a microclimate of a mattress. The method may include determining a time period of expected user sleep; sensing whether a user is present on the mattress; in response to sensing presence during the time period of expected user sleep, flowing air through the mattress in a first operation mode to control microclimate of the mattress while the user is on the mattress; in response to sensing that the user exited the mattress during the time period of expected user sleep, flowing air through the mattress in a second operation mode that is different than the first operation mode; and in response to sensing that the user returned to the mattress during the time period of expected user sleep, resuming the first operation mode.

In some implementations, the system can optionally include one or more of the following features. The mattress may include one or more air distribution layers and one or more air controllers fluidly connected to the one or more air distribution layers. The mattress may include a mattress core having one or more air chambers. The method may include adjusting air pressure on the one or more air chambers during the second operation mode. A fan of an air controller may be operated during both the first operation mode and the second operation mode. The fan may be operated at a different speed in the first operation mode than in the second operation mode. A heater of an air controller may be operated during both the first operation mode and the second operation mode, and the heater may be operated differently in the first operation mode than in the second operation mode. A heater of an air controller may be operated during the first operation mode and not during the second operation mode.

Particular embodiments described herein include a method of controlling a microclimate of a mattress. The method may include sensing whether a user is present on the mattress; determining that a user is exited the mattress during a predetermined time period; and, upon determining that the user exited the mattress during the predetermined time period, initiating activation of an air controller to draw air from an air layer of the mattress to increase distribution of air through a foam layer above the air layer and decrease a temperature at the foam layer.

In some implementations, the system can optionally include one or more of the following features. The method may include, upon determining the user returns onto the mattress, deactivating the air controller. The method may include, upon determining the user returns the mattress, activating the air controller in a mode of operation that was performed before the user exited the mattress. The method may include, prior to determining the user exited the mattress, detecting that the user is on the mattress during the predetermined time period. The predetermined time may range from midnight to 6 AM.

Particular embodiments described herein include a bed system including a mattress, an air controller, a sensor subsystem, and a control subsystem. The mattress has a foam layer and an air layer disposed under the foam layer. The air controller may be configured to cause air to flow through the air layer. The sensor subsystem may be configured to sense whether a user is present on the mattress. The control subsystem may be configured to determine that a user exited the mattress during a predetermined time period; and, upon determining that the user exited the mattress during the predetermined time period, initiate activation of the air controller to draw air from the air layer of the mattress to increase distribution of air through the foam layer above the air layer and decrease a temperature at the foam layer.

In some implementations, the system can optionally include one or more of the following features. The control subsystem may be configured to, upon determining the user returns the mattress, activate the air controller in a mode of operation that was performed before the user exited the mattress. The control subsystem may be configured to, prior to determining the user exited the mattress, detect that the user is on the mattress during the predetermined time period.

Particular embodiments described herein include a mattress system including a mattress having a first climate control zone and a second climate control zone, one or more air controllers in fluid communication with the first and second climate control zones, one or more processors, and a computer-readable storage medium coupled to the one or more processors having instructions stored thereon which, when executed by the one or more processors, cause the one or more processors to perform operations. The operations may include receiving a command to supply air to the first climate control zone that is heated; and, in response to receiving the command, commanding the one or more air controllers to supply heated air to the first climate control zone and to supply ambient air to the second climate control zone. A flow rate of ambient air to the second climate control zone may be configured to reduce an amount of heat transferred from the first climate control zone to the second climate control zone.

In some implementations, the system can optionally include one or more of the following features. The processor may command the one or more air controllers to supply ambient air to the second climate control zone without receiving any user request to supply air to the second climate control zone. The operations may include, in response to sensing a user's presence on the second climate control zone, commanding the one or more controllers to stop supplying ambient air to the second climate control zone. The operations may include, in response to sensing a user's presence on the second climate control zone, commanding the one or more controllers to reduce supply of ambient air to the second climate control zone. The operations may include, in response to sensing a user's presence on the second climate control zone, commanding the one or more controllers to stop supplying heated air to the first climate control zone and to stop supplying ambient air to the second climate control zone. The operations may include, in response to sensing a user's presence on the second climate control zone, commanding the one or more controllers to reduce supply of heated air to the first climate control zone and to reduce supply of ambient air to the second climate control zone. The operations may include, in response to sensing a user's presence on the first climate control zone, commanding the one or more controllers to stop supplying heated air to the first climate control zone and to stop supplying ambient air to the second climate control zone. The operations may include, in response to sensing a user's presence on the first climate control zone, commanding the one or more controllers to reduce supply of heated air to the first climate control zone and to reduce supply of ambient air to the second climate control zone. The flow rate of ambient air to the second climate control zone may be substantially less than a flow rate of heated air to the first climate control zone.

Particular embodiments described herein include a mattress system including a mattress, one or more air controllers, one or more processors, and a computer-readable storage medium. The mattress may have a first climate control zone, a second climate control zone, a third climate control zone, and a fourth climate control zone. The one or more air controllers may be in fluid communication with each of the first, second, third, and fourth climate control zones and configured to independently supply air to or draw air from each of the first, second, third, and fourth climate control zones. The computer-readable storage medium may be coupled to the one or more processors having instructions stored thereon which, when executed by the one or more processors, cause the one or more processors to perform operations. The operations may include commanding the one or more air controllers to operate in a first mode whereby heated or cooled air is supplied to the first zone while air is simultaneously drawn from the second zone; and commanding the one or more air controllers to operate in a second mode whereby heated or cooled air is supplied to the third zone while air is simultaneously drawn from the fourth zone.

In some implementations, the system can optionally include one or more of the following features. The operations may include commanding the one or more air controllers to operate in a third mode whereby heated air is supplied to the first and third zones while air is simultaneously drawn from the second and fourth zones; and commanding the one or more air controllers to operate in a fourth mode whereby heated air is supplied to the first zone, cooled air is supplied to the third zone, and air is simultaneously drawn from the second and fourth zones. The first and second zones may be on a first side of the mattress for supporting a first user and the third and fourth zones are on a second side of the mattress for supporting a second user.

Particular embodiments described herein include a climate-controlled mattress system including a mattress core configured to support a user, an air distribution layer configured to facilitate air flow for climate control of a mattress top surface, an air hose, an air controller fluidly connected to the air distribution layer via the air hose, and a mattress cover that encloses the mattress core, the air distribution layer, and at least part of the air hose. The mattress cover may include a top surface, a bottom surface, and side surfaces. At least a portion of the mattress cover may include fabric with thread having a first heat capacity that is relatively low. The top surface of the mattress cover may include stitching via a stitching material having a second heat capacity that is relatively high as compared to the first heat capacity.

In some implementations, the system can optionally include one or more of the following features. The stitching material may include polypropylene. The stitching material may include nylon.

Particular embodiments described herein include a climate-controlled mattress system including a mattress core configured to support a user, an air distribution layer, an air hose, an air controller, and a gel layer. The air distribution layer may be configured to facilitate air flow for climate control of a mattress top surface. The air distribution layer may have a first heat capacity. The air controller may be fluidly connected to the air distribution layer via the air hose. The gel layer may be positioned proximate the mattress top surface and have a second heat capacity. The second heat capacity may be substantially higher than the first heat capacity.

In some implementations, the system can optionally include one or more of the following features. The climate-controlled mattress system may include a foam layer positioned above the air distribution layer and under the gel layer. The foam layer may have a third heat capacity that is less than the second heat capacity of the gel layer.

Particular embodiments described herein include a mattress system including a mattress cover layer, a foam layer, an airflow insert, and an air controller. The mattress cover layer may include a surface with stitches formed of a material having a first heat capacity. The foam layer has a top surface and an opposite bottom surface. The top surface may be covered by the mattress cover. The foam layer may be configured to permit a first airflow rate. The foam layer may be formed of a material having a second heat capacity that is less than the first heat capacity. The airflow insert pad may be arranged under the bottom surface of the first foam layer, and configured to permit a second airflow rate being higher than the first airflow. The air controller may be configured to draw air from the airflow insert pad to increase distribution of air through the first foam layer and decrease a temperature at the top surface of the first foam layer.

In some implementations, the system can optionally include one or more of the following features. The stitches may be made with polypropylene threads or nylon threads. The mattress cover layer may include a layer of material having a heat capacity greater than a threshold value. The layer of material may include a gel.

Particular embodiments described herein include a bed including a mattress. The mattress may include an inflatable air chamber, an air distribution layer positioned above the inflatable air chamber, a foam layer positioned above the air distribution layer and proximate a top of the mattress, a first air hose, and a second air hose. The foam layer and the air distribution layer may be both configured to allow airflow therethrough. The air distribution layer may resist air flow less than the foam layer. The first air hose may be connected to the inflatable air chamber for inflating the inflatable air chamber. The second air hose may be connected to the air distribution layer for moving air through the air distribution layer. The second air hose may extend from a location that is lower than the inflatable air chamber, around a first side of the inflatable air chamber, to the air distribution layer above the inflatable air chamber.

In some implementations, the system can optionally include one or more of the following features. The mattress may include a mattress cover, and the first and second air hoses may enter the mattress through a common hole in the mattress cover. The inflatable air chamber may include a first inflatable air chamber, and the air distribution layer may include first and second air distribution zones. The first inflatable air chamber may be positioned under the first air distribution zone. The mattress may include a second inflatable air chamber positioned under the second air distribution zone. The mattress may include an insulator positioned between the first air chamber and the second air chamber to reduce heat transfer between the first air chamber and the second air chamber. The mattress may include an insulator positioned between the first and second air chambers and also between the first and second air distribution layers to reduce heat transfer between left and right sides of the mattress. The mattress may include a third air hose connected to the second inflatable air chamber for inflating the second inflatable air chamber; and a fourth air hose connected to the second air distribution layer for moving air through the second air distribution layer. The fourth air hose may extend from a second location that is lower than the second inflatable air chamber, around a second side of the second inflatable air chamber, to the second air distribution layer above the second inflatable air chamber. The mattress may include a mattress cover, and the first and second air hoses may enter the mattress through a first common hole in the mattress cover and the third and fourth air hoses may enter the mattress through a second common hole in the mattress cover. The mattress may include a first rail and a second rail. The first rail may be positioned on the first side of the first inflatable air chamber. The first rail may define a first hose passage, and the first and second hoses may enter the mattress proximate the first hose passage. The second rail may be positioned on the second side of the second inflatable air chamber. The second rail may define a second hose passage, and the third and fourth hoses may enter the mattress proximate the second hose passage. The bed may include a foundation, a pump assembly, and an air controller. The foundation has a support platform configured for supporting the mattress and includes a first foundation opening extending through the support platform and configured to receive the first and second air hoses. The pump assembly may be fluidly connected to an end hose end of the first air hose and configured to supply fluid to the inflatable air chamber. The pump assembly may be positioned in the foundation. The air controller may be fluidly connected to the second air hose and configured to move air through the air distribution layer. The air controller may be positioned in the foundation.

Particular embodiments described herein include a bed that includes a mattress, a foundation, a pump assembly, and an air controller. The mattress may include a foam layer configured to permit a first airflow rate; an inflatable chamber arranged under the foam layer; a hose having first and second hose ends, the first hose end fluidly connected to the inflatable chamber; a foam rail structure including top, bottom, and opposite side form rails extending between the top and bottom foam rails, and configured to surround the inflatable chamber; an airflow insert pad arranged under the foam layer and configured to permit a second airflow rate being higher than the first airflow; and an air duct having first and second duct ends, the first duct end being fluidly connected to the airflow insert pad. The foundation may support the mattress and include a duct opening configured to mate with the second duct end of the air duct. The pump assembly may be fluidly connected to the second hose end of the hose and configured to supply fluid to the chamber. The air controller may be fluidly connected to the duct opening and configured to draw air from the airflow insert pad through the air duct to increase distribution of air through the foam layer and decrease a temperature at a top surface of the foam layer.

In some implementations, the system can optionally include one or more of the following features. The hose may be at least partially routed adjacent the air duct. The airflow insert pad may include a pad cover, and the air duct may be fastened to the pad cover at the first duct end to fluidly connect the air duct with the airflow insert pad. The air duct may be stitched to the pad cover at the first duct end. The air duct may extend from the airflow insert pad is routed around the chamber. The bed may include a duct connector including a base fixed to a top surface of the foundation, and a rib extending from the base away from the top surface of the foundation. The rib may be configured to be inserted into the air duct and maintain a width of at least the second duct end of the air duct against the hose running adjacent the air duct, when the second duct end of the air duct is connected to the duct connector. The foam rail structure may include a notch configured to at least partially receive the air duct extending from the airflow insert pad and around the chamber.

Particular embodiments described herein include a mattress including a mattress core, an air distribution layer, an air hose, and a mattress cover. The mattress core may be configured to support a user. The air distribution layer may be configured to facilitate air flow for climate control of a mattress top surface. The air distribution layer may be positioned above the mattress core. The air hose may be connected to the air distribution layer. The mattress cover has a mattress cover top surface. The mattress cover top surface may include a fabric configured to allow flow of air between the air distribution layer and a space above the mattress top and to resist flow of liquid water into the mattress when the liquid water is positioned on top of the mattress cover top surface.

In some implementations, the system can optionally include one or more of the following features. The fabric may substantially prevent flow of liquid water into the mattress at atmospheric pressure. The fabric may completely prevent flow of liquid water into the mattress at atmospheric pressure. The mattress cover may have a plurality of mattress cover side surfaces that each may include one or more second fabrics configured to allow flow of air and flow of water through the one or more second fabrics. The fabric on the mattress cover top surface may be significantly more liquid resistant than the one or more second fabrics on the mattress cover side surfaces. The fabric on the mattress cover top surface may be water resistant enough to prevent user perspiration from flowing through the fabric into the air distribution layer when air is blown from the air distribution layer through the fabric. The fabric on the mattress cover top surface may be water resistant enough to prevent user perspiration from flowing through the fabric into the air distribution layer when air is drawn from above the fabric into the air distribution layer.

Particular embodiments described herein include a bed system having a mattress. The bed system may include a first air system, a second air system, and a controller. The first air system may be configured for controlling pressure of a first air chamber of the mattress. The second air system may be configured for conditioning air at a top of the mattress. The controller has one or more processors and a computer-readable storage medium coupled to the one or more processors having instructions stored thereon which, when executed by the one or more processors, cause the one or more processors to perform operations. The operations may include operating the second air system as a function of data from the first air system.

In some implementations, the system can optionally include one or more of the following features. The first air system may include a pressure sensor in fluid communication with the first air chamber and configured to sense air pressure. The data may include the air pressure sensed by the pressure sensor of the first air system. The second air system may include a fan, a heater, and an air distribution layer positioned above the first air chamber. The second air system may include a heater, and the heater may be operated as a function of pressure data sensed by the first air system. The operations may include receiving a user input for a desired pressure setpoint of the first air chamber; and operating the first air system to achieve the desired pressure setpoint. Operating the second air system as a function of data from the first air system may include operating the second air system to maintain pressure of the first air chamber to a pressure that is near the desired pressure setpoint. Operating the second air system as a function of data from the first air system may include operating the second air system to maintain pressure of the first air chamber to a pressure that is near a desired pressure setpoint. Operating the second air system as a function of data from the first air system may include operating the second air system to maintain pressure of the first air chamber to a pressure that is within a tolerance range of a desired pressure setpoint. Operating the second air system as a function of data from the first air system may include stopping operation of a heater in response to determining that pressure in the first air chamber is at or has exceeded a threshold. The mattress may include a first layer above the first air chamber, an air distribution layer comprising Qshion™ material above the first layer, a second layer above the air distribution layer, a mattress cover enclosing the first air chamber, the first and second layers, and the air distribution layer, an air hose connected to the first air chamber, and an air duct connected to the air distribution layer. The operations may include determining a desired pressure setpoint and a pressure limit. Operating the second air system as a function of data from the first air system may include operating at least one of a heater and a fan intermittently in a manner configured to avoid exceeding the pressure limit.

Particular embodiments described herein include a method including sensing pressure of an air chamber of a mattress; and controlling operation of an air system as a function of the pressure of the air chamber. The air system may include an air mover fluidically connected to an air layer that is positioned external to and above the air chamber.

In some implementations, the system can optionally include one or more of the following features. The air system may include a fan and a heater, and the heater may be operated as the function of the pressure of the air chamber. The air chamber may be a first air chamber, and the air system may be a first air system. The method may include controlling operation of a second air system as a function of the pressure of the first air chamber. The air chamber may be a first air chamber, and the air system may be a first air system. The method may include receiving a user input for a desired pressure setpoint of the first air chamber; operating the first air system to achieve the desired pressure setpoint; and operating a second air system to maintain pressure of the first air chamber to a pressure that is near the desired pressure setpoint. The air chamber may be a first air chamber, and the air system may be a first air system. The method may include receiving a user input for a desired pressure setpoint of the first air chamber; operating the first air system to achieve the desired pressure setpoint; and operating the second air system to maintain pressure of the first air chamber to a pressure that is within a tolerance range of a desired pressure setpoint.

Particular embodiments described herein include a bed system having a mattress. The bed system may include a first air system configured for controlling pressure of a first air chamber of the mattress; a second air system configured for conditioning air at a top of the mattress; and a controller having one or more processors and a computer-readable storage medium coupled to the one or more processors having instructions stored thereon which, when executed by the one or more processors, cause the one or more processors to perform operations. The operations may include monitoring a temperature of air supplied from the second air system; detecting presence of a user on the mattress; and generating a signal usable by the second air system to change the temperature of air supplied from the second air system by an offset value. The offset value may be configured to achieve no or limited deviation from a set point of the pressure of the first air chamber of the mattress.

In some implementations, the system can optionally include one or more of the following features. Detecting presence of a user on the mattress may include monitoring a pressure of the first air chamber of the mattress; and detecting a change in the pressure of the first air chamber.

Particular embodiments described herein include a method including monitoring a temperature of air supplied from the second air system; detecting presence of a user on the mattress; and changing the temperature of air supplied from the second air system by an offset value. The offset value may be configured to achieve no or limited deviation from a set point of the pressure of the first air chamber of the mattress.

In some implementations, the system can optionally include one or more of the following features. Changing the temperature of air may include changing the temperature of air by the offset value in a single step. Changing the temperature of air may include changing the temperature of air by the offset value in multiple steps. Changing the temperature of air may include changing the temperature of air by the offset value gradually.

Particular embodiments described herein include a bed system having a mattress. The bed system may include a first air system configured for controlling pressure of a first air chamber of the mattress; a second air system configured for conditioning air at a top of the mattress; and a controller having one or more processors and a computer-readable storage medium coupled to the one or more processors having instructions stored thereon which, when executed by the one or more processors, cause the one or more processors to perform operations. The operations may include detecting presence of a user on the mattress; determining an expected temperature offset relating to user presence; when the user is not detected on the mattress, operating the second air system in a first mode to control temperature at the top of the mattress; and when the user is detected on the mattress, operating the second air system in a second mode to control temperature at the top of the mattress. The second mode may differ from the first mode at least because the second mode is adjusted according to the expected temperature offset relating to user presence.

In some implementations, the system can optionally include one or more of the following features. The first air system may include a pressure sensor in fluid communication with the first air chamber and configured to sense air pressure. The presence of the user may be detected by the pressure sensor of the first air system. The second air system may include a fan, a heater, and an air distribution layer positioned above the first air chamber. The second air system may include a heater, and the heater may be operated less in the second mode than in the first mode as a function of the expected temperature offset relating to user presence. The second air system may include a fan, and the fan may be operated less in the second mode than in the first mode as a function of the expected temperature offset relating to user presence. The mattress may include a first layer above the first air chamber, an air distribution layer comprising Qshion™ material above the first layer, a second layer above the air distribution layer, a mattress cover enclosing the first air chamber, the first and second layers, and the air distribution layer, an air hose connected to the first air chamber, and an air duct connected to the air distribution layer. The operations may include determining a desired pressure setpoint and a pressure limit. Operating the second air system in the second mode may include operating at least one of a heater and a fan in a manner configured to avoid exceeding the pressure limit while considering the expected temperature offset relating to user presence. The second air system may include a fan, and the fan may be operated more in the second mode than in the first mode as a function of the expected temperature offset relating to user presence. The operations may include determining a desired pressure setpoint and a pressure limit. Operating the second air system in the second mode may include adjusting an intermittent operation frequency or duration of at least one of a heater and a fan as a function of the expected temperature offset relating to user presence.

Particular embodiments described herein include a bed system having a mattress. The bed system may include a first system configured to consume power; a second air system configured for conditioning air at a top of the mattress; and a controller having one or more processors and a computer-readable storage medium coupled to the one or more processors having instructions stored thereon which, when executed by the one or more processors, cause the one or more processors to perform operations. The operations may include monitoring power consumption by the second air system; calculating energy costs by the second air system; and displaying the power consumption and the energy costs of the second air system.

In some implementations, the system can optionally include one or more of the following features. Monitoring power consumption may include detecting voltage and/or current used in the second air system; and calculating the power consumption based on the voltage and/or current detected. The operations may include monitoring power consumption by the first system; calculating energy costs by the first system; and displaying the power consumption and the energy costs of the first system. The first system may be a first air system for controlling air pressure of a first air chamber of the mattress. The bed system may include a third bed articulation control system. The operations may include monitoring power consumption by the third bed articulation control system; calculating energy costs by the third bed articulation control system; and displaying the power consumption and the energy costs of the third bed articulation control system. The operations may include displaying the power consumption and the energy costs of the bed system. The operations may include receiving information regarding the cost of energy from a utility provider, wherein the energy costs are calculated as a function of the cost of energy.

Particular embodiments described herein include a bed system having a mattress. The bed system may include an air system configured for conditioning air at a top of the mattress, and a controller having one or more processors and a computer-readable storage medium coupled to the one or more processors having instructions stored thereon which, when executed by the one or more processors, cause the one or more processors to perform operations. The operations may include monitoring power consumption by the air system; controlling the air system as a function of the power consumption; and displaying an indication of the power consumption.

In some implementations, the system can optionally include one or more of the following features. The air system may be controlled as a function of the power consumption to prevent causing fire. The operations may include sending a power consumption signal over the internet that indicates the power consumption of the air system. The indication of power consumption may include a total cost of energy consumed during a single sleep session. The total cost of energy consumed during the single sleep session may be calculated as a function of the power consumption for the single sleep session and cost of energy. The operations may include displaying an indication of cost savings by using the air system in lieu of using a second system. The second system may be a whole home system configured for at least heating or air conditioning. The operations may include sending a signal to a second system to control the second system as a function of the power consumption by the air system.

The devices, systems, and techniques described herein may provide one or more of the following advantages. Some embodiments described herein include an airflow pad system that is used with a bed for delivering ambient and/or conditioned (heated or cooled) air to the bed, or suctioning air from the bed, to control the temperature of a user lying on the bed. The airflow pad system can include one or more features that help increase air flow through an airflow insert pad disposed in the bed, thereby improving user comfort while potentially using less energy. Other advantages of the systems, methods, and techniques are further described herein.

The details of one or more implementations are set forth in the accompanying drawings and the description below. Other features and advantages will be apparent from the description and drawings, and from the claims.

BRIEF DESCRIPTION OF THE DRAWINGS

FIG. 19 illustrates an example foundation of the bed system.

FIG. 28 is a schematic end view of the mattress and the foot warming system.

FIG. 29 is a schematic side view of the mattress and the foot warming system.

FIGS. 56A-D illustrate an example air duct.

FIGS. 57A-B illustrate an example piece that can be attached to a rail to keep an air duct securely in place.

FIGS. 58A-C illustrate an example mattress system.

FIG. 65 illustrates another example of a connection portion of a foundation for connecting a connection portion of a mattress.

DETAILED DESCRIPTION OF ILLUSTRATIVE EMBODIMENTS

Overview of Bed Structure with Airflow Pads

Figure 1:
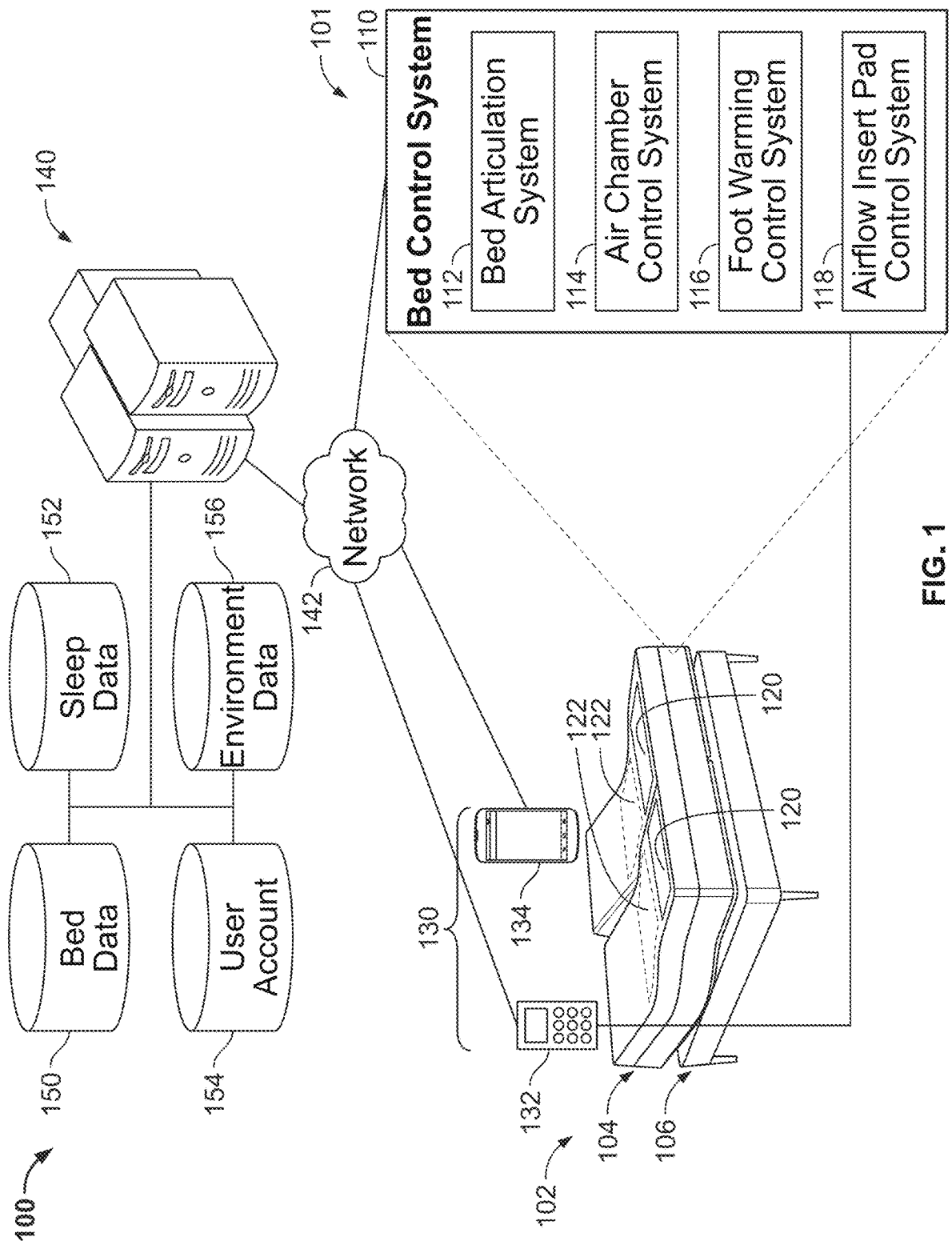
FIG. 1 illustrates an example bed system for providing a quality sleep experience with an example local bed system.

FIG. 1 illustrates an example bed system 100 for providing a quality sleep experience with an example local bed system 101. The local bed system 101 can include a bed 102 and a bed control system 110 used in conjunction with the bed 102 and configured to control one or more user comfort features of the bed 102.

The bed 102 can include a mattress 104 and a foundation 106. In some embodiments, the mattress 104 can be an air mattress having an inflatable air chamber and a controller for controlling inflation of the inflatable air chamber. In other embodiments, the mattress 104 does not include an air chamber. For example, the mattress 104 may include foam and/or springs instead of or in addition to an inflatable air chamber. The mattress 104 can be sized and shaped as a twin mattress, full mattress, queen mattress, king mattress, California king mattress, split king mattresses, partially split mattress (e.g. a mattress that is split at the head and/or foot ends and joined in the middle), and/or other mattress as suitable for the application. The foundation 106 is positioned under the mattress 104 to support the mattress 104. In some embodiments, the foundation 106 can be an adjustable foundation with one or more articulable sections, such as for raising the head and foot of the foundation 106 and the mattress 104. In other embodiments, the foundation 106 can be a stationary foundation.

The bed 102 can be configured to provide a microclimate control of the mattress 104. In some implementations, the bed 102 provides a foot warming function. For example, the bed 102 can include a foot warming device 120 which is disposed on the mattress 104 or incorporated in the mattress 104 and at a foot side of the bed 102. The foot warming device 120 can be disposed on a top of the mattress 104, included in the mattress 104, or disposed at other locations of the bed 102 and/or in other configurations. The foot warming device 120 can include an electronic heating element in some implementations. The foot warming device 120 can include an air circulation element through which heating air is circulated in other implementations. Other configurations are also possible.

In addition or alternatively, the bed 102 can be configured to provide a body cooling/heating function. For example, the bed 102 can include an airflow insert pad 122 that can be included in the mattress 104 and configured to circulate ambient or conditioned air through the mattress under the user at rest. The airflow insert pad 122 can be arranged at various locations in the mattress 104. In the illustrated example, the airflow insert pad 122 is disposed between the head and foot of the mattress 104 (e.g., in the middle of the mattress).

The bed control system 110 operates to control features available for the bed 102. In some implementations, the bed control system 110 includes a bed articulation system 112, an air chamber control system 114, a foot warming control system 116, and an airflow insert pad control system 118.

The bed articulation system 112 operates to articulate the foundation 106 and/or the mattress 104. For example, the bed articulation system 112 can adjust one or more articulable sections of the foundation 106 to raise the head and foot of the foundation 106 and/or the mattress 104. The bed articulation system 112 can include a controller and an actuator (e.g., a motor) operated by the controller and coupled to the articulable sections of the foundation 106 so that the sections of the foundation 106 are automatically adjusted to desired positions. Alternatively or in addition, the articulable sections of the foundation 106 can be manually adjusted.

The air chamber control system 114 operates to control the air chamber of the mattress 104. The air chamber control system 114 can include a controller and an actuator (e.g., a pump) operated by the controller and fluidly connected to the air chamber. The actuator is controlled to inflate or deflate the air chamber to provide and maintain a desired pressure in the air chamber, thereby providing a desired firmness of the air chamber.

The foot warming control system 116 operates to control the foot warming device 120 disposed in the mattress 104. The foot warming control system 116 can include a controller configured to activate a heating element of the foot warming device 120 and maintain a desired temperature of the heating element.

The airflow insert pad control system 118 operates to control the airflow insert pad 122 disposed in the mattress 104. The airflow insert pad control system 118 can include an air controller configured to cause ambient or conditioned air to flow into or out of the airflow insert pad 122 so that a top layer of the mattress above or adjacent the airflow insert pad 122 have a desired temperature and/or humidity.

In some implementations, the bed articulation system 112, the air chamber control system 114, the foot warming control system 116, and the airflow insert pad control system 118 can be independently configured and operated. In other implementations, some or all of the bed articulation system 112, the air chamber control system 114, the foot warming control system 116, and the airflow insert pad control system 118 are at least partially combined so that they share at least part of their components such as actuators (e.g., motors, pumps, etc.) and/or controllers (e.g., control circuits, processors, memory, network interfaces, etc.).

The bed control system 110 can be accessed by a user via one or more control devices 130, such as a bed-side controller 132 and a mobile computing device 134. The bed-side controller 132 is wired to, or wirelessly connected to, the bed control system 110 to enable the user to at least partially control the bed control system 110. The bed-side controller 132 includes an input device (e.g., a keypad, buttons, switches, etc.) for receiving a user input of controlling various settings of the bed control system 110, such as articulation positions, temperature settings, air chamber pressure settings, etc. The bed-side controller 132 can further include an output device (e.g., a display, a speaker, etc.) for outputting the statuses and conditions of the bed control system 110 and other information useful to the user, such as articulation positions, temperature settings, air chamber pressure settings, sleep analysis results, etc. The same or similar functionalities can be implemented with the mobile computing device 134, such as a mobile device running a dedicated software application. For example, the user can use a mobile device as an input device to control various settings of the bed control system 110, such as articulation positions, temperature settings, air chamber pressure settings, etc., and further use the mobile device as an output device to see the statuses and conditions of the bed control system 110 and other useful information, such as articulation positions, temperature settings, air chamber pressure settings, sleep analysis results, etc.

Referring still to FIG. 1, the system 100 can include a server system 140 connected to the local bed system 101 and configured to provide one or more services associated with the bed 102. The server system 140 can be connected to the local bed system 101, such as the bed 102, the bed control system 110, and/or the control devices 130, via a network 142. The server system 140 can be of various forms, such as a local server system with one or more computing devices dedicated to one or more beds, or a cloud server. The network 142 is an electronic communication network that facilitates communication between the local bed system 101 and the server system 140. An electronic communication network is a set of computing devices and links between the computing devices. The computing devices in the network use the links to enable communication among the computing devices in the network. The network 142 can include routers, switches, mobile access points, bridges, hubs, intrusion detection devices, storage devices, standalone server devices, blade server devices, sensors, desktop computers, firewall devices, laptop computers, handheld computers, mobile telephones, and other types of computing devices. In various embodiments, the network 142 includes various types of links. For example, the network 142 includes wired and/or wireless links. Furthermore, in various embodiments, the network 142 is implemented at various scales. For example, the network 142 can be implemented as one or more local area networks (LANs), metropolitan area networks, subnets, wide area networks (such as the Internet), or can be implemented at another scale.

In some implementations, the server system 140 can provide a bed data service that can be used in a data processing system associated with the local bed system 101. The server system 140 can be configured to collect sensor data and sleep data from a particular bed, and match the sensor and sleep data with one or more users that use the bed when the sensor and sleep data were generated. The sensor and sleep data, and the matching data, can be stored as bed data 150 in a database. The bed data 150 can include user identification data usable to identify users of beds. The users can include customers, owners, or other users registered with the server system 140 or another service. Each user can have, for example, a unique identifier, user credentials, contact information, billing information, demographic information, or any other technologically appropriate information. The bed data 150 can include management data usable to identify data related to beds or other products associated with data processing systems. For example, the beds can include products sold or registered with a system associated with the server system 140. Each bed can have, for example, a unique identifier, model and/or serial number, sales information, geographic information, delivery information, a listing of associated sensors and control peripherals, etc. Additionally, an index or indexes stored in the bed data 150 can identify users that are associated with beds. For example, this index can record sales of a bed to a user, users that sleep in a bed, etc. The bed data 150 can include sensor data that record raw or condensed sensor data recorded by beds with associated data processing systems. For example, a bed's data processing system can have a temperature sensor, pressure sensor, and light sensor. Readings from these sensors, either in raw form or in a format generated from the raw data (e.g. sleep metrics) of the sensors, can be communicated by the bed's data processing system to the server system 140 for storage in the bed data 150. Additionally, an index or indexes stored by the server system 140 can identify users and/or beds that are associated with the sensor data. In some implementations, the server system 140 can use any of its available data to generate advanced sleep data. The advanced sleep data includes sleep metrics and other data generated from sensor readings. Some of these calculations can be performed in the server system 140 instead of locally on the bed's data processing system, for example, because the calculations are computationally complex or require a large amount of memory space or processor power that is not available on the bed's data processing system. This can help allow a bed system to operate with a relatively simple controller and still be part of a system that performs relatively complex tasks and computations.

In addition or alternatively, the server system 140 can provide a sleep data service that can be used in a data processing system that can be associated with the local bed system 101. In this example, the server system 140 is configured to record data related to users' sleep experience and store the data as sleep data 152. The sleep data 152 can include pressure sensor data related to the configuration and operation of pressure sensors in beds. For example, the pressure sensor data can include an identifier of the types of sensors in a particular bed, their settings and calibration data, etc. The sleep data 152 can include pressure based sleep data which can be calculated based on raw pressure sensor data and represent sleep metrics specifically tied to the pressure sensor data. For example, user presence, movements, weight change, heart rate, and breathing rate can be determined from raw pressure sensor data. Additionally, an index or indexes stored by the server system 140 can identify users that are associated with pressure sensors, raw pressure sensor data, and/or pressure based sleep data. The sleep data 152 can include non-pressure sleep data which can be calculated based on other sources of data and represent sleep metrics obtained from such other sources of data. For example, user entered preferences, light sensor readings, and sound sensor readings can all be used to track sleep data 152. Additionally, an index or indexes stored by the server system 140 can identify users that are associated with other sensors and/or non-pressure sleep data 152.

In addition or alternatively, the server system 140 can provide a user account service that can be used in a data processing system associated with the local bed system 101. For example, the server system 140 can record a list of users and to identify other data related to those users, and store such data as user account data 154. The user account data 154 are related to users of beds with associated data processing systems. For example, the users can include customers, owners, or other users registered with the server system 140 or another service. Each user can have, for example, a unique identifier, user credentials, demographic information, or any other technologically appropriate information. The user account data 154 can include engagement data usable to track user interactions with the manufacturer, vendor, and/or manager of the bed and/or cloud services. This engagement data can include communications (e.g., emails, service calls), data from sales (e.g., sales receipts, configuration logs), and social network interactions. The user account data 154 can include usage history data related to user interactions with one or more applications and/or remote controls of a bed. For example, a monitoring and configuration application can be distributed to run on, for example, the control devices 130. This application can log and report user interactions for storage. Additionally, an index or indexes stored by the server system 140 can identify users that are associated with each log entry.

In addition or alternatively, the server system 140 can provide an environment service that can be used in a data processing system associated with the local bed system 101. For example, the server system 140 can record data related to users' home environment, and store such data as environment data 156. The environment data 156 can be obtained using one or more sensors installed in or around the bed. Such sensors can be of various types that can detect environmental variables, such as light sensors, noise sensors, vibration sensors, thermostats, etc. The environment data 156 can include historical readings or reports from those sensors. By way of example, a light sensor is used to collect data indicative of the frequency and duration of instances of increased lighting when the user is asleep.

Referring to FIGS. 2-10, an example mattress system 200 is described. The mattress system 200 can be used to implement the mattress 104 of FIG. 1.

Figure 2:
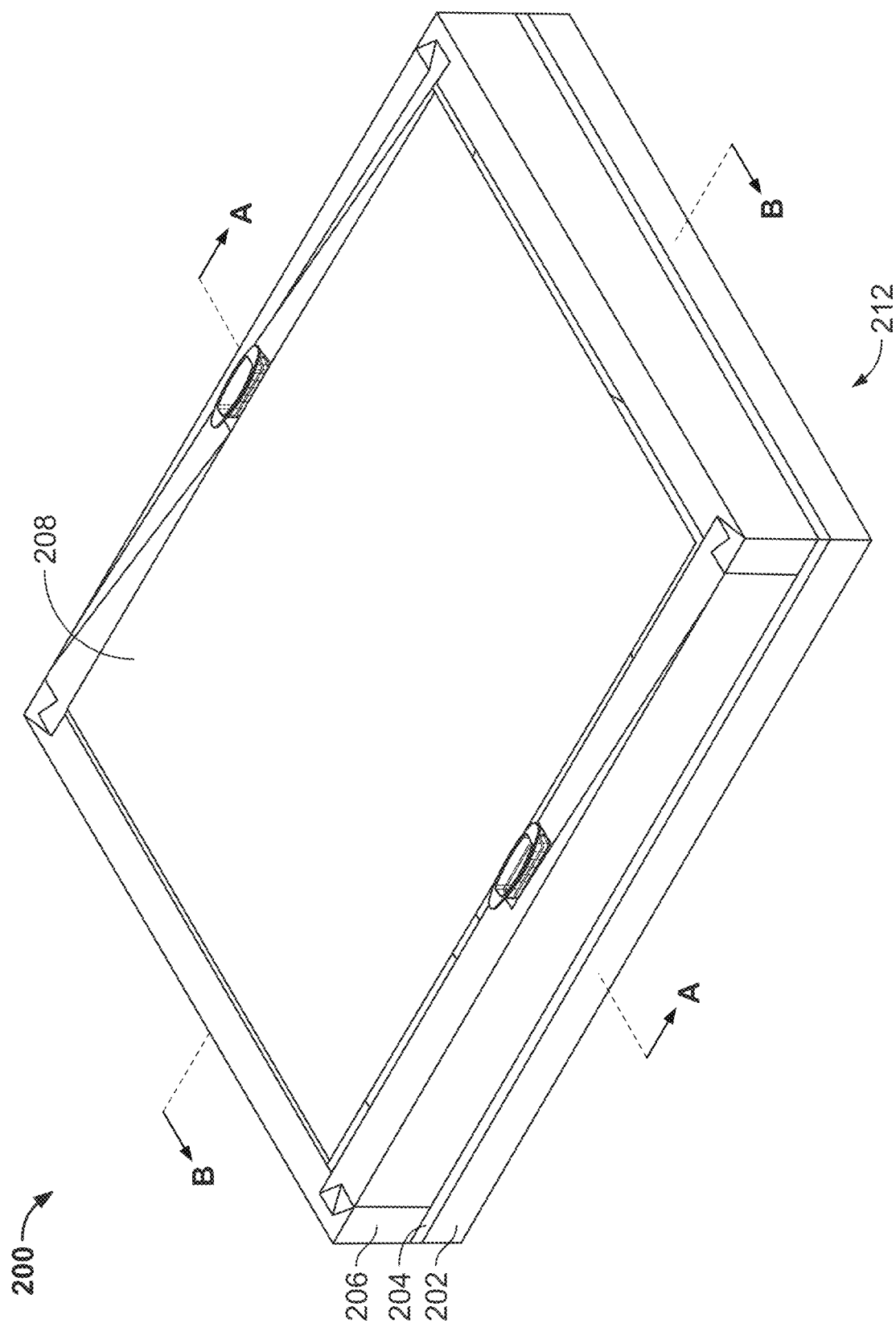
FIG. 2 is a bottom perspective view of the mattress system, illustrating the mattress system upside down.
Figure 3:
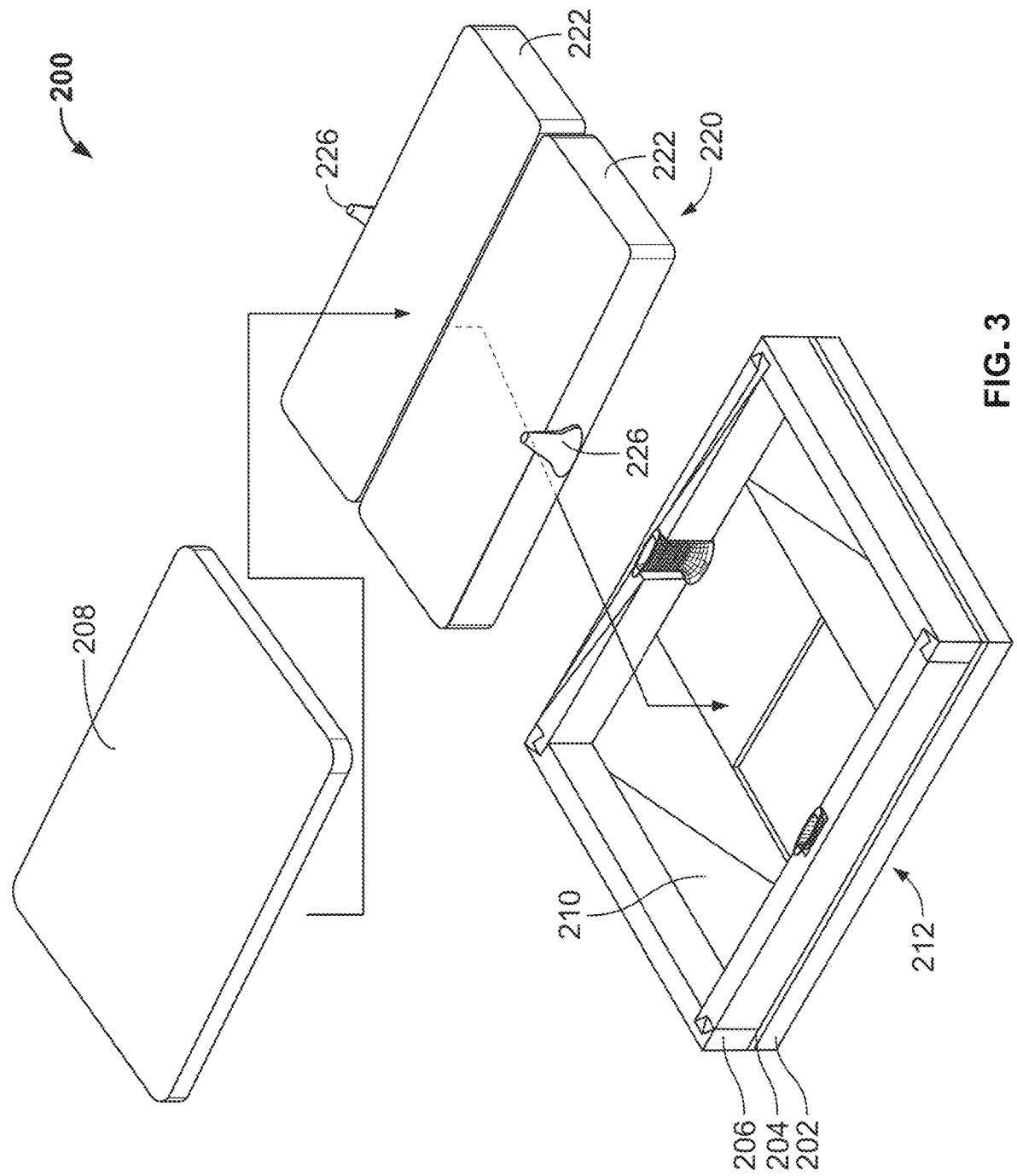
FIG. 3 is a partial exploded view of the mattress system of FIG. 2.

FIG. 2 is a bottom perspective view of the mattress system 200, illustrating the mattress system 200 upside down. The mattress system 200 can include a top layer (e.g., a first layer) 202, an intermediate layer (e.g., a second layer) 204, a rail structure 206, and a bottom layer (e.g., a third layer) 208. In some implementations, the top layer 202, the intermediate layer 204 and the bottom layer 208 are arranged in order from the top to the bottom of the mattress system 200. The rail structure 206 is arranged around a periphery of the mattress system 200 and configured to at least partially surround an air chamber assembly 220 (FIG. 3). As illustrated in FIG. 2, the bottom layer 208 can be disposed to be at least partially surrounded by the rail structure 206. The bottom layer 208 can be configured to close a space 210 (FIG. 3) defined by the rail structure 206. In other implementations, the bottom layer 208 can be configured and disposed above the rail structure 206.

FIG. 3 is a partial exploded view of the mattress system 200 of FIG. 2 (disposed upside down). The mattress system 200 can include the air chamber assembly 220. In the illustrated example, the air chamber assembly 220 includes a pair of air chambers 222 disposed between the top layer 202 and the bottom layer 208. The air chambers 222 can be arranged to be surrounded by the rail structure 206. The air chamber assembly 220 can further include a pump system 224 (FIGS. 10 and 19) configured to inflate and/or deflate the air chambers 222.

The mattress system 200 further includes an airflow layer 230 configured to distribute ambient or conditioned air therethrough and into the top layer 202, and/or draw ambient or conditioned air therethrough and from the top layer 202. The airflow layer 230 can include one or more airflow pad assemblies 232. An example of the airflow pad assembly 232 is described in more detail herein, for example with reference to FIGS. 11-13. The airflow layer can also be referred to herein as the airflow distribution layer, air distribution layer, or other similar terms. The airflow pad assembly can also be referred to herein as the airflow pad, the airflow insert, or other similar terms.

As depicted in FIG. 3, the rail structure 206 can be disposed on the intermediate layer 204 to define the space 210 for at least partially receiving the air chamber assembly 220. The bottom layer 208 can be disposed at least partially within the space 210 to at least partially cover the space 210 and the air chamber assembly 220 within the space 210.

The top layer 202, the intermediate layer 204, the rail structure 206, and the bottom layer 208 can be made of various materials. For example, at least one of the top layer 202, the intermediate layer 204, the rail structure 206, and the bottom layer 208 can be made of foam, which may be closed-cell, open-cell, or a combination thereof. Other materials, such as one or more coil springs, air chambers, spacer materials, and/or other suitable materials, can be used for at least one of the top layer 202, the intermediate layer 204, the rail structure 206, and the bottom layer 208.

Figure 4:
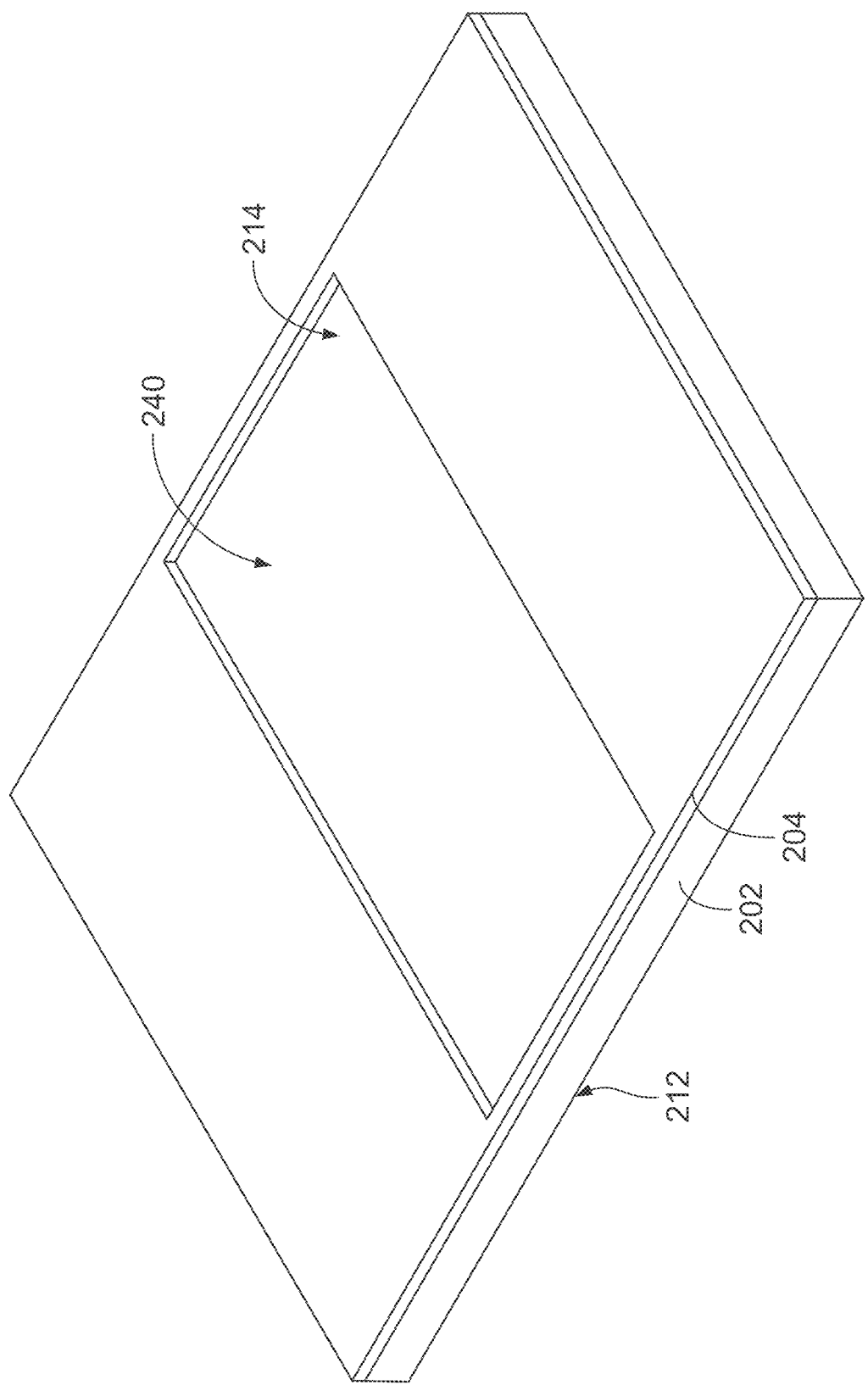
FIG. 4 is a partial exploded view of the mattress system of FIG. 2, illustrating an example top layer and an example intermediate layer.

FIG. 4 is a partial exploded view of the mattress system 200 of FIG. 2 (disposed upside down), illustrating the top layer 202 and the intermediate layer 204. The top layer 202 has a top surface 212 (opposite to a bottom surface 214) on which a user's body can be rested either directly, or indirectly through a mattress cover and/or one or more additional layers disposed on the top surface. The intermediate layer 204 can be disposed opposite to the top surface 212 of the top layer 202. For example, the top layer 202 has the bottom surface 214 opposite to the top layer 212, and the intermediate layer 204 is disposed on the bottom surface 214 of the top layer 202. The intermediate layer 204 can be attached to the top layer 202 in various ways. For example, the intermediate layer 204 can be glued to the top layer 202, or attached to the top layer 202 using fasteners, such as hook-and-loop fasteners (e.g., VELCRO®), zippers, clips, pins, buttons, straps, ties, snap fasteners, and other suitable types of fasteners.

In some implementations, the intermediate layer 204 provides a cutout section 240 configured to receive the airflow layer 230. The cutout section 240 is described in further detail with reference to FIGS. 5-7.

Figure 5:
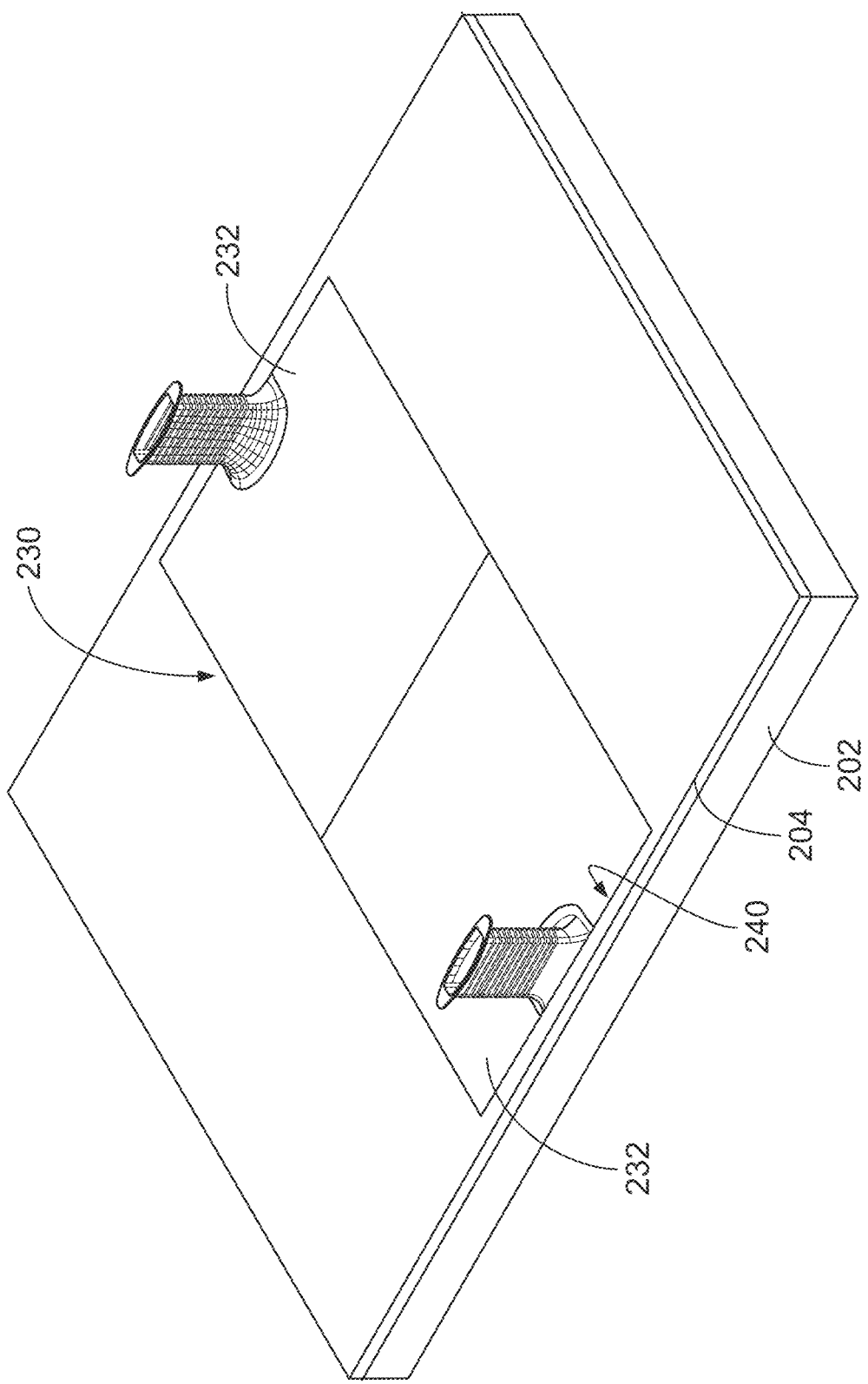
FIG. 5 is a partial exploded view of the mattress system of FIG. 2, illustrating the top layer, the intermediate layer, and an example airflow layer.

FIG. 5 is a partial exploded view of the mattress system 200 of FIG. 2 (disposed upside down), illustrating the top layer 202, the intermediate layer 204, and the airflow layer 230. The airflow pad assemblies 232 can be disposed in the cutout section 240 of the intermediate layer 204. The airflow pad assemblies 232 can be enclosed in the cutout section 240 and surrounded by the intermediate layer 204 such that the airflow pad assemblies 232 are not exposed on the lateral sides of the mattress system 200. In other words, the airflow pad assemblies 232 are not visible from any lateral side of the mattress system 200, and the intermediate layer 204 is instead visible from the lateral sides of the mattress system 200, as shown in FIGS. 2 and 3. The airflow pad assemblies 232 can be attached to the bottom surface 214 of the top layer 202 through the cutout section 240 of the intermediate layer 204. The airflow pad assemblies 232 can be attached to the bottom surface 214 the top layer 202 in various ways. For example, the airflow pad assemblies 232 can be glued to the bottom surface 214 of the top layer 202, or attached to the bottom surface 214 of the top layer 202 using fasteners, such as hook-and-loop fasteners (e.g., VELCRO®), zippers, clips, pins, buttons, straps, ties, snap fasteners, and other suitable types of fasteners.

Figure 6:
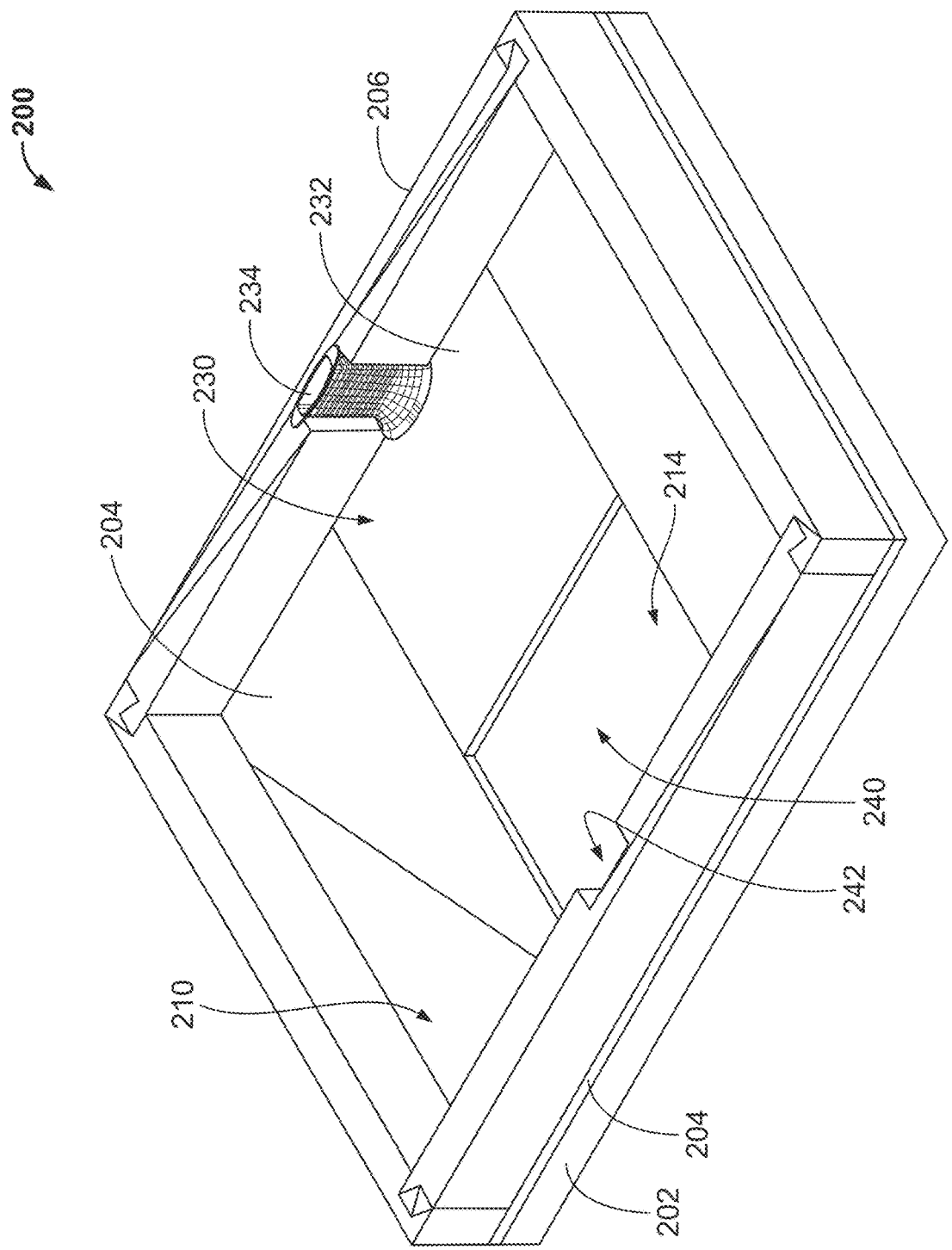
FIG. 6 is a partial exploded view of the mattress system of FIG. 2, illustrating the top layer, the intermediate layer, an example rail structure, and an example airflow pad assembly.
Figure 7:
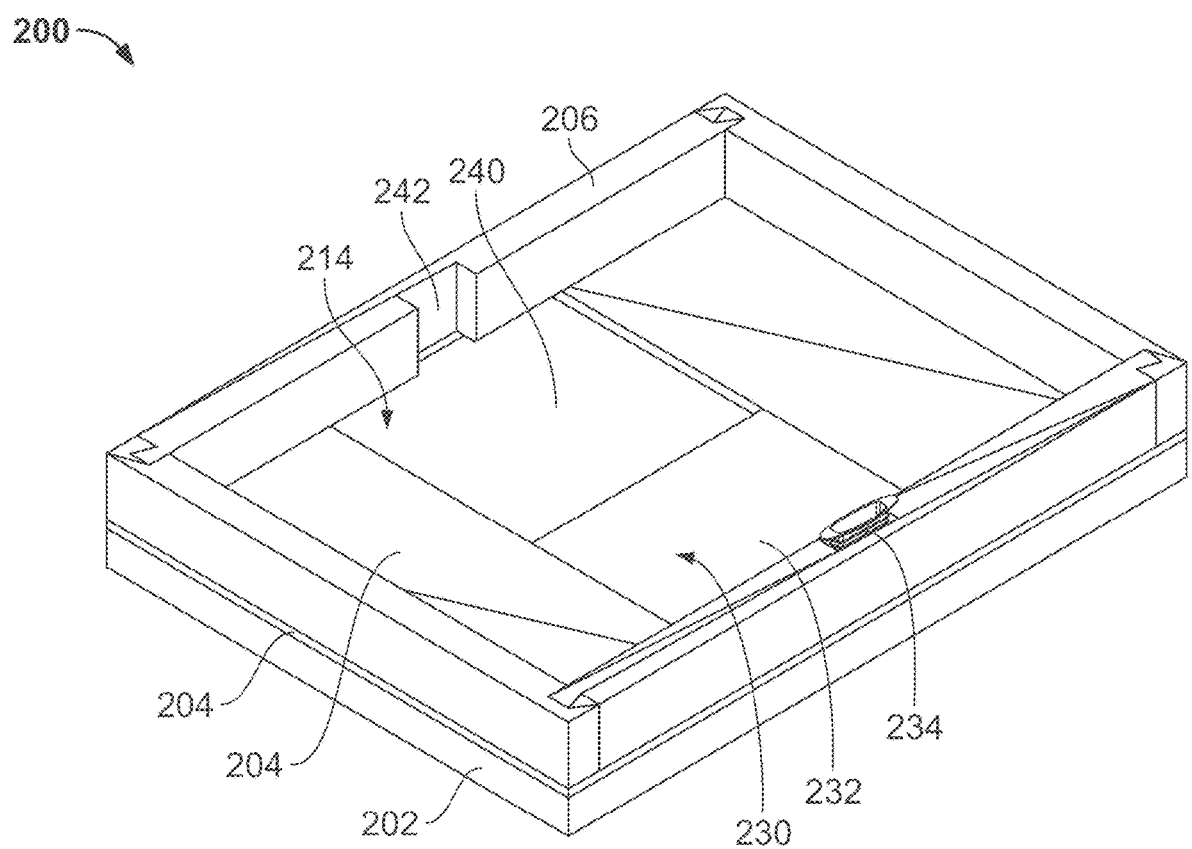
FIG. 7 is a partial exploded view of the mattress system of FIG. 2 from a different angel.

FIGS. 6 and 7 are partial exploded views of the mattress system 200 of FIG. 2 (disposed upside down), illustrating the top layer 202, the intermediate layer 204, the rail structure 206, and one of the airflow pad assemblies 232. As illustrated, the rail structure 206 includes one or more notches 242, each configured to receive an air duct 234 of the airflow pad assembly 232. The notches 242 can be sized to fully receive the air duct 234 so that the air duct 234 does not protrude from the interior surface of the rail structure 206. For example, the notches 242 can be dimensioned to receive the air duct 234 such that the air duct 234 is flushed with the interior surface of the rail structure 206 or disposed below the level of the interior surface of the rail structure 206. As such, the air duct 234 being received within the notch 242 does not interfere with other components of the mattress system 200, such as the air chambers 222 being received within the space 210 of the rail structure 206. The notches 242 can be arranged in locations of the rail structure 206 which correspond to the positions of the air ducts 234 of the airflow pad assemblies 232. In the illustrated example, the notches 242 are arranged in the rail structure 206 between the head and the foot of the mattress system 200, such as in the middle of the length of the mattress system 200.

In alternative embodiments, the mattress system 200 does not include the top layer 202. In this configuration, the bottom layer 208 can function as a top layer of the mattress. Alternatively, the top layer 202 can have different sizes (e.g., thickness) to provide different comfort levels or for other purposes.

In some implementations, the intermediate layer 204 can be arranged in parallel to the airflow layer 230 (e.g., air distribution layer). For example, the intermediate layer 204 can be configured to be parallel with the airflow pad assemblies 232 when assembled.

Airflow Mattress with Air Chamber (Feature Group #13)

Figure 8A:
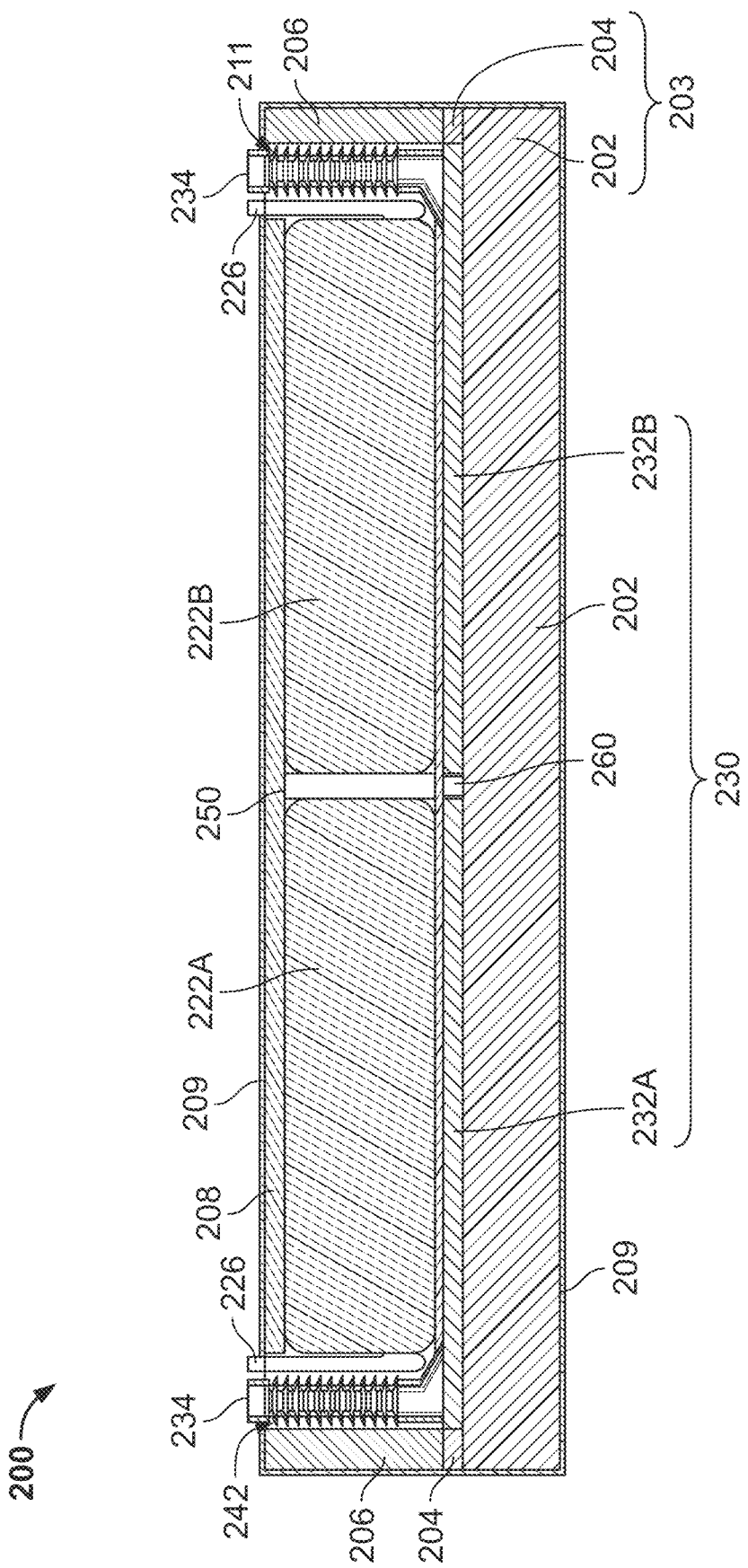
FIG. 8A is a cross sectional view of the top layer, the intermediate layer, the rail structure, the air chamber, the airflow layer, and an example bottom layer of the mattress system, taken along line A-A in FIG. 2.
Figure 8B:
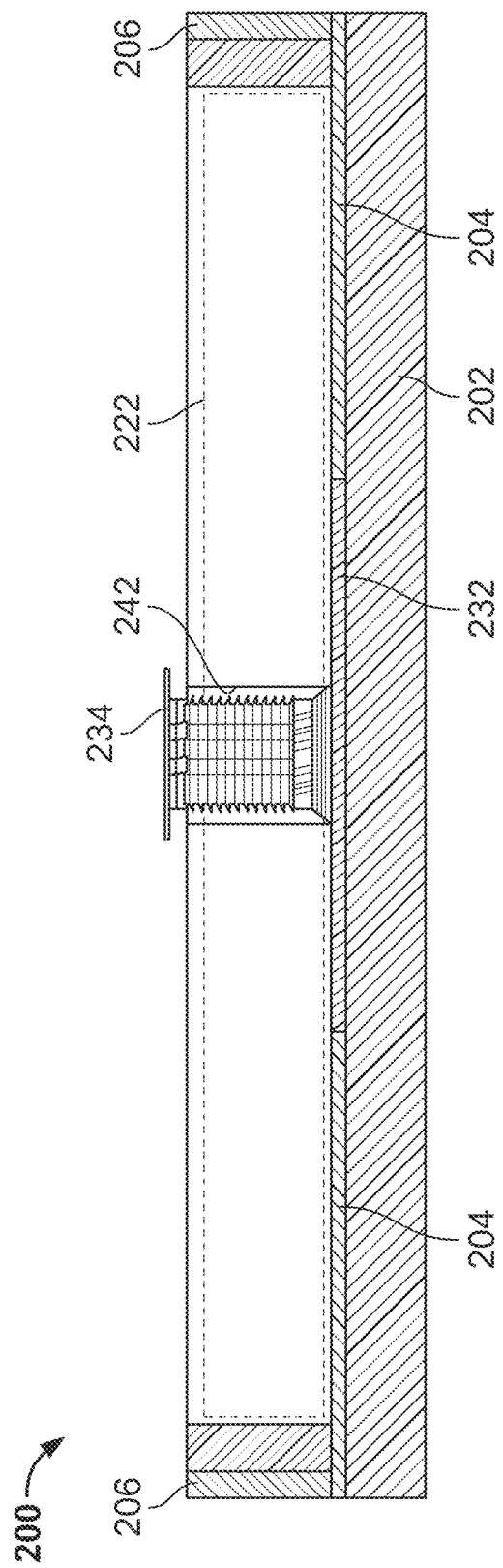
FIG. 8B is a cross sectional view of the top layer, the intermediate layer, the rail structure, and the airflow layer of the mattress system, taken along line B-B in FIG. 2.
Figure 9:
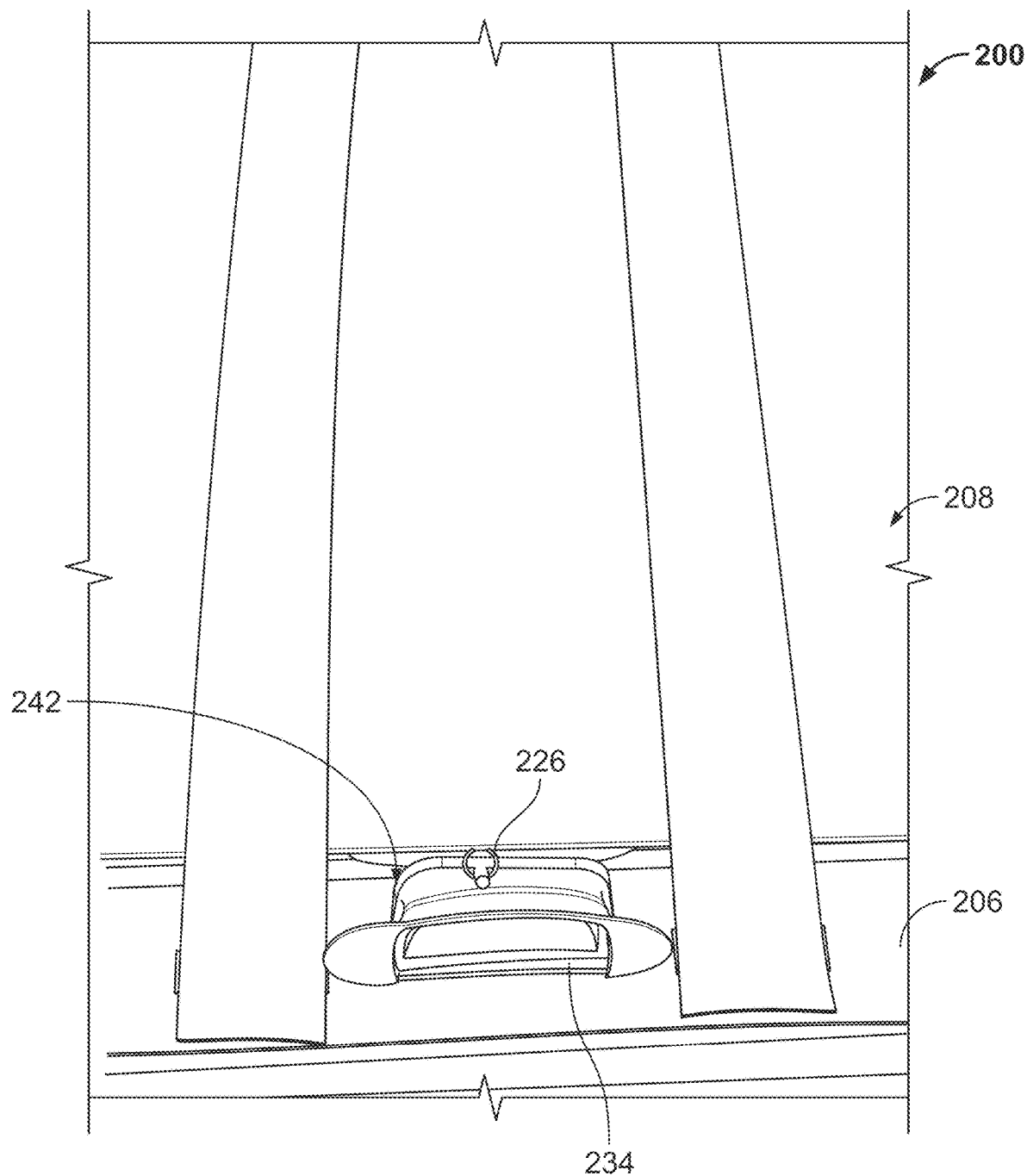
FIG. 9 is a bottom partial view of the mattress of FIG. 2.

Referring to FIGS. 8A, 8B, and 9, an example arrangement of components of the mattress 200 is described. FIG. 8A is a cross sectional view of the top layer 202, the intermediate layer 204, the rail structure 206, the air chamber 222, the airflow layer 230, and the bottom layer 208 of the mattress system 200, taken along line A-A in FIG. 2. In FIG. 8A, an example mattress cover 209 is illustrated. FIG. 8B is a cross sectional view of the top layer 202, the intermediate layer 204, the rail structure 206, and the airflow layer 230 of the mattress system 200, taken along line B-B in FIG. 2. In FIG. 8B, the air chamber 222 is schematically illustrated with dotted lines.

Figure 10:
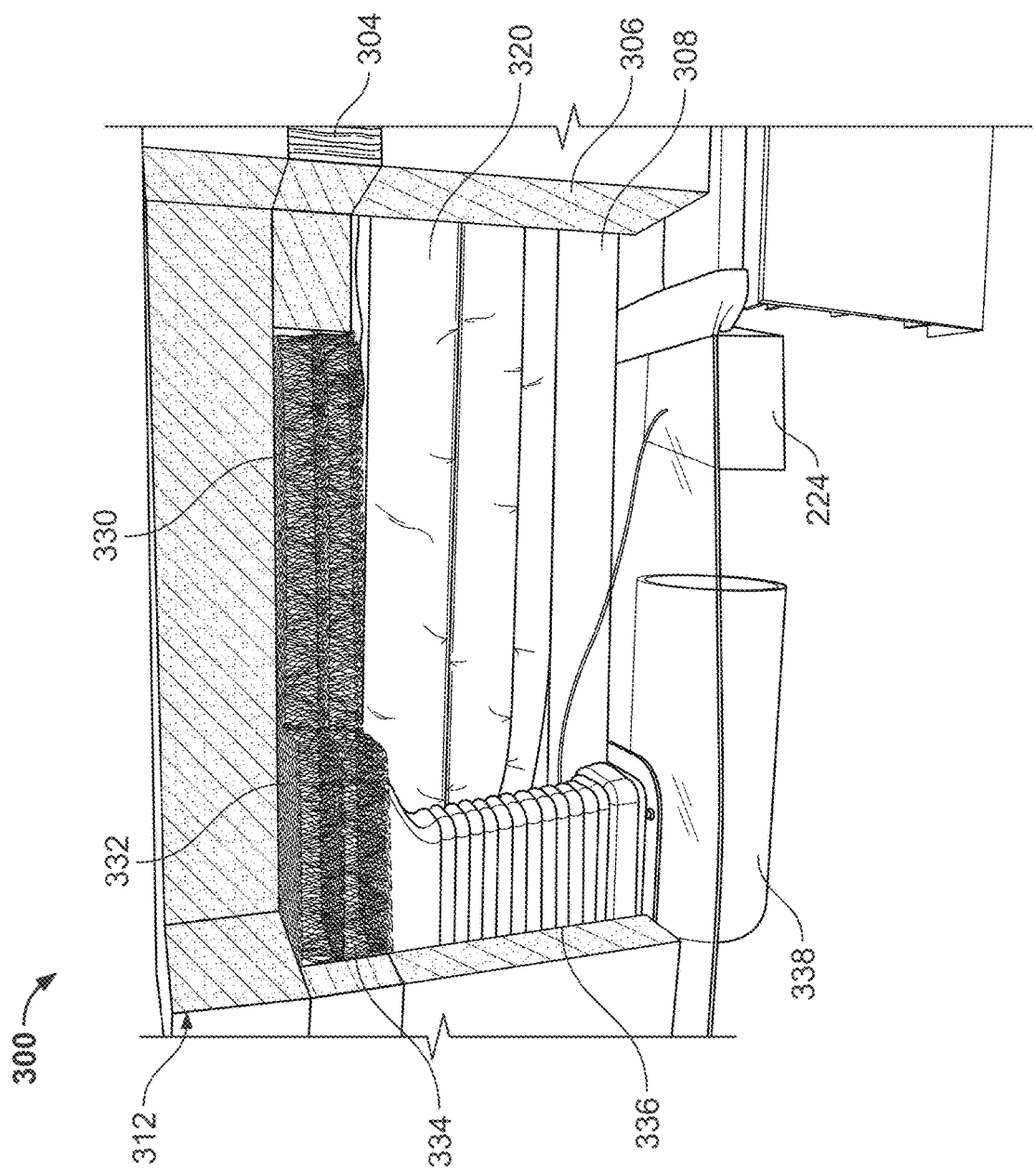
FIG. 10 illustrates a cutaway view of an example mattress system.

As described, the mattress 200 includes the inflatable air chamber 222, the airflow layer 230 (e.g., an air distribution layer), and a foam layer 203. The foam layer 203 can include the top layer 202. The foam layer 203 can further include the intermediate layer 204. The air distribution layer is positioned above the inflatable air chamber 222. The foam layer 203 is positioned above the air distribution layer and proximate a top of the mattress. As described herein, the foam layer 203 and the air distribution layer (e.g., the airflow layer 230) can permit airflow therethrough. The air distribution layer resists air flow less than the foam layer. For example, the air distribution layer can allow a higher airflow rate than the foam layer above the air distribution layer. The mattress 200 further includes an air chamber hose (e.g., the air chamber hose 226) connected to the inflatable air chamber for inflating or deflating the inflatable air chamber 222. For example, one end of the air chamber hose 226 is connected to the air chamber 222 to be in fluid communication with the interior of the air chamber 222, and the other end of the air chamber hose is fluidly connected to the pump system (e.g., the pump system 224 as shown in FIGS. 10 and 19). The mattress 200 further includes an air distribution hose (e.g., the air duct 234) fluidly connected to the air distribution layer (e.g., the airflow layer 230) for moving air into, from, and through the air distribution layer. In some implementations, in a direction from the bottom to the top, the air distribution hose extends from a location below the inflatable air chamber, and is routed around a side of the inflatable air chamber and to the air distribution layer above the inflatable air chamber. In other words, in the reverse direction (from the top to the bottom), the air distribution hose is connected to the air distribution layer above the inflatable air chamber, and routed around the side of the inflatable air chamber and extends to a location below the lowest level of the inflatable air chamber so that the air distribution layer extends over the lowest level of the inflatable air chamber. For example, as illustrated in FIG. 8A, the air distribution hose (e.g., the air duct 234) is connected to the air distribution layer (e.g., the airflow layer 230) above the inflatable air chamber 222, and then routed along a side of the air chamber 222, extending up to a location lower than the inflatable air chamber 222.

In some implementations, the mattress 200 includes the mattress cover 209 that at least partially encloses the components of the mattress 200, such as the top layer 202, the intermediate layer 204, the rail structure 206, the air chamber 222, the airflow layer 230, and the bottom layer 208. The mattress cover 209 includes a common hole 211 through which the air distribution hose and the air chamber hose can extend out together.

In some implementations, the mattress 200 includes a plurality of inflatable air chambers, and the air distribution layer includes a plurality of air distribution zones or pads corresponding to the plurality of inflatable air chambers. In the illustrated examples, the mattress 200 includes first and second air chambers 222A and 222B, and the air distribution layer includes two air distribution pads 232A and 232B (defining two air distribution zones) that are positioned under the first and second air chambers 222A and 222B, respectively, from the view of FIG. 8A. The air chamber hose and the air distribution hose described above are similarly provided to each set of the inflatable air chamber and the air distribution pad.

In some implementations, the mattress 200 includes a chamber insulator 250 positioned between the first and second air chambers 222A and 222B and configured to reduce heat transfer between the first and second air chambers 222A and 222B. In addition or alternatively, the mattress 200 includes an air distribution insulator 260 positioned between the first and second air distribution pads 232A and 232B and configured to reduce heat transfer between the first and second air distribution pads 232A and 232B. The chamber insulator 250 and the air distribution insulator 260 can reduce heat transfer between two different areas (e.g., left and right sides) of the mattress 200, thereby improving independent temperature controls for different users resting on such different areas of the mattress top.

As shown in FIGS. 8B and 9 (a bottom partial view of the mattress 200), as described herein, the rail structure 206 includes the notches 242 (e.g., hose passages) configured to receive and route the air distribution hoses (e.g., the air ducts 234). For example, the notches 242 are provided on the side rails of the rail structure 206. In some implementations, the air chamber hoses (e.g., the air chamber hoses 226) can be routed within or adjacent the notches 242 along with the air distribution hoses.

In some implementations, a foundation (e.g., the foundation 106) can be provided to support the mattress 200. For example, the foundation provides a support platform configured for supporting the mattress 200. The support platform can include a first foundation opening extending through the support platform and configured to receive the air chamber hose and/or the air distribution hose. A pump assembly (e.g., the pump assembly 224 as shown in FIGS. 10 and 19) can be fluidly connected to an end hose end of the chamber air hose and configured to supply fluid (e.g., air) to the inflatable air chamber 222. The pump assembly can be positioned in the foundation. Further, an air controller (e.g., the air controller 338 as shown in FIGS. 10 and 19) can be fluidly connected to the air distribution hose and configured to move air into or from the air distribution layer through the air distribution hose. The air controller can be positioned in the foundation. An example of the foundation is further described herein, for example with reference to FIGS. 17A-B, 18A-B, and 19.

FIG. 10 illustrates a cutaway view of an example mattress system 300. The mattress system 300 can be used to implement the mattress system 200 of FIGS. 2-9 or the mattress 104 of FIG. 1. Similarly to the mattress system 200, the mattress system 300 includes a top layer 302, an intermediate layer 304, a rail structure 306, an air chamber assembly 320, an airflow layer 330, and a bottom layer 308, which can be configured similarly to the top layer 202, the intermediate layer 204, the rail structure 206, the air chamber assembly 220, the airflow layer 230, and the bottom layer 208, respectively.

Similarly to the airflow layer 230 described herein, the airflow layer 330 can include an airflow pad assembly 332. The airflow pad assembly 332 can include one or more airflow pads 334 and an air duct 336 extending from the airflow pad 334 and fluidly connecting the airflow pad 334 with an air controller 338. The air controller 338 is configured to move ambient or conditioned air through the airflow pad 334 and further through the top layer 302 to control a temperature at a top surface 312 of the top layer 302. For example, the air controller 338 can operate to draw air from the airflow pad 334 and the top layer 302 through the air duct 336, thereby decreasing a temperature at the top surface 312 of the top layer 302. Alternatively, the air controller 338 can operate to supply ambient or cooling air to the airflow pad 334 through the air duct 336, thereby enabling such ambient or cooling air to be distributed through the top layer 302 and decreasing a temperature at the top surface 312 of the top layer 302. Alternatively, the air controller 338 can operate to supply heating air to the airflow pad 334 through the air duct 336, thereby enabling such heating air to be distributed through the top layer 302 and increasing a temperature at the top surface 312 of the top layer 302.

In the illustrated implementations, the air chamber hoses 226 are routed at the side locations of the mattress. In alternative implementations, the air chamber hoses 226 can be routed at different locations of the mattress, such as the head or foot of the mattress, or other suitable locations of the mattress.

In the illustrated implementations, the air ducts 234 are positioned at the side locations of the mattress. In alternative implementations, the air ducts 234 can be routed at other locations of the mattress. For example, at least one of the air ducts 234 can be arranged in the middle of the mattress and travel between the air chambers 222 of the mattress.

Airflow Pad (Feature Group #2)

Figure 11A:
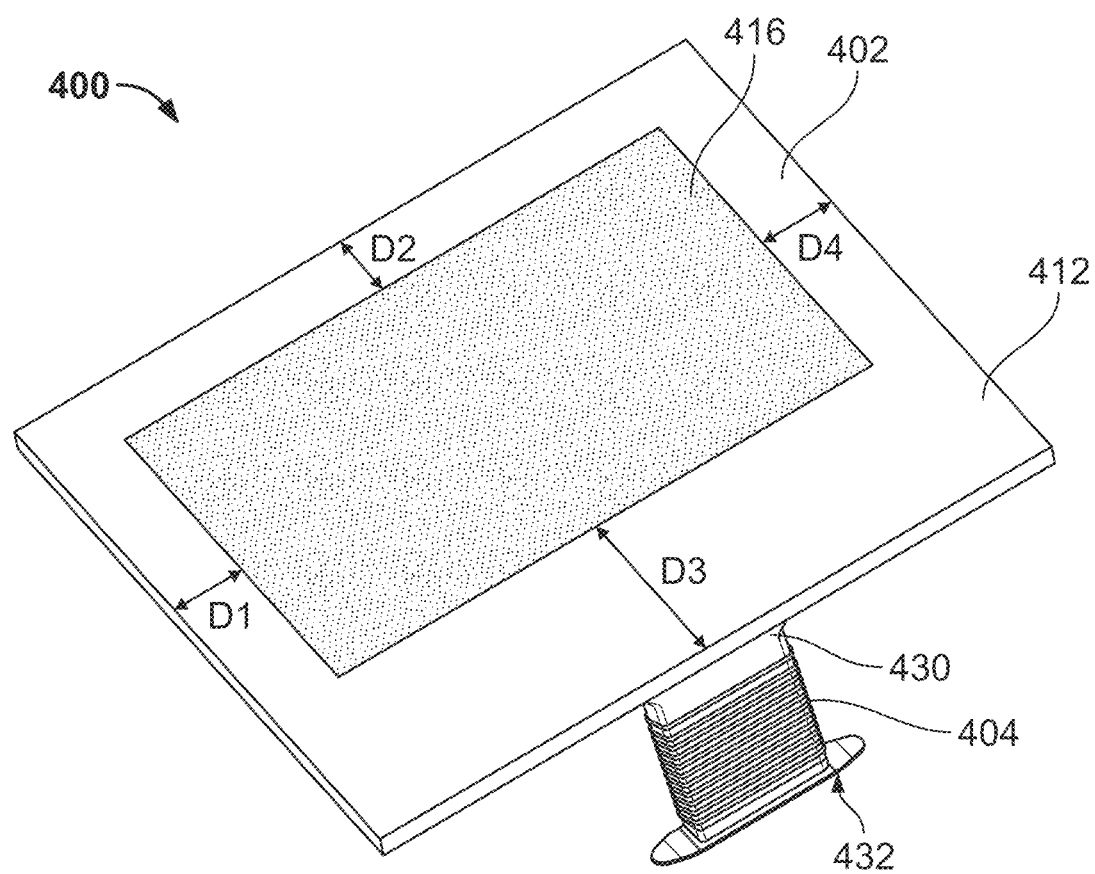
FIGS. 11A-C are perspective views of an example airflow pad assembly that is used with a mattress system.
Figure 11B:
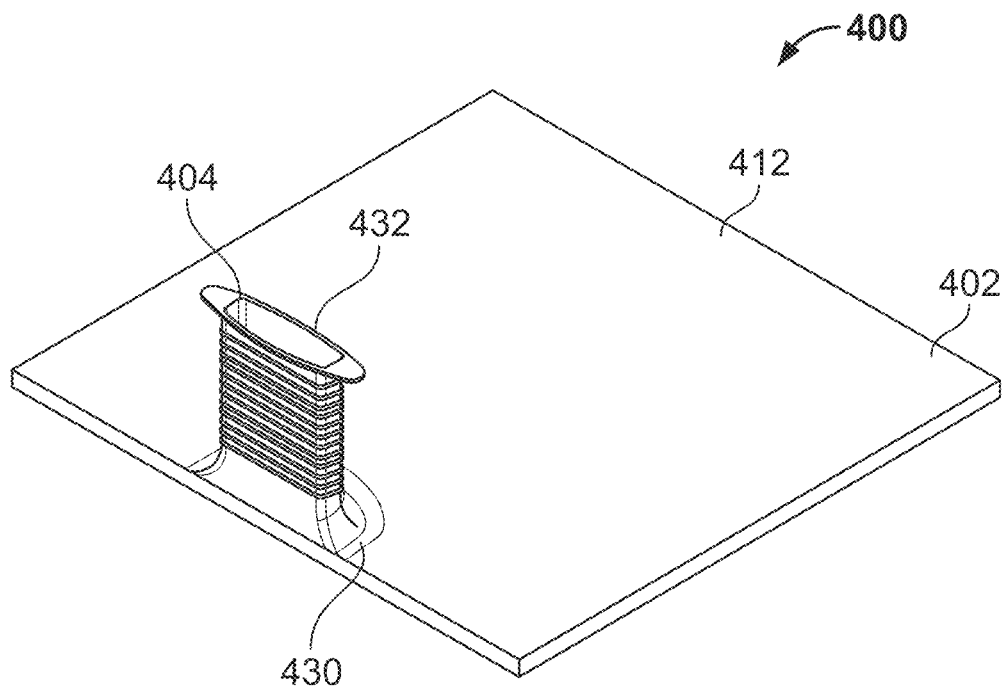
Figure 11C:
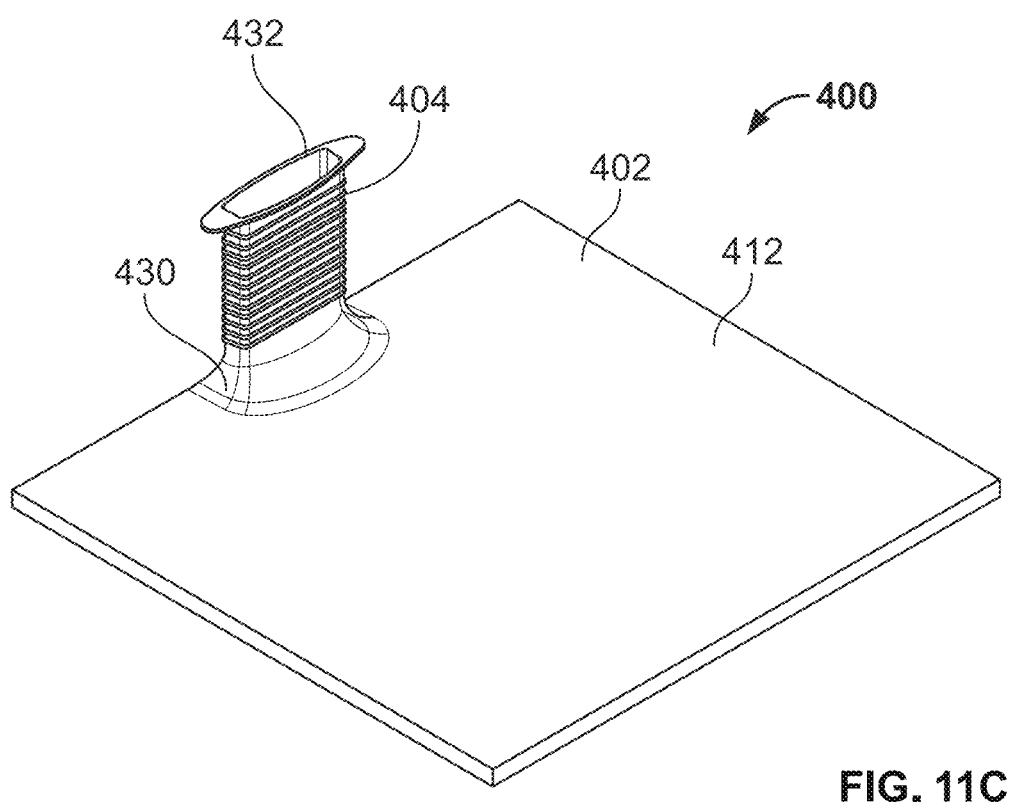

Referring to FIGS. 11A-C, 12, and 13, an example airflow pad assembly 400 is illustrated. FIGS. 11A-C are perspective views of an example airflow pad assembly 400 that is used with a mattress system, such as the mattress 104, the mattress system 200, or the mattress system 300. The airflow pad assembly 400 can be used to implement the airflow pad assembly 232, 332 described above.

Similarly to the airflow pad assembly 232, 332, the airflow pad assembly 400 includes an airflow pad 402 and an air duct 404. The airflow pad 402 is arranged under a top layer of a mattress system, such as the top layer 202, 302 of the mattress system 200, 300. The airflow pad 402 is configured to permit air to flow therethrough and further through the top layer above the airflow pad 402. In this example, the top layer of the mattress system can be made of foam, which may be closed-cell, open-cell, or a combination thereof, so that air can be distributed through the top layer. In some implementations, the airflow pad 402 is configured to permit an airflow rate that is higher than an airflow rate of the top layer above the airflow pad 402.

The airflow pad 402 can permit ambient or conditioned air to flow therethrough and further through the top layer above the airflow pad 402 to control a temperature at a top surface (e.g., a surface opposite to the airflow pad 402) of the top layer. In some implementations, air can be drawn from the airflow pad 402 and thus from the top layer above the airflow pad 402, thereby decreasing a temperature at the top surface of the top layer above the airflow pad 402. For example, when a user rests on the top surface of the top layer in the mattress system, drawing air from the airflow pad 402 causes air to be further drawn from the top layer, and thus cools both the top layer and the user's body contacting the top layer. In other implementations, ambient or cooling air can be supplied to the airflow pad 402 and thus distributed through the top layer above the airflow pad 402, thereby decreasing a temperature at the top surface of the top layer above the airflow pad 402. In a similar example where a user rests on the top surface of the top layer in the mattress system, supplying ambient or cooling air to the airflow pad 402 causes air to be further distributed into and throughout the top layer, and thus cools the user's body contacting the top layer. In yet other implementations, heating air can be supplied to the airflow pad 402 and thus distributed through the top layer above the airflow pad 402, thereby increasing a temperature at the top surface of the top layer above the airflow pad 402. In a similar example where a user rests on the top surface of the top layer in the mattress system, supplying heating air to the airflow pad 402 causes air to be further distributed into and throughout the top layer, and thus warms the user's body contacting the top layer.

Figure 13:
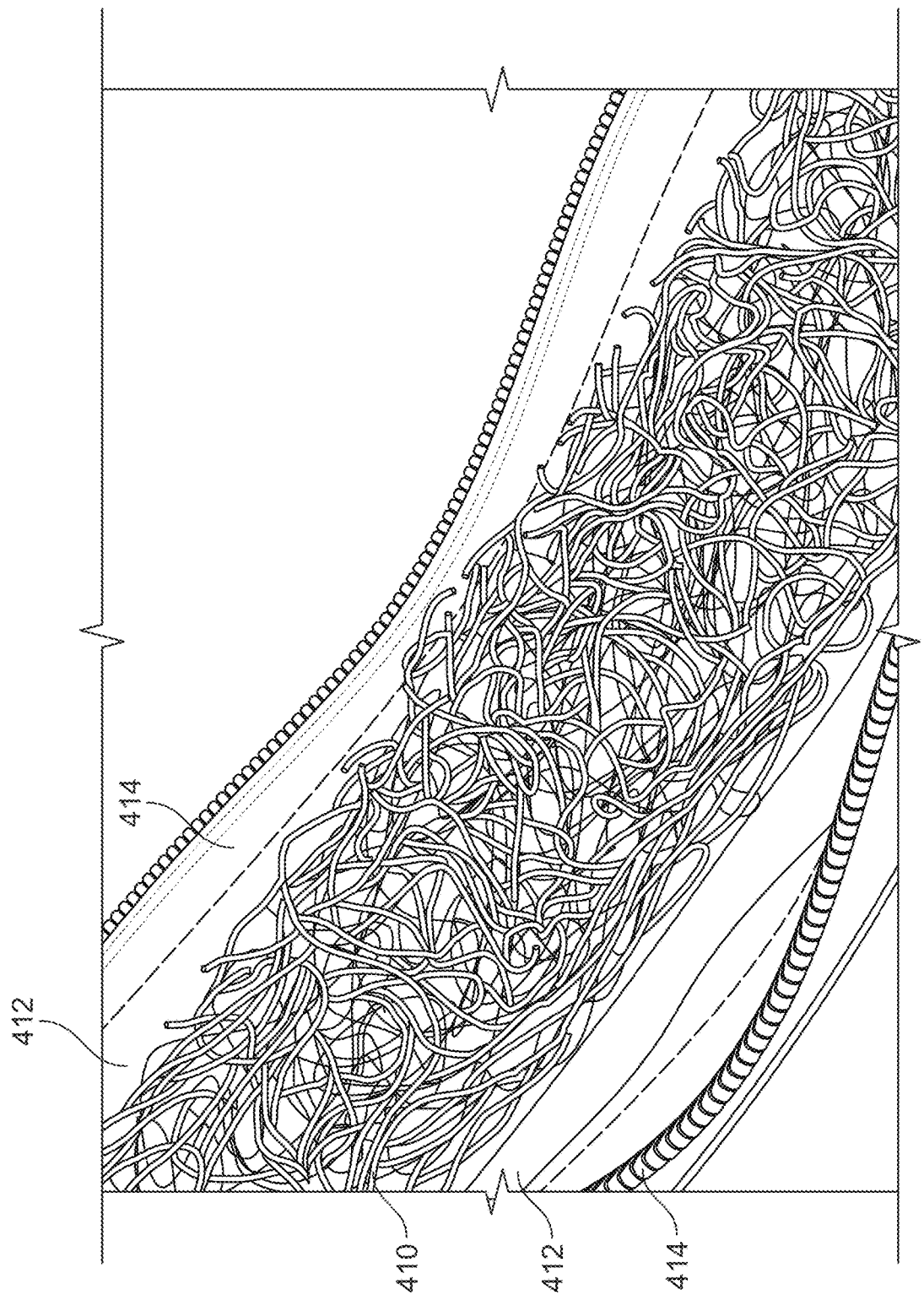
FIG. 13 illustrates an example airflow material and an example pad cover of the airflow pad.

Referring to FIG. 13, the airflow pad 402 can include an airflow material 410 and a pad cover 412 that at least partially wraps the airflow material 410. The airflow material 410 can be a material that is different from the material of the top layer above the airflow pad 402. As described herein, the airflow material 410 is configured to provide an airflow rate that is higher than an airflow rate of the top layer above the airflow pad 402. In addition, the airflow material 410 can be made of a water-resistant material so that the airflow pad 402 can avoid water intrusion while permitting for air distribution. Further, the airflow pad 402 is made to be breathable. In addition, the airflow material 410 is made to be resilient enough to provide desired support for a user resting on the mattress system, along with other layers of the mattress system.

In some implementations, the airflow material 410 can have three-dimensional structures with elastic polyolefin fibers. In addition or alternatively, the airflow material 410 is made of 100% polyolefin. In addition or alternatively, the airflow material 410 is configured to provide a resilience rate of thickness no less than 95% after 80,000 times of repeated compressions. In addition or alternatively, the airflow material 410 includes Qshion™ material, which is available from Qshion 4D, Taiwan, R.O.C. The Qshion™ material provides complex three-dimensional structures with elastic polyolefin fibers which provide desired ventilation and sleeping environment. Further, the Qshion™ material includes a breathable, non-toxic, recyclable POE material which can provide full support and comfort. The Qshion™ material is washable and dries quickly. The Qshion™ material allows airflow to keep a user cool and comfortable for an extended period of time (e.g., overnight). Further, the Qshion™ material is configured to help relieve joint and muscle pressure of a user. The Qshion™ material is a nontoxic, recyclable material which allows a user to sleep in a safe and healthy environment. The Qshion™ material is more breathable than form materials. Further, the Qshion™ material has a resilience rate of thickness no less than 95% after 80,000 times of repeated compressions, while foam materials typically have resilience rates of thickness of 90% or less after the same repeated compressions. The Qshion™ material does not absorb moisture and free of dust mites, while foam materials keep humidity and lead to mold. In other embodiments, the airflow material 410 can be different than Qshion™ material in some ways and yet include one, more than one, or all of the above-identified properties of Qshion™ material.

The pad cover 412 is configured to cover the airflow material 410. For example, the pad cover 412 is configured to at least partially enclose the airflow material 410. In some implementations, the pad cover 412 can include a zip fastener 414 (FIG. 13) configured to open the pad cover 412 to receive or remove the airflow material 410. In other implementations, the pad cover 412 does not include the zip fastener 414 or other fastener for reopening the pad cover.

Figure 12:
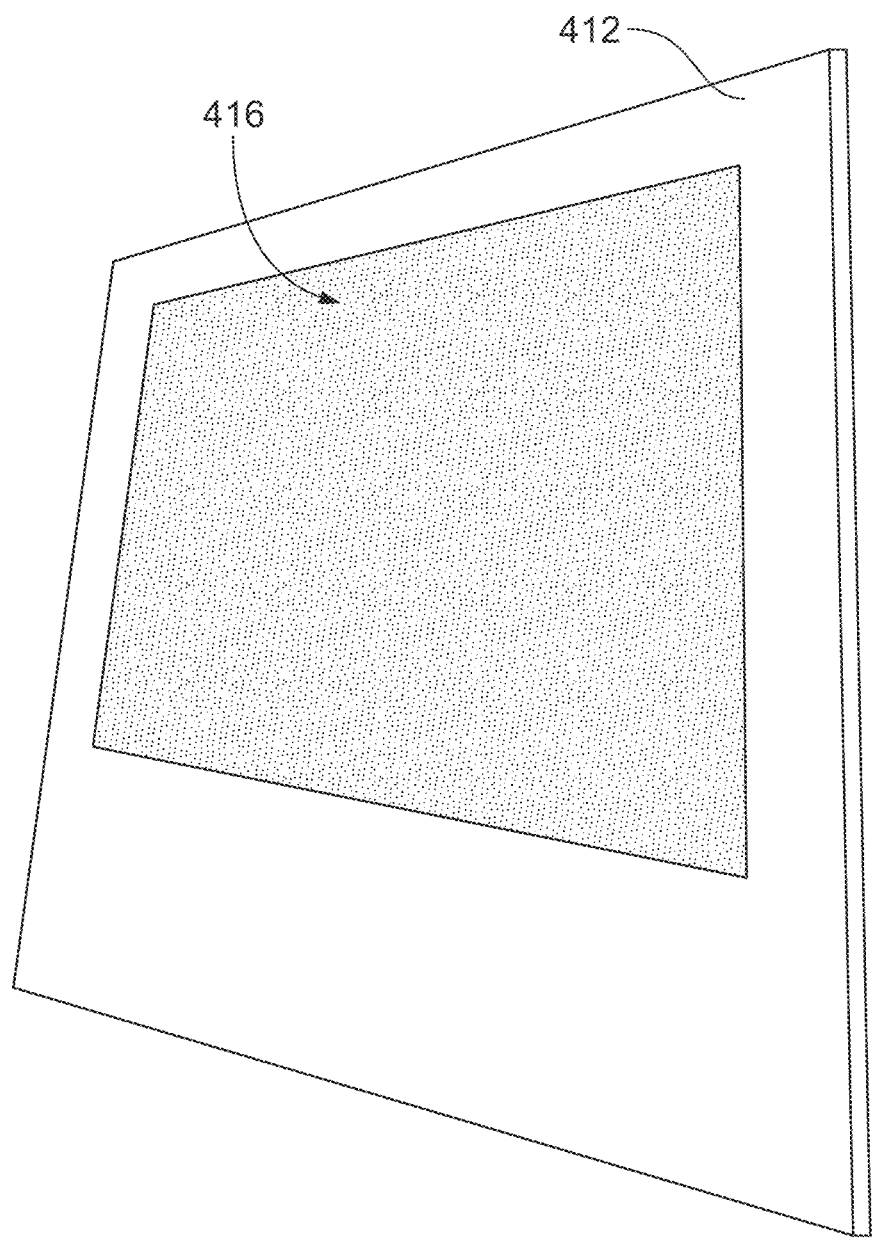
FIG. 12 is a perspective view of the airflow pad assembly of FIG. 11.

As illustrated in FIGS. 11A and 12, the pad cover 412 can include a vent 416 configured to permit for air to pass through. The vent 416 can be provided in a top of the pad cover 412 so that the vent 416 faces a bottom surface of the top layer (e.g., the bottom surface 214, 314 of the top layer 202, 302) above the airflow pad 402. The pad cover 412 can be made of an air restrictive material so that air can flow at least substantially through the vent 416. The pad cover 412 can be free of holes that would significantly direct airflow therethrough, except for the vent 416. Alternatively, the pad cover 412 is made of a material that permits for air flow, but at a slower rate than the vent 416. In some implementations, the vent 416 is configured in the form of a window provided in the pad cover 412. In some implementations, the vent 416 is an opening covered by a meshed material. In other implementations, the vent 416 is an opening with or without any material covering the opening. The vent 416 can be of various shapes, such as a square window, a rectangular window, a circular or oval window, and other suitable polygonal shapes. In addition or alternatively, the vent 416 can be made in a plurality of holes and/or or slits that are arranged in one or more groups.

In some implementations, the edges of the vent 416 can be spaced inward of the perimeter of the airflow pad 402 to form a border around the vent 416. The boarder around the vent 416 can ensure that the surface (e.g., the top surface) of the airflow pad 402 is not entirely the vent 416. For example, the vent 416 is sized to have edges spaced at widths D1-D4 from the perimeter of the pad cover 412. The widths D1-D4 can be determined such that the border around the vent 416 is wider on the side so as to have less or no flow near the outer side of the airflow pad 402, and more flow in the middle and near the inner side of the airflow pad 402. In some implementations, the inlet/outlet (e.g., the pad-side end 430) of the air duct 404 are arranged in a portion of the airflow pad 402 that corresponds with (e.g., aligned with) the border around the vent 416. For example, the pad-side end 430 of the air duct 404 is arranged opposite side of a boarder (the portion having the width D3) of the airflow pad 402. Such arrangement of the inlet/outlet of the air duct 404 can prevent airflow from just blasting upwards from the air duct 404 directly through the vent 416 in an air supply mode, or from suctioning downwards into the air inlet/outlet of the air duct 404 directly through the vent 416 in an air draw mode. Rather, the arrangement of the inlet/outlet of the air duct 404 can allow air to evenly distributed through the entire airflow material 410 (or a majority thereof) as it flows between the inlet/outlet of the air duct 404 and the vent 416.

The pad cover 412 can be configured to provide a plenum chamber that substantially surround a core of the airflow material 410. For example, the pad cover 412 is made of a material that limits airflow while permitting for air to flow through the vent 416. As illustrated, the airflow material 410 can be configured as a layer generally having a top, a bottom, and sides. The pad cover 412 is positioned on at least part of the top, the bottom, and the sides of the airflow material 410, and provides an opening through the vent 416 arranged on the pad cover 412 abutted with the top of the airflow material 410. The vent 416 can be covered by a meshed material or other materials that permit airflow, so that air can flow through the vent 416 and out of or into the airflow material 410 surrounded by the pad cover 412.

The airflow pad 402 is fluidly connected to the air duct 404 at one end. The other end of the air duct 404 can be fluidly connected to an air controller (e.g., the air controller 338) configured to supply ambient or conditioned air into the airflow pad 402 through the air duct 404, or draw air from the airflow pad 402 through the air duct 404.

Referring to FIGS. 11A-C, the air duct 404 includes a pad-side end 430 connected to the airflow pad 402 and fluidly communicating with the airflow material 410 within the airflow pad 402. The air duct 404 has a fan-side end 432 configured to be fluidly connected to a fan assembly (e.g., the air controller 338), or mate with a connection point of the mattress foundation as described in FIGS. 18A and 18B. In some implementations, the air duct 404 can be a bellows-style hose with a repeating series of alternating flex points along the duct. This can allow the air duct to expand and contract as well as to bend to accommodate an air controller being used in different applications.

As described herein, the airflow pad 402 can be configured to include various features that permit for the airflow pad 402 to have a small form factor. For example, the airflow material 410 and the pad cover 412 are configured to provide a smaller thickness of the airflow pad 402 than a layer (e.g., the top layer 202) above the airflow pad 402. For example, the intermediate layer 204 that incorporates the airflow layer 206 (including one or more airflow pads 402) can be configured to have a smaller thickness than the top layer 202 so that the comfort that the top layer 202 can provide is not reduced or otherwise compromised by the inclusion of the intermediate layer 204 and/or the airflow layer 206 (including the airflow pads 402). In some implementations, a ratio in thickness of the top layer 202 over the intermediate layer 204 can range between about 1.2 to about 10. By way of example, the top layer 202 can be made to be 4 inches thick while the intermediate layer 204 (including the airflow layer 206) can be made to be 1 inch thick.

Figure 62:
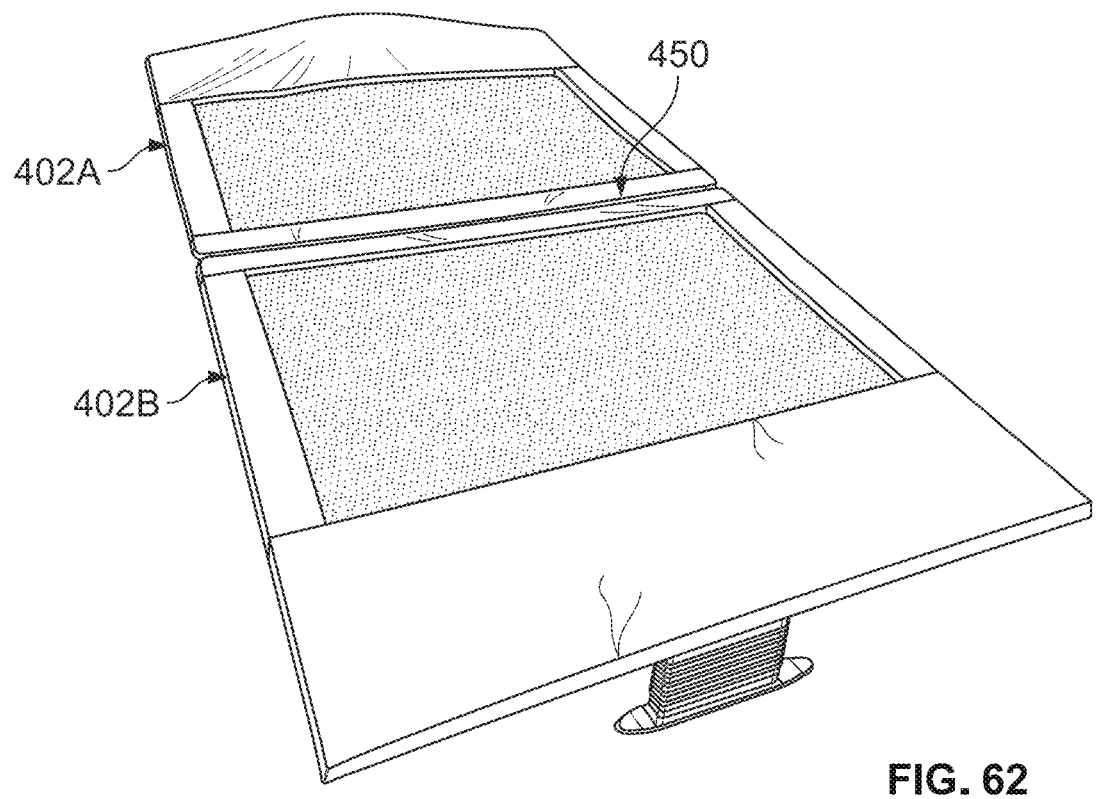
FIG. 62 illustrates an example interconnection between airflow pads.
Figure 63:
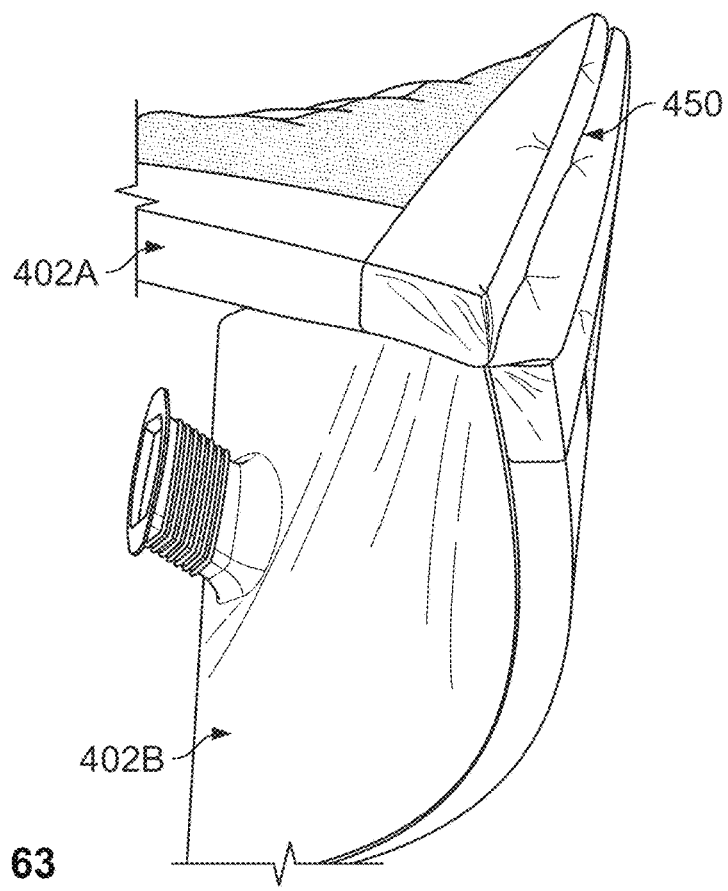
FIG. 63 illustrates the interconnection between the airflow pads of FIG. 62.

Referring to FIGS. 62 and 63, the air distribution layer can include two airflow pads 402 (including 402A and 402B) that can be connected together. For example, the airflow pad 402A and the airflow pad 402B are mechanically connected at an interface 450. Various methods can be used to mechanically attach the airflow pads 402A and 402B together at the interface 450, such as stitching, adhesives, fasteners, and other suitable mechanisms. The interconnected interface 450 between the airflow pads 402A and 402B can prevent unstable placement (e.g., wobbling, dislocation, displacement, etc.) of the airflow pads 402A and 402B that may otherwise result from the compression from the mattress top (e.g., resulting from the body weight), the user's movement on the mattress top, the air movement or change in pressure in the air chambers, etc. For example, while the user moves on the mattress top, either or both of the airflow pads 402A and 402B can wobble, or be displaced or dislocated from proper positions, thereby resulting in a separation between the airflow pads 402A and 402B. The interconnection at the interface 450 can prevent such separation between the airflow pads 402A and 402B and hold them in place.

Reinforcement Straps (Feature Group #3)

Figure 14:
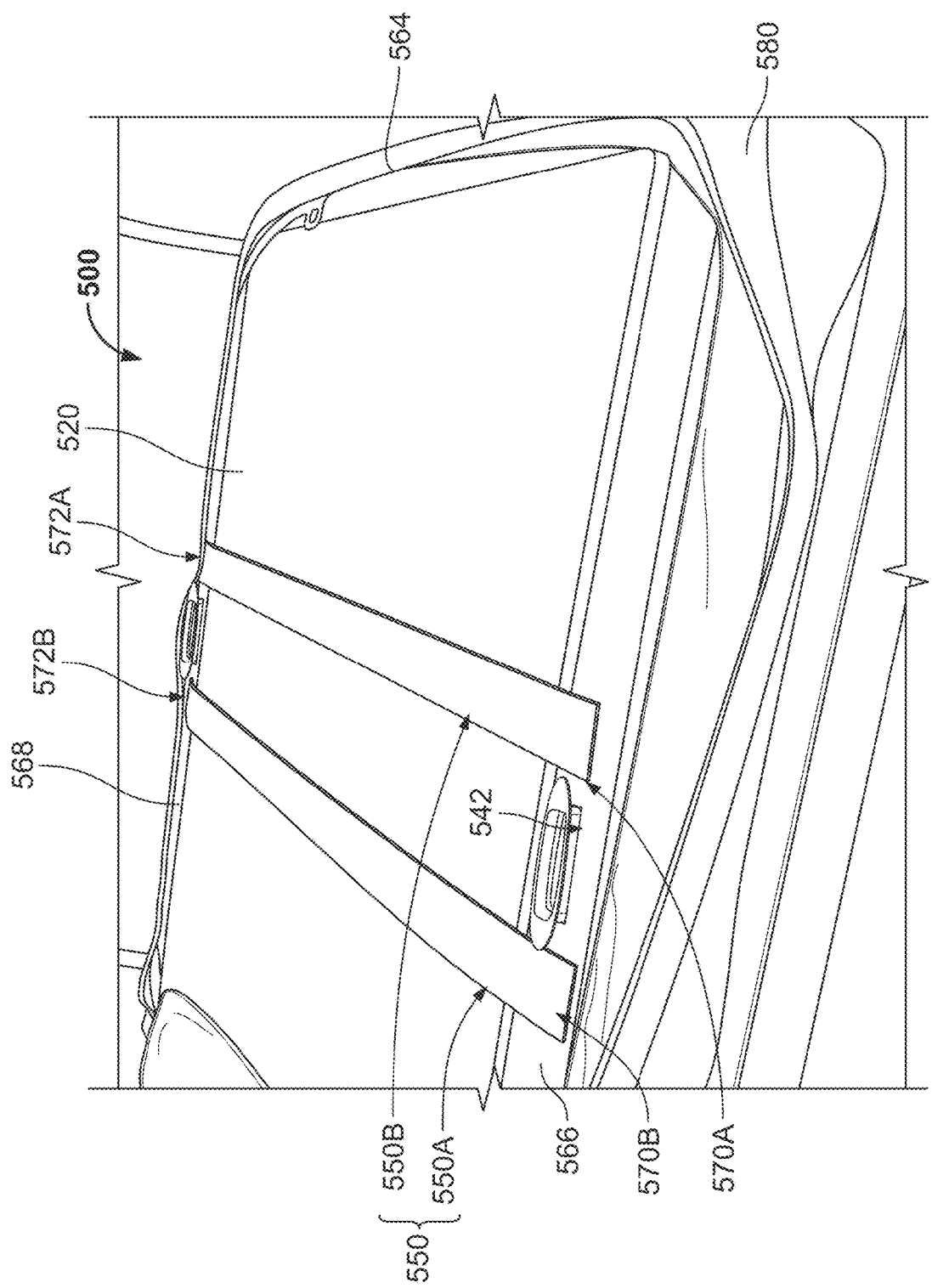
FIG. 14 illustrates a bottom perspective view of an example mattress system with a set of reinforcement straps attached in place.
Figure 15:
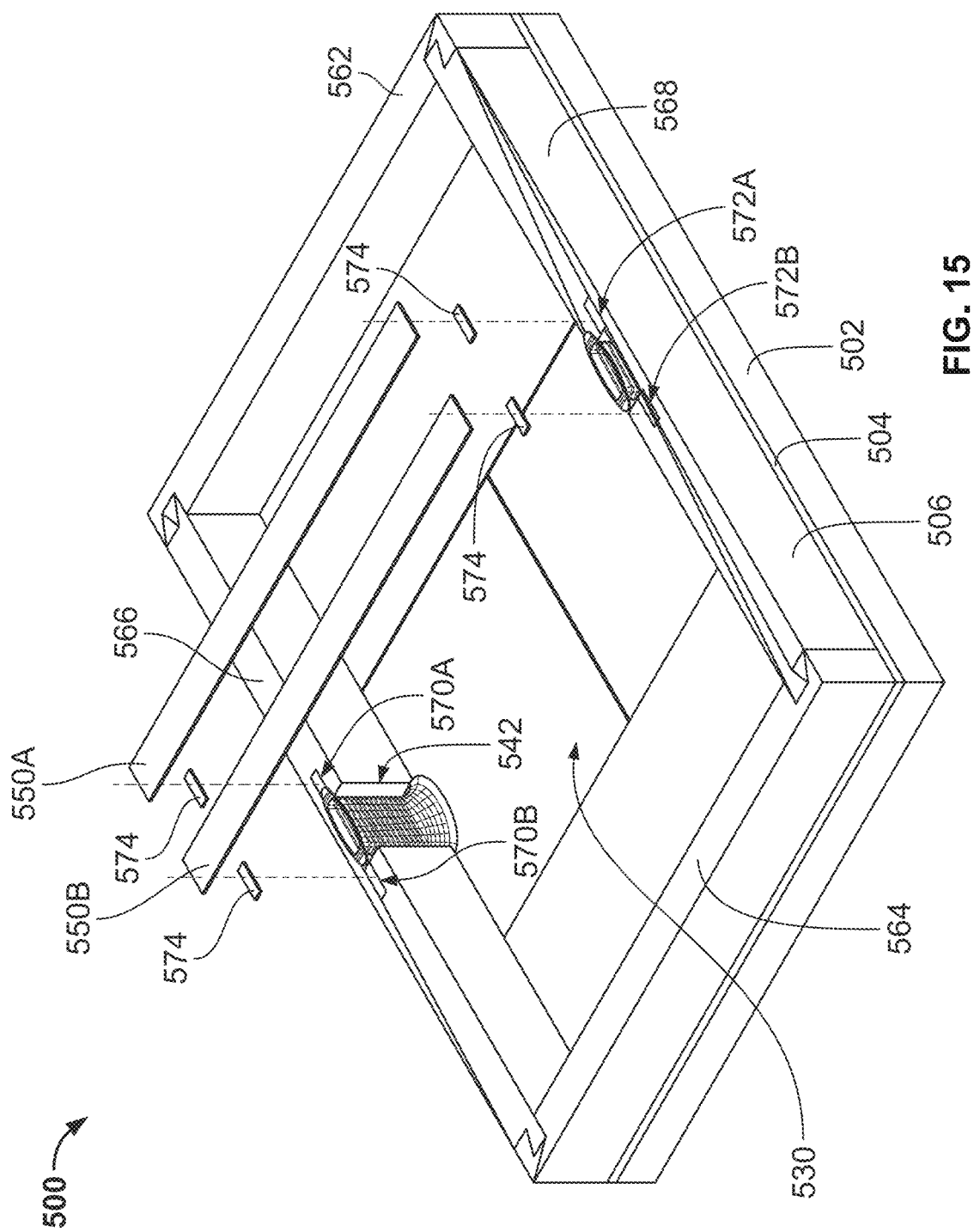
FIG. 15 illustrates a bottom perspective view of the mattress system with the reinforcement straps removed.

Referring to FIGS. 14 and 15, example reinforcement straps 550 are described. FIG. 14 illustrates a bottom perspective view of an example mattress system 500 with a set of reinforcement straps 550 attached in place. FIG. 15 illustrates a bottom perspective view of the mattress system 500 with the reinforcement straps 550 removed.

One or more reinforcement straps 550 can be used to hold the mattress system 500 in place and keep it from bowing outwards when used. For example, the mattress system 500 can include a layer and a rail structure attached to the layer. The layer can have a layer top and a layer bottom opposite to the layer top. The layer can extend between a first layer edge and a second layer edge. Examples of the first and second layer edges are opposite side edges of the layer. In addition, the layer can extend between a third layer edge and a fourth layer edge, examples of which are head-side and foot-side edges. The rail structure can include a first side rail attached to the layer bottom proximate the first layer edge, and a second side rail attached to the layer bottom proximate the second layer edge. For example, the first and second side rails can be rails arranged at opposite sides along the length of the mattress. In addition, the rail structure can include a third side rail attached to the layer bottom proximate the third layer edge, and a fourth side rail attached to the layer bottom proximate the fourth layer edge. For example, the third and fourth side rails can be rails arranged at the head-side edge and the foot-side edge. A core of the mattress, such as one or more air chambers, foams, and/or spring assemblies, can be positioned under the layer bottom between the first side rails and the second side rails. In addition, the core can be positioned under the layer bottom between the third side rails and the fourth side rails.

In the illustrated examples, two reinforcement straps 550 can be used, including a first strap 550A and a second strap 550B. For example, the first strap 550A can be connected to the first side rail and the second side rail and extend under the core from the first side rail to the second side rail. One end of the first strap 550A can be connected to a first connection point located on a bottom of the first side rail, and the other end of the first strap 550A can be connected to a second connection point located on a bottom of the second side rail. Similarly, the second strap 550B can be connected to the first side rail and the second side rail and extend under the core from the first side rail to the second side rail. One end of the second strap 550B can be connected to a third connection point located on a bottom of the first side rail, and the other end of the second strap 550B can be connected to a fourth connection point located on a bottom of the second side rail. The first strap 550A and the second strap 550B can be relatively arranged in various configurations. For example, the first strap 550A is arranged close to the second strap 550B and extends to be parallel with the second strap 550B. The first strap 550A can be arranged at a distance from the second strap 550B extending parallel with the first strap 550A. An example of the distance can range from about 5 inches to about 70 inches. Although two reinforcement straps are primarily illustrated in the illustrated examples, more than two reinforcement straps 550 can be used in similar manners in other implementations. In yet alternative implementations, a single reinforcement strap 550 can be used in a desired configuration.

As illustrated in FIGS. 14 and 15, the mattress system 500 can be configured similarly to the mattress 104 or the mattress system 200, 300. For example, the mattress system 500 includes a top layer 502, an intermediate layer 504, a rail structure 506, and an airflow layer 530, which are configured similarly to the top layer 202, 302, the intermediate layer 204, 304, the rail structure 206, 306, and the airflow layer 230, 330, respectively. The mattress system 500 can be configured to include a core of various types, such as one or more inflatable air chambers, foams, and/or spring assemblies, that can be received in a space defined by the rail structure 506 in the same or similar manner as described herein.

The rail structure 506 can include a head rail 562, a foot rail 564, and opposite side rails 566, 568 extending between the head rail 562 and the foot rail 564. In some implementations, the rail structure 506 can be made of one or more foam materials. In this example, the rail structure 506 is attached to the intermediate layer 504. When attached to the intermediate layer 504, the rail structure 506 may be also engaged with, or attached to, the airflow layer 530 that is positioned in a cutout section of the intermediate layer 504 (e.g., to be flushed with the intermediate layer 504). For example, the head rail 562 is attached to a bottom of the intermediate layer 504 at (or proximate) a head edge of the intermediate layer 504, and the foot rail 565 is attached to the bottom of the intermediate layer 504 at (or proximate) a foot edge of the intermediate layer 504 (opposite to the head edge of the intermediate layer 504). The side rails 566, 568 are attached to the bottom of the intermediate layer 504 at (or proximate) opposite sides of the intermediate layer 504. Similarly to the rail structure 206, 306, the rail structure 506 forms an upside-down foam tub, along with the layers (e.g., the intermediate layer 504, the airflow layer 530, and/or the top layer 502). For example, the rail structure 506 defines a space for receiving a mattress core 520, such as one or more inflatable air chambers, foams, and/or spring assemblies.

The reinforcement straps 550 can include the first strap 550A. The first strap 550A can be connected to the opposite side rails 566, 568 so as to extend under the mattress core 520 between bottoms of the side rails 566, 568. The first strap 550A can be attached to the opposite side rails 566, 568 at predetermined connection locations 570A, 572A. Further, the reinforcement straps 550 can include the second strap 550B. Similarly to the first strap 550A, the second strap 550B can be connected to the opposite side rails 566, 568 so as to extend under the mattress core 520 between bottoms of the side rails 566, 568. The second strap 550B can be attached to the opposite side rails 566, 568 at predetermined connection locations 570B, 572B. In some implementations, the first strap 550A and the second strap 550B are positioned in a longitudinal middle section of the mattress. The first strap 550A can extend to be parallel with the second strap 550B and spaced at a predetermined distance from the second strap 550B.

Figure 16:
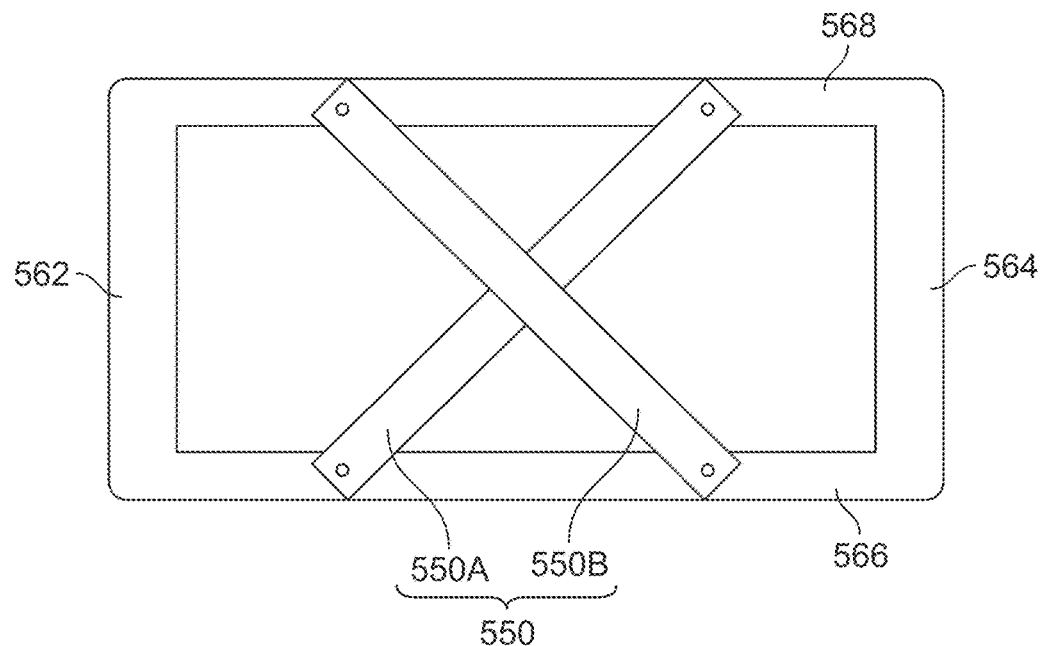
FIG. 16 illustrates an alternative configuration of the reinforcement straps.

Other configurations of the straps 550 can be possible. In some implementations, the straps 550 can be routed to cross each other. For example, the first strap 550A and the second strap 550B are connected to the opposite side rails 566, 568 to extend under the mattress core 520 between the bottoms of the side rails 566, 568. The first strap 550A can be routed to cross the second strap 550B by connecting one end of the first strap 550A to one of the side rails 566, 568 between the head rail 562 and the second strap 550B, and connecting the other end of the first strap 550a to the other side rail 566, 568 between the foot rail 562 and the second strap 550B. An example of the cross routing of the straps 550 is illustrated in FIG. 16.

In other configurations, one or more straps 550 can extend to one or both of the head rail 562 and the foot rail 564. In one example, one or more straps 550 can extend from the head rail 562 to the foot rail 564 rather than extending between the opposite side rails 566 and 568. In another example, one or more straps 550 can extend from the head rail 562 to the foot rail 564 in addition to having one or more straps 550 extending between the opposite side rails 566 and 568.

In some implementations, the rail structure 506 can include one or more cutouts for various purposes. For example, the rail structure 506 includes cutouts 542 configured to receive air ducts of the airflow pad assemblies 530 and/or other components (e.g., air passages, electronic wires, etc.) of the mattress system. The cutouts 542 can be configured similarly to the notches 242 described herein. The cutouts 542 of the rail structure 506 can structurally weaken the rail structure 506 at or around the cutouts. The straps 550 can be attached to the rail structure 506 on opposite side of the cutouts 542, thereby reinforcing or maintaining the rail structure 506 at or around the cutouts 542. For example, in the illustrated example, the cutouts 542 are provided in the opposite side rails 566, 568, and the first strap 550A and/or the second strap 550B are connected to the opposite side rails 566, 568 proximate the cutouts 542, as illustrated in FIGS. 14 and 15.

The straps 550 can be attached to the rail structure 506 using one or more fastening elements 574. The fastening elements 574 can be of various types. For example, the fastening elements 574 include adhesive tapes. Alternatively or in addition, the fastening elements 574 can be hook-and-loop fasteners (e.g., VELCRO®), zippers, clips, pins, buttons, straps, ties, snap fasteners, and other suitable types of fasteners. The fastening elements 574 can be applied at the connection locations 570A-B, 572A-B, or at desired locations (e.g., the ends) of the straps 550, so that such desired location of the straps 550 are attached to the connection points of the rail structure 506. For example, adhesive tapes can be applied between the connection locations 570A-B, 572A-B of the rail structure and the ends of the straps 550.

As illustrated in FIG. 14, the mattress system 500 can further include a mattress cover 580 configured to cover components of the mattress system 500, such as the top layer 502, the intermediate layer 504, the rail structure 506, the mattress core 520, an airflow layer 530, and the straps 550.

As such, the reinforcement straps that extend between rails and run across the bottom of the mattress can help hold the mattress core and other mattress components in place and keep them from bowing outwards after repeated edge of bed stress from a user entering and exiting. The reinforcement straps can be used with pieces of hook materials (e.g., 3M hook materials) with adhesive backing. The hook materials can be placed along the bottom side of the perimeter side rails. In some implementations, the reinforcement straps can include a scrim material and attach to the hook materials and extend from one side of the bed to the other side. The straps are removable to allow other components (e.g., the air chambers, layers, etc.) to be assembled without interference. The straps can be adjustable to accommodate for stretch or changes over time, varying tolerances of the foam tub and its cover, or general aesthetic preference impact. The straps can have a width of varying sizes, such as a width ranging between about 1 inch and about 7 inches.

Connection Interface Between Mattress and Foundation (Feature Group #4)

Referring to FIGS. 17-20, an example connection interface is described which connects a mattress with a foundation. In general, the mattress has a mattress top and a mattress bottom opposite to the mattress top, and defines a mattress interior between the mattress top and the mattress bottom. When the mattress is placed on the foundation, a user can rest on or above the mattress top. In some implementations, the mattress has a first connection portion positioned on the mattress bottom and defines a first air hole configured to allow airflow through the first connection portion. The mattress can include an air hose extending from the first air hole of the first connection portion into the mattress interior. For example, as illustrated in FIGS. 18A-B, a mattress 600 is configured to provide a first connection portion 652 on a bottom of the mattress. The first connection portion 652 is in fluid communication with an interior hole 654 located with the interior of the mattress 600. The interior hole 654 can be provided for multiple purposes. In one example, the interior hole 654 is an air hole that permits for air to flow into or out from an air-fillable or air-distributable component, such as an inflatable air chamber (e.g. the air chamber 222) and/or an airflow layer (e.g., the airflow layer 230, 330, 530). Alternatively or in addition, the interior hole 654 can be a hole that permits for other elements, such as wires, cables, etc., to route through. The mattress 600 can further include a duct (or hose) 656 extending from the interior hole 654 within the interior of the mattress 600 and out from the bottom of the mattress through the first connection portion 652. In some implementations, the duct 656 can be an air hose or duct that is configured to be similar to the air duct 234, 336, 404. The duct 656 can be made of a flexible material. The duct 656 can have a mating end 658 configured to mate a second connection portion 672 provided in a foundation 670. As described below, the mating end 658 can be made of a flexible material and snap fit with the second connection portion 672.

The foundation 670 is sized and configured to be positioned under the bottom of the mattress 600 and support the mattress 600 on a support surface 673. The foundation 670 includes the second connection portion 672 positioned on the support surface 673. The second connection portion 672 defines an interface hole 676 for one or more purposes. For example, the interface hole 676 is an air hole configured to permit for air to flow through the second connection portion 672. Alternatively or in addition, the interface hole 676 can be a hole that permits for other elements, such as wires, cables, etc. The second connection portion 672 can be arranged to be aligned with the first connection portion 652 when the mattress 600 is positioned on the foundation 670. The second connection portion 672 can be configured to be connected to the first connection portion 652. For example, the second connection portion 672 is configured to couple the mating end 658 of the duct 656 at or adjacent the first connection portion 652, such that the second connection portion 672 is directly or indirectly engaged with the first connection portion 652. When the first connection portion 652 is coupled with the second connection portion 672, the interior hole 654 (e.g., the air hole) in the mattress 600 is fluidly connected with the interface hole 676 (e.g., the air hole) in the foundation 670 so that air can flow between the foundation and the mattress through the interior hole 654 and the interface hole 676. In some implementations, the interior hole 654 (e.g., the air hole) in the mattress 600 can be configured to align with the interface hole 676 (e.g., the air hole) in the foundation 670.

Figure 17A:
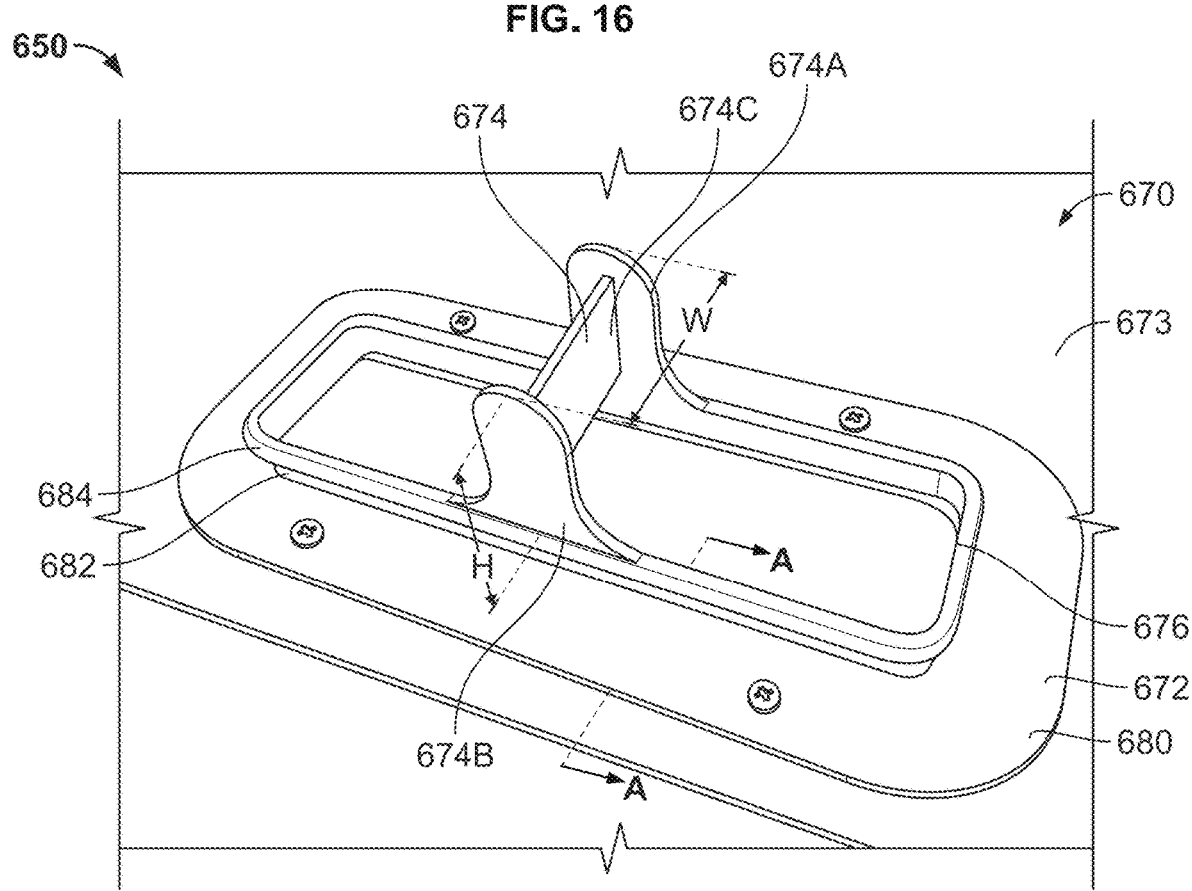
FIGS. 17A and 17B illustrate an example connection interface for connecting a mattress with a foundation.
Figure 17B:
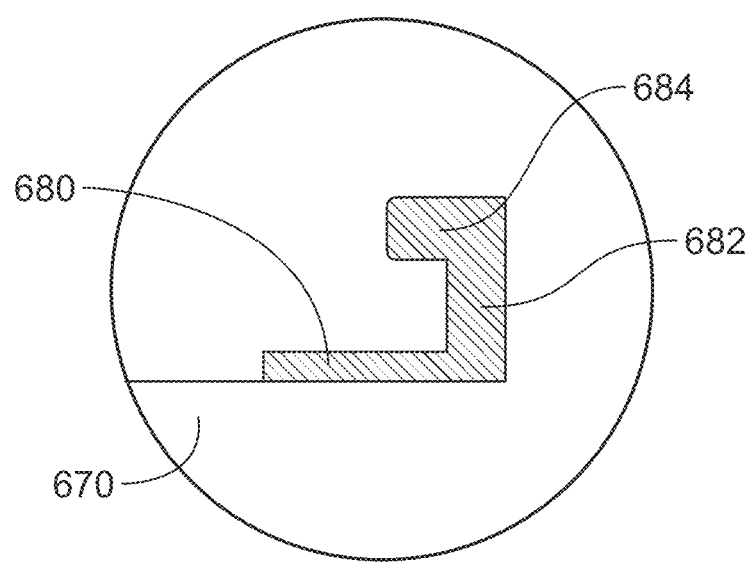
Figure 18B:
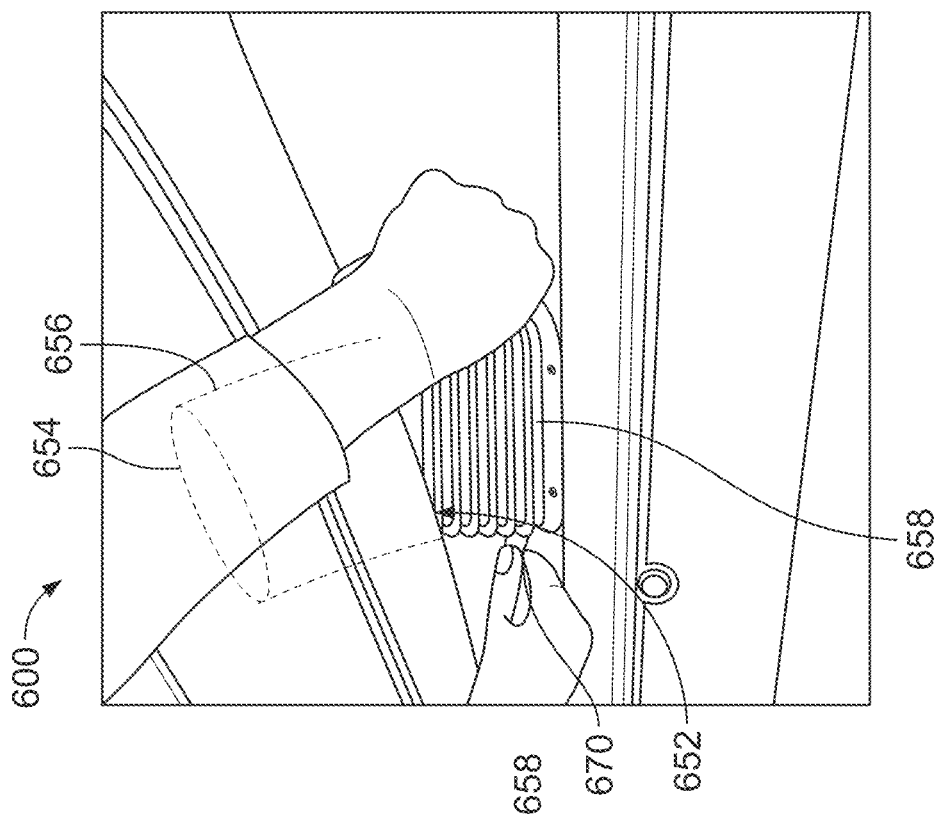
FIGS. 18A-B illustrate an example configuration of the connection interface, and an example process of connecting the mattress with the foundation.
Figure 18A:
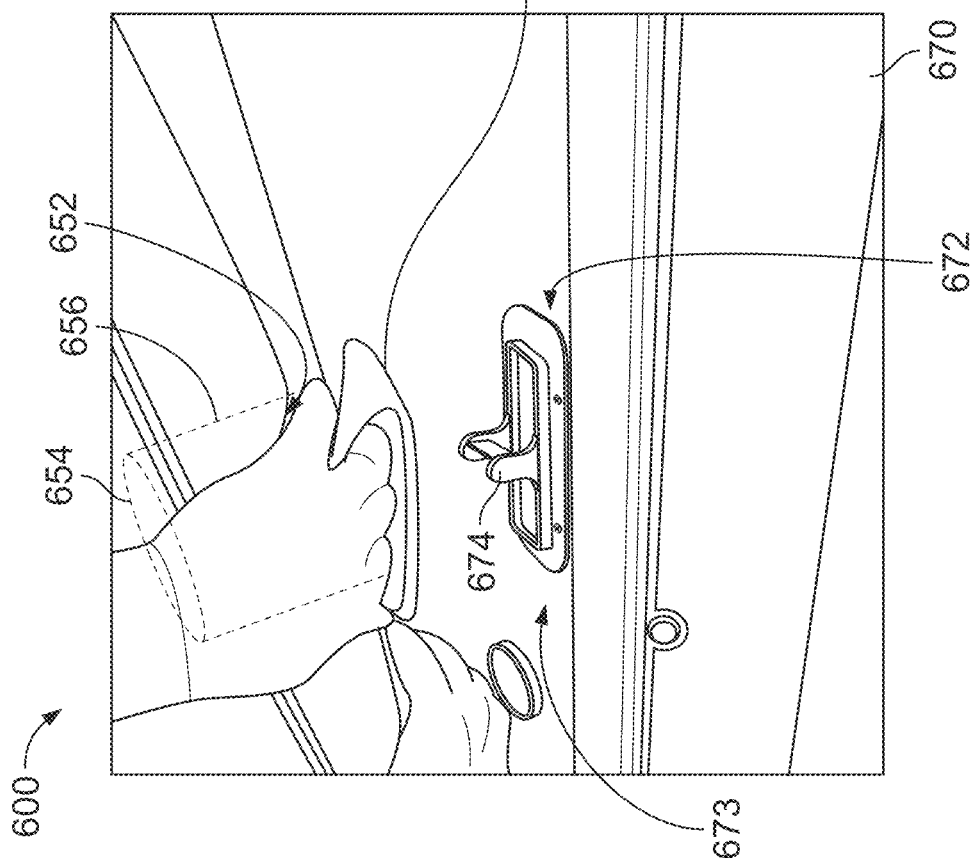

In some implementations, the duct 656 extending from the mattress 600 is sized and shaped to snap fit with the second connection portion 672 of the foundation 670. For example, the second connection portion 672 can include a base 680 and a lip 682 protruding from the base 680 and defining the interface hole 676 thereunder. The second connection portion 672 can further include a mating flange 684 extending radially outwardly at a top edge of the lip 682, as illustrated in FIG. 17B, which is a partial cross sectional view taken along line A-A in FIG. 17A. As illustrated in FIG. 18B, the mating end 658 of the duct 656 can include gripping portions 670 that permit a user (e.g., an installer, customer, etc.) to grip to bring the mating end 658 of the duct 656 over the second connection portion 672. The mating end 658 can be made to be flexible so as to be flexed out to enable the mating end 658 to cover up the lip 682 of the second connection portion 672. As the mating end 658 slides over the lip 682, the mating flange 684 engages with the mating end 658 so that the mating end 658 fits the lip 682. In some implementations, the mating end 658 of the duct 656 can include a groove that corresponds with the mating flange 684 so that the mating end 658 is secured to the lip 682 of the second connection portion 672.

The mattress 600 can be configured similarly to the mattress 104 or the mattress system 200, 300, 500, and include one or more components similar to the top layer 202, 302, 502, the intermediate layer 204, 304, 504, the rail structure 206, 306, 506, and/or the airflow layer 230, 330, 530. The mattress system 600 can be configured to include a core of various types, such as one or more inflatable air chambers, foams, and/or spring assemblies, that can be received in a space defined by the rail structure in the same or similar manner as described herein. For example, the duct 656 of the mattress 600 is configured to fluidly connect to an airflow layer (similar to the airflow layer 230, 330, 530) of the mattress 600, and configured similarly to the air duct 234, 336, 404.

A plurality of second connection portions 672 can be provided in embodiments wherein the mattress 600 includes a plurality of first connection portions 652. For example, in embodiments where two airflow layers (and thus two first connection portions 652) are provided in the mattress 600 (as described with respect to the mattress 200, 300 herein), two second connection portions 672 can be provided to correspond with the first connection portions 652.

The foundation 670 can be an adjustable foundation. For example, the foundation 670 can be configured to raise or lower a head of the mattress 600 supported on the foundation 670. In addition or alternatively, the foundation 670 can be configured to raise or lower a foot of the mattress 600 supported on the foundation 670. As illustrated in FIG. 19, the foundation 670 can include a head panel 690, a foot panel 692, and one or more middle panel 694A and 694B between the head panel 690 and the foot panel 692. The head panel 690 is configured to raise or lower the head of the mattress 600, and the foot panel 692 is configured to raise or lower the foot of the mattress 600. The middle panel 694A is configured to remain substantially stationary when either or both of the head panel 690 and the foot panel 692 are articulated. The middle panel 694B is configured to connect the middle panel 694A to the foot panel 692, and consequently, can also raise or lower when the foot panel 692 raises or lowers. In some implementations, the second connection portion 672 is arranged in the middle panel 694A of the foundation 670. The second connection portion 672 can be fluidly connected to the air controller 338 mounted to the bottom of the foundation 670. In some implementations, the foundation 670 further includes one or more air chamber interface conduit 696s configured to permit for components (e.g., air hose, wiring, etc.) of the air chamber assembly to pass through to connect to the pump assembly 224 that can be mounted to the bottom of the foundation 670. The air chamber interface conduits 696 can also be arranged in the middle panel 694A.

In some implementations, all panels of the foundation 670, including the middle panel 694A, can be configured to be raised or lowered. In some implementations, more or fewer than four panels can be included in the foundation 670, such as having only three panels (e.g. head, middle, and foot) or five or more panels.

The connection interface between the first connection port 652 and the second connection portion 672 (e.g., the mating of the duct 656 with the second connection portion 672) described above can provide sufficient strength to hold the mattress 600 to the foundation 670 when the foundation 670 is articulated to raise or lower the head and/or the foot of the mattress 600. In some implementations, the connection(s) between the first connection port(s) 652 and the second connection portion(s) 672 (e.g., the mating of the duct 656 with the second connection portion 672) is a sole connection mechanism between the mattress 600 and the foundation 670 without any additional connector, such as adhesives, hook-and-loop fasteners (e.g., VELCRO®), zippers, clips, pins, buttons, straps, ties, snap fasteners, and other suitable types of fasteners.

Referring again to FIG. 17A, the second connection portion 672 can include a duct support rib 674 extending from the base 680. The duct support rib 674 can be sized and shaped to extend upward into the duct 656 at the mating end 658 when the mating end 658 of the duct 656 fits with the second connection portion 672. The duct support rib 674 is configured to provide structural rigidity to the duct 656 when the duct 656 is connected to the second connection portion 672. For example, the duct support rib 674 can have a width W similar to a corresponding inner width W of the duct 656, and a height H from the base 680, so that the shape (e.g., the width) of the duct 656 is maintained at least along the height H when the duct 656 fits with the second connection portion 672.

The duct support rib 674 can be sized and shaped to provide suitable support to the duct 656 without restricting air flow much or at all. For example, the duct support rib 674 can have first and second side walls 674A and 674B extending upward from opposite sides of the interface hole 676 and can have a cross wall 674C extending from the side wall 674A to the side wall 674B, substantially across the interface hole 676. The cross wall 674C can have a relatively thin cross section so as to cause relatively little restriction of flow into or out of the interface hole 676.

Figure 20A:
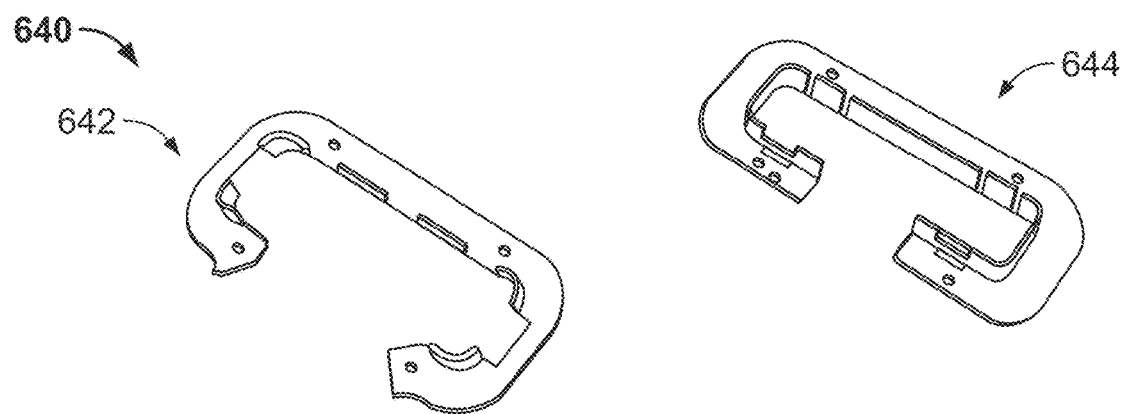
FIGS. 20A-C illustrate an example mattress coupling assembly.
Figure 20B:
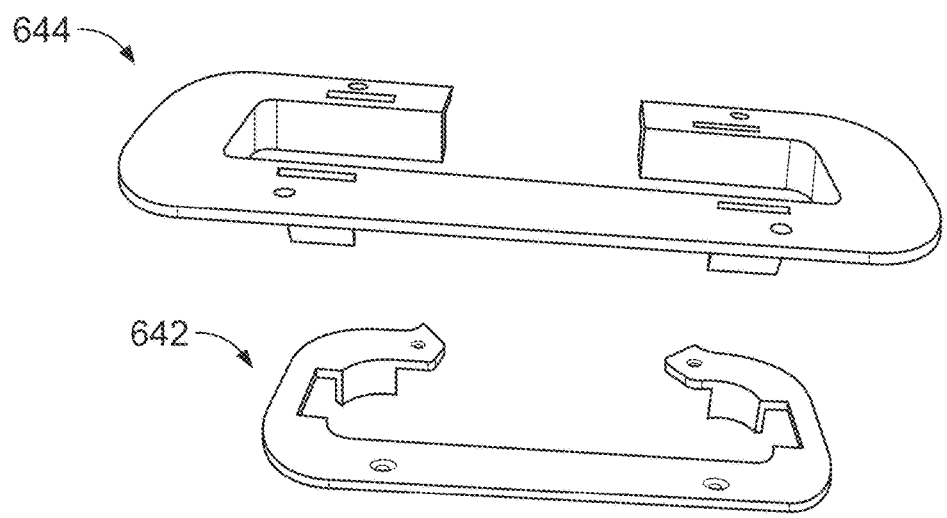
Figure 20C:
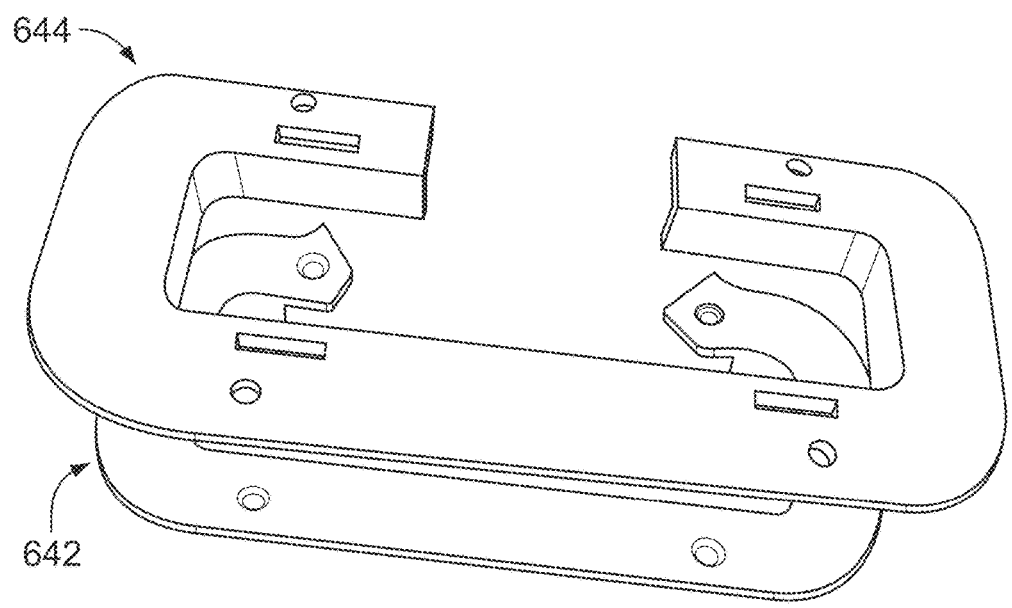

FIGS. 20A-C illustrates an example mattress coupling assembly 640. In some implementations, the mattress coupling assembly 640 includes a first coupling element 642 and a second coupling element 644. The first coupling element 642 can be arranged on the bottom of the mattress 600 and around the air duct 656 extending from the bottom of the mattress 600. For example, the first coupling element 642 can be positioned on the exterior surface of a mattress cover or other sheet that wraps the bottom of the mattress 600. In addition, the second coupling element 644 can be positioned on the interior surface of the mattress cover or other sheet and arranged around the air duct 656 so that the second coupling element 644 is aligned with the first coupling element 644 with the mattress cover or other sheet therebetween. The first coupling element 642 is configured to snap fit the second coupling element 644 with the mattress cover or other sheet therebetween so that the first coupling element 642 is exposed at the bottom of the mattress (outside the mattress cover or sheet) while the second coupling element 644 is positioned at least partially inside the mattress and at least partially hidden from the exterior of the mattress bottom. The first coupling element 642 is configured to fit to a corresponding connection portion, such as the second connection portion 672 (of various configurations), provided at the foundation 670. For example, the first coupling element 642 can be slid into and coupled with the connection portion of the foundation 670. In other examples, the first coupling element 642 can be snap fit with the connection portion of the foundation 670.

In some implementations, the first coupling element 642 can include one or more protruding clips configured to extend down into the connection portion (e.g., the second connection portion 672) of the foundation and engage with the connection portion for coupling the mattress to the foundation. In alternative implementations, the second coupling element 644 can include one or more protruding clips configured to extend down into the connection portion (e.g., the second connection portion 672) of the foundation and engage with the connection portion for coupling the mattress to the foundation. In yet alternative implementations, the first coupling element 642 and the second coupling element 644 can both include one or more protruding clips configured to extend down into the connection portion (e.g., the second connection portion 672) of the foundation and engage with the connection portion for coupling the mattress to the foundation.

Figure 20D:
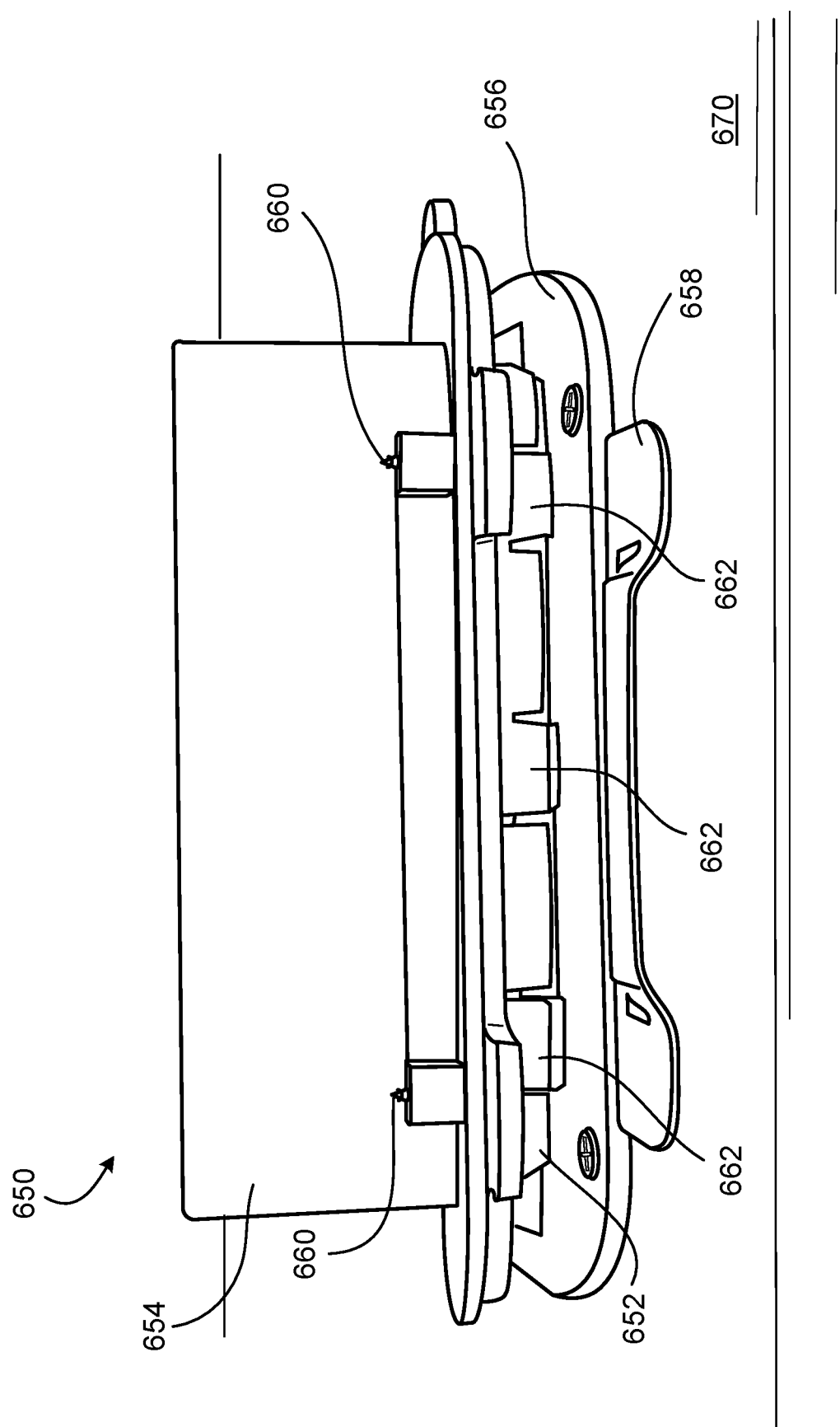
FIG. 20D illustrates another example mattress coupling assembly.

FIG. 20D illustrates another example mattress coupling assembly 650. Similarly to the mattress coupling assembly 640 illustrated in FIGS. 20A-C, the mattress coupling assembly 650 includes a first coupling element 652 and a second coupling element 654. The first coupling element 652 can be arranged on the bottom of the mattress 600 and around the air duct 656 extending from the bottom of the mattress 600. For example, the first coupling element 652 can be positioned on the exterior surface of a mattress cover or other sheet that wraps the bottom of the mattress 650. In addition, the second coupling element 654 can be positioned on the interior surface of the mattress cover or other sheet and arranged around the air duct 656 so that the second coupling element 654 is aligned with the first coupling element 654 with the mattress cover or other sheet therebetween. The first coupling element 642 can be connected to the second coupling element 644 with one or more fasteners 660 while the mattress cover or other sheet is engaged between the first coupling element 642 and the second coupling element 644. Other connecting mechanisms, such as snap-fitting, interference-fitting, adhesion, latches, etc., can be used to connect the first coupling element 642 to the second coupling element 644. When assembled, the first coupling element 652 is exposed at the bottom of the mattress (outside the mattress cover or sheet) while the second coupling element 654 is positioned at least partially inside the mattress and at least partially hidden from the exterior of the mattress bottom. The first coupling element 652 is configured to fit to a corresponding connection portion 656 (e.g., the second connection portion 672) provided at the foundation 670. The connection portion 656 can be fixed around an air passage of the foundation 670. In some implementations, the first coupling element 652 include hooks or clips 662 configured to removably engage with the inner periphery of the connection portion 656. In some implementations, the connection portion 656 can include portions (e.g., recesses) for removably locking the hooks or clips 662 of the first coupling element 652.

The mattress coupling assembly 650 can further include a removal tool 658 configured to easily unlock the mattress from the foundation. For example, the removal tool 658 can be slid under the connection portion 656 to push the hooks or clips 662 of the first coupling element 652 inward, thereby disengaging the hooks or clips 662 of the first coupling element 652 from the connection portion 656 so that the mattress is detached from the foundation 670.

FIG. 65 illustrates another example of the second connection portion 672 for connecting with the first connection portion 652 from the mattress 600. In this example, the second connection portion 672 is configured similarly to the second connection portion 672 of FIG. 17A with a few modifications. For example, the second connection portion 672 in FIG. 65 does not include the duct support rib 674. Instead, the second connection portion 672 has an extended lip 682 extending from the base 680 so that the lip 682 can provide reinforcement of the air duct that fits over the second connection portion 672. As illustrated, the lip 682 in FIG. 65 is longer than the lip 682 in FIG. 17A. In alternative implementations, the extended lip 682 can be provided together with the duct support rib 674.

In some implementations, the connection interface can include a mechanism for mechanically coupling the mattress with the foundation, which may be used independently or in combination with the other types of connection interface described herein. For example, the coupling mechanism can include one or more magnets that are arranged at the bottom of the mattress and correspondingly arranged at the top of the foundation, so that the mattress can be arranged in place and immovable relative to the foundation when the magnets of the mattress are engaged with the corresponding magnets of the foundation. Unless a force exceeding a threshold value is applied to the magnet connection, the mattress can stay in position relative to the foundation. In addition or alternatively, the coupling mechanism can include one or more hooks, clips, buttons, or other suitable locking means. For example, the mattress can include a set of hooks around the side, bottom, and/or other suitable areas of the mattress, and the foundation can include pieces (e.g., rings, holes, hooks, clips, buttons, etc.) with which the hooks or clips are engaged. The pieces can be arranged around the side, top, and/or bottom of the foundation to correspond with the locations of the hooks of the mattress. The mattress can be coupled or locked onto the foundation by engaging the hooks of the mattress with the corresponding pieces of the foundation.

Figure 64:
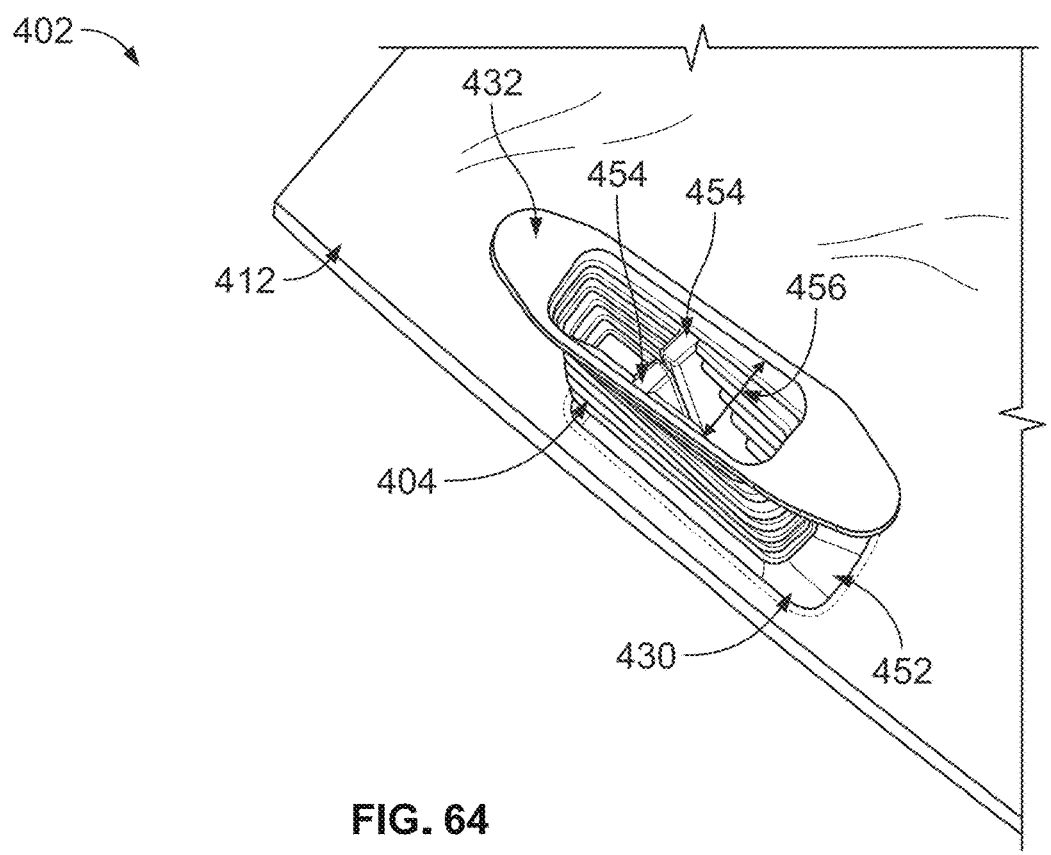
FIG. 64 illustrates an example airflow pad assembly.

Referring to FIG. 64, the air duct 404 can be affixed directly to the pad cover 412 (e.g., envelop). For example, the pad-side end 430 of the air duct 404 can be fixed to the pad cover 412 with stitching 452. Other fastening methods can be used to fix the pad-side end 430 directly to the pad cover 412.

In some implementations, the air duct 404 can include one or more ribs 454 configured to maintain a passage width 456 of the air duct 404. As illustrated in FIG. 64, the air duct 404 can include two ribs 454 that are arranged on the opposing wider inner surfaces of the air duct 404 and at the center of the wider inner surfaces of the air duct 404, so that the ribs 454 face each other. In embodiments where the air duct 404 is made to be flexible, the air duct 404 may be compressed or bent to block the passage of the air duct 404. The ribs 454 are configured to reinforce the air duct 404 while allowing flexibility of the air duct 404. When the air duct 404 are compressed from one or both of the opposite wider sides, the ribs 454 can contact with each other and resist such compression, thereby ensuring the air passage through the air duct 404.

In some implementations, the ribs 454 can be arranged through the entire length of the air duct 404. The ribs 454 can be configured continuously through the entire length of the air duct 404. Alternatively, multiple sets of ribs 454 can be arranged to be spaced apart along the entire length of the air duct 404. Alternatively, the ribs 454 can be arranged along a portion of the length of the air duct 404. For example, the ribs 454 can be positioned adjacent the fan-side end 432 of the air duct 404. In other examples, the ribs 454 can be positioned in the middle of the air duct 404 along its length, or close to the pad-side end 430.

Air Controller Assembly (Feature Group #5)

Referring to FIGS. 21-26, an example air controller 700 is described which is used with a mattress system, such as the mattress 104 or the mattress system 200, 300, 500, 600. For example, the air controller 700 can be used to implement the air controller 338 in FIGS. 10 and 19. The air controller 700 is configured to move air into or from an airflow layer (e.g., the airflow layer 230, 330, 530) in the mattress system. For example, the air controller 700 can be configured to draw air from the airflow layer of the mattress, and/or supply ambient or conditioned air to the airflow layer. In addition, the air controller 700 can condition air before supplying it to the airflow layer. For example, the air controller 700 can operate to heat or cool air and cause the heated or cooled air to flow into the airflow layer.

Figure 21:
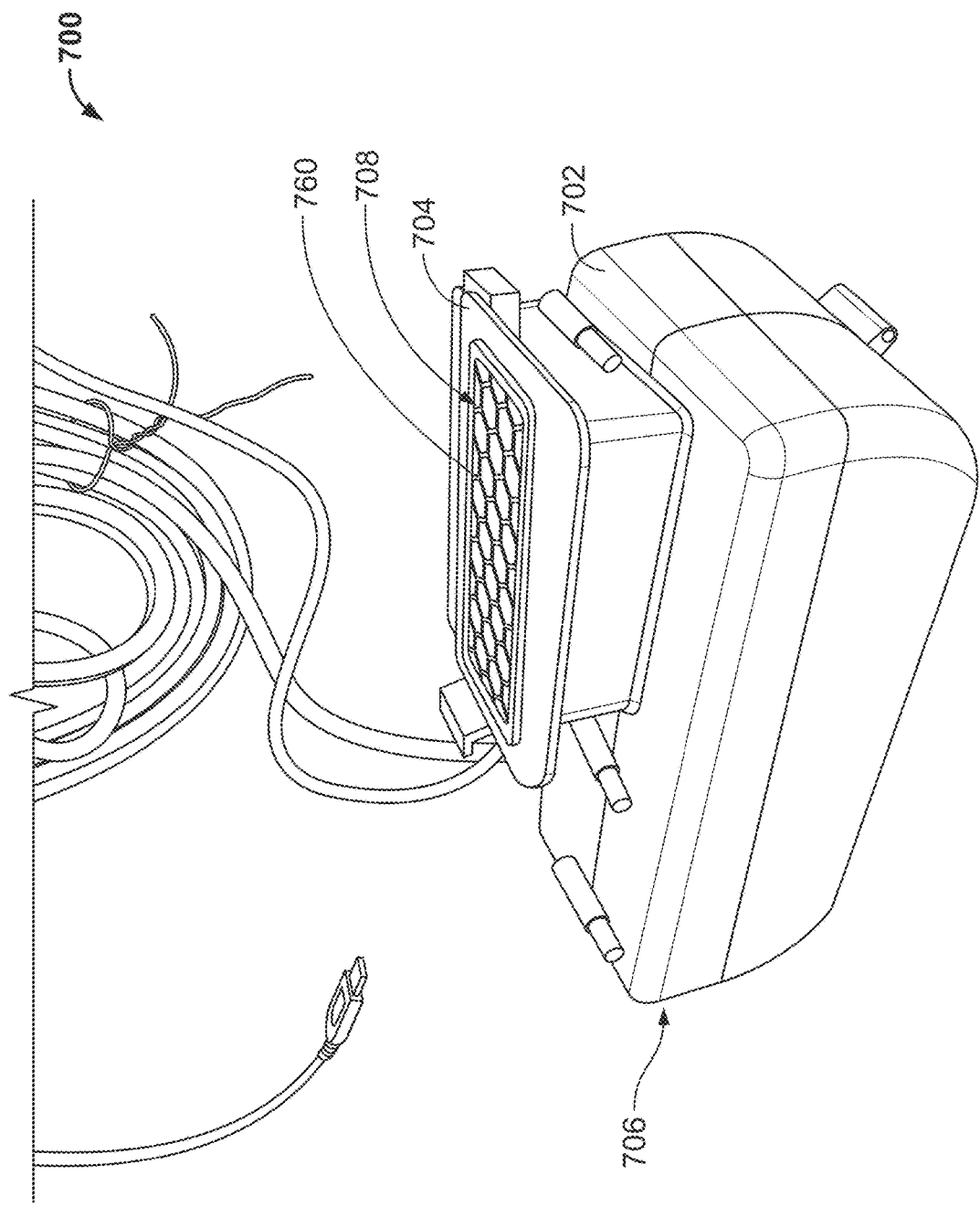
FIG. 21 is a perspective view of an example air controller that is used with a mattress system.

Referring to FIG. 21, the air controller 700 includes a housing 702 having a connection side (e.g., a mattress side) 704 and an ambient side 706. The connection side 704 of the housing 702 is configured to attach to a desired location, such as an underside of a foundation that supports the mattress. The housing 702 includes a connection-side opening (e.g., a mattress-side opening) 708 at the connection side 704, and an ambient-side opening 710 at the ambient side 706. In embodiments where the air controller 700 is used with the foundation 670 described herein, the housing 702 can be attached to the foundation 670 at the connection side 704 so that the connection-side opening 708 is in fluid communication with the interface hole 676 of the second connection portion 672 of the foundation 670, and thus in fluid communication with the interior hole 654 of the mattress 600 when the mattress 600 is supported on the foundation 670 and the duct 656 from the mattress 600 is coupled to the second connection portion 672 of the foundation 670. The ambient side 706 of the housing 702 can be exposed to the atmosphere, and air can be drawn from, or discharged into, the surroundings through the ambient-side opening 710.

Figure 22A:
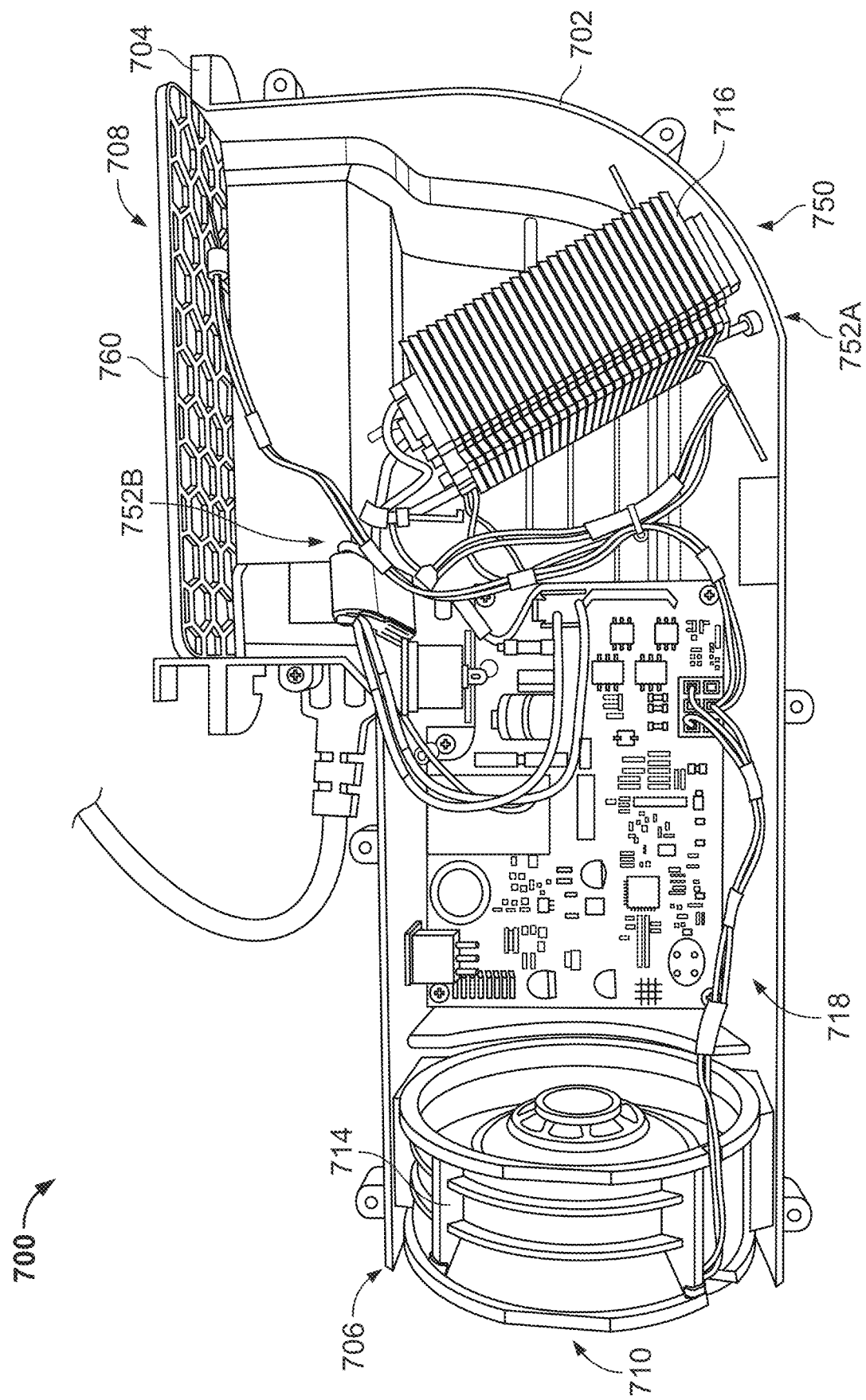
FIGS. 22A-B illustrate example components in the air controller.
Figure 22B:
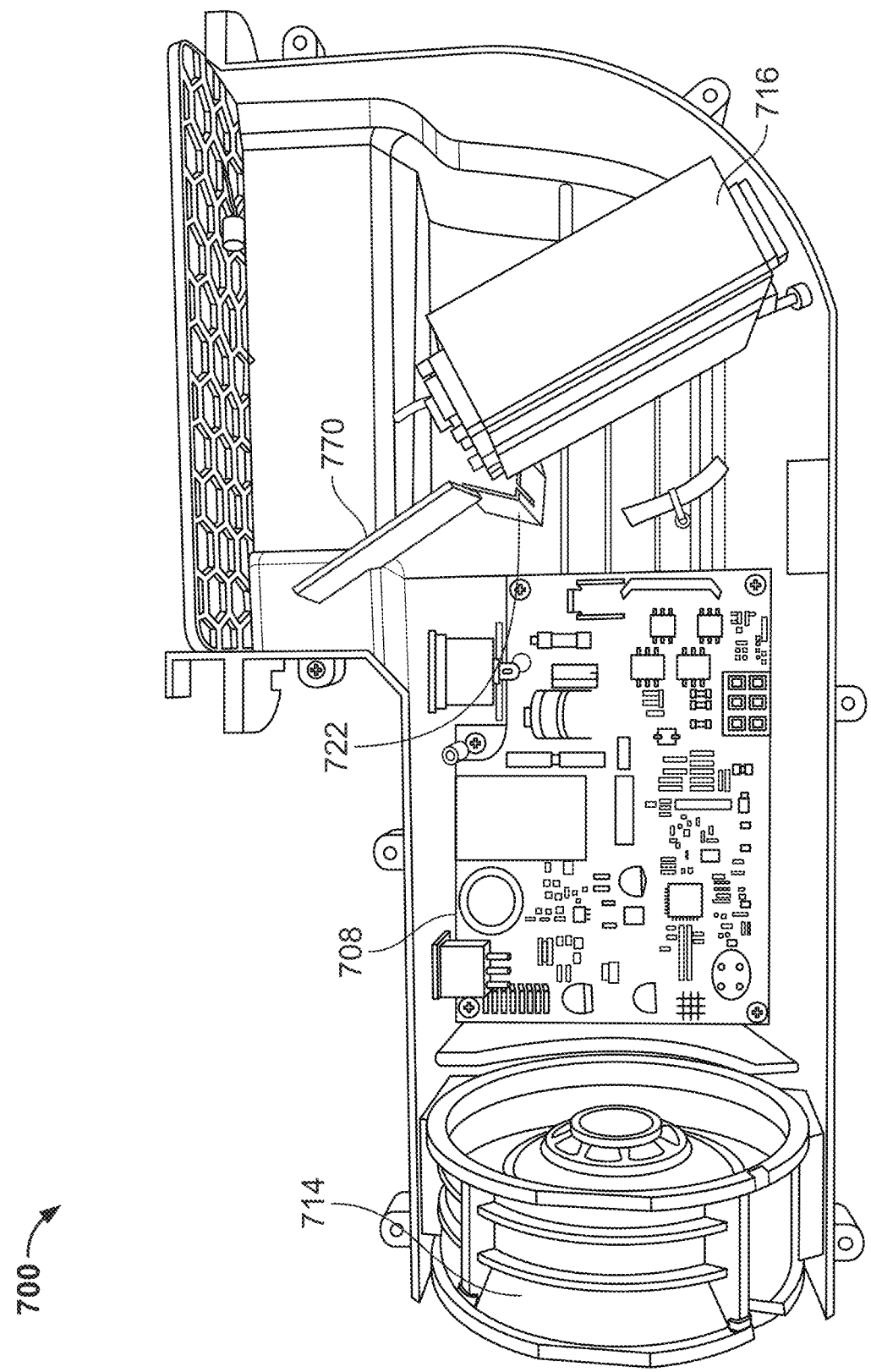

Referring to FIGS. 22A-B, the air controller 700 can include a fan assembly 714 mounted in the housing 702 and configured to cause air to flow through the housing 702. In some implementations, the fan assembly 714 is configured as a reversible fan assembly configured to cause air to flow in opposite directions. For example, the fan assembly 714 can be operated to rotate a fan in one direction to cause air to flow from the ambient side 706 to the connection side 704 of the housing 702. Further, the fan assembly 714 can be operated to rotate the fan in the opposite direction to cause air to flow from the connection side 704 to the ambient side 706 of the housing 702. In some implementations, the fan assembly 714 is positioned at the ambient side 706 of the housing 702 as illustrated in FIGS. 22A-B. Other locations of the fan assembly 714 are possible in other implementations. For example, the fan assembly 714 can be positioned adjacent a heating element 716, such as between the heating element 716 and a PCB board (e.g., a control unit 718).

The air controller 700 can include a heating element 716 mounted in the housing 702 and configured to heat air that passes through the heating element 716. In some implementations, the heating element 716 includes a plurality of fins that allow air flow in between the fins to be heated by the heating element. As described herein, the heating element 716 can be mounted in the housing 702 in a location that is at least partially spaced from an inner wall of the housing 702 so as to define a bypass flow path that allows air to flow around the heating element 716 while air simultaneously flows through the heating element 716. Such a bypass flow path can allow effective air flow through the housing when air is drawn from the mattress and flows from the connection-side opening 708 to the ambient-side opening 710, or when air is supplied and flows from the ambient-side opening 710 toward the connection-side opening 708 with or without activating the heating element 716.

The air controller 700 can include a control unit 718 mounted in the housing 702 and configured to control the air controller 700 in one or more operational modes. For example, the control unit 718 can operate the air controller 700 in a first mode (e.g., ambient-air-drawing mode) in which the control unit 718 controls the fan assembly 714 to cause air to flow from the connection side 704 to the ambient side 706 so that air is drawn from the airflow layer of the mattress. Alternatively or in addition, the control unit 718 can operate the air controller 700 in a second mode (e.g., heating-air-supplying mode) in which the control unit 718 activates the heating element 716 and controls the fan assembly 714 to cause air to flow from the ambient side 706 to the connection side 704 so that the air passes through the heating element 716 and the heating air is supplied to the airflow layer of the mattress. Alternatively or in addition, the control unit 718 can operate the air controller 700 in a third mode (e.g., ambient-air-supplying mode) in which the control unit 718 controls the fan assembly 714 to cause air to flow from the ambient side 706 to the connection side 704 (without activating the heating element 716) so that ambient air is supplied to the airflow layer of the mattress.

In alternative embodiments, the air controller 700 can include a cooling unit with or without the heating element 716, so that the air controller 700 can be operated in additional operational modes. For example, the control unit 718 can operate the air controller 700 in a fourth mode (e.g., cooling-air-supplying mode) in which the control unit 718 activates the cooling element and controls the fan assembly 714 to cause air to flow from the ambient side 706 to the connection side 704 so that the air passes through the cooling element and the cooling air is supplied to the airflow layer of the mattress.

The air controller 700 can be configured with a printed circuit board. The printed circuit board can be positioned in the housing 702 between the ambient-side opening 710 and the heating element 716. The fan assembly 714 can be positioned in the housing 702 between the ambient-side opening 710 and the heating element 716. The air controller 700 can be electrically connected to the fan assembly 714 and the heating element 716 to control operation of the fan assembly 714 and the heating element 716.

The air controller 700 can include one or more temperature sensors configured to detect temperatures at different locations. For example, the air controller 700 can include a first temperature sensor 720 configured to detect a temperature of the heating element 716 and generate a sensor signal 730 representative of the heating element temperature. The air controller 700 can include a second temperature sensor 722 configured to detect an outlet temperature of air existing the housing 702, such as a temperature of air existing at the connection side 704, and generate a sensor signal 732 representative of the outlet air temperature. The control unit 718 can receive the sensor signals 730 and 732 from the first and second temperature sensors 720 and 722, and control the heating element 716 based at least in part on the sensors signals 730 and 732 to achieve a predetermined outlet air temperature. For example, the control unit 718 can determine an offset value of the detected outlet air temperature from the predetermined outlet air temperature, and controls the heating element 716 to compensate the offset value so that the outlet air temperature reaches the predetermined outlet air temperature.

The second temperature sensor 722 can be used to detect a temperature of air drawn into the housing 702 from, for example, the airflow layer of the mattress, and generate a sensor signal 732 representative of the drawn air temperature. Alternatively, the air controller 700 can include a separate temperature sensor (e.g., a third temperature sensor) for detecting the drawn air temperature. The air controller 700 can further include a fourth temperature sensor 724 configured to detect an ambient temperature and generate a sensor signal 734 representative of the ambient temperature. The control unit 718 can receive the sensor signals 732 and 734 from the second (or third) and fourth temperature sensors 722 and 724, and control the fan assembly 714 based at least in part on the sensors signals 732 and 734 to achieve a predetermined drawn air temperature. For example, the control unit 718 can determine an offset value of the detected drawn air temperature from the predetermined drawn air temperature, and controls the fan assembly 714 to compensate the offset value so that the drawn air temperature reaches the predetermined drawn air temperature. In addition, the control unit 718 can calculate an amount of heat extracted from the airflow layer of the mattress based on the sensor signals 732 and 734.

In addition, the air controller 700 can include one or more humidity sensors 726 configured to detect a humidity value and generate a sensor signal 736 representative of the humidity value. The control unit 718 can receive the sensor signal 736 and control the fan assembly 714 and/or the heating element 716 based in part on the sensor signal 736 to achieve a predetermined humidity value. For example, the control unit 718 can determine an offset value of the detected humidity value from the predetermined humidity value, and controls the fan assembly 714 and/or the heating element 716 to compensate the offset value so that the humidity reaches the predetermined humidity value.

Figure 23:
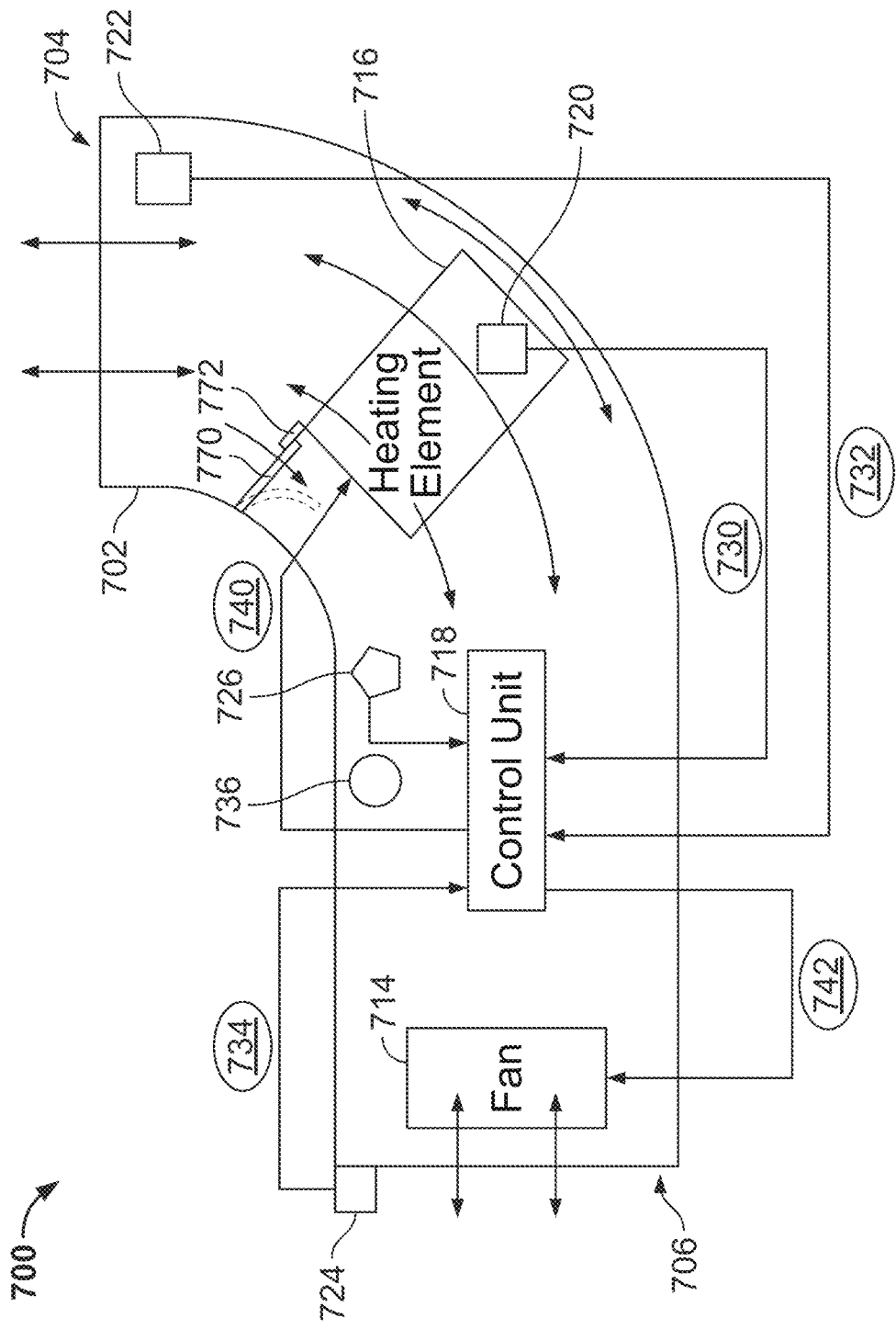
FIG. 23 is a diagram of an example control of the air controller.
Figure 24:
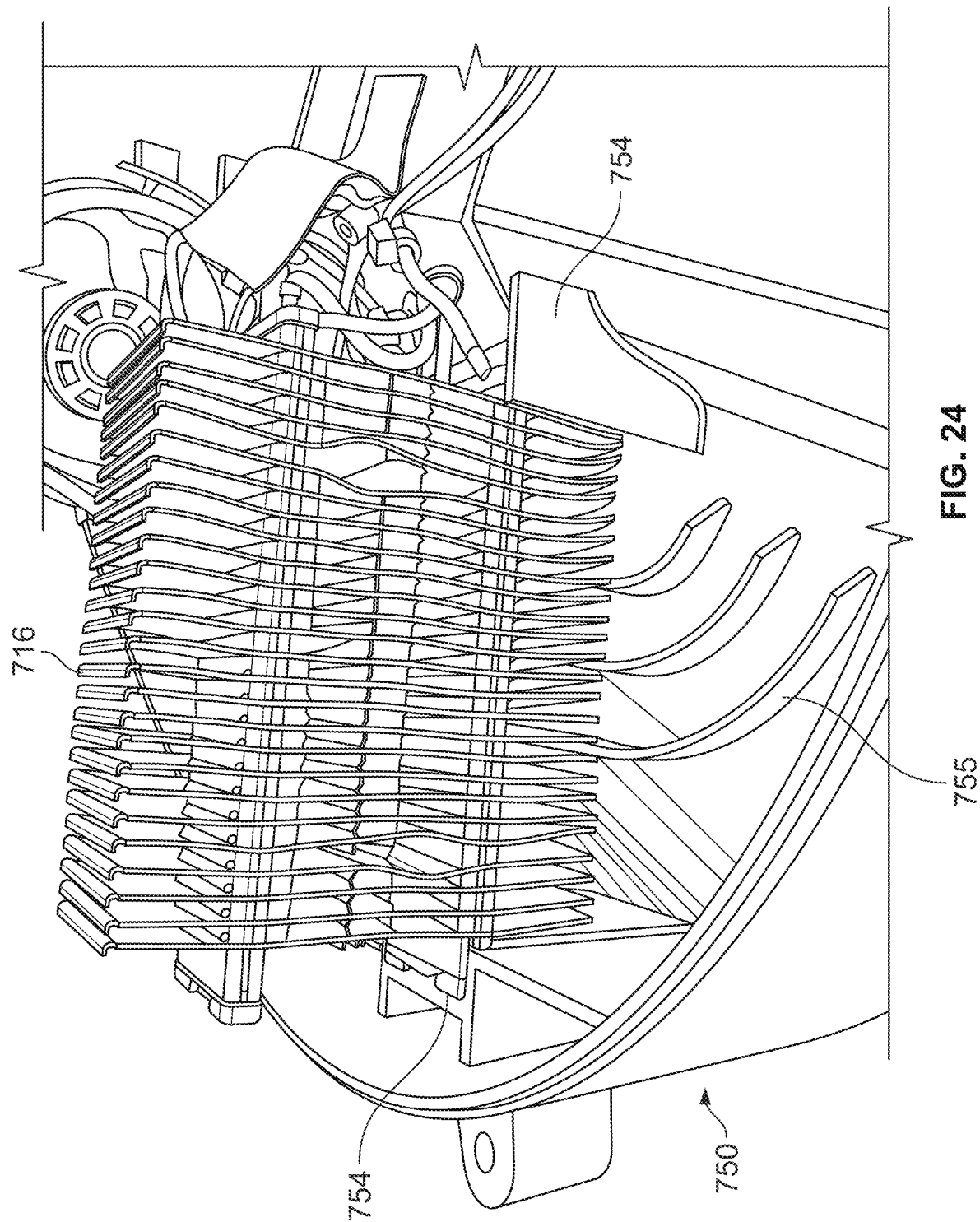
FIG. 24 illustrates an example heating element and associated components in the air controller.

Referring again to FIGS. 22 and 23, the housing 702 includes a curved conduit 750 between the connection side 704 and the ambient side 706. In some implementations, the heating element 716 is arranged at the curved conduit 750. The heating element 716 can be sized to be smaller than a cross section of the curved conduit 750. For example, as illustrated in FIG. 24, the primary area of the heating element 716 is smaller than a cross section of the curved conduit 750 to open an area around the heating element 716, thereby permitting airflow without interference. In some implementations, the housing 702 includes opposite spacers 754 extending from an inner surface of the housing 702 and configured to interference-fit the heating element 716 therebetween. In some implementations, as illustrated in FIGS. 22A-B, the heating element 716 can be arranged closer to an outer corner 752A of the curved conduit 750 than an inner corner 752B of the curved conduit 750. In some implementations, the housing 702 can include one or more vanes 755 (FIG. 24) configured to direct flow of air that bypasses the heating element 716.

Figure 25:
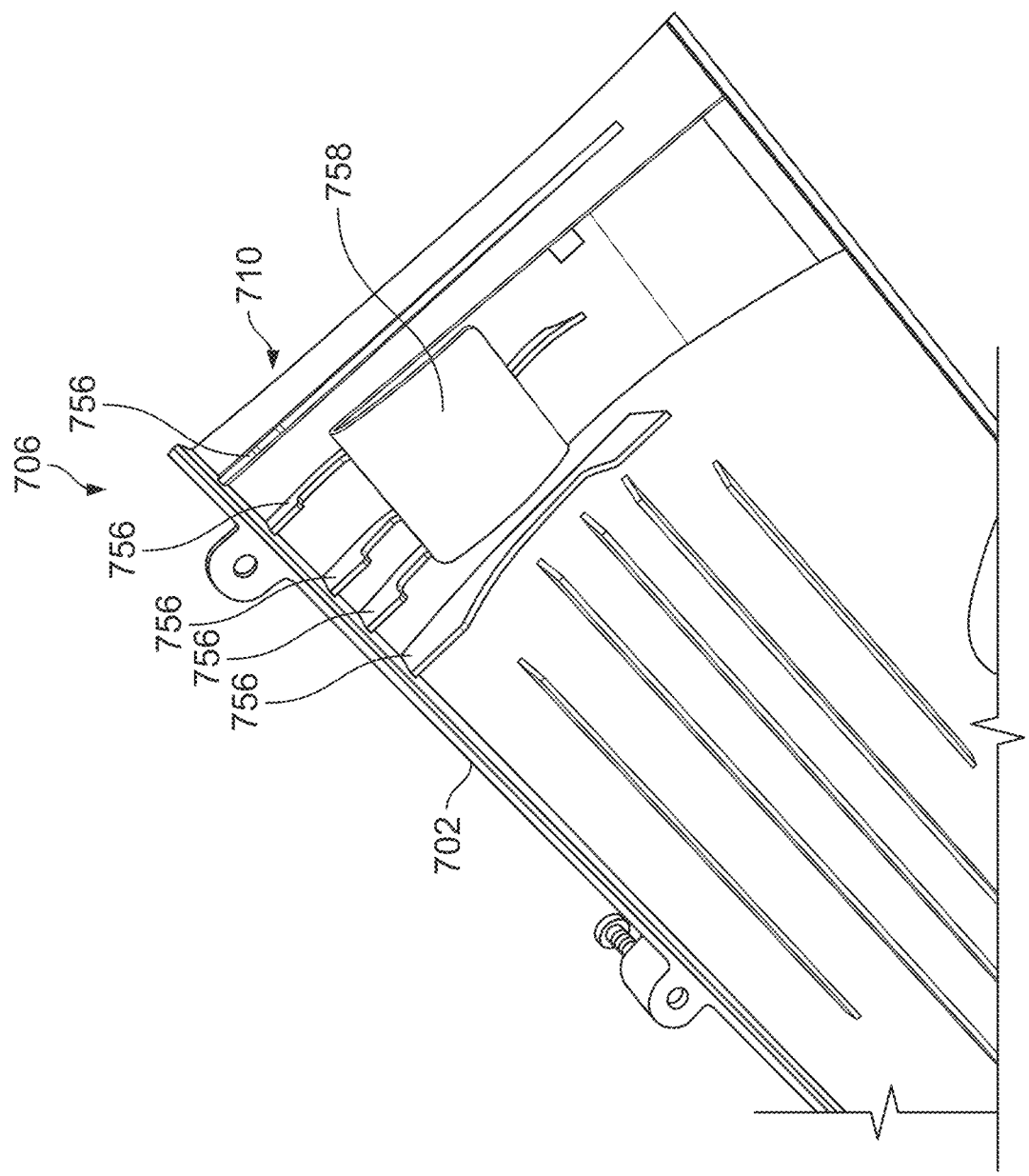
FIG. 25 illustrates an example mechanism for mounting a fan assembly in the air controller.

As illustrated in FIGS. 22A-B, the fan assembly 714 can be arranged at the ambient-side opening 710 of the housing 702. In some implementations, as shown in FIG. 25, the housing 702 includes ribs 756 extending from an inner surface of the housing 702 at the ambient side 706 and configured to engage the fan assembly 714 to secure the fan assembly 714 at the ambient-side opening 710 of the housing 702. Further, the air controller 700 can include a foam material 758 disposed between the fan assembly 714 and the ribs 756 at the ambient-side opening 710. Along with the ribs 756, the foam material 758 can secure the fan assembly 714 at the ambient-side opening 710 of the housing 702, and further absorb vibration of the fan assembly 714 so that it does not transfer to the housing 702 and the rest of the bed (e.g., the foundation and the mattress).

Figure 26:
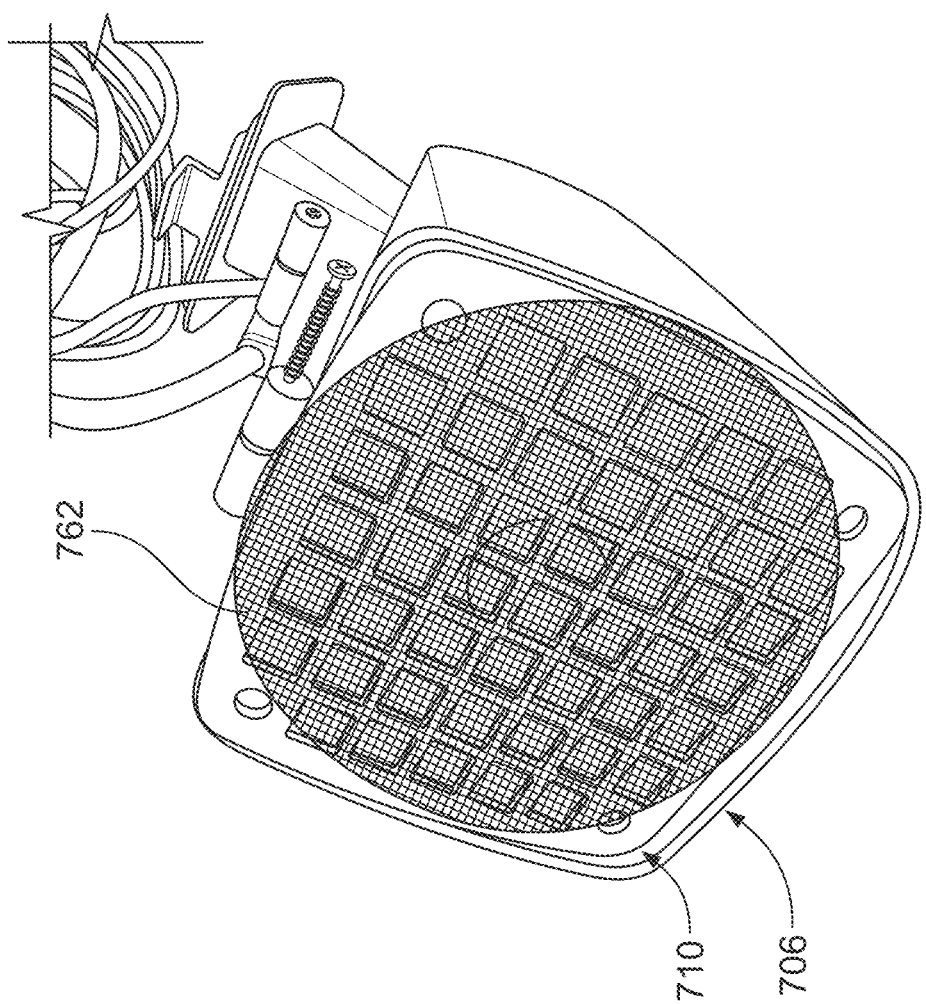
FIG. 26 illustrates an example configuration of an opening of the air controller.

The air controller 700 can include one or more air screens. For example, as shown in FIGS. 21 and 22, the air controller 700 can include a first screen 760 arranged at the connection-side opening 708 of the housing 702. As shown in FIG. 26, the air controller 700 can include a second screen 762 arranged at the ambient-side opening 710 of the housing 702. The first and second screens 760 and 762 are configured to filter debris, dirt, and contaminants from air passing through the air controller 700, thereby preventing them from entering the air controller 700 and/or the mattress to which the air controller 700 is coupled.

Referring to FIG. 22B, the air controller 700 can include one or more air deflectors 770 configured to improve distribution of conditioned air to the mattress. The air deflectors 770 can be disposed in various locations along one or more air flow paths through the air controller 700. For example, the air deflector 770 can be arranged around the heating element 716 to restrict airflow in one direction and facilitate airflow in the opposite direction. In the illustrated example, the air deflector 770 is arranged in an airflow path around the heating element 716 and configured to open the airflow path around the heating element 716 when air is drawn from the mattress. The opened airflow path around the heating element 716 can facilitate the airflow into the air controller 700 by routing all or a majority of air around the heating element 716 and reducing or eliminating the air passing through the heating element 716. In contrast, when the air controller 700 is operated to supply heated air to the mattress, the air deflector 770 is configured to prevent airflow around the heating element 716 so that air can flow through the heating element 716 and becomes heated before being discharged from the air controller 700.

In some implementations, the air deflectors 770 can be at least partially made with flexible materials so that it flexes open or closed depending on the direction of air. Alternatively or in addition, the air deflectors 770 can be hingedly coupled to a structure of the air controller 700 so that the air deflectors 770 hinges to open when air flows in one direction, and hinges back to close when air flows in the other direction. In some implementations, the air controller 700 can include a stopper 772 that is configured to engage a portion (e.g., a free end) of the air deflector 770 to close the air path and prevent airflow along the air path.

Example System with Air and Foot Warming
(Feature Group #1)

Referring to FIGS. 27-30, an example foot warming system is described which can be used for a mattress, such as the mattress 104 or the mattress system 200, 300, 500, 600. The foot warming system can be used together with an airflow layer in a mattress, such as the airflow layer 230, 330, 530 described herein. For example, the foot warming system can be disposed in the mattress to provide heating in a foot area of the mattress, and the airflow layer can be disposed in the mattress to provide cooling or heating in a predetermined area (e.g., a middle area and/or a head area) of the mattress. Separate control systems can be provided for the foot warming system and the airflow layer for independent operations. Alternatively, a single control system is connected to the foot warming system and the airflow layer while it can independently control the foot warming system and the airflow layer. In some implementations, the operations of the foot warming system and the airflow layer can be coordinated to provide a desired effect to a user resting on the mattress.

Figure 27:
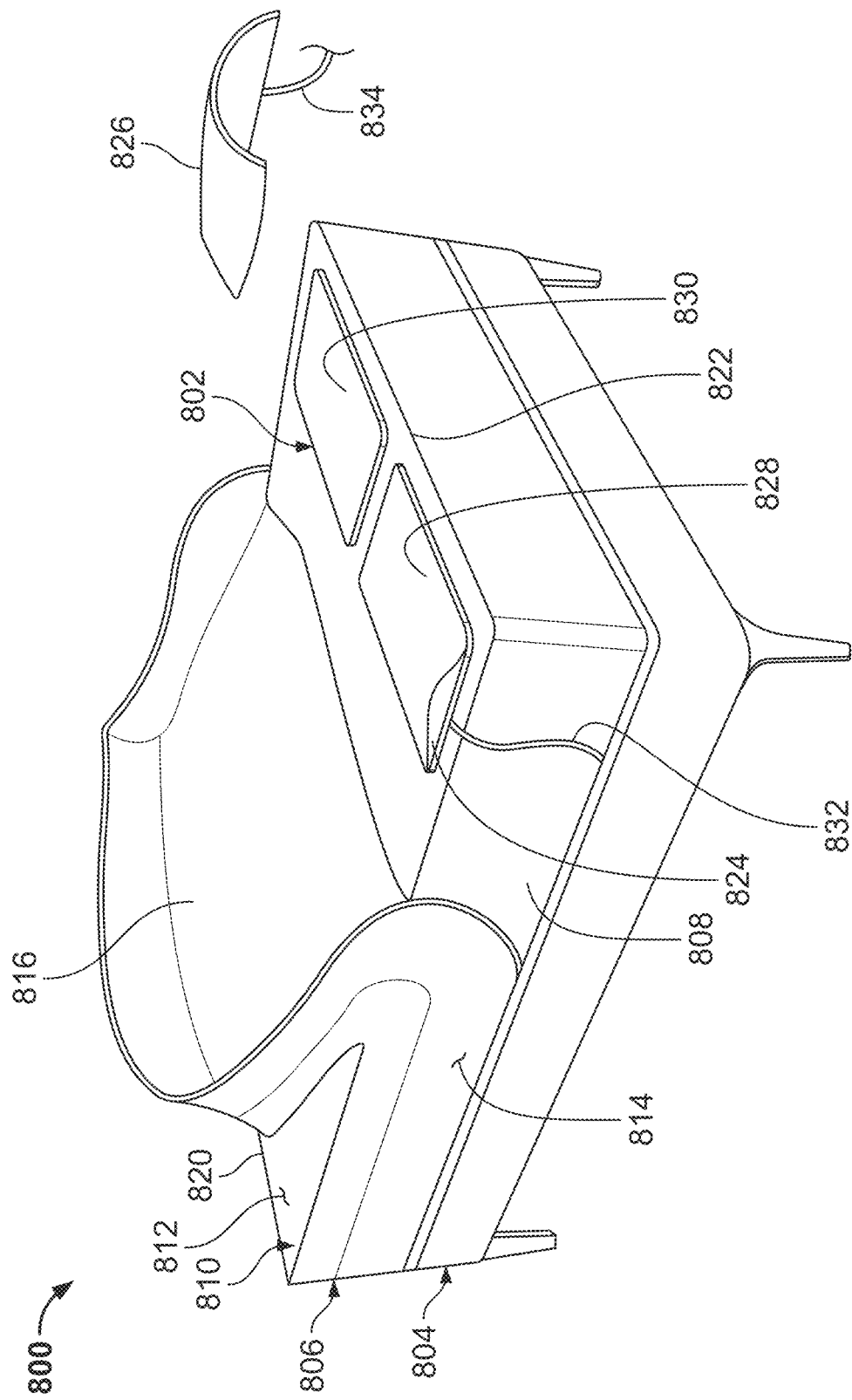
FIG. 27 is a perspective view of an example bed having an example foot warming system.

FIG. 27 is a perspective view of an example bed 800 having a foot warming system 802. The bed 800 can have a foundation 804 and a mattress 806 supported by the foundation 804. In some embodiments, the bed 800 can be an air bed system such as the air bed system 100 shown in FIG. 1 and having one, more than one, or all of the features described above with respect to FIGS. 1-26. In other embodiments, the bed 800 can be another type of bed suitable for the application, such as a bed having foam and/or springs without inflatable air chambers. In some embodiments, the foundation 804 can be an articulable foundation. In other embodiments, the foundation 804 need not be articulable. In some embodiments, the bed 800 need not include any foundation at all.

In the embodiment shown in FIG. 27, the mattress 806 includes a support structure 808 and a cover 810 configured to cover the support structure 808. The cover 810 has a top portion 812 positioned on a top of the support structure 808, side portions 814 extending around the outside of the support structure 808, and a bottom portion (not shown) so as to substantially enclose the support structure 808. The support structure 808 is configured to support a user sleeping or otherwise resting on the mattress 806, and can include foam, springs, inflatable air chambers, and/or one or more other suitable mattress components. The cover 810 can also include an additional padding layer 816 at the top portion 812, such as a pillow top layer, a ticking layer, and/or other material suitable for the application.

The mattress 806 can include a head 820 and a foot 822. The foot warming system 802 can be positioned at or near the foot 822 of the mattress 806 in a location configured for warming feet of a user laying on the mattress 806. As shown in FIG. 21, the foot warming system 802 can include one or more heating units 824 and 826, envelopes 828 and 830, electrical connectors 832 and 834 (such as one or more cables or wires), and one or more power sources (shown in FIG. 27). In some embodiments, the power source can be a pump controller (such as air chamber controller 1300 shown in FIGS. 1 and 2) or an articulation controller (such as for controlling articulation of an adjustable base). In other embodiments, the power source can be another controller or power source suitable for the application.

The heating units 824 and 826 can be positioned inside the mattress 806. In some embodiments, the heating units 824 and 826 can comprise an electrically conductive fabric, such as a carbon-filled polymer material, for generating heat. In other embodiments, the heating units 824 and 826 can comprise another electrical assembly suitable for the application, such as resistance wiring and fabrics. The heating units 824 and 826 can be positioned inside the mattress cover 810 and on top of the support structure 808 so as to be between the support structure 808 and the mattress cover 810. The electrically conductive fabric can be relatively flexible and can heat relatively evenly, to provide a positive foot warming experience for the user with little to no adverse impact on the softness and overall comfort of the mattress 806.

In some embodiments, the heating units 824 and 826 can be attached to the support structure 808. For example, FIG. 27 shows the heating unit 824 attached to the support structure 808 via the envelope 828. The heating unit 824 can be positioned inside the envelope 828, which can be affixed to a top of the support structure 808 via adhesive, thread, or another mechanism suitable for the application.

In the illustrated example, the heating unit 824 is removably attached to the support structure because it is removably inserted into the envelope 828. For example, the heating unit 826 is shown removed from its corresponding envelope 830. Accordingly, the envelopes 828 and 830 allow for the heating units 824 and 826 to be held in place with respect to the mattress 806 while also being removable for repair or replacement.

In some embodiments, the envelopes 828 and 830 can be omitted. For example, in some embodiments the heating units 824 and 826 can be affixed to the support structure 808 without the envelopes 828 and 830. In other embodiments, the heating units 824 and 826 can be attached to the cover 810, the fire resistant cap 836 (FIGS. 28-29), or other layer inside the mattress 806. Such attachments can be via adhesive, stitching, or other fastening mechanism suitable for the application.

While FIG. 27 shows the mattress 806 with the cover 810 partially removed to show internal components, the cover 810 would be closed during normal operation of the mattress 806, substantially concealing the foot warming system 802.

The power source can be electrically connected to the heating units 824 and 826 so as to selectively drive (or power) the heating units 824 and 826 to heat the mattress 806 at or near the foot 822 of the mattress 806. This can warm the mattress 806 at a user's feet, for example, to improve comfort and/or help induce sleep more rapidly.

In some implementations, the envelopes 838 can be embedded into the mattress. For example, the envelopes 838 can be positioned inside a foam layer of the mattress (e.g., a top layer similar to the top layer 902), and the wires from the envelopes 838 can be routed through, and extend out from, the foam layer (e.g., the side of the foam layer). With this configuration, the mattress can provide or maintain comfort from the foam layer, as opposed to another embodiment where the embedded envelopes 838 are exposed on the top of the mattress (or the top of the foam layer).

FIG. 28 is a schematic end view of the mattress 806 and the foot warming system 802. FIG. 29 is a schematic side view of the mattress 806 and the foot warming system 802. As shown in FIGS. 22 and 23, the mattress 806 can include a fire resistant cap 836 positioned inside the cover 810. The fire resistant cap 836 can cover internal components of the mattress, including the support structure 808 and components of the foot warming system 802 (including the envelopes 828 and 830 and the heating units 824 positioned therein.). In some embodiments, the fire resistant cap 836 can include a 4 ounce jersey knit material. In other embodiments, the fire resistant cap 836 can include one or more other materials suitable for the application. In still other embodiments, the fire resistant cap 836 can be omitted.

Referring to FIG. 28, an embodiment of the support structure 808 can include a foam 838 and air chambers 840 and 842. In the embodiment shown, the foam 838 is an upside-down foam tub covering the air chambers 840 and 842. The air chambers 840 and 842 are adjustably inflatable air chambers each sized for supporting first and second users respectively, and can be the same as or similar to the air chambers 222 (FIG. 3) described above. The envelopes 828 and 830 can be adhered or otherwise attached to the foam 838, with the heating units 824 and 826 positioned inside.

Referring to FIGS. 28 and 29, an example embodiment of positioning of the electrical connectors 832 and 834 is illustrated. As shown in FIGS. 22A-B, the electrical connectors 832 and 834 include wires extending along the sides of the mattress 806, partially through the foam 838. The foam 838 can define pathways allowing the electrical connectors 832 to be routed through. In one embodiment, the electrical connector 832 can be routed through a slit cut in the foam 838. In another embodiment, the electrical connector 832 can be routed through a hole bored through the foam 838. The electrical connectors 832 and 834 can terminate at connector ends 844 and 846, which can connect to one or more power sources (not shown in FIGS. 22 and 23) for powering the heating units 824 and 826.

Referring to FIG. 29, the connector 834 (from a side view) can extend from the envelope 830 (with the heating unit 826 positioned inside) near the foot 822 of the mattress 806 to the connector end 846 positioned near a longitudinal center of the mattress 806. By positioning the connector end 846 near the longitudinal center of the mattress 806, the mattress 806 can be used with adjustable foundations to raise and lower the head 820 and foot 822 of the mattress 806 while allowing the connector end 846 to remain relatively stationary during articulation. This can allow the heating units 824 and 826 to be raised and lowered with the mattress 806 while being connected to and powered by a power source that is relatively stationary during articulation.

Figure 30:
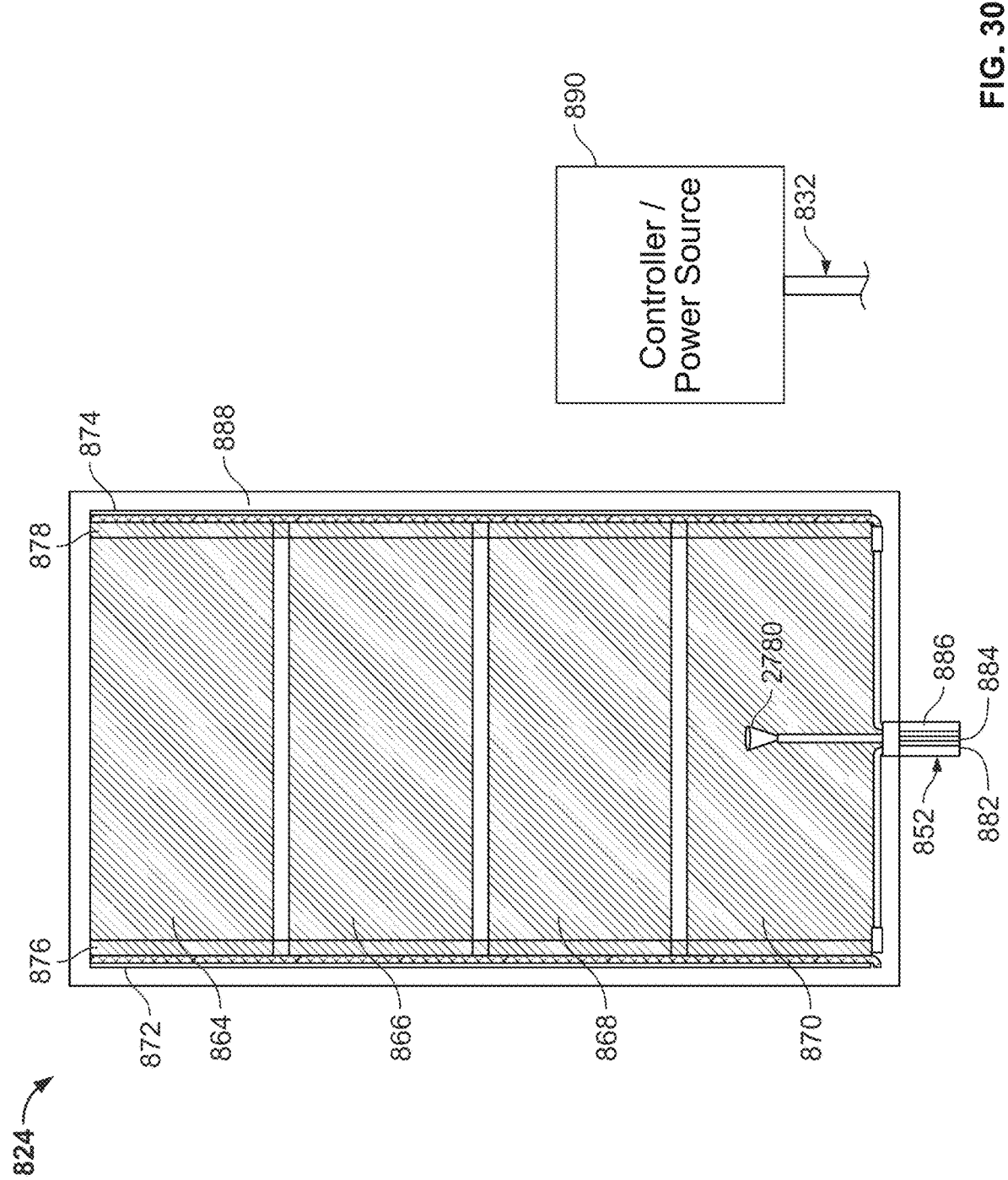
FIG. 30 is a top view of components of the foot warming system.

FIG. 30 is a top view of components of the foot warming system 802. In the embodiment shown in FIG. 30, the heating unit 824 includes electrically conductive fabric heating elements (heating elements 864, 866, 868, and 870), bus bars 872 and 874, reinforcing tape 876 and 878, temperature sensor 880, wires 882, 884, and 886, and bonding film 888. The connector 832 can be a wire harness that includes the wires 882, 884, and 886. The wire 882 electrically connects the bus bar 872 to a controller (power source) 890 and the wire 886 electrically connects the bus bar 874 to the controller 890. The wire 884 electrically connects the temperature sensor 880 to the controller 890, which can receive temperature signals from the temperature sensor 880 and power the heating unit 824 as a function of the received temperature signals. While only one wire 884 is shown connecting to the temperature sensor 880, multiple wires can be used. In some embodiments, the controller 890 can include or be part of the foot warming control system 116 (FIG. 1). Alternatively, the controller 890 can be included in a pump controller (such as the air chamber control system 114 shown in FIG. 1), an articulation controller (such as the bed articulation system 112 shown in FIG. 1), or an airflow layer control system (such as the airflow insert pad control system 118 shown in FIG. 1). In some of such embodiments, the controller 890 can perform none, some, or all of the functions described above with respect to those controllers. In other embodiments, the controller 890 can be another controller or power source suitable for the application. For example, the controller 890 can be a controller dedicated to operating the foot warming system 802 alone, or operating the foot warming system 802 in conjunction with one or more other systems.

In some embodiments, multiple electrically conductive fabric heating elements can extend from bus bar 872 to bus bar 874. In the illustrated embodiment, four separate fabric heating elements (the heating elements 864, 866, 868, and 870) are included. Gaps are shown spacing adjacent ones of the heating elements 864, 866, 868, and 870. In some embodiments, gaps between adjacent ones of the heating elements 864, 866, 868, and 870 can be about 0.5 inch. In some embodiments, gaps between adjacent ones of the heating elements 864, 866, 868, and 870 can be between 0.2 inch and 0.8 inch. In other embodiment, more or fewer heating elements can be used.

In some embodiments, the heating elements 864, 866, 868, and 870 can comprise carbon-based electrically conductive fabric, which can conduct electricity between the bus bars 872 and 874 and which has a suitable resistance to generate heat. The heating elements 864, 866, 868, and 870 can operate at relatively low power and heat relatively uniformly, thus warming a mattress with reduced risk of fire. For example, in some embodiments the power for the heating unit 824 can be about 0.085-0.095 W/inch$^2$.

In some embodiments, the bus bars 872 and 874 can be tinned copper bus wires having a relatively thin diameter so as to allow for repeated bending when the mattress is in use. In some of such embodiments, the bus bars 872 and 874 can comprise wire braids. In other embodiments, the bus bars 872 and 874 can comprise conductive ink. In other embodiments, the bus bars 872 and 874 can have a different configuration as suitable for the application.

The temperature sensor 880 can sense temperature at and around the heating unit 824, to provide feedback to the controller 890 for powering the heating unit 824. In some embodiments, the temperature sensor 880 can be placed proximate the heating element 870. In some of such embodiments, the temperature sensor 880 can be proximate to but slightly spaced from the heating element 870 via a layer of material, such as a layer of polyimide film. In various embodiments, the temperature sensor 880 can be a thermistor, a thermocouple, or another suitable temperature sensor.

The reinforcing tape 876 and 878 can be placed along edges of the heating elements 864, 866, 868, and 870 and the bus bars 872 and 874 to reinforce the heating unit 824. The bonding film 888 can include top and bottom layers of film that enclose the heating elements 864, 866, 868, and 870, the bus bars 872 and 874, the reinforcing tape 876 and 878, the temperature sensor 880, and part of the wires 882, 884, and 886. The bonding film 888 can protect components contained therein from moisture and tampering. In some examples, the bonding film 888 can be polyurethane or another polymer material suitable to encase the flexible heating elements 864, 866, 868, and 870.

The heating unit 824 can be a relatively thin layer sized and configured for being positioned inside a mattress for warming feet of a user of the mattress. In some embodiments, the heating unit 824 can be sized and positioned for heating only a limited portion of the mattress including the feet of the user but not the head and torso of the user. In some embodiments, the heating unit 824 can have a width of between 21 inches and 31 inches and a depth of between 10 inches and 20 inches. In some embodiments, the heating unit 824 can have a width of between 25 inches and 28 inches and a depth of between 14 inches and 18 inches. In other embodiments, the size and position of the heating unit 824 can be varied as suitable for the application.

In operation, the controller 890 can selectively power the heating unit 824 (and/or the heating unit 826) to generate heat and warm the mattress 806. The foot warming system 802 can be controlled automatically, via inputs from a user interface (such as a mobile device or other remote control), or both. Automatic control can be performed as a function of a number of sensed events, such as the user entering or leaving the bed and/or the user falling asleep or waking.

The controller 890 can have intelligence to allow for benefits such as pre-heating, timed shut off, temperature regulation via the temperature sensor 880, or other features that may enhance the user experience. For example, the foot warming system 802 can be controlled as a function of when the user goes to sleep. In one example, the user can identify an earliest time that they go to sleep. The controller 890 can then drive the heating unit 824 to warm for a predetermined time prior to this sleep time (e.g., 30 minutes) so that the mattress 806 is warm when the user enters the mattress 806. In another example, the foot warming system 802 may be turned on via an instruction from the user through a user interface indicating the intent of user going to bed. Upon the user entering the mattress 806, the foot warming system 802 can shut off automatically based on sensing the user entered in the mattress 806, or can continue to run for a given amount of time. In another example, the foot warming system 802 can run until the user falls asleep as determined by one or more sensors.

During the operation, the warming system 802 can maintain a constant temperature level or adjust to a preset level in response to one or more timed or sensed events. The foot warming system 802 can operate at different power levels as appropriate for the situation. For example, the foot warming system 802 can operate a high power level in order to initially heat the mattress 806 quickly, and then to operate at a lower power to maintain a target temperature, such as operating via pulse wave modulation.

In another example, the controller 890 can determine an expected bed time for a user of the bed. This determination can be made as a function of user inputs regarding bed time. Alternatively, this determination can be made automatically by the controller 890 as a function of a learned sleep schedule that is based on sensed data of the user historically entering bed night after night. Based on this information, the controller 890 can drive the foot warming system 802 to heat the foot of the mattress 806 to reach a target temperature prior to the expected bed time.

In some of such applications, the controller 890 can reduce power upon a sensor detecting the user enters the mattress 806. For example, the controller 890 can cut power immediately such that the foot warming system 802 only warms before the user enters the bed. Alternatively, the controller 890 could slowly reduce power or reduce power after a given time period after the user enters the mattress 806.

In another example, the controller 890 can determine whether the user is asleep as a function of sensed data and then drive the foot warming system 802 as a function of whether the user is determined to be asleep. For example, the foot warming system 802 can be driven until the user falls asleep and shut off in response to determining that the user is asleep based on sensed data.

In another example, the controller 890 can drive the foot warming system 802 automatically in order to improve sleep quality. For example, the controller 890 can access historical sleep metrics that represent sleep quality of a user while the user was sleeping in the bed and/or access historical sensor data that represent sensor readings that measure environmental conditions affecting the user while the user was sleeping in the bed, such as sensed temperature. The controller 890 can identify in the historical sleep metrics incidences of low quality sleep experienced by the user and incidences of high quality sleep by the user and then generate a corrective plan that specifies a change to the foot warming system to improve sleep quality based on historical sleep metric incidences associated with high quality sleep. The controller 890 can then drive the foot warming system 802 according to the generated corrective plan. The corrective plan can be based on the user's own sleep data and/or aggregate sleep data from other individuals.

In another example the controller 890 can achieve a desired temperature as a function of sensed temperature, as sensed by the temperature sensor 880. The controller 890 can drive the heating unit 824 as a function of a difference between the sensed temperature and a target temperature such that the controller 890 supplies more power to the electrically conductive fabric in response to determining a relatively large difference between the sensed temperature and the target temperature and the controller 890 supplies less power to the heating unit 824 in response to determining a relatively small difference between the sensed temperature and the target temperature.

In various embodiments, the foot warming system 802 can be operated to improve user comfort and/or to induce rapid sleep onset. By warming the user's feet upon entering the bed, some users have been shown to fall asleep more quickly, thus improving sleep quality. The foot warming system 802 can be integrated into a mattress at a location suitable for a particular user with little or no negative impact on the comfort of the mattress. The foot warming system 802 can actively monitor microclimate to maintain appropriate temperature. The foot warming system 802 can be automatically controlled via sensed data, reducing or removing the need for user inputs. Various embodiments described herein can achieve one or more of these benefits, among others.

The bed 800 can combine the foot warming system 802 with one or more other features described herein. For example, the bed 800 can include the foot warming system 802 in the mattress system 200 (described above with respect to FIGS. 1-10), including some or all of the features described with respect to the mattress system 200 such as the airflow pad assemblies 232 and the airflow insert pad control system 118. Accordingly, the bed 800 can supply or draw heated, cooled, and/or ambient air using the airflow insert pad control system 118 and can separately warm feet using the foot warming system 802. In some embodiments, including both air and foot warming in the bed 800 can achieve many of the benefits described herein and can do so efficiently and effectively compared to using just air or just foot warming.

In some embodiments the bed 800 can be configured to heat via the foot warming system 802 and can cool via the airflow insert pad control system 118. In one example, the airflow insert pad control system 118 can be configured to draw air from the user (or supply ambient air to the user) in order to cool the user when appropriate. Consequently, the airflow insert pad control system 118 need not include a heating or cooling device and can use lower energy as a result. When desired, heat can be provided via the foot warming system 802. For example, heat can be provided via the foot warming system 802 prior to the user entering the bed 800 in order to help induce rapid sleep onset and then turned off when no longer required. Later, cooling can be provided via the airflow insert pad control system 118 while the user is sleeping to avoid (or to remedy) excess heat buildup. Alternatively, the foot warming system 802 can be used at the same time that the airflow insert pad control system 118 is used to draw air, which can have the effect of drawing air from the foot warming system 802 over and across the user's body to heat the user's body without requiring any heating unit to be added to the airflow insert pad control system 118. In further alternative, the foot warming system 802 can be used at the same time that the airflow insert pad control system 118 is used to supply air, which can have the effect of simultaneously heating the user's feet while cooling the user's core.

In some implementations, the heating elements 864, 866, 868, and 870 can include resistive wire elements, alternatively to or in addition to the conductive materials described herein. In some implementations, the heating unit 824 can include thermostats integrated therewith.

Mattress Surface Treatment (Feature Group #12)

Figure 31:
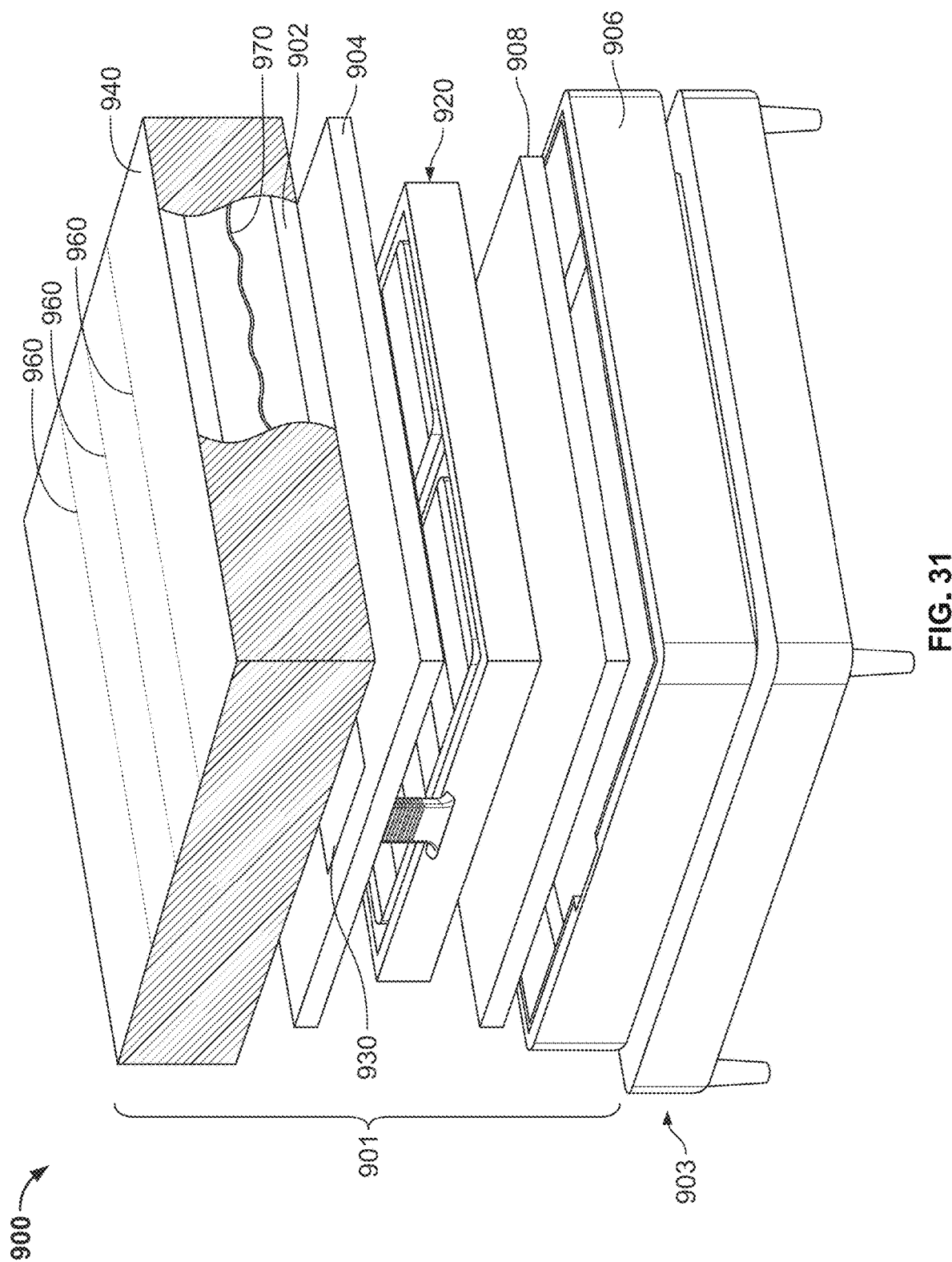
FIG. 31 illustrates example mattress surface treatments for improving climate control of a mattress top surface.

FIG. 31 illustrates example mattress surface treatments for improving climate control of a mattress top surface. In this example, an example bed 900 includes a mattress 901 and a foundation 903, which can be configured to be identical or similar to the mattresses and the foundations described herein, for example with reference to FIGS. 1-30. In general, the mattress 901 can be configured as a climate-controlled mattress, and include a mattress core, an air distribution layer, an air hose, an air controller, and a mattress cover. The mattress core is configured to support a user resting on the mattress. The air distribution layer is configured to facilitate air flow for climate control of a top surface of the mattress. The air hose is configured to route ambient or conditioned air into and from the air distribution layer. The air controller is fluidly connected to the air distribution layer via the air hose, and operates to cause ambient or conditioned air to flow into or from the air distribution layer. The mattress cover is used to enclose the mattress core, the air distribution layer, and at least part of the air hose.

The mattress can further include one or more mattress surface treatment mechanisms for improving effects of climate control of the mattress. In some implementations, the mattress includes stitching with relatively high heat capacity that is provided on the mattress cover. For example, the mattress cover is at least partially made of fabric with thread having a first heat capacity that is relatively low, and further includes stitching on the top surface of the mattress. The stitching can be made of a material having a second heat capacity that is relatively high compared to the first heat capacity, so that the stitching can better resist temperature change on the mattress top. For example, the stitching can help better preserve energy of cooling air or ambient air (cooler than a body temperature), and resist being warmed by a user's body temperature when the user rests on the mattress top. The stitching material can be of various types. Examples of the stitching materials include polypropylene threads, nylon threads, etc. In addition, a foam layer can be positioned below the mattress cover. The foam layer can be made of a material having a heat capacity that is less than the heat capacity of the stitching material.

Another example of the mattress surface treatment mechanisms includes a gel layer. The gel layer can be positioned proximate the mattress top surface. For example, the gel layer is positioned under the mattress cover. Alternatively, the gel layer can be configured as part of the mattress cover. The gel layer can have a heat capacity that is substantially higher than a heat capacity of the air distribution layer. In some implementations, the gel layer can be selected such that a ratio of the heat capacity of the gel layer over the heat capacity of one of the other layers or mattress components (e.g., the top layer 902, the intermediate layer 904, the rail structure 906, the bottom layer 908, the air chamber assembly 920, and the airflow layer 930) can be greater than about 1.05, about 1.50, about 2.00, or about 5.00. Therefore, the gel layer can better resist temperature change on the mattress top surface. For example, the gel layer can help better preserve energy of cooling air or ambient air (cooler than a body temperature), and resist being warmed by a user's body temperature when the user rests on the mattress top. In addition, a foam layer can be positioned above the air distribution layer and under the gel layer. The foam layer can have a heat capacity that is less than the heat capacity of the gel layer.

Referring to FIG. 31, the mattress 901 can include a top layer 902, an intermediate layer 904, a rail structure 906, a bottom layer 908, an air chamber assembly 920, and an airflow layer 930, which can be configured to be identical or similar to the top layer, the intermediate layer, the rail structure, the bottom layer, the air chamber assembly, and the airflow layer, respectively, described above. Further, the mattress 901 includes a mattress cover 940 having a top surface, a bottom surface, and side surfaces, which are configured to at least partially cover the top layer 902, the intermediate layer 904, the rail structure 906, the bottom layer 908, the air chamber assembly 920, and the airflow layer 930.

The mattress cover 940 can include stitching 960. The stitching 960 has relatively high heat capacity. For example, the mattress cover 940 is at least partially made of fabric with thread having a heat capacity that is lower than a heat capacity of the stitching 960. The stitching 960 can be made of various types of stitching materials. Examples of the stitching materials include polypropylene threads, nylon threads, etc. In addition, the top layer 902 that is positioned under the mattress cover 940 can be made of a foam material having a heat capacity that is less than the heat capacity of the stitching 960. The stitching 960 can be arranged in various patterns on the mattress cover 940. For example, the stitching 980 can be routed on or around the mattress in various sizes (e.g., widths, heights, etc.) and/or lengths. In addition, the stitching 980 can have different colors.

In addition or alternatively, the mattress 901 can include a gel layer 970. The gel layer 970 can be positioned under the mattress cover 940. In addition, the gel layer 970 can be arranged above the top layer 902, the intermediate layer 904, and the airflow layer 930. For example, the gel layer 970 can be positioned on the top of a top foam layer (e.g., the top layer 902). In some implementations, the gel layer 970 can be configured as part of the mattress cover 940. The gel layer 970 can have a heat capacity that is higher than heat capacities of the top layer 902, the intermediate layer 904, and/or the airflow layer 930. The gel layer 970 can be made of various types of gel materials.

Figure 61:
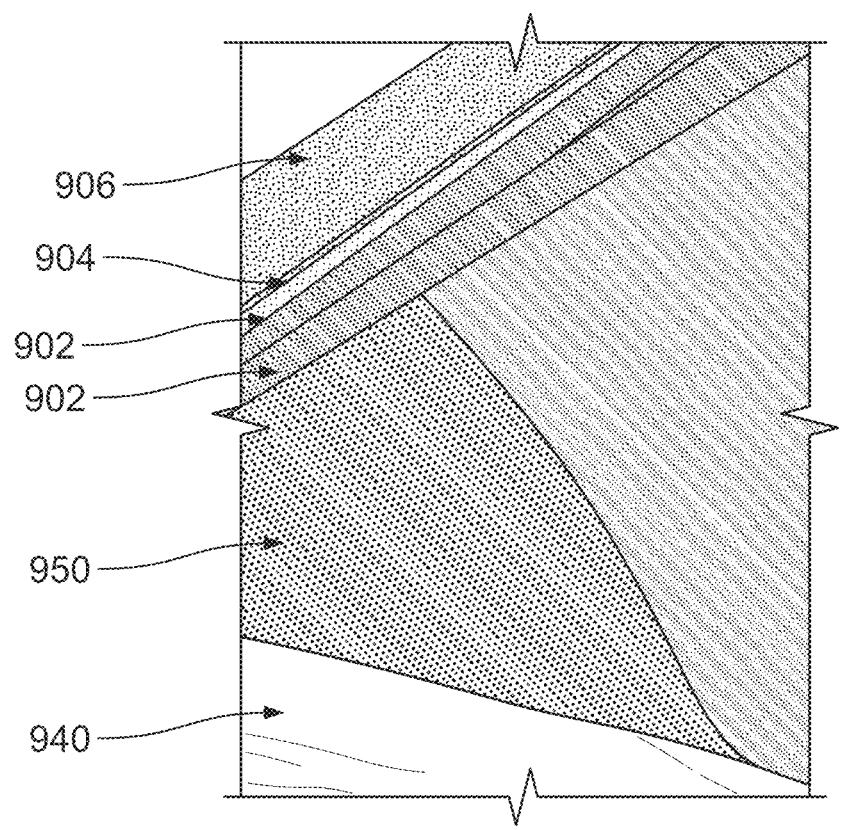
FIG. 61 illustrates an example mattress layer that is treated with a gel material.

Alternatively or in addition, the top layer 902 (e.g., made of foam materials) can be surface-treated with one or more gel materials that have different heat capacities than the top layer 902. For example, the heat capacity of the gel material incorporated in the top layer 902 can have a higher heat capacity than the top layer 902 to provide prolonged warmth or coolness through the mattress when the bed is in a heated air supply mode or a cooled air supply mode, and also facilitate heat absorption from the user's body on the mattress or the surroundings around the mattress when the bed is in a cooling mode in which ambient air is suctioned from the top of the mattress. In some implementations, one or more gel materials can be incorporated into the top layer 902 by surface-infusion. For example, as illustrated in FIG. 61 (in which the top layer 902 is folded to partially show the top surface of the top layer 902), a portion 950 of the top layer 902 can be surface-treated with a gel material to provide a higher heat capacity than the other portion of the top layer 902. The portion 950 being surface-treated can be a portion of the top layer 902 that is arranged to correspond with the airflow layer 930 under the top layer 902.

For example, the top layer 902 (e.g., the portion 950 thereof) can be treated with a water-based surface infusion so that the top layer 902 includes a water-based surface coating with a high content of phase-change material. Various coatings can be used. An example of such coating is AquaCool™, available from Peterson Chemical Technology. In some implementations, the coating can be applied to the top layer 902 and configured to create a breathable, flexible, and durable coating with adhesion for various applications such as mattress layers, toppers, and other comfort products. In addition, the coating is configured to promote heat flow for cooling or maintaining temperature for comfort. The coating can be configured to provide various coating thicknesses, and easy to cure with water or other liquid. Further, the coating can be applied to the top layer by roll coating or spraying. The coating is configured to provide breathable layer of cool, flexible phase-change coating to the top layer to help maintaining air flow and moisture transmission. Further, the coating can function as a medium for lateral heat transfer. The coating is configured to enhance cooling without excessive weight, and improve heat capacity, conductivity, and thermal effusivity. The coating can be augmented with additives for added conductivity to help regenerate a phase change material (PCM) or for antimicrobial effects. Examples of such conductive additives include LumaCool™, Black Diamond, ceramic, titanium, copper, etc. Examples of antimicrobial performance additives include copper, silver, etc.

In addition or alternatively, other layers and components in the mattress, such as the intermediate layer 904, the rail structure 906, the bottom layer 908, the air chamber assembly 920, and the airflow layer 930, can be treated to incorporate one or more gel materials in the same or similar manner as the top layer 902 as described above.

Airflow Mattress with Water Resistant Layer (Feature Group #14)

Figure 32:
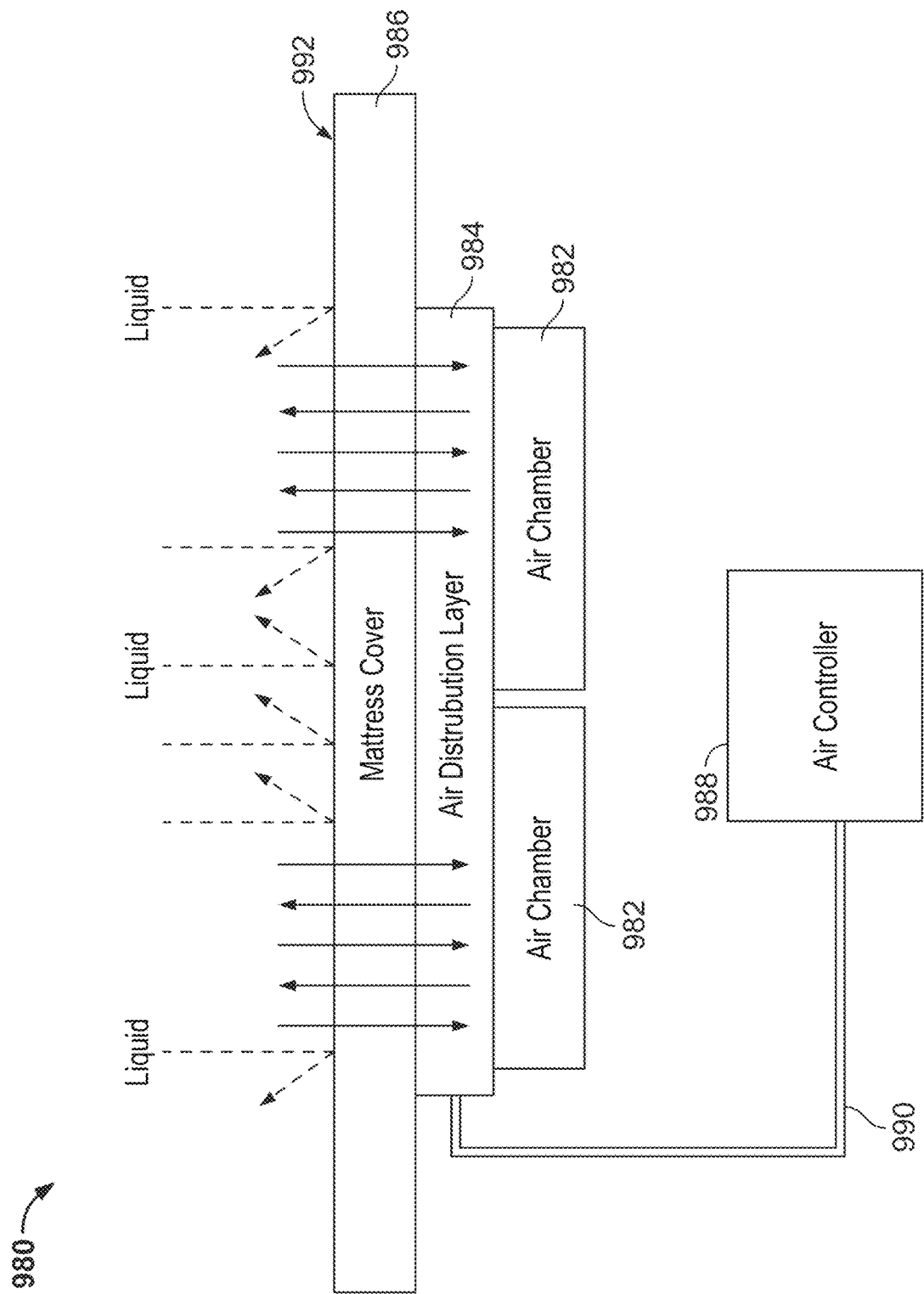
FIG. 32 schematically illustrates an example water resistant layer that can be used with a mattress.

FIG. 32 schematically illustrates an example water resistant layer that can be used with the mattresses described herein, for example with reference to FIGS. 1-31. In general, a mattress with a water resistant layer includes a mattress core, an air distribution layer, an air hose, and a mattress cover. The mattress core is configured to support a user and can be of various types, such as one or more inflatable air chambers, foams, and/or spring assemblies. The air distribution layer is positioned above the mattress core, and configured to facilitate air flow for climate control of a mattress top surface. The air hose is connected to the air distribution layer and configured to route ambient or conditioned air between the air distribution layer and an air controller. The mattress cover has a mattress cover top surface, at least a portion of which is made of a fabric configured to allow flow of air between the air distribution layer and a space above the mattress top and to resist flow of liquid water into the mattress when the liquid water is positioned on top of the mattress cover top surface. In some implementations, the fabric of the mattress cover can substantially prevent flow of liquid water into the mattress at atmospheric pressure.

Referring to FIG. 32, a mattress 980 can include a set of inflatable air chambers 982 (or other mattress core) and an air distribution layer 984 positioned above the air chambers 982. The air distribution layer 984 is fluidly connected to an air controller 988 via an air duct 990. The air controller 988 is configured to cause ambient or conditioned air to flow into or from the air distribution layer 984. The mattress 980 can further include a mattress cover 986 that at least partially covers the air chambers 982, the air distribution layer 984, and other components of the mattress 980. The mattress cover 986 has a top surface 992 made of a fabric that allows airflow therethrough while resisting liquid flow into the mattress when the liquid is positioned on the mattress top surface.

Alternatively or in addition to the mattress cover 986, the mattress 980 can include a mattress protector that is separate from the mattress cover 986 and configured to allow airflow therethrough and resist liquid flow into the mattress when the liquid is positioned on the top of the mattress protector.

Overview of Bed Control

Figure 33:
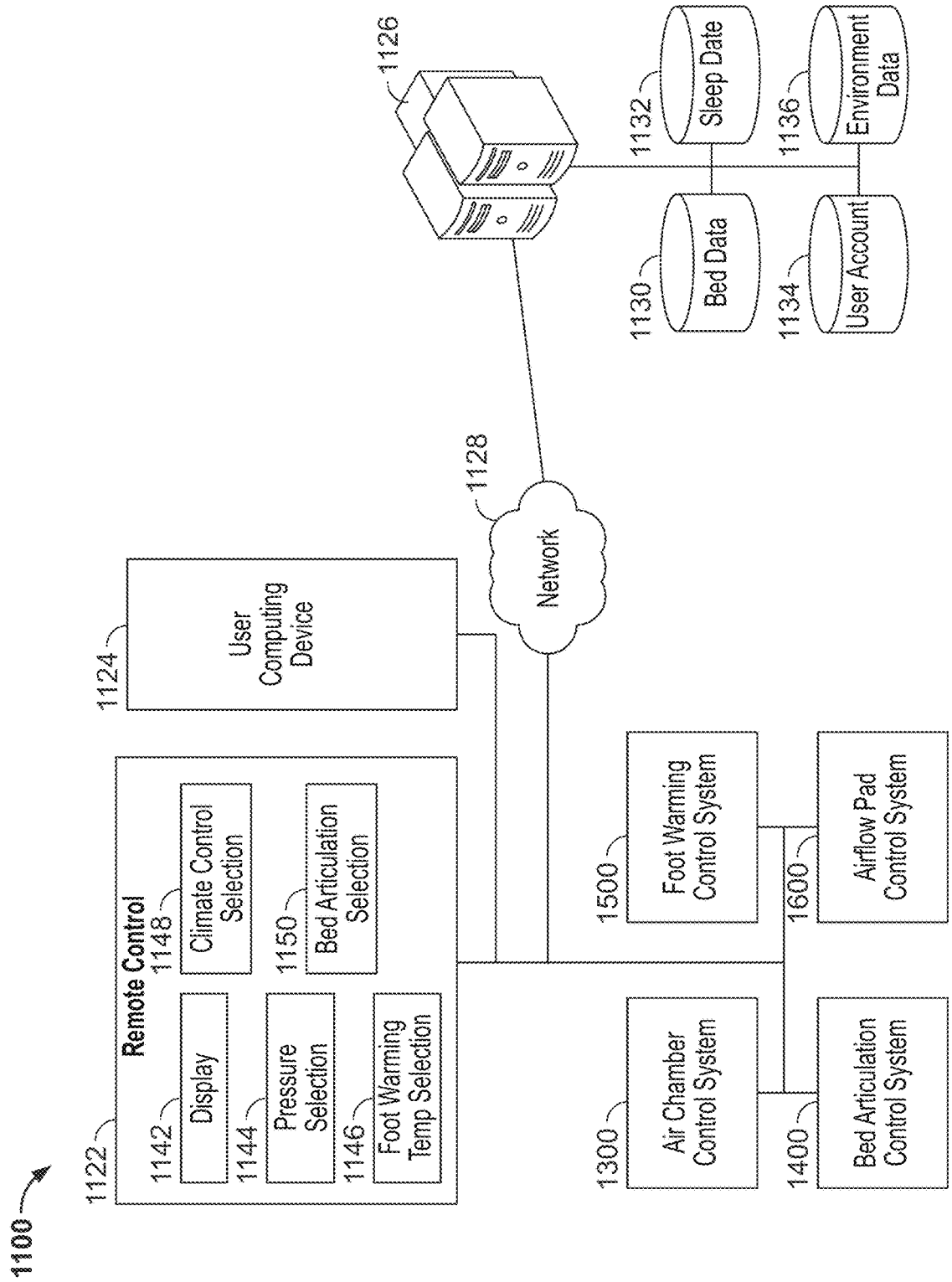
FIG. 33 is a block diagram of an example of various components of a bed system.

FIG. 33 is a block diagram of an example of various components of a bed system. For example, these components can be used in the example bed system 1100. The bed system 1100 can be used to implement the beds described herein, for example with reference to FIGS. 1-32. The bed system 1100 can include multiple components to provide various functionalities of the bed system 1100. For example, the bed system 1100 includes an air chamber control system 1300, a bed articulation control system 1400, a foot warming control system 1500, and an airflow pad control system 1600. The bed system 1100 can include a server system 1126 that can communicate with at least one of the systems 1300, 1400, 1500, 1600 via a network 1128. The bed system 1100 can further include a remote control 1122 and a user computing device 1124 that are configured to enable a user to interact with the bed system 1100. The remote control 1122 and/or the user computing device 1124 can communicate with the server system 1126 with the network 1128.

The air chamber control system 1300 can control one or more air chambers included in a mattress and configured to provide desired firmness of the mattress for the user. The bed articulation control system 1400 can control the position of an adjustable foundation of the bed system 1100. The foot warming control system 1500 can control one or more foot heating elements included in the mattress to provide desired temperature at the foot of the mattress. The airflow pad control system 1600 can control airflow through airflow pads included in the mattress to provide desired temperature and/or humidity at the top of the mattress. The systems 1300, 1400, 1500, 1600 are described in more detail with reference to FIGS. 34-37.

The user of the bed system 1100 can use one or more input devices, such as the remote control 1122 and the user computing device 1124, to input a desired mode of operation, a desired temperature setting, a desired humidity setting, a desired bed position setting, and other suitable settings, in the bed system 1100. For example, the remote control 1122 can be used to implement the bed-side controller 132 as shown in FIG. 1.

The remote control 1122 can include a display 1142, a pressure selection input device 1144, a foot temperature selection input device 1146, a climate control selection input device 1148, and a bed articulation input device 1150. The pressure selection input device 1144 is configured to allow a user to increase or decrease the pressure in the air chamber of the air chamber control system 1300. Adjusting the pressure within the air chamber can cause a corresponding adjustment to the firmness of the respective air chamber. The foot temperature selection input device 1146 is configured to allow a user to increase or decrease the temperature of the heating unit of the foot warming control system 1500. The climate control selection input device 1148 is configured to enable a user to select one or more mode of operation for the airflow layer (e.g., airflow pad), and/or adjust the temperature of the airflow layer, in the airflow pad control system 1600. The bed articulation input device 1150 is configured to enable a user to adjust the bed position (inclined, reclined, etc.) in the bed articulation control system 1400. The input devices of the remote control 1122 can be of various types, such as mechanical and/or virtual buttons, switches, etc. In some implementations, the bed system 1100 includes a plurality of remote controls 1122 for separately controlling different sections of the bed (e.g., left and right sides of the bed). In other implementations, a single remote control 1122 is configured to permit for a user to control different sections of the bed. The remote control 1122 can be a dedicated wireless remote control, a dedicated wired remote control, a smart phone or other mobile device running a remote control application, or other remote control that is suitable to function for remotely controlling. The remote control 1122 can be omitted or modified as appropriate for an application. For example, in some embodiments the bed 1112 can be controlled by a computer, tablet, smart phone, or other device in wired or wireless communication with the bed 1112 in addition to or instead of using one or more remote controls 1122.

In some implementations, data can be transmitted from a component back to one or more processors (e.g., processors in the systems 1300, 1400, 1500, 1600) or to one or more display devices, such as the display 1142. For example, various pieces of information associated with the bed, such as the current foot warming temperature as determined by a sensor element of the temperature controller, the current airflow layer temperature as determined by a sensor element of the air controller, the pressure of the bed, sensed user biometrics, the current position of the foundation or other information, can be transmitted to respective controllers in the control systems 1300, 1400, 1500, 1600. Such controllers can then transmit the received information to remote control 1122 where it can be displayed to the user (e.g., on the display 1142).

Similarly, the user computing device 1124 can be used by a user of a bed and/or a user located remotely from the bed. Example user computing devices 1124 include, but are not limited to, mobile computing devices (e.g., mobile phones, tablet computers, laptops) and desktop computers. The user computing device 1124 includes one or more power supplies, processors, and computer readable memory. User input and output can be transmitted by one or more user interfaces such as speakers, a touchscreen, a pointing device or keyboard, and other suitable input and output devices. The user computing device 1124 can run one or more applications for allowing the user to interact with the bed system 1100. These applications can allow a user to view information about the bed (e.g., sensor readings, sleep metrics), or configure the behavior of the bed system 1100 (e.g., set a desired firmness to the bed, set a desired temperature of a foot warming unit, set a desired temperature or airflow mode of an airflow pad, set desired behavior for peripheral devices, etc.). In some cases, the user computing device 1124 can be used in addition to, or to replace, the remote control 1122 described previously. In some implementations, the user computing device 1124 can be used to implement the mobile computing device 134 as shown in FIG. 1.

The server 1126 can include one or more computing devices. The server 1126 can be used to implement the server system 140 as shown in FIG. 1. The server 1126 can be connected to the bed system 1100. For example, the server 1126 can be connected to at least one of the systems 1300, 1400, 1500, 1600 via the network 1128. The server 1126 can further communicate with the remote control 1122 and/or the user computing device 1124 via the network 1128 for permitting the user to interact with the components of the bed system 1100. The network 1128 can be similar to the network 142 of FIG. 1. The server 1126 can be connected to databases to provide various services. For example, the server 1126 is configured to access bed data 1130 for a bed data service, sleep data 1132 for a sleep data service, user account data 1134 for a user account service, and environment data 1136 for an environment service. The bed data 1130, the sleep data 1132, the user account data 1134, and the environment data 1136 can be similar to the bed data 150, the sleep data 152, the user account data 154, and the environment data 156 as shown in FIG. 1. The bed data service, the sleep data service, the user account service, and the environment service performed using the server 1126 can be similar to the bed data service, the sleep data service, the user account service, and the environment service as described with reference to FIG. 1.

Although the systems 1300, 1400, 1500, 1600 are illustrated herein as separate systems or units, it is understood that some or all of these systems can be combined and operated as a single unit. For example, one or more components and/or functions of the controllers in the systems 1300, 1400, 1500, 1600 can be integrated and configured as a single control box that are in communication with, and control, other components, such as the pump, the adjustable foundation, the foot heating elements, and the airflow pads.

Figure 34:
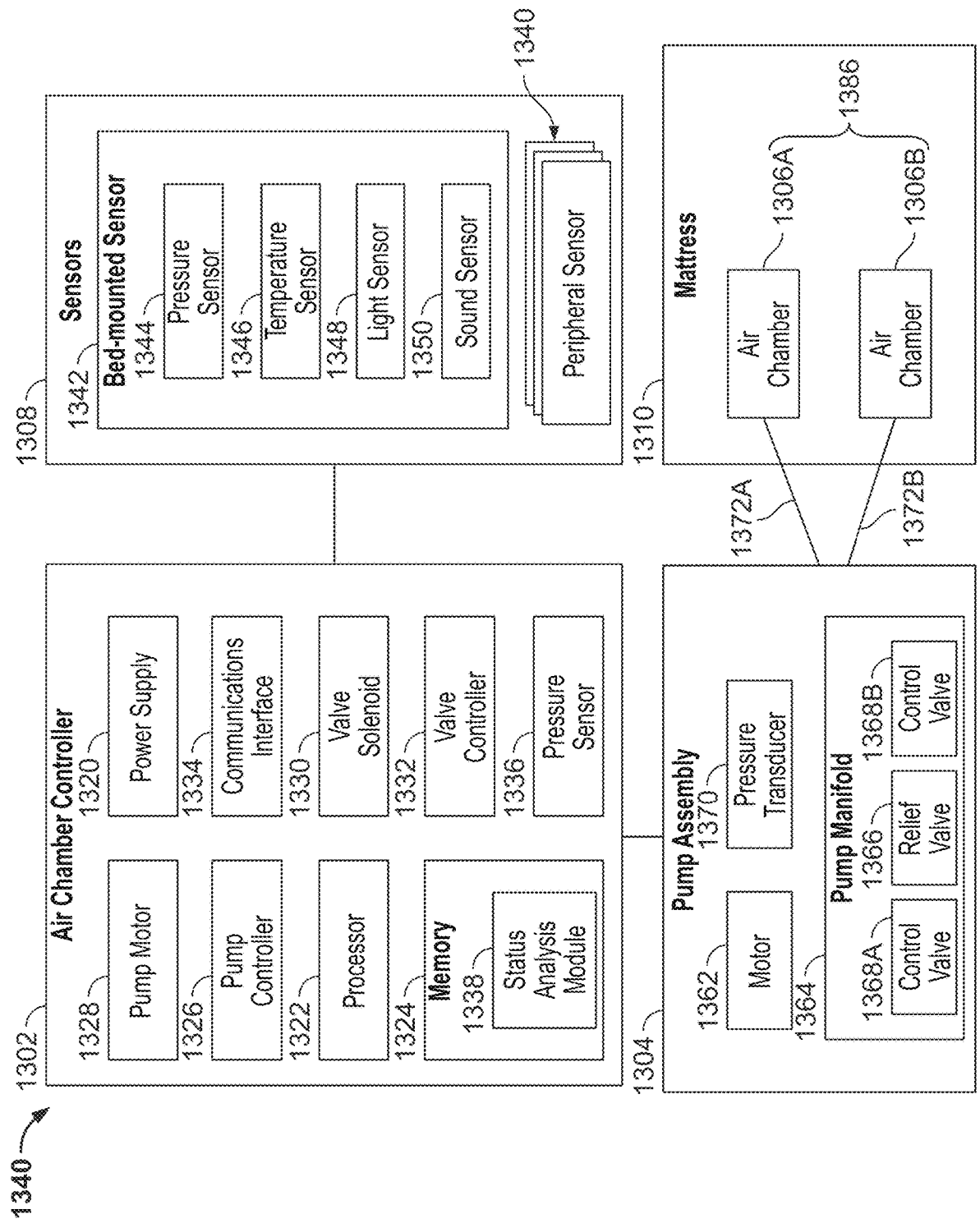
FIG. 34 is a block diagram of an example air chamber control system that can be associated with a bed system.

FIG. 34 is a block diagram of an example of the air chamber control system 1300 that can be associated with a bed system, including those described herein, for example with reference to FIGS. 1, 8-10, 19, and 33. The air chamber control system 1300 can include an air chamber controller 1302, a pump assembly 1304, one or more air chambers 1306, and a set of sensors 1308.

The air chamber controller 1302 can control the pump assembly 1304 to activate and control the pressures of the air chambers 1306 included in a mattress 1310. The air chamber controller 1302 can be used to implement at least part of the air chamber control system 114 shown in FIG. 1. In some implementations, the air chamber controller 1302 can be configured as a center or hub of the bed system 1100 to activate and control various functionalities provided in the bed system, such as at least some functionalities of the foot warming control system 1500 and the airflow pad control system 1600.

In some implementations, the air chamber controller 1302 can include a power supply 1320, a processor 1322, and memory 1324. The power supply 1320 includes hardware used to receive electrical power from an outside source and supply it to components of the air chamber controller 1302. The power supply 1320 can include, for example, a battery pack and/or wall outlet adapter, an AC to DC converter, a DC to AC converter, a power conditioner, a capacitor bank, and/or one or more interfaces for providing power in the current type, voltage, etc., needed by other components of the air chamber controller 1302.

The processor 1322 can be one or more processors that operate to receive input, perform logical determinations, and provide output. The processor 1322 can be a central processing unit, a microprocessor, general purpose logic circuitry, application-specific integrated circuitry, a combination of these, and/or other hardware for performing the functionality needed.

The memory 1324 is used to store data and software and/or firmware code executable by the processor 1322. The memory 1324 can include long term stable data storage (e.g., on a hard disk), short term unstable (e.g., on Random Access Memory) or any other technologically appropriate configuration.

The air chamber controller 1302 can include a pump controller 1326 and a pump motor 1328, which can be housed with a common housing (such as a plastic or metal pump housing). The pump controller 1326 can receive commands from the processor 1322 and, in response, control the function of the pump motor 1328. For example, the pump controller 1326 can receive, from the processor 1322, a command to increase the pressure of an air chamber 1306 by 0.3 pounds per square inch (PSI). The pump controller 1326, in response, engages a valve so that the pump motor 1328 is configured to pump air into the selected air chamber 1306, and can engage the pump motor 1328 for a length of time that corresponds to 0.3 PSI or until a sensor indicates that pressure has been increased by 0.3 PSI. In an alternative configuration, the message can specify that the air chamber 1306 should be inflated to a target PSI, and the pump controller 1326 can engage the pump motor 1328 until the target PSI is reached.

In some implementations, the air chamber controller 1302 can include one or more valve solenoids 1330 that can control connections between a pump and one or more air chambers. In some cases, the solenoid 1330 can be controlled by the processor 1322 directly. In some cases, the solenoid 1330 can be controlled by the pump controller 1326. In some implementations, a valve controller 1332 can be provided to convert commands from the processor 1322 into control signals for the valve solenoid 1330. In one example, the processor 1322 can issue a command to the valve controller 1332 to connect the pump to a particular air chamber out of the group of air chambers in an air bed. The valve controller 1332 can control the position of the valve solenoid 1330 so that the pump is connected to the indicated air chamber.

The air chamber controller 1302 can include a communications interface 1334 to permit the air chamber controller 1302 to communicate with other components of the system 1300. For example, the air chamber controller 1302 can communicate with one or more peripheral sensors, peripheral controllers, circuitries (e.g., foot heater control circuitry, airflow pad control circuitry, etc.), and/or computing devices over one or more wired or wireless networks. The communications interface 1334 can provide any technologically appropriate communication interface, including but not limited to multiple communication interfaces such as Wi-Fi, Bluetooth, and copper wired networks.

The air chamber controller 1302 can include a pressure sensor 1336 configured to read pressure readings from one or more air chambers 1306 of the air bed. The pressure sensor 1336 can also preform digital sensor conditioning. The pressure sensor 1336 can be native to the air chamber controller 1302. Alternatively or in addition, a pressure sensor can be provided as a peripheral sensor as described below.

The air chamber controller 1302 can provide a status analysis module 1338. For example, the status analysis module 1338 can be one or more software components stored on the computer memory 1324 and executed by the processor 1322. The status analysis module 1338 can receive data from a wide variety of sources (e.g., sensors, non-sensor local sources, cloud data services) and analyze various statuses and operational conditions in the bed system 1100. The status analysis module 1338 can further generate one or more actions to be taken (e.g., commands to send to peripheral controllers, data to send to cloud services). This can be useful, for example, in tracking user behavior and automating devices in communication with the user's bed.

The status analysis module 1338 can collect data from any technologically appropriate source, for example, to gather data about features of a bed, the bed's environment, and/or the bed's users. Some such sources include any of the sensors of the set of sensors 1308. For example, this data can provide the status analysis module 1338 with information about the current state of the environment around the bed. For example, the status analysis module 1338 can access readings from the pressure sensor 1336, 1344 to determine the pressure of the air chamber in the bed. From this reading, and potentially other data, user presence in the bed can be determined. In another example, the status analysis module can access the light sensor 1348 to detect the amount of light in the bed's environment.

Similarly, the status analysis module 1338 can access data from cloud services through for example the server system 1126 (FIG. 33). For example, the status analysis module 1338 can access the bed cloud service to access historical sensor data and/or advanced sleep data. Other cloud services, including those not previously described, can be accessed by the status analysis module 1338. For example, the status analysis module 1338 can access a weather reporting service, a 3rd party data provider (e.g., traffic and news data, emergency broadcast data, user travel data), and/or a clock and calendar service.

Similarly, the status analysis module 1338 can access data from non-sensor sources. For example, the status analysis module 1338 can access a local clock and calendar service (e.g., a component of the processor 1322).

The status analysis module 1338 can aggregate and prepare this data for use by one or more behavioral algorithms. The behavioral algorithms can be used to learn a user's behavior and/or to perform some action based on the state of the accessed data and/or the predicted user behavior. For example, the behavior algorithm can use available data (e.g., pressure sensor, non-sensor data, clock and calendar data) to create a model of when a user goes to bed every night. Later, the same or a different behavioral algorithm can be used to determine if an increase in air chamber pressure is likely to indicate a user going to bed and, if so, send some data to a third-party cloud service and/or engage a peripheral controller.

In the illustrated example, the status analysis module 1338 (including the behavioral algorithms) are shown as components of the air chamber controller 1302. Alternatively, the status analysis module 1338 can be included in other components in the bed system 1100. For example, the same or a similar status analysis module and/or behavior algorithms can be run in one or more cloud services (e.g., in the server system 1126), and the resulting output can be sent to the air chamber controller 1302, other components in the bed system 1100 or any other technologically appropriate recipient.

Referring still to FIG. 34, the pump assembly 1304 is in two-way communication with the air chamber controller 1302. The pump 1304 can include a motor 1362, a pump manifold 1364, a relief valve 1366, a first control valve 1368A, a second control valve 1368B, and a pressure transducer 1370. The pump 1304 is fluidly connected with the first air chamber 1306A and the second air chamber 1306B via a first tube 1372A and a second tube 1372B, respectively. The first and second control valves 1368A and 1368B can be controlled by switching mechanism, and are operable to regulate the flow of fluid between the pump 1304 and first and second air chambers 1306A and 1306B, respectively. The switching mechanism can be included in the air chamber controller 1302, and can include, for example, a relay or a solid state switch. In other implementations, the switching mechanism can be located in another component, such as the pump 1304, rather than the air chamber controller 1302.

In some implementations, the pump 1304 and the air chamber controller 1302 can be provided and packaged as a single unit in a common pump housing. In some alternative implementations, the pump 1304 and the air chamber controller 1302 can be provided as physically separate units. In some implementations, the air chamber controller 1302, the pump 1304, or both are integrated within or otherwise contained within a bed frame or bed support structure that supports the bed 1112. In some implementations, the air chamber controller 1302, the pump 1304, or both are located outside of a bed frame or bed support structure.

The example bed system 1100 depicted in FIG. 33 includes the two air chambers 1306A and 1306B and the single pump 1304. However, other implementations can include an air bed system having two or more air chambers and one or more pumps incorporated into the air bed system to control the air chambers. For example, a separate pump can be associated with each air chamber of the bed system or a pump can be associated with multiple chambers of the bed system. Separate pumps can allow each air chamber to be inflated or deflated independently and simultaneously. Furthermore, additional pressure transducers can also be incorporated into the bed system such that, for example, a separate pressure transducer can be associated with each air chamber.

In use, the processor 1322 can, for example, send a decrease pressure command to decrease the pressure in one of air chambers 1306A or 1306B, and a switching mechanism can be used to convert the low voltage command signals sent by the processor 1322 to higher operating voltages sufficient to operate the relief valve 1366 of the pump 1304 and open the control valve 1368A or 1368B. Opening the relief valve 1366 can allow air to escape from the air chamber 1306A or 1306B through the respective air tube 1372A or 1372B. During deflation, the pressure transducer 1370 can send pressure readings to the processor 1322 via an A/D converter. The A/D converter can receive analog information from pressure transducer 1370 and can convert the analog information to digital information useable by the processor 1322. The processor 1322 can send the digital signal to the remote control 1122 and/or the user computing device 1124 to update the display in order to convey the pressure information to the user.

As another example, the processor 1322 can send an increase pressure command. The pump motor 1362 can be energized in response to the increase pressure command and send air to the designated one of the air chambers 1306A or 1306B through the air tube 1372A or 1372B via electronically operating the corresponding valve 1368A or 1368B. While air is being delivered to the designated air chamber 1306A or 1306B in order to increase the firmness of the chamber, the pressure transducer 1370 can sense pressure within the pump manifold 1364. Again, the pressure transducer 1370 can send pressure readings to the processor 1322 via the A/D converter. The processor 1322 can use the information received from the A/D converter to determine the difference between the actual pressure in air chamber 1306A or 1306B and the desired pressure. The processor 1322 can send the digital signal to the remote control 1122 and/or the user computing device 1124 to update the display in order to convey the pressure information to the user.

During an inflation or deflation process, the pressure sensed within the pump manifold 1364 can provide an approximation of the pressure within the respective air chamber that is in fluid communication with the pump manifold 1364. An example method of obtaining a pump manifold pressure reading that is substantially equivalent to the actual pressure within an air chamber includes turning off pump 1304, allowing the pressure within the air chamber 1306A or 1306B and the pump manifold 1364 to equalize, and then sensing the pressure within the pump manifold 1364 with the pressure transducer 1370. Thus, providing a sufficient amount of time to allow the pressures within the pump manifold 1364 and chamber 1306A or 1306B to equalize can result in pressure readings that are accurate approximations of the actual pressure within air chamber 1306A or 1306B. In some implementations, the pressure of the air chambers 1306A and/or 1306B can be continuously monitored using multiple pressure sensors (not shown).

In some implementations, information collected by the pressure transducer 1370 can be analyzed to determine various states and/or biometric information of a person lying on the bed. For example, the processor 1322 can use information collected by the pressure transducer 1370 to determine a heart rate or a respiration rate for a person lying in the bed. For example, a user can be lying on a side of the bed that includes the chamber 1306A. The pressure transducer 1370 can monitor fluctuations in pressure of the chamber 1306A and this information can be used to determine the user's heart rate and/or respiration rate. As another example, additional processing can be performed using the collected data to determine a sleep state of the person (e.g., awake, light sleep, deep sleep). For example, the processor 1322 can determine when a person falls asleep and, while asleep, the various sleep states of the person.

Additional information associated with a user of the bed system 1100 that can be determined using information collected by the pressure transducer 1370 includes motion of the user, presence of the user on a surface of the bed, weight of the user, heart arrhythmia of the user, and apnea. Taking user presence detection for example, the pressure transducer 1370 can be used to detect the user's presence on the bed, e.g., via a gross pressure change determination and/or via one or more of a respiration rate signal, heart rate signal, and/or other biometric signals. For example, a simple pressure detection process can identify an increase in pressure as an indication that the user is present on the bed. As another example, the processor 1322 can determine that the user is present on the bed if the detected pressure increases above a specified threshold (so as to indicate that a person or other object above a certain weight is positioned on the bed). As yet another example, the processor 1322 can identify an increase in pressure in combination with detected slight, rhythmic fluctuations in pressure as corresponding to the user being present on the bed. The presence of rhythmic fluctuations can be identified as being caused by respiration or heart rhythm (or both) of the user. The detection of respiration or a heartbeat can distinguish between the user being present on the bed and another object (e.g., a suit case) being placed upon the bed.

In some implementations, fluctuations in pressure can be measured at the pump 1304. For example, one or more pressure sensors can be located within one or more internal cavities of the pump 1304 to detect fluctuations in pressure within the pump 1304. The fluctuations in pressure detected at the pump 1304 can indicate fluctuations in pressure in one or both of the chambers 1306A and 1306B. One or more sensors located at the pump 1304 can be in fluid communication with the one or both of the chambers 1306A and 1306B, and the sensors can be operative to determine pressure within the chambers 1306A and 1306B. The air chamber controller 1302 can be configured to determine at least one vital sign (e.g., heart rate, respiratory rate) based on the pressure within the chamber 1306A or the chamber 1306B.

In some implementations, the air chamber controller 1302 can analyze a pressure signal detected by one or more pressure sensors to determine a heart rate, respiration rate, and/or other vital signs of a user lying or sitting on the chamber 1306A or the chamber 1306B. For example, when a user lies on the bed positioned over the chamber 1306A, each of the user's heart beats, breaths, and other movements can create a force on the bed 1112 that is transmitted to the chamber 1306A. As a result of the force input to the chamber 1306A from the user's movement, a wave can propagate through the chamber 1306A and into the pump 1304. A pressure sensor located at the pump 1304 can detect the wave, and thus the pressure signal output by the sensor can indicate a heart rate, respiratory rate, or other information regarding the user.

With regard to sleep state, the bed system 1100 can determine a user's sleep state by using various biometric signals such as heart rate, respiration, and/or movement of the user. While the user is sleeping, the processor 1322 can receive one or more of the user's biometric signals (e.g., heart rate, respiration, and motion) and determine the user's present sleep state based on the received biometric signals. In some implementations, signals indicating fluctuations in pressure in one or both of the chambers 1306A and 1306B can be amplified and/or filtered to allow for more precise detection of heart rate and respiratory rate.

The air chamber controller 1302 can perform a pattern recognition algorithm or other calculation based on the amplified and filtered pressure signal to determine the user's heart rate and respiratory rate. For example, the algorithm or calculation can be based on assumptions that a heart rate portion of the signal has a frequency in the range of 0.5-4.0 Hz and that a respiration rate portion of the signal a has a frequency in the range of less than 11 Hz. The air chamber controller 1302 can also be configured to determine other characteristics of a user based on the received pressure signal, such as blood pressure, tossing and turning movements, rolling movements, limb movements, weight, the presence or lack of presence of a user, and/or the identity of the user.

For example, the pressure transducer 1370 can be used to monitor the air pressure in the chambers 1306A and 1306B of the bed 1112. If the user on the bed is not moving, the air pressure changes in the air chamber 1306A or 1306B can be relatively minimal, and can be attributable to respiration and/or heartbeat. When the user on the bed is moving, however, the air pressure in the mattress can fluctuate by a much larger amount. Thus, the pressure signals generated by the pressure transducer 1370 and received by the processor 1322 can be filtered and indicated as corresponding to motion, heartbeat, or respiration.

In some implementations, rather than performing the data analysis in the air chamber controller 1302 with the processor 1322, a digital signal processor (DSP) can be provided to analyze the data collected by the pressure transducer 1370. Alternatively, the data collected by the pressure transducer 1370 could be sent to a cloud-based computing system for remote analysis.

Referring still to FIG. 34, the set of sensors 1308 can include one or more sensors configured to sense physical phenomenon of the environment and/or bed, and to report such sensing back to the air chamber controller 1302 for analysis or other purposes. The sensors can include peripheral sensors 1340 that communicate with the air chamber controller 1302. Such peripheral sensors of the set of sensors 1308 can communicate with the air chamber controller 1302 through one or more of the network interfaces of the air chamber controller 1302, including but not limited to a USB stack, a Wi-Fi radio, a Bluetooth Low Energy (BLE) radio, a ZigBee radio, and a Bluetooth radio, as is appropriate for the configuration of the particular sensor. For example, a sensor that outputs a reading over a USB cable can communicate through the USB stack. In addition or alternatively, the sensors can include sensors that are native to the air chamber controller 1302.

Some of the peripheral sensors 1340 of the set of sensors 1308 can be bed mounted sensors 1342. The bed mounted sensors 1342 can be, for example, embedded into the structure of a bed and sold with the bed, or later affixed to the structure of the bed. Other peripheral sensors 1340 can be in communication with the air chamber controller 1302, but optionally not mounted to the bed. In some cases, some or all of the bed mounted sensors 1342 and/or peripheral sensors 1340 can share networking hardware, including a conduit that contains wires from each sensor, a multi-wire cable or plug that, when affixed to the air chamber controller 1302, connect all of the associated sensors with the air chamber controller 1302. In some embodiments, one, some, or all of sensors can sense one or more features of a mattress, such as pressure, temperature, light, sound, and/or one or more other features of the mattress. In some embodiments, one, some, or all of the sensors can sense one or more features external to the mattress. The bed mounted sensors 1342 can include one or more of a pressure sensor 1344, a temperature sensor 1346, a light sensor 1348, a sound sensor 1350, and other suitable sensors for detecting one or more features of the mattress and/or external to the mattress. In this example, the pressure sensor 1344 is configured as a peripheral sensor, which can be used as an alternative to, or addition to, the pressure sensor 1336 in the air chamber controller 1302.

Figure 35:
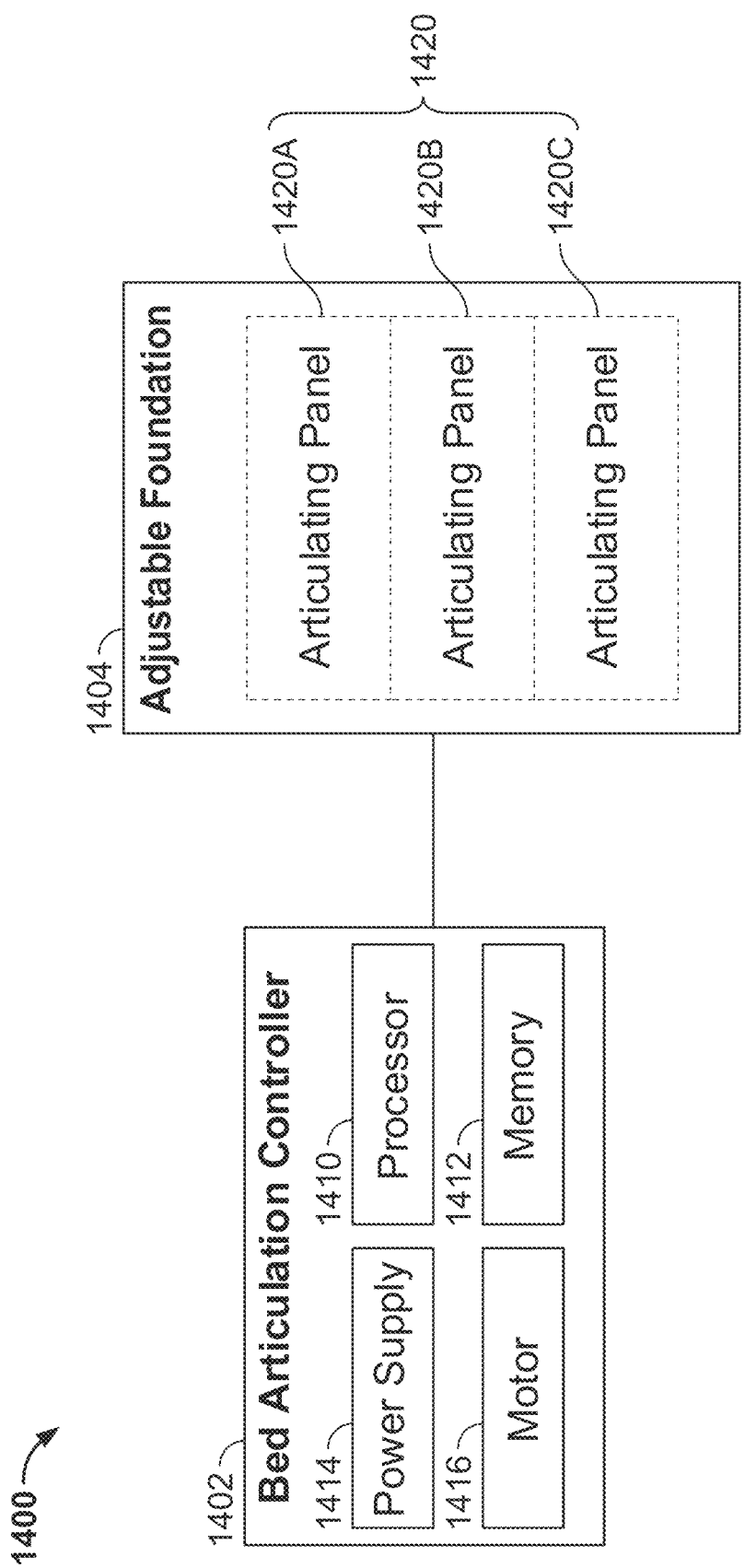
FIG. 35 is a block diagram of an example bed articulation control system that can be associated with a bed system.

FIG. 35 is a block diagram of an example of the bed articulation control system 1400 that can be associated with a bed system, including those described herein, for example with reference to FIGS. 1, 19, and 33. The bed articulation control system 1400 can include a bed articulation controller 1402 and an adjustable foundation 1404. The articulation controller 1402 is configured to adjust the position of a bed by adjusting the adjustable foundation that supports the bed. The adjustable foundation 1404 can include one or more adjustable panels 1420, the positions of which can be controlled by the articulation controller 1402. The articulation controller 1402 can be used to implement at least part of the bed articulation system 112 of the bed control system 110 shown in FIG. 1. In some implementations, the articulation controller 1402 can include a processor 1410, a memory 1412, a power supply 1414, and a motor 1416. In some implementations, the motor 1416 can be located in another component, such as the adjustable foundation 1404.

For example, the articulation controller 1402 can adjust the foundation 1404 from a flat position to a position in which a head portion of a mattress of the bed is inclined upward (e.g., to facilitate a user sitting up in bed and/or watching television). In some implementations, the foundation 1404 includes multiple separately articulable sections or panels. For example, portions of the foundation corresponding to the locations of the air chambers 1306A and 1306B can be articulated independently from each other, to allow one person positioned on the bed surface to rest in a first position (e.g., a flat position) while a second person rests in a second position (e.g., a reclining position with the head raised at an angle from the waist). In some implementations, separate positions can be set for two different beds (e.g., two twin beds placed next to each other). The foundation 1404 of the bed can include more than one zone that can be independently adjusted. The articulation controller 1402 can include the motor 1416 that can be energized in response to an articulation command transmitted from the processor 1410. The motor 1416 is operatively engaged with one or more articulating panels of the foundation 1404, and adjust the positions of the articulating panels based on the articulation command. The articulation controller 1402 can also be configured to provide different levels of massage to one or more users on the bed. The articulation command can be generated by the processor 1410 based on a user input of bed articulation settings via, e.g., the remote control 1122 and/or the user computing device 1124.

Referring again to FIG. 33, the bed system 1100 can include one or more temperature control systems configured to increase, decrease, or maintain the temperature of a bed, for example for the comfort of the user. As described, such temperature control systems can include the foot warming control system 1500 and the airflow pad control system 1600.

Figure 36:
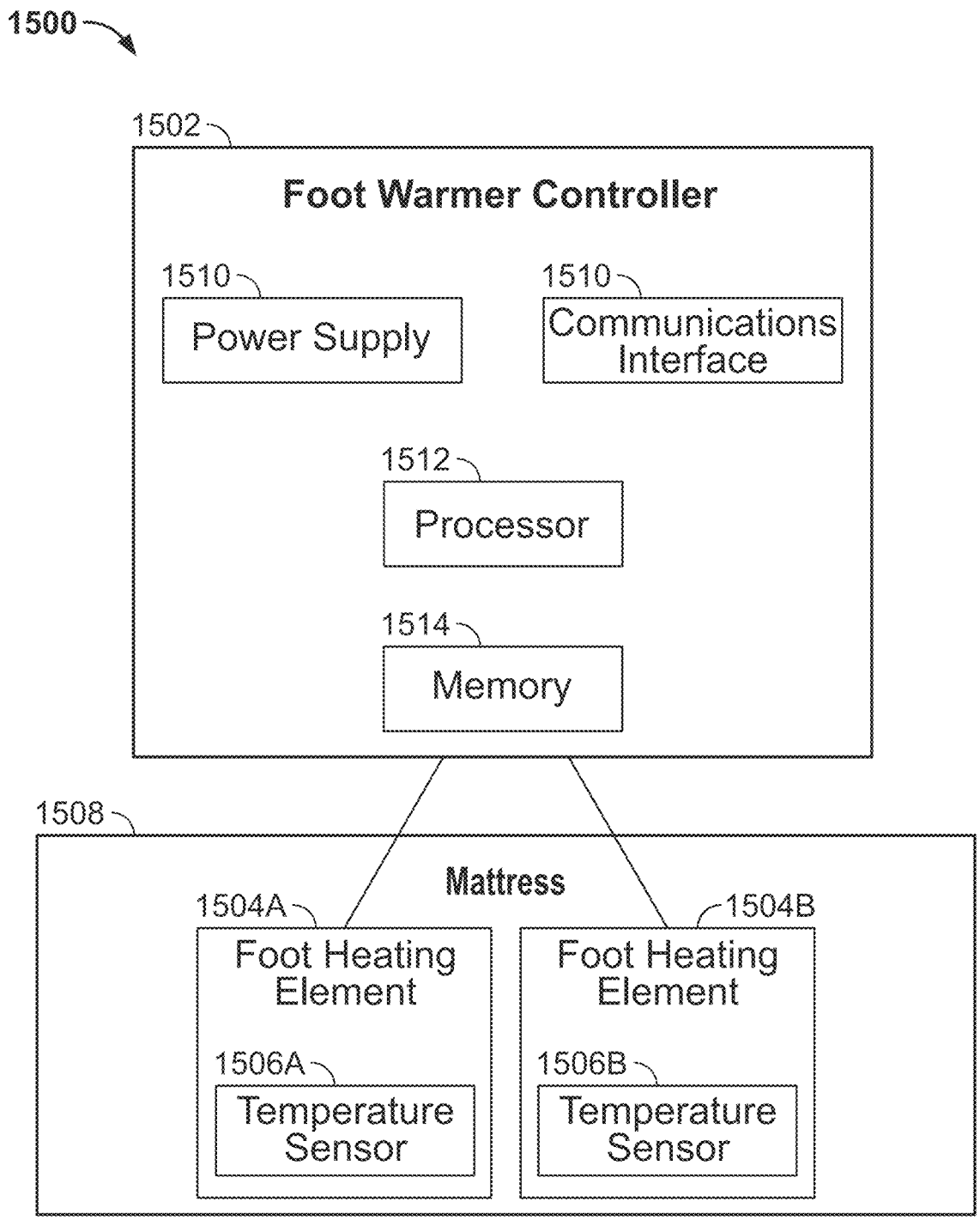
FIG. 36 is a block diagram of an example foot warming control system that can be associated with a bed system.

FIG. 36 is a block diagram of an example of the foot warming control system 1500 that can be associated with a bed system, including those described above with reference to FIGS. 1, 27-30, and 33. The foot warming control system 1500 can include a foot warming controller 1502 and one or more foot warming pads 1504A and 1504B that can be placed on the top or be part of a mattress 1508 at the foot of the mattress. The mattress 1508 can be implemented by the mattress 1310 of FIG. 34. The foot warming pads 1504A and 1504B can include heating elements used to keep the pads warm at desired temperatures. The foot warming controller 1502 is coupled to the foot warming pads 1504A and 1504B and operable to warm the heating elements of the pads at desired temperatures. The foot warming controller 1502 can include a processor 1512 and a memory 1514, and the processor 1512 can generate a control command to energize the heating elements according to a user input of foot temperature settings via, e.g., the remote control 1122 or the user computing device 1124. The foot warming controller 1502 can include a communications interface 1516 to permit for the foot warming controller 1502 to communicate with other components in the bed system 1100, such as at least one of the systems 1300, 1400, 1600, the remote control 1122, the user computing device 1124, and the server system 1126.

The processor 1512 can generate a foot warming command according to the user input of foot temperature settings (e.g., via the remote control 1122 or the user computing device 1124), and transmit the foot warming command to the foot warming controller 1502. The foot warming controller 1502 can selectively activate the heating elements of the foot warming pads 1504A and 1504B to raise, lower, or maintain the desired temperatures of the foot warming pads 1504A and 1504B. The foot warming controller 1502 can include a power supply 1510 to supply electronic power to activate the heating elements of the foot warming pads 1504A and 1504B.

In some implementations, temperature sensors 1506A and 1506B are provided to detect the temperature at the foot warming pads 1504A and 1504B, and transmit the temperature readings to the foot warming controller 1502. The processor 1512 can use the temperature readings at the foot warming pads 1504A and 1504B to adjust the operation of the pads 1504A and 1504B as necessary. Separate foot warming pads can be used for the different sides of the bed 1112 (e.g., corresponding to the locations of the air chambers 1306A and 1306B) to provide for differing temperature control for the different sides of the bed.

The user of the bed system 1100 can use an input device, such as the remote control 1122 and the user computing device 1124, to input a desired temperature for the foot warming at the foot of the bed. The desired temperature can be encapsulated in a command data structure that includes the desired temperature as well as identifies the foot warming controller 1502 as the desired component to be controlled. The command data structure can then be transmitted via Bluetooth or another suitable communication protocol to the processor 1512. In various examples, the command data structure is encrypted before being transmitted. The foot warming controller 1502 can then configure its elements to increase or decrease the temperature of the foot warming pads depending on the temperature input into the remote control 1122 or the user computing device 1124 by the user.

Figure 37:
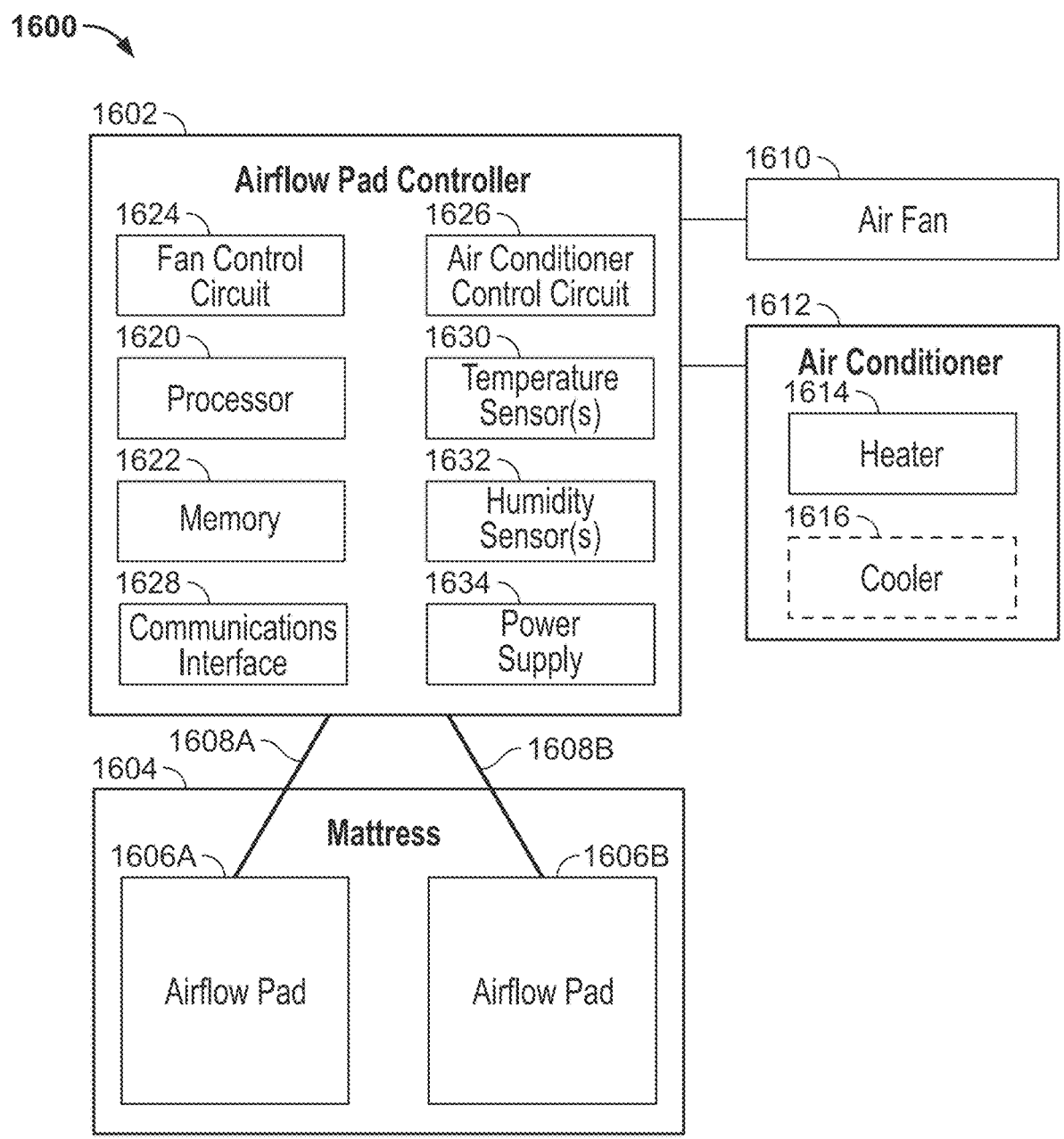
FIG. 37 is a block diagram of an example airflow pad control system that can be associated with a bed system.

FIG. 37 is a block diagram of an example of the airflow pad control system 1600 that can be associated with a bed system, including those described above with reference to FIGS. 1-33. The airflow pad control system 1600 can include an airflow pad controller 1602 and one or more airflow pads 1606. The airflow pads 1606A and 1606B can be arranged in a mattress 1604 and configured to cool or warm at least part of the mattress top. The mattress 1604 can be implemented by the mattress 1310 (FIG. 34) or the mattress 1508 (FIG. 36). The airflow pads 1606A and 1606B can be used together with the foot warming pads 1504A and 1504B. For example, the foot warming pads 1504A and 1504B are arranged at the foot of the mattress, and the airflow pads 1606A and 1606B can be arranged in other areas of the mattress, such as the head of the mattress or the middle section between the head and the foot of the mattress. The airflow pads 1606A and 1606B can be configured to be identical or similar to the airflow layers described herein, for example with reference to FIGS. 1-3, 5-13, and 31-33. The airflow pads 1606A and 1606B are configured to permit for ambient or conditioned air to flow therethrough so that the air can be distributed through one or more layers above the airflow pads, or that the air can be drawn from the layers above the airflow pads.

The airflow pad controller 1602 can be fluidly connected to the airflow pads 1606A and 1606B via air hoses 1608A and 1608B. The airflow pad controller 1602 is configured to move ambient or conditioned air through the airflow pads 1606A and 1606B and further through the top layer of the mattress to control a temperature at a top surface of the top layer. For example, the airflow pad controller 1602 can operate to draw air from the airflow pads 1606A and 1606B and the top layer through the air hoses 1608A and 1608B, thereby decreasing a temperature at the top surface of the top layer. Alternatively, the airflow pad controller 1602 can operate to supply ambient or cooling air to the airflow pads 1606A and 1606B through the air hoses 1608A and 1608B, thereby enabling such ambient or cooling air to be distributed through the top layer and decreasing a temperature at the top surface of the top layer. Alternatively, the airflow pad controller 1602 can operate to supply heating air to the airflow pads 1606A and 1606B through the air hoses 1608A and 1608B, thereby enabling such heating air to be distributed through the top layer and increasing a temperature at the top surface of the top layer.

In some implementations, the airflow pad controller 1602 can include, or be coupled to, an air fan 1610 and an air conditioner 1612. The air conditioner 1612 can include an air heater 1614. In addition, the air conditioner 1612 can include an air cooler 1616. The fan 1610 is configured to cause air to flow into or from the airflow pads 1606A and 1606B. The heater 1614 is configured to heat air flowing into or from the airflow pads 1606A and 1606B. The cooler 1616 is configured to cool air flowing into or from the airflow pads 1606A and 1606B. The air fan 1610 can be implemented by the air controller 700 described with reference to FIGS. 21-26 above. The heater 1614 can be implemented by the heating element 716 described with reference to FIGS. 22-26 above.

The airflow pad controller 1602 can include a processor 1620, a memory 1622, a fan control circuit 1624, an air conditioner control circuit 1626, a communications interface 1628, one or more temperature sensors 1630, one or more humidity sensors 1632, and a power supply 1634. The fan control circuit 1624 is configured to permit communication between the processor 1620 and the fan 1610 to control the fan 1610. The air conditioner control circuit 1626 is configured to permit communication between the processor 1620 and the air conditioner 1612 to control the air conditioner 1612. The communications interface 1628 is configured to permit for the airflow pad controller 1602 to communicate with other components in the bed system 1100, such as at least one of the systems 1300, 1400, 1500, the remote control 1122, the user computing device 1124, and the server system 1126.

The temperature sensors 1630 are configured and arranged to detect the temperature of air flowing into and/or drawing from the airflow pads 1606A and 1606B, the temperature of the air conditioner 1612 (e.g., the heater 1614 or the cooler 1616), the temperature of ambient air, and/or other temperatures at different locations in the bed system. Such temperature measurements can be used to adjust the operations of the airflow pads 1606A and 1606B and/or other components in the bed system 1100. The temperature sensors 1630 can be arranged in various locations. In some implementations, one or more temperature sensors 1630 can be disposed in a housing of the airflow pad controller 1602, which may also houses the air fan 1610 and/or the air conditioner 1612 (e.g., the heater 1614 and/or the cooler 1616). For example, at least one of the temperature sensors 1630 can be arranged adjacent the fan 1610 and/or the air conditioner 1612. In addition or alternatively, one or more temperature sensors 1630 can be disposed outside of the mattress, such as below the bottom of the mattress. In addition or alternatively, one or more temperature sensors 1630 can be mounted to a desired location of the mattress (e.g., on the bottom of the mattress. In addition or alternatively, one or more temperature sensors 1630 can be arranged in an airflow path between the fan 1610 and the airflow pads 1606.

The humidity sensors 1632 are configured and arranged to detect the humidity value of air flowing into and/or drawing from the airflow pads 1606A and 1606B, the humidity value of ambient air, and/or the humidity values at different locations in the bed system. Such humidity measurements can be used to adjust the operations of the airflow pads 1606A and 1606B and/or other components in the bed system 1100. For example, the processor 1620 can use the temperature measurements and/or the humidity measurements to adjust various operations of the airflow pad controller 1602, such as conditioning air, supplying or drawing air to/from the airflow pads 1606A and 1606B, etc., and/or operations of other components in the bed system 1100. The humidity sensors 1632 can be arranged in various locations. In some implementations, one or more humidity sensors 1632 can be disposed in a housing of the airflow pad controller 1602, which may also houses the air fan 1610 and/or the air conditioner 1612 (e.g., the heater 1614 and/or the cooler 1616). For example, at least one of the humidity sensors 1632 can be arranged adjacent the fan 1610 and/or the air conditioner 1612. In addition or alternatively, one or more humidity sensors 1632 can be disposed outside of the mattress, such as below the bottom of the mattress. In addition or alternatively, one or more humidity sensors 1632 can be mounted to a desired location of the mattress (e.g., on the bottom of the mattress. In addition or alternatively, one or more humidity sensors 1632 can be arranged in an airflow path between the fan 1610 and the airflow pads 1606.

Example Bed in a Bedroom Environment

Figure 38:
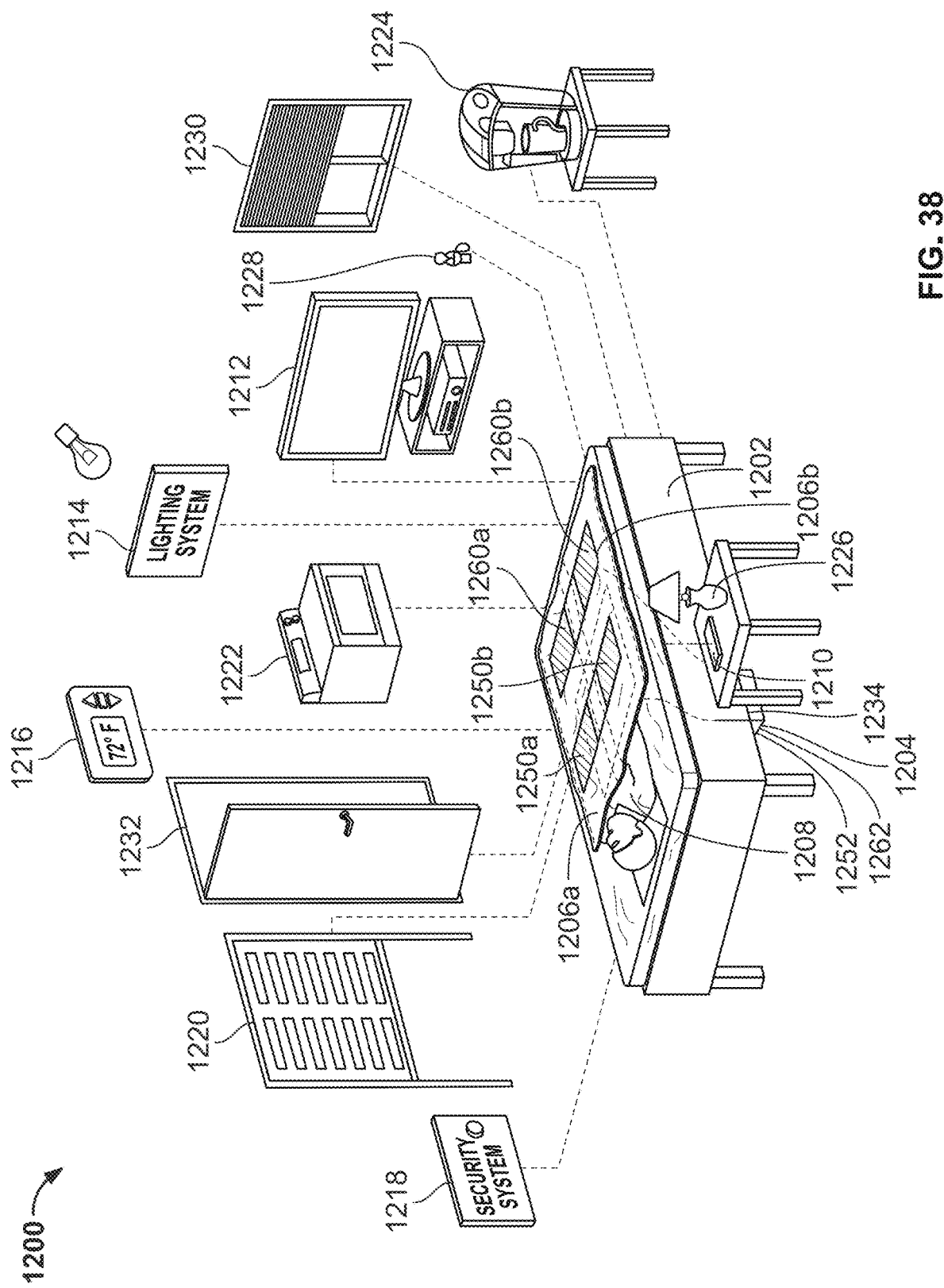
FIG. 38 illustrates an example environment including a bed in communication with devices located in and around a home.

FIG. 38 illustrates an example environment 1200 including a bed 1202 in communication with devices located in and around a home. In the example shown, the bed 1202 includes a pump 1204 for controlling air pressure within two air chambers 1206a and 1206b (as described with respect to the air chambers herein). The pump 1204 additionally includes circuitry for controlling inflation and deflation functionality performed by the pump 1204. The circuitry is further programmed to detect fluctuations in air pressure of the air chambers 1206a-b and used the detected fluctuations in air pressure to identify bed presence of a user 1208, sleep state of the user 1208, movement of the user 1208, and biometric signals of the user 1208 such as heart rate and respiration rate. In the example shown, the pump 1204 is located within a support structure of the bed 1202 and the control circuitry 1234 for controlling the pump 1204 is integrated with the pump 1204. In some implementations, the control circuitry 1234 is physically separate from the pump 1204 and is in wireless or wired communication with the pump 1204. In some implementations, the pump 1204 and/or control circuitry 1234 are located outside of the bed 1202. In some implementations, various control functions can be performed by systems located in different physical locations. For example, circuitry for controlling actions of the pump 1204 can be located within a pump casing of the pump 1204 while control circuitry 1234 for performing other functions associated with the bed 1202 can be located in another portion of the bed 1202, or external to the bed 1202. As another example, control circuitry 1234 located within the pump 1204 can communicate with control circuitry 1234 at a remote location through a LAN or WAN (e.g., the Internet). As yet another example, the control circuitry 1234 can be included in the air chamber controller 1302 of FIG. 34.

In some implementations, one or more devices other than, or in addition to, the pump 1204 and control circuitry 1234 can be utilized to identify user bed presence, sleep state, movement, and biometric signals. For example, the bed 1202 can include a second pump in addition to the pump 1204, with each of the two pumps connected to a respective one of the air chambers 1206a-b. For example, the pump 1204 can be in fluid communication with the air chamber 1206b to control inflation and deflation of the air chamber 1206b as well as detect user signals for a user located over the air chamber 1206b such as bed presence, sleep state, movement, and biometric signals while the second pump is in fluid communication with the air chamber 1206a to control inflation and deflation of the air chamber 1206a as well as detect user signals for a user located over the air chamber 1206a.

In addition, the bed 1202 can include airflow pads 1250a and 1250b (as described with respect to the airflow pads herein). The bed 1202 includes an air controller 1252 for controlling airflow into or from the airflow pads 1250a and 1250b as described herein. The air controller 1252 can be located together with the pump 1204 or the control circuitry 1234. In another example, the air controller 1252 can be located remotely from the pump 1204 and/or the control circuitry 1234. In yet another example, the air controller 1252 can be included in the airflow pad controller 1602 of FIG. 37.

Further, the bed 1202 can include foot warming pads 1260a and 1260b (as described with respect to the foot warming pads herein). For example, the foot warming pads 1260 can be configured similarly to the foot heating elements 1504 or the heating units 824 described herein. Alternatively or in addition, the foot warming pads 1260 can be configured with the airflow pads 1250 and associated components. The bed 1202 includes a foot warming control circuitry 1262 for controlling the temperatures of the foot warming pads 1260a and 1260b. The foot warming controller 1262 can be located together with the pump 1204, the control circuitry 1234, and/or the air controller 1252. In another example, the foot warming controller 1262 can be located remotely from the pump 1204, the control circuitry 1234, and/or the air controller 1252. In yet another example, the foot warming controller 1262 can be included in the foot warming controller 1502 of FIG. 36.

Alternatively or in addition, the bed 1202 can include one or more pressure sensitive pads or surface portions that are operable to detect movement, including user presence, user motion, respiration, and heart rate. For example, a first pressure sensitive pad can be incorporated into a surface of the bed 1202 over a left portion of the bed 1202, where a first user would normally be located during sleep, and a second pressure sensitive pad can be incorporated into the surface of the bed 1202 over a right portion of the bed 1202, where a second user would normally be located during sleep. The movement detected by the one or more pressure sensitive pads or surface portions can be used by control circuitry 1234 to identify user sleep state, bed presence, or biometric signals.

In some implementations, information detected by the bed (e.g., motion information) is processed by control circuitry 1234 (e.g., control circuitry 1234 integrated with the pump 1204) and provided to one or more user devices such as a user device 1210 for presentation to the user 1208 or to other users. In the example depicted in FIG. 38, the user device 1210 is a tablet device; however, in some implementations, the user device 1210 can be a personal computer, a smart phone, a smart television (e.g., a television 1212), or other user device capable of wired or wireless communication with the control circuitry 1234. The user device 1210 can be in communication with control circuitry 1234 of the bed 1202 through a network or through direct point-to-point communication. For example, the control circuitry 1234 can be connected to a LAN (e.g., through a Wi-Fi router) and communicate with the user device 1210 through the LAN.

As another example, the control circuitry 1234 and the user device 1210 can both connect to the Internet and communicate through the Internet. For example, the control circuitry 1234 can connect to the Internet through a Wi-Fi router and the user device 1210 can connect to the Internet through communication with a cellular communication system. As another example, the control circuitry 1234 can communicate directly with the user device 1210 through a wireless communication protocol such as Bluetooth. As yet another example, the control circuitry 1234 can communicate with the user device 1210 through a wireless communication protocol such as ZigBee, Z-Wave, or another wireless communication protocol suitable for the application. As another example, the control circuitry 1234 can communicate with the user device 1210 through a wired connection such as, for example, a USB connector or another wired connection suitable for the application.

The user device 1210 can display a variety of information and statistics related to sleep, or user 1208's interaction with the bed 1202. For example, a user interface displayed by the user device 1210 can present information including amount of sleep for the user 1208 over a period of time (e.g., a single evening, a week, a month, etc.) amount of deep sleep, ratio of deep sleep to restless sleep, time lapse between the user 1208 getting into bed and the user 1208 falling asleep, total amount of time spent in the bed 1202 for a given period of time, heart rate for the user 1208 over a period of time, respiration rate for the user 1208 over a period of time, or other information related to user interaction with the bed 1202 by the user 1208 or one or more other users of the bed 1202. In some implementations, information for multiple users can be presented on the user device 1210, for example information for a first user positioned over the air chamber 1206a can be presented along with information for a second user positioned over the air chamber 1206b. In some implementations, the information presented on the user device 1210 can vary according to the age of the user 1208. For example, the information presented on the user device 1210 can evolve with the age of the user 1208 such that different information is presented on the user device 1210 as the user 1208 ages as a child or an adult.

The user device 1210 can also be used as an interface for the control circuitry 1234 of the bed 1202 to allow the user 1208 to enter information. The information entered by the user 1208 can be used by the control circuitry 1234 to provide better information to the user or to various control signals for controlling functions of the bed 1202 or other devices. For example, the user can enter information such as weight, height, and age and the control circuitry 1234 can use this information to provide the user 1208 with a comparison of the user's tracked sleep information to sleep information of other people having similar weights, heights, and/or ages as the user 1208. As another example, the user 1208 can use the user device 1210 as an interface for controlling air pressure of the air chambers 1206a and 1206b, for controlling various recline or incline positions of the bed 1202, for controlling temperature of one or more surface temperature control devices of the bed 1202, or for allowing the control circuitry 1234 to generate control signals for other devices (as described in greater detail below).

In some implementations, control circuitry 1234 of the bed 1202 (e.g., control circuitry 1234 integrated into the pump 1204) can communicate with other devices or systems in addition to or instead of the user device 1210. For example, the control circuitry 1234 can communicate with the television 1212, a lighting system 1214, a thermostat

1216, a security system 1218, or other house hold devices such as an oven 1222, a coffee maker 1224, a lamp 1226, and a nightlight 1228. Other examples of devices and/or systems that the control circuitry 1234 can communicate with include a system for controlling window blinds 1230, one or more devices for detecting or controlling the states of one or more doors 1232 (such as detecting if a door is open, detecting if a door is locked, or automatically locking a door), and a system for controlling a garage door 1220 (e.g., control circuitry 1234 integrated with a garage door opener for identifying an open or closed state of the garage door 1220 and for causing the garage door opener to open or close the garage door 1220). Communications between the control circuitry 1234 of the bed 1202 and other devices can occur through a network (e.g., a LAN or the Internet) or as point-to-point communication (e.g., using Bluetooth, radio communication, or a wired connection). In some implementations, control circuitry 1234 of different beds 1202 can communicate with different sets of devices. For example, a kid bed may not communicate with and/or control the same devices as an adult bed. In some embodiments, the bed 1202 can evolve with the age of the user such that the control circuitry 1234 of the bed 1202 communicates with different devices as a function of age of the user.

The control circuitry 1234 can receive information and inputs from other devices/systems and use the received information and inputs to control actions of the bed 1202 or other devices. For example, the control circuitry 1234 can receive information from the thermostat 1216 indicating a current environmental temperature for a house or room in which the bed 1202 is located. The control circuitry 1234 can use the received information (along with other information) to determine if a temperature of all or a portion of the surface of the bed 1202 should be raised or lowered. The control circuitry 1234 can then cause a heating or cooling mechanism (e.g., the foot warming system and/or the airflow system described herein) of the bed 1202 to raise or lower the temperature of the surface of the bed 1202. For example, the user 1208 can indicate a desired sleeping temperature of 74 degrees while a second user of the bed 1202 indicates a desired sleeping temperature of 72 degrees. The thermostat 1216 can indicate to the control circuitry 1234 that the current temperature of the bedroom is 72 degrees. The control circuitry 1234 can identify that the user 1208 has indicated a desired sleeping temperature of 74 degrees, and send control signals to a heating device (e.g., the foot warming pad and/or the airflow pad described herein) located on the user's side of the bed to raise the temperature of the portion (e.g., the foot or the middle) of the surface of the bed 1202 where the user 1208 is located to raise the temperature of the user's sleeping surface to the desired temperature.

The control circuitry 1234 can also generate control signals controlling other devices and propagate the control signals to the other devices. In some implementations, the control signals are generated based on information collected by the control circuitry 1234, including information related to user interaction with the bed 1202 by the user 1208 and/or one or more other users. In some implementations, information collected from one or more other devices other than the bed 1202 are used when generating the control signals. For example, information relating to environmental occurrences (e.g., environmental temperature, environmental noise level, and environmental light level), time of day, time of year, day of the week, or other information can be used when generating control signals for various devices in communication with the control circuitry 1234 of the bed 1202. For example, information on the time of day can be combined with information relating to movement and bed presence of the user 1208 to generate control signals for the lighting system 1214. In some implementations, rather than or in addition to providing control signals for one or more other devices, the control circuitry 1234 can provide collected information (e.g., information related to user movement, bed presence, sleep state, or biometric signals for the user 1208) to one or more other devices to allow the one or more other devices to utilize the collected information when generating control signals. For example, control circuitry 1234 of the bed 1202 can provide information relating to user interactions with the bed 1202 by the user 1208 to a central controller (not shown) that can use the provided information to generate control signals for various devices, including the bed 1202.

Still referring to FIG. 38, the control circuitry 1234 of the bed 1202 can generate control signals for controlling actions of other devices, and transmit the control signals to the other devices in response to information collected by the control circuitry 1234, including bed presence of the user 1208, sleep state of the user 1208, and other factors. For example, control circuitry 1234 integrated with the pump 1204 can detect a feature of a mattress of the bed 1202, such as an increase in pressure in the air chamber 1206*b*, and use this detected increase in air pressure to determine that the user 1208 is present on the bed 1202. In some implementations, the control circuitry 1234 can identify a heart rate or respiratory rate for the user 1208 to identify that the increase in pressure is due to a person sitting, laying, or otherwise resting on the bed 1202 rather than an inanimate object (such as a suitcase) having been placed on the bed 1202. In some implementations, the information indicating user bed presence is combined with other information to identify a current or future likely state for the user 1208. For example, a detected user bed presence at 11:00 am can indicate that the user is sitting on the bed (e.g., to tie her shoes, or to read a book) and does not intend to go to sleep, while a detected user bed presence at 10:00 pm can indicate that the user 1208 is in bed for the evening and is intending to fall asleep soon. As another example, if the control circuitry 1234 detects that the user 1208 has left the bed 1202 at 6:30 am (e.g., indicating that the user 1208 has woken up for the day), and then later detects user bed presence of the user 1208 at 7:30 am, the control circuitry 1234 can use this information that the newly detected user bed presence is likely temporary (e.g., while the user 1208 ties her shoes before heading to work) rather than an indication that the user 1208 is intending to stay on the bed 1202 for an extended period.

In some implementations, the control circuitry 1234 can use collected information (including information related to user interaction with the bed 1202 by the user 1208, as well as environmental information, time information, and input received from the user) to identify use patterns for the user 1208. For example, the control circuitry 1234 can use information indicating bed presence and sleep states for the user 1208 collected over a period of time to identify a sleep pattern for the user. For example, the control circuitry 1234 can identify that the user 1208 generally goes to bed between 9:30 pm and 10:00 pm, generally falls asleep between 10:00 pm and 11:00 pm, and generally wakes up between 6:30 am and 6:45 am based on information indicating user presence and biometrics for the user 1208 collected over a week. The control circuitry 1234 can use identified patterns for a user to better process and identify user interactions with the bed 1202 by the user 1208.

For example, given the above example user bed presence, sleep, and wake patterns for the user 1208, if the user 1208 is detected as being on the bed at 12:00 pm, the control circuitry 1234 can determine that the user's presence on the bed is only temporary, and use this determination to generate different control signals than would be generated if the control circuitry 1234 determined that the user 1208 was in bed for the evening. As another example, if the control circuitry 1234 detects that the user 1208 has gotten out of bed at 12:00 am, the control circuitry 1234 can use identified patterns for the user 1208 to determine that the user has only gotten up temporarily (for example, to use the rest room, or get a glass of water) and is not up for the day. By contrast, if the control circuitry 1234 identifies that the user 1208 has gotten out of the bed 1202 at 6:40 am, the control circuitry 1234 can determine that the user is up for the day and generate a different set of control signals than those that would be generated if it were determined that the user 1208 were only getting out of bed temporarily (as would be the case when the user 1208 gets out of the bed 1202 at 12:00 am). For other users 1208, getting out of the bed 1202 at 12:00 am can be the normal wake-up time, which the control circuitry 1234 can learn and respond to accordingly.

As described above, the control circuitry 1234 for the bed 1202 can generate control signals for control functions of various other devices. The control signals can be generated, at least in part, based on detected interactions by the user 1208 with the bed 1202, as well as other information including time, date, temperature, etc. For example, the control circuitry 1234 can communicate with the television 1212, receive information from the television 1212, and generate control signals for controlling functions of the television 1212. For example, the control circuitry 1234 can receive an indication from the television 1212 that the television 1212 is currently on. If the television 1212 is located in a different room from the bed 1202, the control circuitry 1234 can generate a control signal to turn the television 1212 off upon making a determination that the user 1208 has gone to bed for the evening. For example, if bed presence of the user 1208 on the bed 1202 is detected during a particular time range (e.g., between 8:00 pm and 7:00 am) and persists for longer than a threshold period of time (e.g., 10 minutes) the control circuitry 1234 can use this information to determine that the user 1208 is in bed for the evening. If the television 1212 is on (as indicated by communications received by the control circuitry 1234 of the bed 1202 from the television 1212) the control circuitry 1234 can generate a control signal to turn the television 1212 off. The control signals can then be transmitted to the television (e.g., through a directed communication link between the television 1212 and the control circuitry 1234 or through a network). As another example, rather than turning off the television 1212 in response to detection of user bed presence, the control circuitry 1234 can generate a control signal that causes the volume of the television 1212 to be lowered by a pre-specified amount.

As another example, upon detecting that the user 1208 has left the bed 1202 during a specified time range (e.g., between 6:00 am and 8:00 am) the control circuitry 1234 can generate control signals to cause the television 1212 to turn on and tune to a pre-specified channel (e.g., the user 1208 has indicated a preference for watching the morning news upon getting out of bed in the morning). The control circuitry 1234 can generate the control signal and transmit the signal to the television 1212 to cause the television 1212 to turn on and tune to the desired station (which could be stored at the control circuitry 1234, the television 1212, or another location). As another example, upon detecting that the user 1208 has gotten up for the day, the control circuitry 1234 can generate and transmit control signals to cause the television 1212 to turn on and begin playing a previously recorded program from a digital video recorder (DVR) in communication with the television 1212.

As another example, if the television 1212 is in the same room as the bed 1202, the control circuitry 1234 does not cause the television 1212 to turn off in response to detection of user bed presence. Rather, the control circuitry 1234 can generate and transmit control signals to cause the television 1212 to turn off in response to determining that the user 1208 is asleep. For example, the control circuitry 1234 can monitor biometric signals of the user 1208 (e.g., motion, heart rate, respiration rate) to determine that the user 1208 has fallen asleep. Upon detecting that the user 1208 is sleeping, the control circuitry 1234 generates and transmits a control signal to turn the television 1212 off. As another example, the control circuitry 1234 can generate the control signal to turn off the television 1212 after a threshold period of time after the user 1208 has fallen asleep (e.g., 10 minutes after the user has fallen asleep). As another example, the control circuitry 1234 generates control signals to lower the volume of the television 1212 after determining that the user 1208 is asleep. As yet another example, the control circuitry 1234 generates and transmits a control signal to cause the television to gradually lower in volume over a period of time and then turn off in response to determining that the user 1208 is asleep.

In some implementations, the control circuitry 1234 can similarly interact with other media devices, such as computers, tablets, smart phones, stereo systems, etc. For example, upon detecting that the user 1208 is asleep, the control circuitry 1234 can generate and transmit a control signal to the user device 1210 to cause the user device 1210 to turn off, or turn down the volume on a video or audio file being played by the user device 1210.

The control circuitry 1234 can additionally communicate with the lighting system 1214, receive information from the lighting system 1214, and generate control signals for controlling functions of the lighting system 1214. For example, upon detecting user bed presence on the bed 1202 during a certain time frame (e.g., between 8:00 pm and 7:00 am) that lasts for longer than a threshold period of time (e.g., 10 minutes) the control circuitry 1234 of the bed 1202 can determine that the user 1208 is in bed for the evening. In response to this determination, the control circuitry 1234 can generate control signals to cause lights in one or more rooms other than the room in which the bed 1202 is located to switch off. The control signals can then be transmitted to the lighting system 1214 and executed by the lighting system 1214 to cause the lights in the indicated rooms to shut off. For example, the control circuitry 1234 can generate and transmit control signals to turn off lights in all common rooms, but not in other bedrooms. As another example, the control signals generated by the control circuitry 1234 can indicate that lights in all rooms other than the room in which the bed 1202 is located are to be turned off, while one or more lights located outside of the house containing the bed 1202 are to be turned on, in response to determining that the user 1208 is in bed for the evening. Additionally, the control circuitry 1234 can generate and transmit control signals to cause the nightlight 1228 to turn on in response to determining user 1208 bed presence or whether the user 1208 is asleep. As another example, the control circuitry 1234 can generate first control signals for turning off a first set of lights (e.g., lights in common rooms) in response to detecting user bed presence, and second control signals for turning off a second set of lights (e.g., lights in the room in which the bed 1202 is located) in response to detecting that the user 1208 is asleep.

In some implementations, in response to determining that the user 1208 is in bed for the evening, the control circuitry 1234 of the bed 1202 can generate control signals to cause the lighting system 1214 to implement a sunset lighting scheme in the room in which the bed 1202 is located. A sunset lighting scheme can include, for example, dimming the lights (either gradually over time, or all at once) in combination with changing the color of the light in the bedroom environment, such as adding an amber hue to the lighting in the bedroom. The sunset lighting scheme can help to put the user 1208 to sleep when the control circuitry 1234 has determined that the user 1208 is in bed for the evening.

The control circuitry 1234 can also be configured to implement a sunrise lighting scheme when the user 1208 wakes up in the morning. The control circuitry 1234 can determine that the user 1208 is awake for the day, for example, by detecting that the user 1208 has gotten off of the bed 1202 (i.e., is no longer present on the bed 1202) during a specified time frame (e.g., between 6:00 am and 8:00 am). As another example, the control circuitry 1234 can monitor movement, heart rate, respiratory rate, or other biometric signals of the user 1208 to determine that the user 1208 is awake even though the user 1208 has not gotten out of bed. If the control circuitry 1234 detects that the user is awake during a specified time frame, the control circuitry 1234 can determine that the user 1208 is awake for the day. The specified time frame can be, for example, based on previously recorded user bed presence information collected over a period of time (e.g., two weeks) that indicates that the user 1208 usually wakes up for the day between 6:30 am and 7:30 am. In response to the control circuitry 1234 determining that the user 1208 is awake, the control circuitry 1234 can generate control signals to cause the lighting system 1214 to implement the sunrise lighting scheme in the bedroom in which the bed 1202 is located. The sunrise lighting scheme can include, for example, turning on lights (e.g., the lamp 1226, or other lights in the bedroom). The sunrise lighting scheme can further include gradually increasing the level of light in the room where the bed 1202 is located (or in one or more other rooms). The sunrise lighting scheme can also include only turning on lights of specified colors. For example, the sunrise lighting scheme can include lighting the bedroom with blue light to gently assist the user 1208 in waking up and becoming active.

In some implementations, the control circuitry 1234 can generate different control signals for controlling actions of one or more components, such as the lighting system 1214, depending on a time of day that user interactions with the bed 1202 are detected. For example, the control circuitry 1234 can use historical user interaction information for interactions between the user 1208 and the bed 1202 to determine that the user 1208 usually falls asleep between 10:00 pm and 11:00 pm and usually wakes up between 6:30 am and 7:30 am on weekdays. The control circuitry 1234 can use this information to generate a first set of control signals for controlling the lighting system 1214 if the user 1208 is detected as getting out of bed at 12:00 am and to generate a second set of control signals for controlling the lighting system 1214 if the user 1208 is detected as getting out of bed after 6:30 am. For example, if the user 1208 gets out of bed prior to 6:30 am, the control circuitry 1234 can turn on lights that guide the user 1208's route to a restroom. As another example, if the user 1208 gets out of bed prior to 6:30 am, the control circuitry 1234 can turn on lights that guide the user 1208's route to the kitchen (which can include, for example, turning on the nightlight 1228, turning on under bed lighting, or turning on the lamp 1226).

As another example, if the user 1208 gets out of bed after 6:30 am, the control circuitry 1234 can generate control signals to cause the lighting system 1214 to initiate a sunrise lighting scheme, or to turn on one or more lights in the bedroom and/or other rooms. In some implementations, if the user 1208 is detected as getting out of bed prior to a specified morning rise time for the user 1208, the control circuitry 1234 causes the lighting system 1214 to turn on lights that are dimmer than lights that are turned on by the lighting system 1214 if the user 1208 is detected as getting out of bed after the specified morning rise time. Causing the lighting system 1214 to only turn on dim lights when the user 1208 gets out of bed during the night (i.e., prior to normal rise time for the user 1208) can prevent other occupants of the house from being woken by the lights while still allowing the user 1208 to see in order to reach the restroom, kitchen, or another destination within the house.

The historical user interaction information for interactions between the user 1208 and the bed 1202 can be used to identify user sleep and awake time frames. For example, user bed presence times and sleep times can be determined for a set period of time (e.g., two weeks, a month, etc.). The control circuitry 1234 can then identify a typical time range or time frame in which the user 1208 goes to bed, a typical time frame for when the user 1208 falls asleep, and a typical time frame for when the user 1208 wakes up (and in some cases, different time frames for when the user 1208 wakes up and when the user 1208 actually gets out of bed). In some implementations, buffer time can be added to these time frames. For example, if the user is identified as typically going to bed between 10:00 pm and 10:30 pm, a buffer of a half hour in each direction can be added to the time frame such that any detection of the user getting onto the bed between 9:30 pm and 11:00 pm is interpreted as the user 1208 going to bed for the evening. As another example, detection of bed presence of the user 1208 starting from a half hour before the earliest typical time that the user 1208 goes to bed extending until the typical wake up time (e.g., 6:30 am) for the user can be interpreted as the user going to bed for the evening. For example, if the user typically goes to bed between 10:00 pm and 10:30 pm, if the user's bed presence is sensed at 12:30 am one night, that can be interpreted as the user getting into bed for the evening even though this is outside of the user's typical time frame for going to bed because it has occurred prior to the user's normal wake up time. In some implementations, different time frames are identified for different times of the year (e.g., earlier bed time during winter vs. summer) or at different times of the week (e.g., user wakes up earlier on weekdays than on weekends).

The control circuitry 1234 can distinguish between the user 1208 going to bed for an extended period (such as for the night) as opposed to being present on the bed 1202 for a shorter period (such as for a nap) by sensing duration of presence of the user 1208. In some examples, the control circuitry 1234 can distinguish between the user 1208 going to bed for an extended period (such as for the night) as opposed to going to bed for a shorter period (such as for a nap) by sensing duration of sleep of the user 1208. For example, the control circuitry 1234 can set a time threshold whereby if the user 1208 is sensed on the bed 1202 for longer than the threshold, the user 1208 is considered to have gone to bed for the night. In some examples, the threshold can be about 2 hours, whereby if the user 1208 is sensed on the bed 1202 for greater than 2 hours, the control circuitry 1234 registers that as an extended sleep event. In other examples, the threshold can be greater than or less than two hours.

The control circuitry 1234 can detect repeated extended sleep events to determine a typical bed time range of the user 1208 automatically, without requiring the user 1208 to enter a bed time range. This can allow the control circuitry 1234 to accurately estimate when the user 1208 is likely to go to bed for an extended sleep event, regardless of whether the user 1208 typically goes to bed using a traditional sleep schedule or a non-traditional sleep schedule. The control circuitry 1234 can then use knowledge of the bed time range of the user 1208 to control one or more components (including components of the bed 1202 and/or non-bed peripherals) differently based on sensing bed presence during the bed time range or outside of the bed time range.

In some examples, the control circuitry 1234 can automatically determine the bed time range of the user 1208 without requiring user inputs. In some examples, the control circuitry 1234 can determine the bed time range of the user 1208 automatically and in combination with user inputs. In some examples, the control circuitry 1234 can set the bed time range directly according to user inputs. In some examples, the control circuitry 1234 can associate different bed times with different days of the week. In each of these examples, the control circuitry 1234 can control one or more components (such as the lighting system 1214, the thermostat 1216, the security system 1218, the oven 1222, the coffee maker 1224, the lamp 1226, and the nightlight 1228), as a function of sensed bed presence and the bed time range.

The control circuitry 1234 can additionally communicate with the thermostat 1216, receive information from the thermostat 1216, and generate control signals for controlling functions of the thermostat 1216. For example, the user 1208 can indicate user preferences for different temperatures at different times, depending on the sleep state or bed presence of the user 1208. For example, the user 1208 may prefer an environmental temperature of 72 degrees when out of bed, 70 degrees when in bed but awake, and 68 degrees when sleeping. The control circuitry 1234 of the bed 1202 can detect bed presence of the user 1208 in the evening and determine that the user 1208 is in bed for the night. In response to this determination, the control circuitry 1234 can generate control signals to cause the thermostat to change the temperature to 70 degrees. The control circuitry 1234 can then transmit the control signals to the thermostat 1216. Upon detecting that the user 1208 is in bed during the bed time range or asleep, the control circuitry 1234 can generate and transmit control signals to cause the thermostat 1216 to change the temperature to 68. The next morning, upon determining that the user is awake for the day (e.g., the user 1208 gets out of bed after 6:30 am) the control circuitry 1234 can generate and transmit control circuitry 1234 to cause the thermostat to change the temperature to 72 degrees.

In some implementations, the control circuitry 1234 can similarly generate control signals to cause one or more heating or cooling elements (e.g., the foot warming pads and/or the airflow pads described herein) on the surface of the bed 1202 to change temperature at various times, either in response to user interaction with the bed 1202 or at various pre-programmed times. For example, the control circuitry 1234 can activate a heating element to raise the temperature of one side of the surface of the bed 1202 to 73 degrees when it is detected that the user 1208 has fallen asleep. As another example, upon determining that the user 1208 is up for the day, the control circuitry 1234 can turn off a heating or cooling element. As yet another example, the user 1208 can pre-program various times at which the temperature at the surface of the bed should be raised or lowered. For example, the user can program the bed 1202 to raise the surface temperature to 76 degrees at 10:00 pm, and lower the surface temperature to 68 degrees at 11:30 pm.

In some implementations, in response to detecting user bed presence of the user 1208 and/or that the user 1208 is asleep, the control circuitry 1234 can cause the thermostat 1216 to change the temperature in different rooms to different values. For example, in response to determining that the user 1208 is in bed for the evening, the control circuitry 1234 can generate and transmit control signals to cause the thermostat 1216 to set the temperature in one or more bedrooms of the house to 72 degrees and set the temperature in other rooms to 67 degrees.

The control circuitry 1234 can also receive temperature information from the thermostat 1216 and use this temperature information to control functions of the bed 1202 or other devices. For example, as discussed above, the control circuitry 1234 can adjust temperatures of heating elements included in the bed 1202 in response to temperature information received from the thermostat 1216.

In some implementations, the control circuitry 1234 can generate and transmit control signals for controlling other temperature control systems. For example, in response to determining that the user 1208 is awake for the day, the control circuitry 1234 can generate and transmit control signals for causing floor heating elements to activate. For example, the control circuitry 1234 can cause a floor heating system for a master bedroom to turn on in response to determining that the user 1208 is awake for the day.

The control circuitry 1234 can additionally communicate with the security system 1218, receive information from the security system 1218, and generate control signals for controlling functions of the security system 1218. For example, in response to detecting that the user 1208 in is bed for the evening, the control circuitry 1234 can generate control signals to cause the security system to engage or disengage security functions. The control circuitry 1234 can then transmit the control signals to the security system 1218 to cause the security system 1218 to engage. As another example, the control circuitry 1234 can generate and transmit control signals to cause the security system 1218 to disable in response to determining that the user 1208 is awake for the day (e.g., user 1208 is no longer present on the bed 1202 after 6:00 am). In some implementations, the control circuitry 1234 can generate and transmit a first set of control signals to cause the security system 1218 to engage a first set of security features in response to detecting user bed presence of the user 1208, and can generate and transmit a second set of control signals to cause the security system 1218 to engage a second set of security features in response to detecting that the user 1208 has fallen asleep.

In some implementations, the control circuitry 1234 can receive alerts from the security system 1218 and indicate the alert to the user 1208. For example, the control circuitry 1234 can detect that the user 1208 is in bed for the evening and in response, generate and transmit control signals to cause the security system 1218 to engage or disengage. The security system can then detect a security breach (e.g., someone has opened the door 1232 without entering the security code, or someone has opened a window when the security system 1218 is engaged). The security system 1218 can communicate the security breach to the control circuitry 1234 of the bed 1202. In response to receiving the communication from the security system 1218, the control circuitry 1234 can generate control signals to alert the user 1208 to the security breach. For example, the control circuitry 1234 can cause the bed 1202 to vibrate. As another example, the control circuitry 1234 can cause portions of the bed 1202 to articulate (e.g., cause the head section to raise or lower) in order to wake the user 1208 and alert the user to the security breach. As another example, the control circuitry 1234 can generate and transmit control signals to cause the lamp 1226 to flash on and off at regular intervals to alert the user 1208 to the security breach. As another example, the control circuitry 1234 can alert the user 1208 of one bed 1202 regarding a security breach in a bedroom of another bed, such as an open window in a kid's bedroom. As another example, the control circuitry 1234 can send an alert to a garage door controller (e.g., to close and lock the door). As another example, the control circuitry 1234 can send an alert for the security to be disengaged.

The control circuitry 1234 can additionally generate and transmit control signals for controlling the garage door 1220 and receive information indicating a state of the garage door 1220 (i.e., open or closed). For example, in response to determining that the user 1208 is in bed for the evening, the control circuitry 1234 can generate and transmit a request to a garage door opener or another device capable of sensing if the garage door 1220 is open. The control circuitry 1234 can request information on the current state of the garage door 1220. If the control circuitry 1234 receives a response (e.g., from the garage door opener) indicating that the garage door 1220 is open, the control circuitry 1234 can either notify the user 1208 that the garage door is open, or generate a control signal to cause the garage door opener to close the garage door 1220. For example, the control circuitry 1234 can send a message to the user device 1210 indicating that the garage door is open. As another example, the control circuitry 1234 can cause the bed 1202 to vibrate. As yet another example, the control circuitry 1234 can generate and transmit a control signal to cause the lighting system 1214 to cause one or more lights in the bedroom to flash to alert the user 1208 to check the user device 1210 for an alert (in this example, an alert regarding the garage door 1220 being open). Alternatively, or additionally, the control circuitry 1234 can generate and transmit control signals to cause the garage door opener to close the garage door 1220 in response to identifying that the user 1208 is in bed for the evening and that the garage door 1220 is open. In some implementations, control signals can vary depend on the age of the user 1208.

The control circuitry 1234 can similarly send and receive communications for controlling or receiving state information associated with the door 1232 or the oven 1222. For example, upon detecting that the user 1208 is in bed for the evening, the control circuitry 1234 can generate and transmit a request to a device or system for detecting a state of the door 1232. Information returned in response to the request can indicate various states for the door 1232 such as open, closed but unlocked, or closed and locked. If the door 1232 is open or closed but unlocked, the control circuitry 1234 can alert the user 1208 to the state of the door, such as in a manner described above with reference to the garage door 1220. Alternatively, or in addition to alerting the user 1208, the control circuitry 1234 can generate and transmit control signals to cause the door 1232 to lock, or to close and lock. If the door 1232 is closed and locked, the control circuitry 1234 can determine that no further action is needed.

Similarly, upon detecting that the user 1208 is in bed for the evening, the control circuitry 1234 can generate and transmit a request to the oven 1222 to request a state of the oven 1222 (e.g., on or off). If the oven 1222 is on, the control circuitry 1234 can alert the user 1208 and/or generate and transmit control signals to cause the oven 1222 to turn off. If the oven is already off, the control circuitry 1234 can determine that no further action is necessary. In some implementations, different alerts can be generated for different events. For example, the control circuitry 1234 can cause the lamp 1226 (or one or more other lights, via the lighting system 1214) to flash in a first pattern if the security system 1218 has detected a breach, flash in a second pattern if garage door 1220 is on, flash in a third pattern if the door 1232 is open, flash in a fourth pattern if the oven 1222 is on, and flash in a fifth pattern if another bed has detected that a user of that bed has gotten up (e.g., that a child of the user 1208 has gotten out of bed in the middle of the night as sensed by a sensor in the bed 1202 of the child). Other examples of alerts that can be processed by the control circuitry 1234 of the bed 1202 and communicated to the user include a smoke detector detecting smoke (and communicating this detection of smoke to the control circuitry 1234), a carbon monoxide tester detecting carbon monoxide, a heater malfunctioning, or an alert from any other device capable of communicating with the control circuitry 1234 and detecting an occurrence that should be brought to the user 1208's attention.

The control circuitry 1234 can also communicate with a system or device for controlling a state of the window blinds 1230. For example, in response to determining that the user 1208 is in bed for the evening, the control circuitry 1234 can generate and transmit control signals to cause the window blinds 1230 to close. As another example, in response to determining that the user 1208 is up for the day (e.g., user has gotten out of bed after 6:30 am) the control circuitry 1234 can generate and transmit control signals to cause the window blinds 1230 to open. By contrast, if the user 1208 gets out of bed prior to a normal rise time for the user 1208, the control circuitry 1234 can determine that the user 1208 is not awake for the day and does not generate control signals for causing the window blinds 1230 to open. As yet another example, the control circuitry 1234 can generate and transmit control signals that cause a first set of blinds to close in response to detecting user bed presence of the user 1208 and a second set of blinds to close in response to detecting that the user 1208 is asleep.

The control circuitry 1234 can generate and transmit control signals for controlling functions of other household devices in response to detecting user interactions with the bed 1202. For example, in response to determining that the user 1208 is awake for the day, the control circuitry 1234 can generate and transmit control signals to the coffee maker 1224 to cause the coffee maker 1224 to begin brewing coffee. As another example, the control circuitry 1234 can generate and transmit control signals to the oven 1222 to cause the oven to begin preheating (for users that like fresh baked bread in the morning). As another example, the control circuitry 1234 can use information indicating that the user 1208 is awake for the day along with information indicating that the time of year is currently winter and/or that the outside temperature is below a threshold value to generate and transmit control signals to cause a car engine block heater to turn on.

Additionally, functions of the bed 1202 are controlled by the control circuitry 1234 in response to user interactions with the bed 1202. For example, the bed 1202 can include an adjustable foundation and an articulation controller configured to adjust the position of one or more portions of the bed 1202 by adjusting the adjustable foundation that supports the bed. For example, the articulation controller can adjust the bed 1202 from a flat position to a position in which a head portion of a mattress of the bed 1202 is inclined upward (e.g., to facilitate a user sitting up in bed and/or watching television). In some implementations, the bed 1202 includes multiple separately articulable sections. For example, portions of the bed corresponding to the locations of the air chambers 1206a and 1206b can be articulated independently from each other, to allow one person positioned on the bed 1202 surface to rest in a first position (e.g., a flat position) while a second person rests in a second position (e.g., a reclining position with the head raised at an angle from the waist). In some implementations, separate positions can be set for two different beds (e.g., two twin beds placed next to each other). The foundation of the bed 1202 can include more than one zone that can be independently adjusted. The articulation controller can also be configured to provide different levels of massage to one or more users on the bed 1202 or to cause the bed to vibrate to communicate alerts to the user 1208 as described above.

The control circuitry 1234 can adjust positions (e.g., incline and decline positions for the user 1208 and/or an additional user of the bed 1202) in response to user interactions with the bed 1202. For example, the control circuitry 1234 can cause the articulation controller to adjust the bed 1202 to a first recline position for the user 1208 in response to sensing user bed presence for the user 1208. The control circuitry 1234 can cause the articulation controller to adjust the bed 1202 to a second recline position (e.g., a less reclined, or flat position) in response to determining that the user 1208 is asleep. As another example, the control circuitry 1234 can receive a communication from the television 1212 indicating that the user 1208 has turned off the television 1212, and in response the control circuitry 1234 can cause the articulation controller to adjust the position of the bed 1202 to a preferred user sleeping position (e.g., due to the user turning off the television 1212 while the user 1208 is in bed indicating that the user 1208 wishes to go to sleep).

In some implementations, the control circuitry 1234 can control the articulation controller so as to wake up one user of the bed 1202 without waking another user of the bed 1202. For example, the user 1208 and a second user of the bed 1202 can each set distinct wakeup times (e.g., 6:30 am and 7:15 am respectively). When the wakeup time for the user 1208 is reached, the control circuitry 1234 can cause the articulation controller to vibrate or change the position of only a side of the bed on which the user 1208 is located to wake the user 1208 without disturbing the second user. When the wakeup time for the second user is reached, the control circuitry 1234 can cause the articulation controller to vibrate or change the position of only the side of the bed on which the second user is located. Alternatively, when the second wakeup time occurs, the control circuitry 1234 can utilize other methods (such as audio alarms, or turning on the lights) to wake the second user since the user 1208 is already awake and therefore will not be disturbed when the control circuitry 1234 attempts to wake the second user.

Still referring to FIG. 38, the control circuitry 1234 for the bed 1202 can utilize information for interactions with the bed 1202 by multiple users to generate control signals for controlling functions of various other devices. For example, the control circuitry 1234 can wait to generate control signals for, for example, engaging the security system 1218, or instructing the lighting system 1214 to turn off lights in various rooms until both the user 1208 and a second user are detected as being present on the bed 1202. As another example, the control circuitry 1234 can generate a first set of control signals to cause the lighting system 1214 to turn off a first set of lights upon detecting bed presence of the user 1208 and generate a second set of control signals for turning off a second set of lights in response to detecting bed presence of a second user. As another example, the control circuitry 1234 can wait until it has been determined that both the user 1208 and a second user are awake for the day before generating control signals to open the window blinds 1230. As yet another example, in response to determining that the user 1208 has left the bed and is awake for the day, but that a second user is still sleeping, the control circuitry 1234 can generate and transmit a first set of control signals to cause the coffee maker 1224 to begin brewing coffee, to cause the security system 1218 to deactivate, to turn on the lamp 1226, to turn off the nightlight 1228, to cause the thermostat 1216 to raise the temperature in one or more rooms to 72 degrees, and to open blinds (e.g., the window blinds 1230) in rooms other than the bedroom in which the bed 1202 is located. Later, in response to detecting that the second user is no longer present on the bed (or that the second user is awake) the control circuitry 1234 can generate and transmit a second set of control signals to, for example, cause the lighting system 1214 to turn on one or more lights in the bedroom, to cause window blinds in the bedroom to open, and to turn on the television 1212 to a pre-specified channel.

Closed Loop Control (Feature Group #6)

Figure 39A:
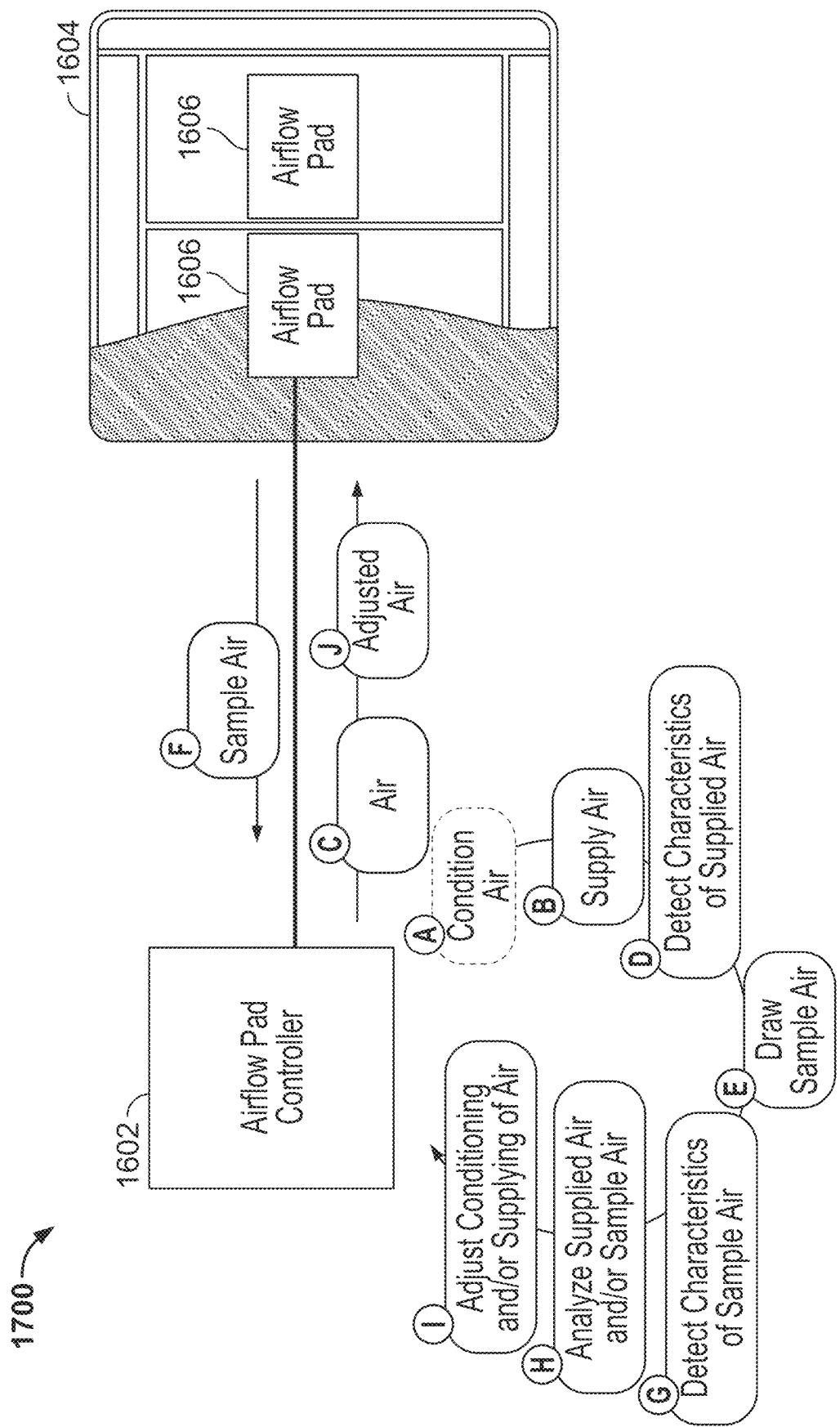
FIG. 39A illustrates an example method for operating an airflow pad controller to control a microclimate of the mattress.

FIG. 39A illustrates an example method 1700 for operating the airflow pad controller 1602 to control a microclimate of the mattress 1604. The airflow pad controller 1602 can draw ambient or conditioned air from, or supply ambient or conditioned air to, the airflow pad 1606 (also referred to as an air layer) arranged in the mattress 1604 (e.g., below the top of the mattress) to control the temperature at the top surface of the mattress.

In some implementations, the airflow pad controller 1602 can operate to condition air (Step A). The air can be conditioned based on one or more values that can be set by a user via, e.g., the remote control or the user computing device. Alternatively, the values can be automatically determined to satisfy the user profile or preference. Examples of such values include temperature values, humidity, and other suitable values that can be manually or automatically determined. In some implementations, the controller 1602 can heat air at a temperature that is set by a user or automatically determined for optimally controlling the microclimate of the mattress 1604. For example, the controller 1602 includes the heater 1614 activated to heat air as the fan 1610 drives the air to pass through or around the heater. In other implementations, the controller 1602 can cool air at a temperature that is manually set or automatically determined for improved or optimal microclimate control of the mattress. For example, the controller 1602 can include the cooler 1616 activated to cool air as the fan drives the air to pass through or around the cooler.

The airflow pad controller 1602 can drive air (Step B) so that the air is supplied to the airflow pad 1606 of the mattress 1604 (Step C). In embodiments where the air is conditioned (as described in Step A), the airflow pad controller 1602 operates to supply the conditioned air to the airflow pad 1606. In other embodiments, the controller 1602 can operate to supply ambient air to the airflow pad 1606. For example, the controller 1602 activates the fan 1610 at a desired speed to drive the ambient or conditioned air to the airflow pad 1606.

The airflow pad controller 1602 operates to detect one or more characteristics of the air supplied from the controller 1602 (Step D). In some implementations, the airflow pad controller 1602 can detect a temperature of the supplied air. For example, the temperature sensor 1630 of the controller 1602 can be used to detect the temperature of the supplied air. Alternatively or in addition, the airflow pad controller 1602 can detect a humidity of the supplied air using, for example, the humidity sensor 1632. Other characteristics of the supplied air can also be detected for various purposes.

The airflow pad controller 1602 can draw air (Step E) so that air is sampled from the airflow pad 1606 (Step F). For example, the airflow pad controller 1602 can operate the air fan 1610 in a reverse direction to draw air from the airflow pad 1606. Alternatively, the airflow pad controller 1602 can include another fan that is separate from the air fan 1610 and operates in an opposite direction to draw air from the airflow pad 1606. The drawing of air can be performed for a predetermined period of time, which can be relatively short to draw a small amount of air from the airflow pad 1606 for sampling.

The airflow pad controller 1602 can detect one or more characteristics of the sample air (Step G). In some implementations, the airflow pad controller 1602 can detect a temperature of the sample air using, for example, the temperature sensor 1630. Alternatively or in addition, the airflow pad controller 1602 can detect a humidity of the sample air using, for example, the humidity sensor 1632. Other characteristics of the supplied air can also be detected for various purposes.

The airflow pad controller 1602 can analyze the supplied air and/or the sample air (Step H). In some implementations, the airflow pad controller 1602 can compare the value(s) of the detected characteristic(s) of the supplied air with predetermined value(s) and identify any difference between the values. Alternatively or in addition, the airflow pad controller 1602 can compare the value(s) of the detected characteristic(s) of the sample air with predetermined value(s) and identify any difference between the values. The predetermined values can represent values for achieving desired microclimate control at the bed. For example, the predetermined values can include a predetermined air temperature value (e.g., at the location of the temperature sensor) required to achieve a desired temperature and/or humidity at a particular area in the bed (e.g., at the top of the mattress). In another example, the predetermined values can include a predetermined air humidity value (e.g., at the location of the temperature sensor) required to achieve a desired temperature and/or humidity at the particular area in the bed (e.g., at the top of the mattress).

Alternatively or in addition, the airflow pad controller 1602 can compare the value(s) of the detected characteristic(s) of the supplied air with the value(s) of the detected characteristic(s) of the sample air and identify any difference between the values.

The airflow pad controller 1602 can operate to adjust conditioning of air and/or supplying of ambient or conditioned air based on the analysis (Step I) so that adjusted air is supplied to the airflow pad 1606 (Step J). For example, the airflow pad controller 1602 can control the air conditioner 1612 to adjust the temperature of air, and/or control the fan 1610 to change the flow rate of the air. The temperature and/or the flow rate of air can be adjusted to reduce or eliminate the difference between the value(s) of the detected characteristic(s) of air (e.g., supplied air or sample air) and the predetermined value(s), so that the desired temperature and/or humidity can be achieved at the particular bed area (e.g., at the top of the mattress). Alternatively, the temperature and/or the flow rate of air can be adjusted so that the difference between the value(s) of the detected characteristic(s) of the supplied air and the value(s) of the detected characteristic(s) of the sample air can meet one or more threshold values representative of desired microclimate control.

In an example process for controlling the microclimate of the mattress 1604, the airflow pad controller 1602 can activate the heater 1614 to heat air and activate the air fan 1610 in a direction to supply the heated air to a top of the mattress. As described herein, for example, the heated air can be supplied to the top of the mattress through the airflow pad 1606. The airflow pad controller 1602 can further control the air fan 1610 in an opposite direction to draw an amount of air from the top of the mattress for a predetermined period time. For example, the air can be drawn from the top of the mattress through the airflow pad 1606. Alternatively, the airflow pad controller 1602 can include a separate air fan operable in such an opposite direction to draw air. The airflow pad controller 1602 can detect a temperature of the amount of air drawn from the top of the mattress, and use the temperature to adjust the operation of the heating element and/or the air fan. For example, the airflow pad controller 1602 can activate the heating element and/or the reversible fan again whereby activation of at least one of the heating element and the reversible fan is adjusted based on the temperature detected.

In another example process for controlling the microclimate of the mattress 1604, the airflow pad controller 1602 supplies air to the mattress 1604 over a first extended period to control a microclimate at a top of the mattress 1604. The airflow pad controller 1602 can sample air temperature at the microclimate over a brief sampling period by reversing airflow to draw air from the mattress to a temperature sensor (e.g., the temperature sensor 1630 in FIG. 37). Then, the airflow pad controller 1602 can supply air to the mattress again over a second extended period so that air is supplied in a manner different than during the first extended period as a function of the air temperature sampled while airflow was reversed. In some implementations, the first and second extended periods can range between 5 and 300 minutes long. In some implementations, the brief sampling period can range between 5 and 300 seconds long.

Figure 39B:
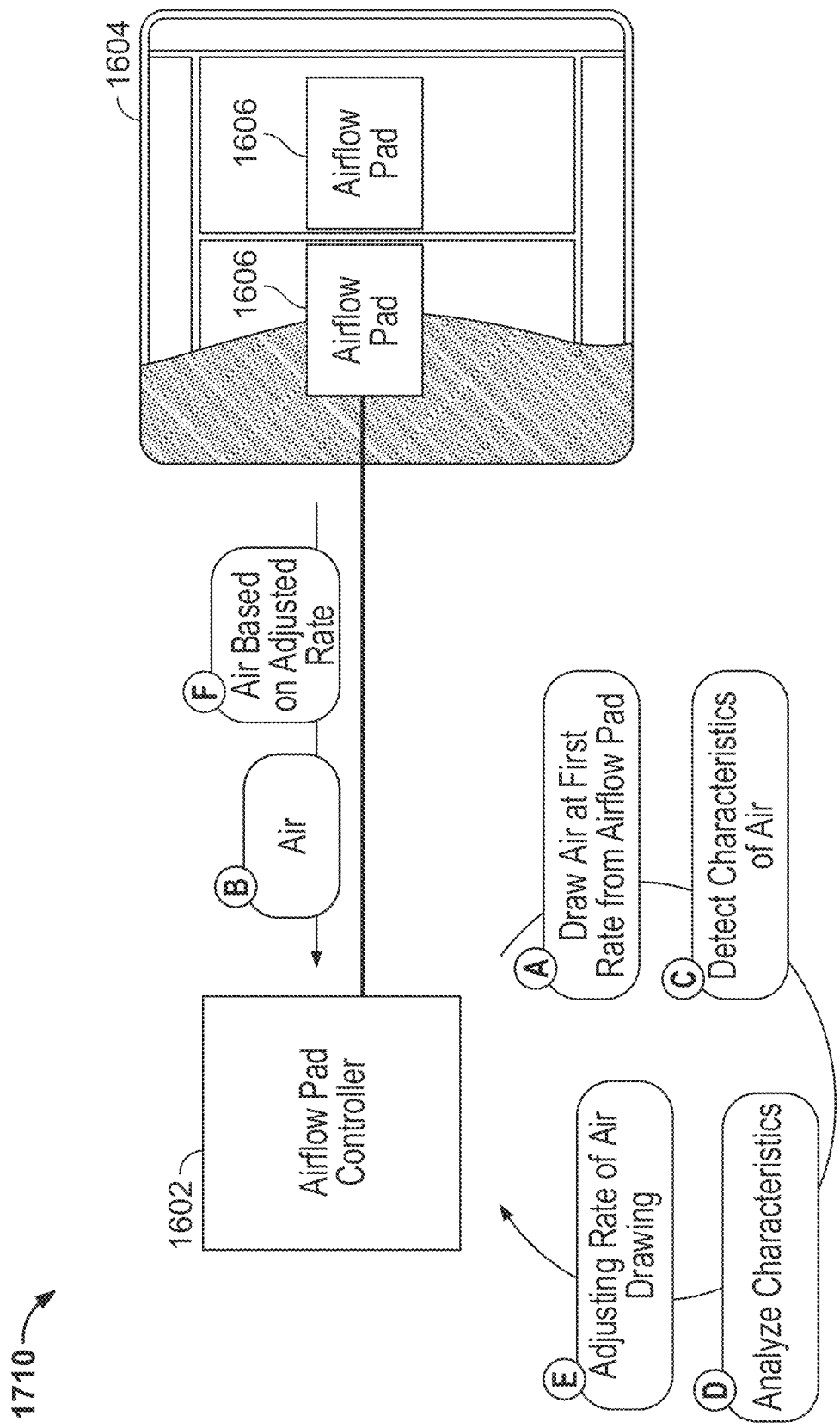
FIG. 39B illustrates another example method for operating the airflow pad controller to control a microclimate of the mattress.

FIG. 39B illustrates another example method 1710 for operating the airflow pad controller 1602 to control a microclimate of the mattress 1604. In this example, the airflow pad controller 1602 can operate to draw air from the airflow pad 1606 at a predetermined flow rate (Step A) so that the air flows back into the airflow pad controller 1602 (Step B). The airflow pad controller 1602 can activate the fan 1610 to draw air from the airflow pad 1606. In some implementations, the airflow pad controller 1602 can be in a normal mode of operation where ambient air is drawn from the airflow pad 1606 at a predetermined flow rate to control a microclimate of the mattress 1604 (e.g., the temperature at the top of the mattress). The predetermined flow rate can be determined to achieve a desired temperature and/or humidity that is manually set or automatically determined. Alternatively, drawing of air can be performed in other modes of operation as described herein.

The airflow pad controller 1602 can operate to detect one or more characteristics of the air drawn from the airflow pad 1606 (Step C). In some implementations, the airflow pad controller 1602 can detect a temperature of the supplied air using, for example, the temperature sensor 1630 of the controller 1602. Alternatively or in addition, the airflow pad controller 1602 can detect a humidity of the drawn air using, for example, the humidity sensor 1632. Other characteristics of the supplied air can also be detected for various purposes.

The airflow pad controller 1602 can analyze the characteristics of the air (Step D). In some implementations, the airflow pad controller 1602 can compare the value(s) of the detected characteristic(s) of the drawn air with predetermined value(s) and identify any difference between the values. The predetermined values can represent values for achieving desired microclimate control at the bed. For example, the predetermined values can include a predetermined air temperature value (e.g., at the location of the temperature sensor) required to achieve a desired temperature and/or humidity at a particular area in the bed (e.g., at the top of the mattress). In another example, the predetermined values can include a predetermined air humidity value (e.g., at the location of the temperature sensor) required to achieve a desired temperature and/or humidity at the particular area in the bed (e.g., at the top of the mattress).

The airflow pad controller 1602 can operate to adjust the flow rate of air being drawn from the airflow pad 1606 based on the analysis (Step E) so that air flows from the airflow pad 1606 into the controller 1602 at the adjusted flow rate (Step F). For example, the airflow pad controller 1602 can control the operation of the fan 1610 so that the fan 1610 can speed up or down to adjust the flow rate. The flow rate can be adjusted to reduce or eliminate the difference between the value(s) of the detected air characteristic(s) and the predetermined value(s), so that the desired temperature and/or humidity can be achieved at the particular bed area (e.g., at the top of the mattress).

In an example process for controlling the microclimate of the mattress 1604, the airflow pad controller 1602 can activate the fan 1610 to draw air from the airflow pad 1606. The airflow pad 1606 can be arranged under a top foam layer of the mattress 1604 and configured to permit an airflow rate being higher than an airflow rate of the top foam layer. The airflow pad controller 1602 can detect a temperature of the air drawn from the airflow pad 1606, and adjust activation of the fan 1610 based on the temperature.

Figure 39C:
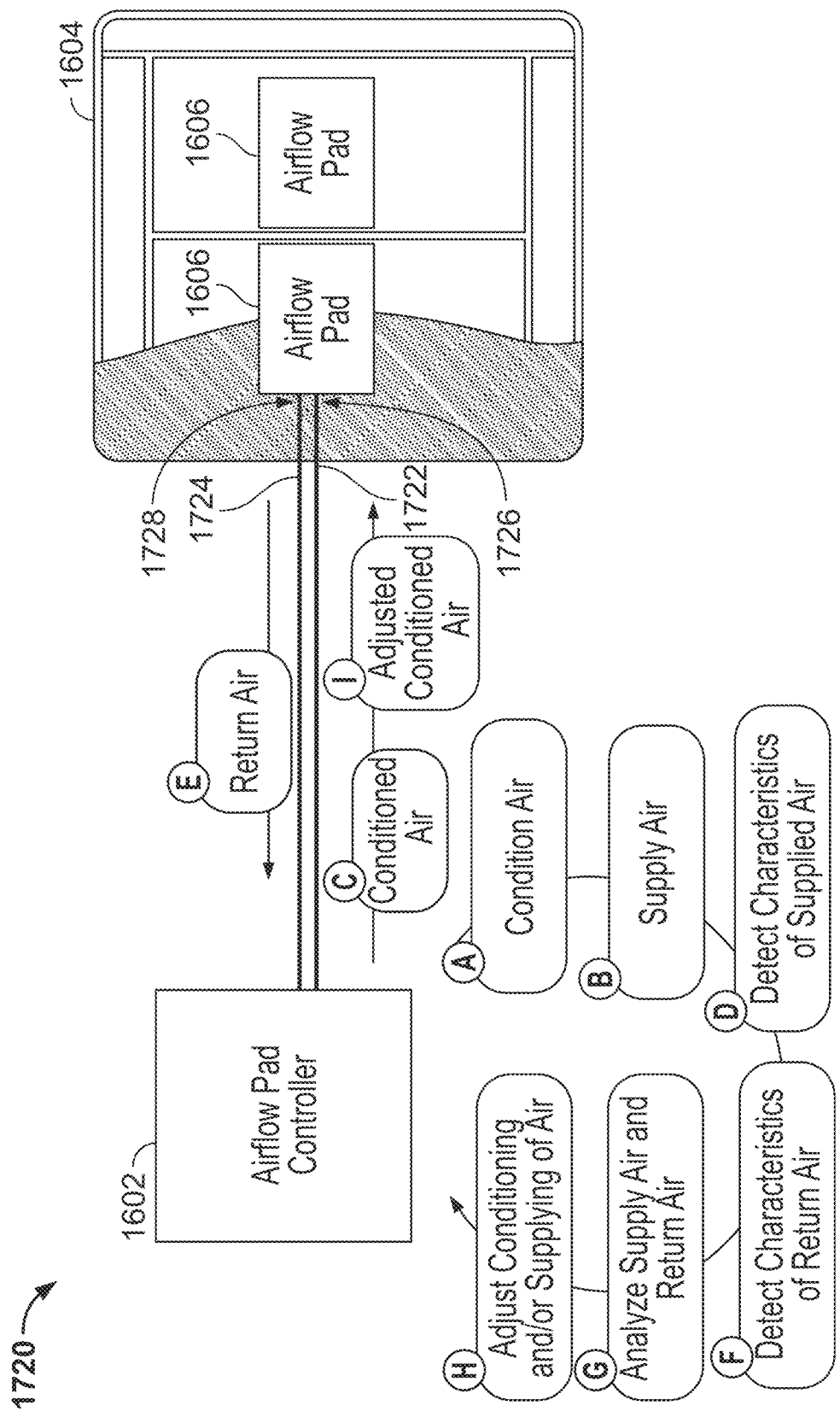
FIG. 39C illustrates yet another example method for operating the airflow pad controller to control a microclimate of the mattress.

FIG. 39C illustrates yet another example method 1720 for operating the airflow pad controller 1602 to control a microclimate of the mattress 1604. In this example, the airflow pad 1606 can be fluidly connected to an inlet conduit 1722 at an air inlet 1726, and a separate outlet conduit 1724 at an air outlet 1728, so that air can flow into the airflow pad 1606 through the inlet conduit 1722 and exit through the outlet conduit 1724.

The airflow pad controller 1602 can operate to condition air (Step A). The air can be conditioned based on one or more values that can be set by a user via, e.g., the remote control or the user computing device. Alternatively, the values can be automatically determined to satisfy the user profile or preference. Examples of such values include temperature values, humidity, and other suitable values that can be manually or automatically determined. In some implementations, the controller 1602 can heat air at a temperature that is set by a user or automatically determined for optimally controlling the microclimate of the mattress 1604. For example, the controller 1602 includes the heater 1614 activated to heat air as the fan 1610 drives the air to pass through or around the heater. In other implementations, the controller 1602 can cool air at a temperature that is manually set or automatically determined for optimal microclimate control of the mattress. For example, the controller 1602 includes the cooler 1616 activated to cool air as the fan drives the air to pass through or around the cooler.

The airflow pad controller 1602 can drive air (Step B) so that the conditioned air is supplied to the airflow pad 1606 of the mattress 1604 through the inlet conduit 1722 (Step C). Alternatively, the controller 1602 can operate to supply ambient air to the airflow pad 1606 without conditioning it. For example, the controller 1602 activates the fan 1610 at a desired speed to drive the air to the airflow pad 1606.

The airflow pad controller 1602 operates to detect one or more characteristics of the air supplied from the controller 1602 (Step D). In some implementations, the airflow pad controller 1602 can detect a temperature of the supplied air. For example, the temperature sensor 1630 of the controller 1602 can be used to detect the temperature of the supplied air. Alternatively or in addition, the airflow pad controller 1602 can detect a humidity of the supplied air using, for example, the humidity sensor 1632. Other characteristics of the supplied air can also be detected for various purposes.

When air flows through the airflow pad 1606, it can return to the airflow pad controller 1602 through the outlet conduit 1724 (Step E). The airflow pad controller 1602 can detect one or more characteristics of the return air (Step F). In some implementations, the airflow pad controller 1602 can detect a temperature of the return air using, for example, the temperature sensor 1630. Alternatively or in addition, the airflow pad controller 1602 can detect a humidity of the return air using, for example, the humidity sensor 1632. Other characteristics of the supplied air can also be detected for various purposes.

The airflow pad controller 1602 can analyze the supplied air and the return air (Step G). In some implementations, the airflow pad controller 1602 can compare the value(s) of the detected characteristic(s) of the return air with the value(s) of the detected characteristic(s) of the supplied air, and identify any difference between the values.

The airflow pad controller 1602 can operate to adjust conditioning of air and/or supplying of ambient or conditioned air based on the analysis (Step H) so that adjusted air is supplied to the airflow pad 1606 through the inlet conduit 1722 (Step I). For example, the airflow pad controller 1602 can control the air conditioner 1612 to adjust the temperature of air, and/or control the fan 1610 to change the flow rate of the air. The temperature and/or the flow rate of air can be adjusted so that the difference between the value(s) of the detected characteristic(s) of the supplied air and the value(s) of the detected characteristic(s) of the return air can meet one or more threshold values representative of desired microclimate control.

In an example process for controlling a microclimate of the mattress 1604, the airflow pad controller 1602 can activate the air conditioner 1612 to condition air, and supply the conditioned air to an inlet of an airflow pad 1606 using, for example, the fan 1610. The airflow pad 1606 can be arranged under a top foam layer of the mattress 1604 and configured to permit an airflow rate being higher than an airflow rate of the top foam layer. The airflow pad controller 1602 can detect supply characteristics of air entering the inlet of the airflow pad 1606, and detect return characteristics of air exiting an outlet of the airflow pad 1606. The airflow pad controller 1602 can adjust activation of the air conditioner 1612 based on the supply characteristics and the return characteristics. For example, the airflow pad controller 1602 can adjust activation of the fan 1610 based on the supply characteristics and the return characteristics. In some examples, the supply characteristics and the return characteristics include at least one of temperature and humidity.

Overview of Multiple Modes

Figure 40:
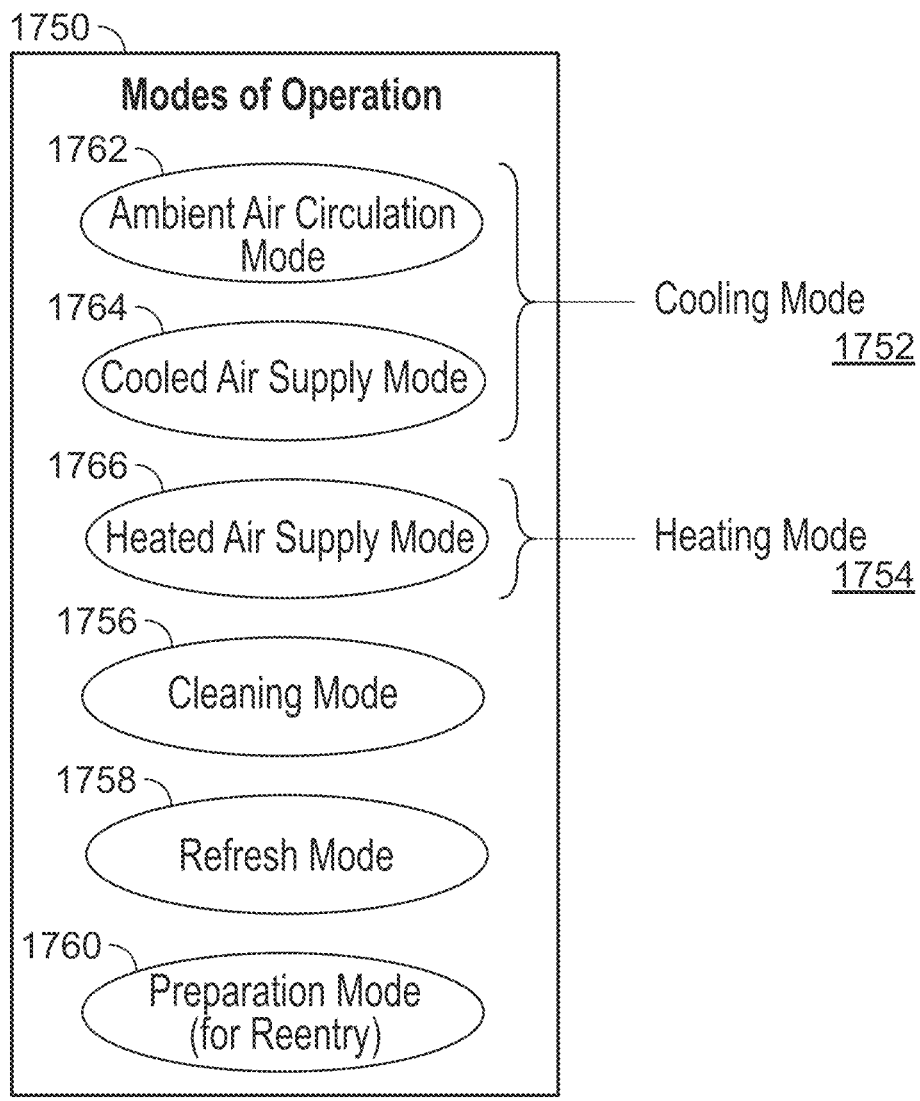
FIG. 40 illustrates example modes of operation that can be performed using the airflow pad control system.

FIG. 40 illustrates example modes of operation 1750 that can be performed using the airflow pad control system 1600.

The airflow pad control system 1600 can selectively perform a cooling mode 1752, a heating mode 1754, a cleaning mode 1756, a refresh mode 1758, and a preparation mode 1760. The cooling mode 1752 can include an ambient air circulation mode 1762 and a cooled air supply mode 1764. The heating mode 1754 can include a heated air supply mode 1766. The airflow pad control system 1600 can receive a user input of selecting one of these modes via, for example, the remote control 1122 or the user computing device 1124, and perform the selected mode of operation. Alternatively, the airflow pad control system 1600 can automatically select a mode of operation based on one or more factors, such as environment factors in or around the bed system 1100, operational conditions of the bed system 1100, and user profiles or preferences.

The modes of operation of the airflow pad control system 1600 can be performed along with other microclimate operations by other systems in the bed system 1100, such as the foot warming system 1500. For example, when the airflow pad control system 1600 performs one of the modes of operation 1750 for a mattress, the foot warming system 1500 can operate to warm the foot heating element mounted in the mattress at the same time.

Figure 41:
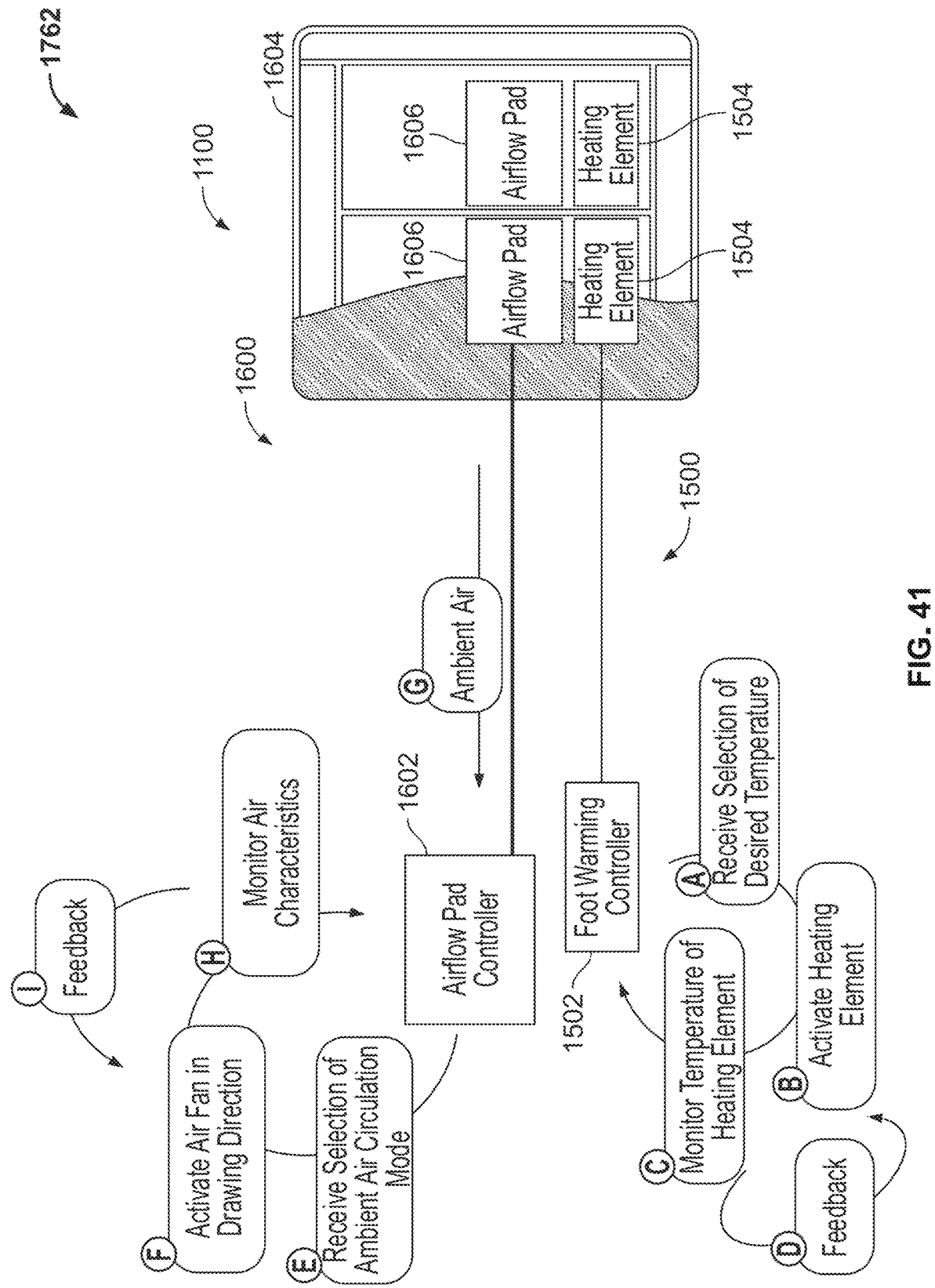
FIG. 41 illustrates an example ambient air circulation mode.

FIG. 41 illustrates an example of the ambient air circulation mode 1762. In the ambient air circulation mode 1762, the airflow pad control system 1600 operates to draw ambient air from the airflow pad 1606 of the mattress 1604 to cool the top of the mattress 1604 to a desired temperature. In some implementations, the airflow pad control system 1600 can be operated together with the foot warming control system 1500.

In an example configuration, the foot warming controller 1502 receives a user selection of a desired temperature at the foot of the mattress (Step A). Alternatively, the desired temperature can be automatically determined based on one or more factors including the user's profile or preference, the room temperature, the mattress top temperature, etc. The foot warming controller 1502 can activate the heating element 1504 based on the user selection (Step B). In some implementations, the foot warming controller 1502 can monitor the temperature of the heating element (Step C), and provide feedback signals (Step D) to modulate the operation of the heating element if necessary to maintain or achieve the desired temperature set point.

In the meantime, the airflow pad controller 1602 can receive a user selection of the ambient air circulation mode 1762 (Step E). In addition, the user can select one or more attributes of the ambient air circulation mode 1762, such as a temperature set point or target point in general, a temperature set point or target point at the top of the mattress, a humidity set point or target point, an airflow rate setting, a fan speed setting, etc. In some implementations, the ambient air circulation mode 1762 can be selected automatically based on one or more factors including the user's profile or preference, the room temperature, the mattress top temperature, etc. The airflow pad controller 1602 can activate the fan in a drawing direction (Step F) so that ambient air is drawn from the mattress 1604 through the airflow pad 1606 (Step G). In some implementations, the airflow pad controller 1602 can monitor one or more characteristics of the air drawn from the mattress (Step H), and provide feedback signals to module the operation of the airflow pad controller 1602 if necessary to maintain or achieve the desired settings (Step I). For example, the airflow pad controller 1602 can monitor the temperature and/or humidity of the drawn air, and control the fan speed, thereby adjusting the flow rate of air drawing from the mattress to achieve the temperature and/or humidity set points at the top of the mattress.

Figure 42:
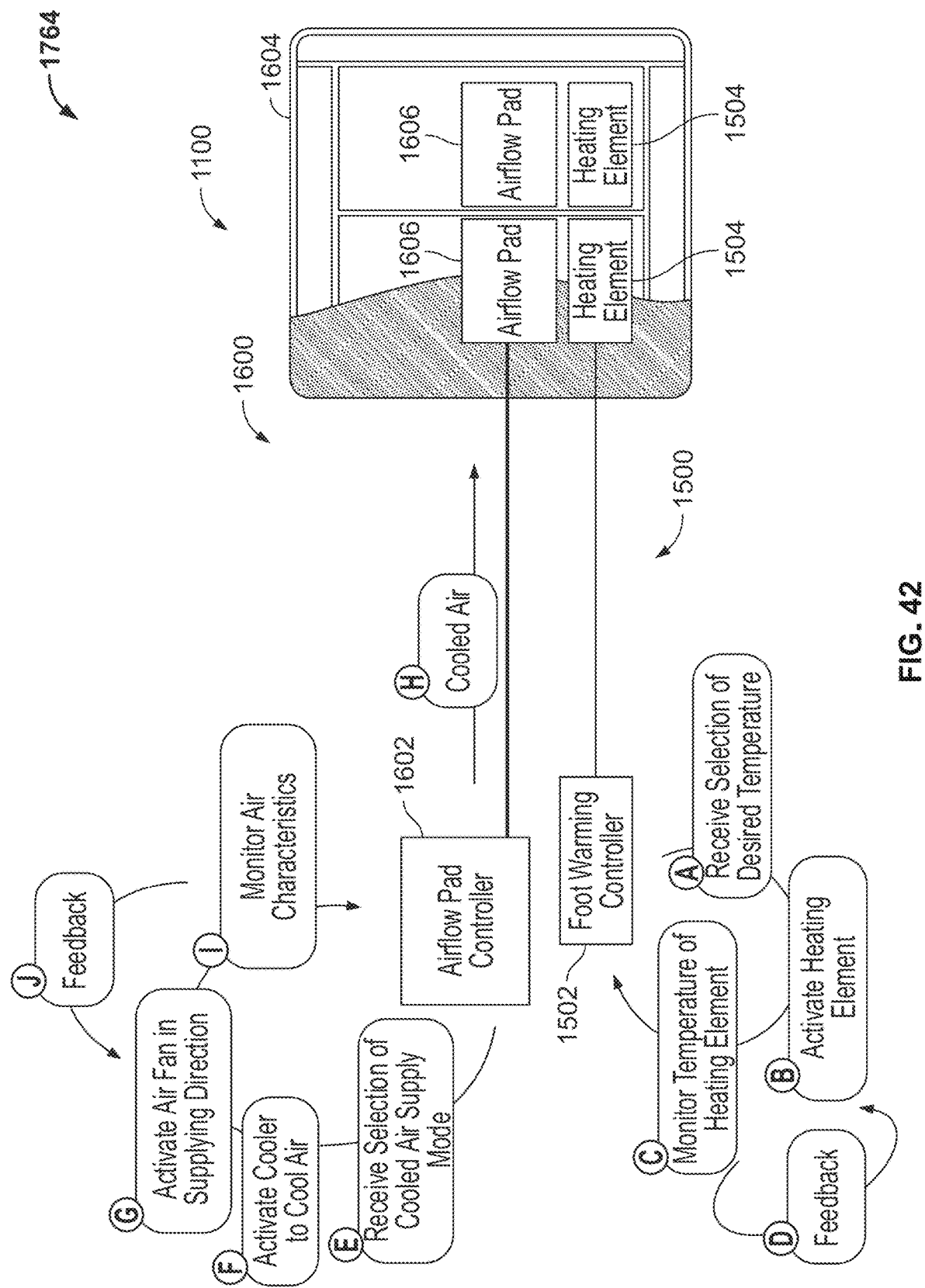
FIG. 42 illustrates an example cooled air supply mode.

FIG. 42 illustrates an example of the cooled air supply mode 1764. In the cooled air supply mode 1764, the airflow pad control system 1600 operates to cool air and supply the cooled air to the airflow pad 1606 of the mattress 1604 to actively cool the top of the mattress 1604 to a desired temperature.

In some implementations, the airflow pad control system 1600 can be operated together with the foot warming control system 1500. In an example configuration, the foot warming controller 1502 receives a user selection of a desired temperature at the foot of the mattress (Step A). Alternatively, the desired temperature can be automatically determined based on one or more factors including the user's profile or preference, the room temperature, the mattress top temperature, etc. The foot warming controller 1502 can activate the heating element 1504 based on the user selection (Step B). In some implementations, the foot warming controller 1502 can monitor the temperature of the heating element (Step C), and provide feedback signals (Step D) to modulate the operation of the heating element if necessary to maintain or achieve the desired temperature set point.

In the meantime, the airflow pad controller 1602 can receive a user selection of the cooled air supply mode 1764 (Step E). In addition, the user can select one or more attributes of the cooled air supply mode 1764, such as a temperature set point or target point in general, a temperature set point or target point at the top of the mattress, a humidity set point or target point, an airflow rate setting, a fan speed setting, etc. In some implementations, the cooled air supply mode 1764 can be selected automatically based on one or more factors including the user's profile or preference, the room temperature, the mattress top temperature, etc. The airflow pad controller 1602 can activate the cooler to cool air to a desired temperature (Step F). The airflow pad controller 1602 can activate the fan in a supplying direction (Step G) so that the cooled air is supplied to the mattress 1604 through the airflow pad 1606 (Step H). In some implementations, the airflow pad controller 1602 can monitor one or more characteristics of the air suppled to the mattress (Step I), and provide feedback signals to module the operation of the airflow pad controller 1602 if necessary to maintain or achieve the desired settings (Step J). For example, the airflow pad controller 1602 can monitor the temperature and/or humidity of the air, and control the cooler and/or the fan speed, thereby adjusting the temperature of the air and/or the flow rate of air supplying to the mattress to achieve the temperature and/or humidity set points at the top of the mattress.

Figure 43:
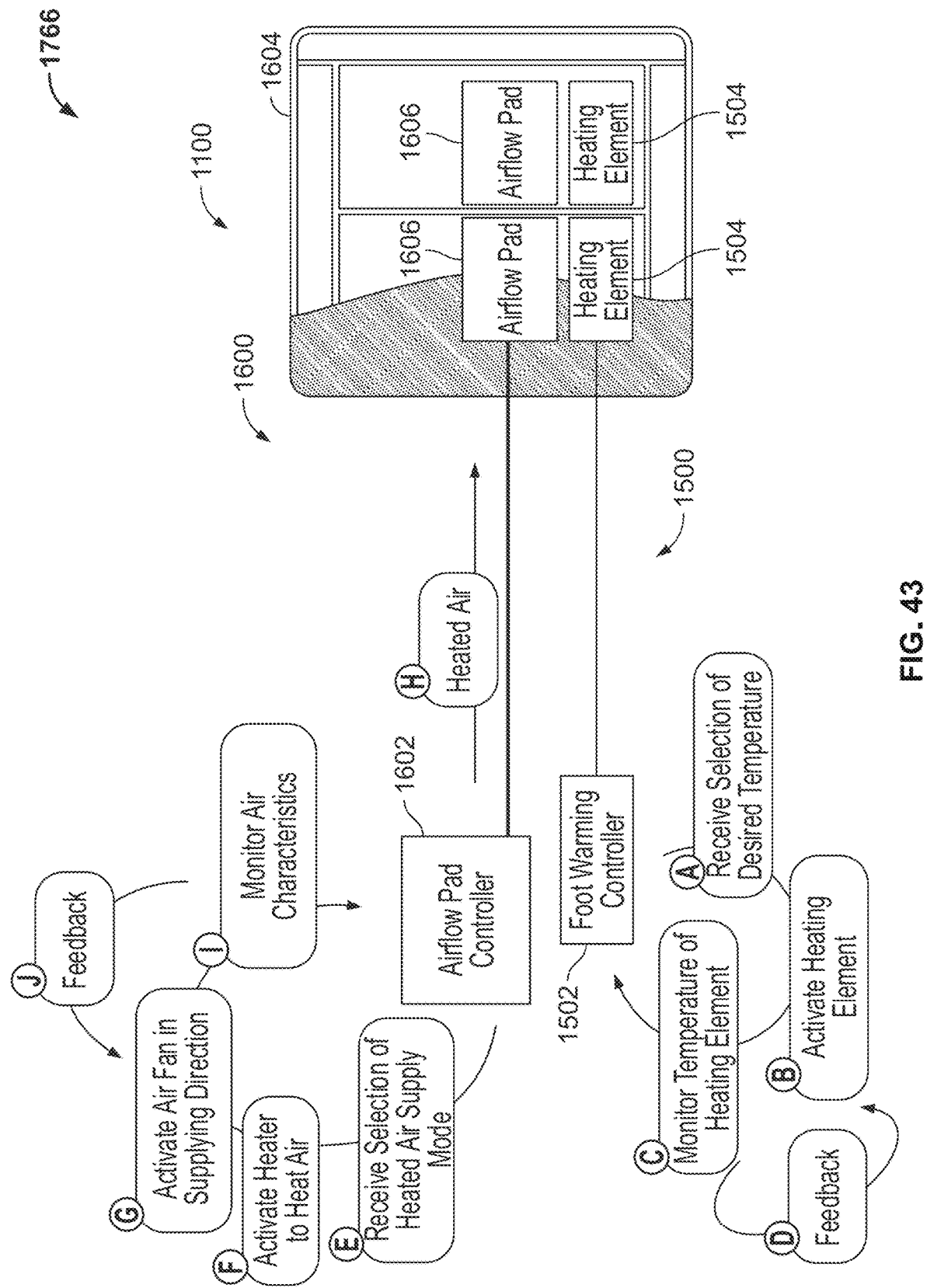
FIG. 43 illustrates an example heated air supply mode.

FIG. 43 illustrates an example of the heated air supply mode 1766. In the heated air supply mode 1766, the airflow pad control system 1600 operates to heat air and supply the heated air to the airflow pad 1606 of the mattress 1604 to actively warm the top of the mattress 1604 to a desired temperature.

In some implementations, the airflow pad control system 1600 can be operated together with the foot warming control system 1500. In an example configuration, the foot warming controller 1502 receives a user selection of a desired temperature at the foot of the mattress (Step A). Alternatively, the desired temperature can be automatically determined based on one or more factors including the user's profile or preference, the room temperature, the mattress top temperature, etc. The foot warming controller 1502 can activate the heating element 1504 based on the user selection (Step B). In some implementations, the foot warming controller 1502 can monitor the temperature of the heating element (Step C), and provide feedback signals (Step D) to modulate the operation of the heating element if necessary to maintain or achieve the desired temperature set point.

In the meantime, the airflow pad controller 1602 can receive a user selection of the heated air supply mode 1766 (Step E). In addition, the user can select one or more attributes of the heated air supply mode 1766, such as a temperature set point or target point in general, a temperature set point or target point at the top of the mattress, a humidity set point or target point, an airflow rate setting, a fan speed setting, etc. In some implementations, the heated air supply mode 1766 can be selected automatically based on one or more factors including the user's profile or preference, the room temperature, the mattress top temperature, etc. The airflow pad controller 1602 can activate the heater to warm air to a desired temperature (Step F). The airflow pad controller 1602 can activate the fan in a supplying direction (Step G) so that the heated air is supplied to the mattress 1604 through the airflow pad 1606 (Step H). In some implementations, the airflow pad controller 1602 can monitor one or more characteristics of the air suppled to the mattress (Step I), and provide feedback signals to module the operation of the airflow pad controller 1602 if necessary to maintain or achieve the desired settings (Step J). For example, the airflow pad controller 1602 can monitor the temperature and/or humidity of the air, and control the cooler and/or the fan speed, thereby adjusting the temperature of the air and/or the flow rate of air supplying to the mattress to achieve the temperature and/or humidity set points at the top of the mattress.

The cleaning mode 1756, the refresh mode 1758, and the preparation mode 1760 are described below with reference to FIGS. 44-46.

Cleaning Operation of Fan/Heater Assembly
(Feature Group #7)

Figure 44:
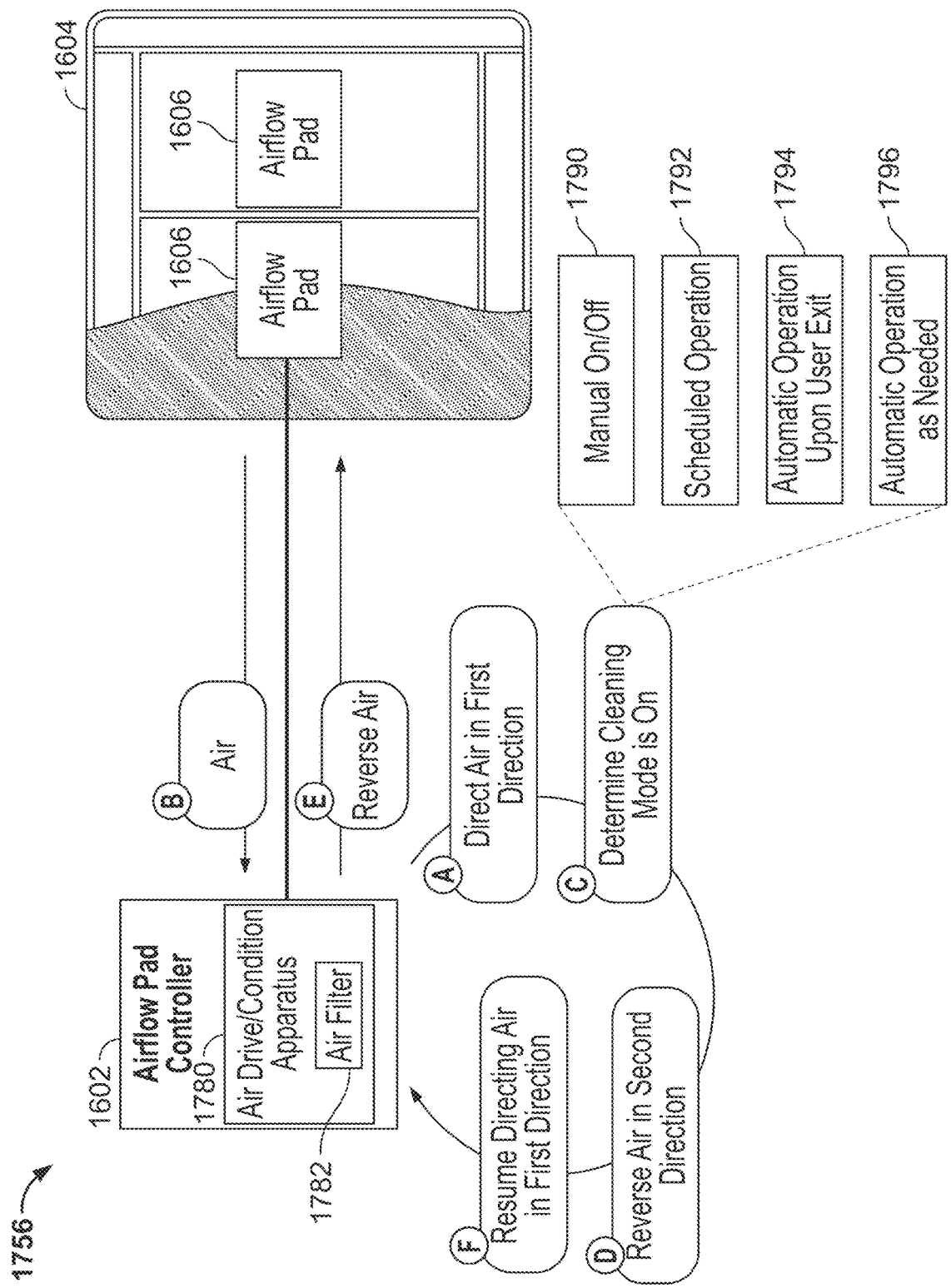
FIG. 44 illustrates an example cleaning mode of the airflow pad control system.

FIG. 44 illustrates an example cleaning mode 1756 of the airflow pad control system 1600. The airflow pad control system 1600 can include an air drive/condition apparatus 1780 having one or more air filters 1782. The air drive/condition apparatus 1780 can be used to implement at least part of the airflow pad controller 1602 including the air fan 1610 and the air conditioner 1612. The air drive/condition apparatus 1780 can be configured similarly to the air controller 700 as shown in FIGS. 21-26. For example, the air drive/condition apparatus 1780 can include a housing containing various components, such as a circuit board, a fan, a heating element, a cooling element, sensors, and other suitable components for controlling airflow into and from the mattress 1604. As described with respect to the air controller 700, the housing of the air drive/condition apparatus 1780 can define an air passage having one or more openings, such as the connection-side opening 708 and the ambient-side opening 710. The air drive/condition apparatus 1780 can arrange the filters 1782 at the openings to filter debris, dirt, and contaminants from air passing through the apparatus, and thus prevent them from entering the apparatus 1780 and/or the mattress to which the apparatus 1780 is coupled. The filters 1782 can be configured similarly to the air screens 760 and 762 as shown in FIG. 26.

The airflow pad control system 1600 can operate in the cleaning mode 1756 to clean up the filters 1782 and other components in the air drive/condition apparatus 1780. The airflow pad control system 1600 can perform the cleaning mode 1756 for a short period of time while the system 1600 operates in another mode such as the cooling mode 1752 or the heating mode 1754. For example, the cleaning mode 1756 can be performed by briefly interrupting the current mode of operation of the system 1600.

In some implementations, the airflow pad controller 1602 can operate to direct air in a first direction (Step A) so that the air flows relative to the airflow pad 1606 of the mattress 1604 accordingly (Step B). In the illustrated example, the air is being drawn from the airflow pad 1606 (e.g., the ambient air circulation mode 1762). However, the air can be driven to flow into the airflow pad 1606 in other modes of operation (e.g., the cooled air supply mode 1764 or the heated air supply mode 1766).

The airflow pad controller 1602 can determine that the cleaning mode is activated (Step C). The cleaning mode can be activated in several ways. For example, the user can activate or deactivate the cleaning mode using for example the remote control 1122 or the user computing device 1124 (Manual On/Off 1790). Alternatively, the cleaning mode can be performed at programmed schedules (Scheduled Operation 1792). For example, the cleaning mode can be periodically performed or performed at scheduled times. Alternatively, the cleaning mode can be automatically activated when (or shortly after) the user is detected to exit the bed (Automatic Operation Upon User Exit 1794). Alternatively, the cleaning mode can be automatically activated when the filters are detected to be clogged enough and need to be cleaned (Automatic Operation As Needed 1796). For example, the airflow pad system 1600 can monitor the air flow through the apparatus 1780 (or through the filters 1782) and determine slowdown of the air flow that can indicate the filters are dirty.

The airflow pad controller 1602 can drive air in a second direction (e.g., the direction opposite to the first direction) (Step D) so that the air flow is reversed (in the direction opposite to the original air flow) (Step E). The reverse air can blow particles out of the filters 1782 and clean the surface of the filters 1782. The air can be driven in the reverse direction for a substantially shorter duration than the original mode of operation as performed in Step A.

The airflow pad controller 1602 can resume the original mode of operation as performed in Step A (Step F). For example, the airflow pad controller 1602 can return to drive air in the first direction under the same conditions as performed in Step A.

The cleaning mode 1756 can be performed for a predetermined period of time that is determined to be sufficient to blow a substantial amount of particles out from the filters while not interfering with the original operational mode for a substantial period of time. Alternatively, the cleaning mode 1756 can be performed independently. For example, the cleaning mode 1756 can be performed while the airflow pad control system 1600 is at rest (not in any other mode).

In an example cleaning mode, the airflow pad controller 1602 can operate to flow air through a housing of the mattress air controller (e.g., the air drive/condition apparatus 1780) in a first direction from a housing inlet to a housing outlet during a first operation mode configured to condition air at a top of a mattress. The airflow pad controller 1602 can reverse flow of air through the housing in a second direction from the housing outlet to the housing inlet in order to blow particles out of a filter positioned at the housing inlet. The filter cleaning mode can be configured to be performed in a substantially shorter duration than the first operation mode.

In addition, the airflow pad controller 1602 can receive information of user presence on or around the bed. For example, the bed system can sense user presence on the mattress, and determine that a user exited the mattress. The airflow pad controller 1602 can operate the filter cleaning mode after determining that the user exited the mattress. Alternatively, the filter cleaning mode is operated daily when the bed system determines that a user is not on the mattress.

In some implementations, the airflow pad controller 1602 can draw air from an airflow insert pad for a mattress and supply conditioned air to the airflow insert pad. The airflow pad controller 1602 can include a housing having a connection-side opening and an ambient-side opening. The connection-side opening is in fluid communication with the airflow insert pad, and the ambient-side opening is exposed to a surrounding. The airflow pad controller 1602 can further include a reversible fan mounted in the housing, a heating element mounted in the housing, and a filtering unit arranged at the ambient-side opening of the housing. In a cooling mode, the airflow pad controller 1602 can be controlled to operate the reversible fan to cause airflow from the connection-side opening to the ambient-side opening through the housing. Further, the airflow pad controller 1602 can operate in a heating mode where the heating element is heated and the reversible fan operates to cause air to flow from the ambient-side opening to the connection-side opening, passing through the heating element. In an example cleaning mode, the airflow pad controller 1602 can be controlled to operate the reversible fan to blow air out through the filtering unit at the ambient-side opening of the housing for a predetermined period of time, thereby cleaning the filtering unit. In some implementations, the airflow pad controller 1602 can be configured to perform the cleaning mode periodically. The airflow pad controller 1602 can further include a second filtering unit arranged at the connection-side opening of the housing.

Refresh Cycle (Feature Group #8)

Figure 45A:
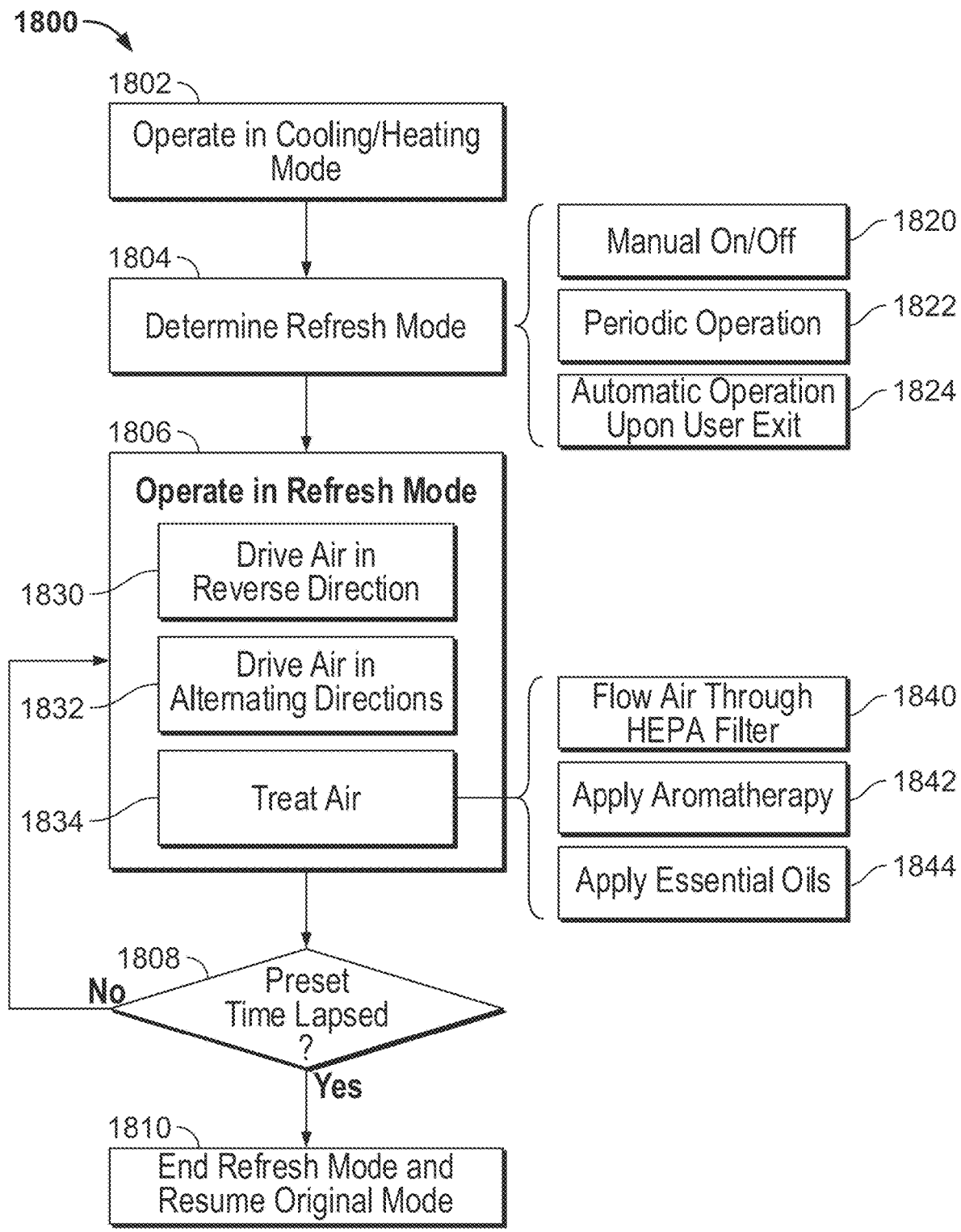
FIG. 45A is a flowchart of an example process for performing a refresh mode of the airflow pad control system.

FIG. 45A is a flowchart of an example process 1800 for performing the refresh mode 1758 of the airflow pad control system 1600. The refresh mode 1758 is a mode in which the airflow pad control system 1600 provides refreshing effects at the top of the mattress.

In this example, the process 1800 can begin with the airflow pad control system 1600 being in certain mode of operation, such as the cooling mode 1752 or the heating mode 1754 (FIG. 40) (Block 1802). The airflow pad control system 1600 can determine that the refresh mode is activated (Block 1804). The refresh mode can be activated in several ways. For example, the user can activate or deactivate the refresh mode using for example the remote control 1122 or the user computing device 1124 (1820). Alternatively, the refresh mode can be performed at programmed schedules (1822). For example, the refresh mode can be periodically performed or performed at scheduled times. Alternatively, the refresh mode can be automatically activated when the user is detected to have exited the bed (1824).

When it is determined that the refresh mode is activated, the airflow pad control system 1600 can operate in the refresh mode (Block 1806). The refresh mode can be performed in one or more manners. In one example, the airflow pad control system 1600 can operate to drive air in a reverse direction (1830), i.e., the direction opposite to the original flow of air. In another example, the airflow pad control system 1600 can operate to drive air in alternating directions (1832). In yet another example, the airflow pad control system 1600 can treat air to provide additional effects to the user on the mattress (1834). Various methods can be used for air treatment. For example, the airflow pad control system 1600 can flow air through a special air filter, such as a high-efficiency particulate (HEPA) filter, to purify air coming in or from the mattress (1840). In addition or alternatively, the airflow pad control system 1600 can apply aromatherapy materials (e.g., oils) to air flowing in or from the mattress (1842). In addition or alternatively, the airflow pad control system 1600 can apply essential oils to air flowing in or from the mattress (1844).

In some implementations, the air reversing 1830, the air alternation 1832, and the air treatment 1834 can be selectively used for the refresh mode. In other implementations, at least two of the air reversing 1830, the air alternation 1832, and the air treatment 1834 can be used simultaneously or in alternating manners.

The process 1800 continues to determine whether a preset period of time has lapsed for the refresh mode (Block 1808). The preset period of time can vary for different purposes or methods of refreshing air. For example, the preset period of time can range between 30 seconds and 5 minutes. In other examples, the preset period of time can be shorter than 30 seconds, or greater than 5 minutes.

If the preset period of time has lapsed, the airflow pad control system 1600 can deactivate the refresh mode, and can resume the original mode of operation (as was in Block 1802). Otherwise, the airflow pad control system 1600 can continue to operate in the refresh mode (as in Block 1806).

Figure 45B:
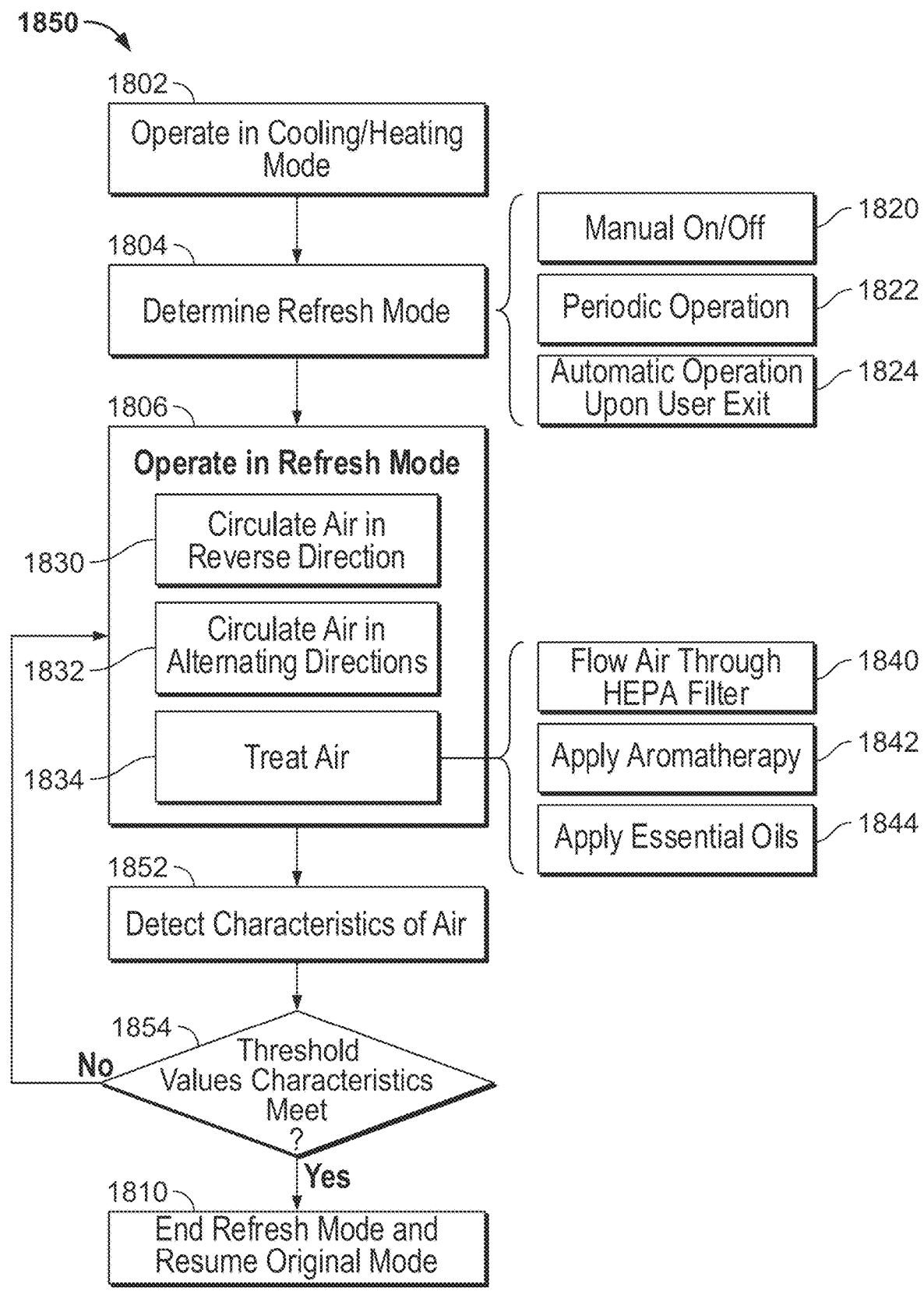
FIG. 45B is a flowchart of another example process for performing the refresh mode of the airflow pad control system.

FIG. 45B is a flowchart of another example process 1850 for performing the refresh mode 1758 of the airflow pad control system 1600. The process 1850 is identical or similar to the process 1800 of FIG. 45A except for operations 1852 and 1854 (instead of operation 1808 in FIG. 45A). In this example, when the refresh mode is activated (1806), the airflow pad control system 1600 can detect one or more characteristics of air (Block 1852), and determine whether the characteristics meet threshold values (Block 1854). For example, the airflow pad control system 1600 can detect a temperature and/or humidity of air during the refresh mode, and determine the detected temperature and/or humidity reaches threshold values, such as desired temperature value and/or humidity value (e.g., temperature and humidity that are comfortable to the user). The threshold values can be manually set by the user using, for example, the remote control 1122 or the user computing device 1124. Alternatively, the threshold values can be automatically determined based on one or more factors, such as environmental status, operational conditions, and user profile or preference. If the detected characteristics meet the threshold values, the airflow pad control system 1600 can deactivate the refresh mode, and can resume the original mode of operation (as was in Block 1802). Otherwise, the airflow pad control system 1600 can continue to operate in the refresh mode (as in Block 1806).

In some implementations, the airflow pad control system 1600 can operate to draw air from an air distribution layer (e.g., the airflow pad) for a mattress and supply ambient or conditioned air to the air distribution layer. As described herein, the airflow pad control system 1600 can include a reversible fan and a heating element. The airflow pad control system 1600 can operate in a cooling mode by operating the reversible fan to draw air from the air distribution layer, and also operate in a refresh mode by operating the reversible fan to cause air to circulate through the air distribution layer for a predetermined period of time. The airflow pad control system 1600 can be controlled in the refresh mode for a predetermined period of time, which can range between 30 minutes to 60 minutes.

In some implementations, the refresh mode can be performed based on user presence on the mattress. For example, the bed system can sense user presence on or around the mattress, and determine whether the user is not present on or around the mattress. The refresh mode can be activated when the user is determined not to be present on or around the mattress.

The airflow pad control system 1600 can operate to detect a humidity level in the air in the refresh mode, and continue the refresh mode until the humidity level reaches a predetermined value. The refresh mode can be performed by controlling the reversible fan to draw air from the air distribution layer for the predetermined period of time. Alternatively or in addition, the refresh mode can be performed by controlling the reversible fan to supply air to the air distribution layer for the predetermined period of time. Alternatively or in addition, the refresh mode can be performed by flowing air through a HEPA filter during the refresh mode. Alternatively or in addition, the refresh mode can be performed by applying aromatherapy to circulated air during the refresh mode. Alternatively or in addition, the refresh mode can be performed by applying essential oils to air circulated into the mattress during the refresh mode.

In addition or alternatively, the mattress being used may not include any material treated with antimicrobial chemicals. In such cases, the refresh mode can be automatically operated regularly at intervals configured to reduce microbial growth.

Prep Cycle for Reentry (Feature Group #10)

Figure 46:
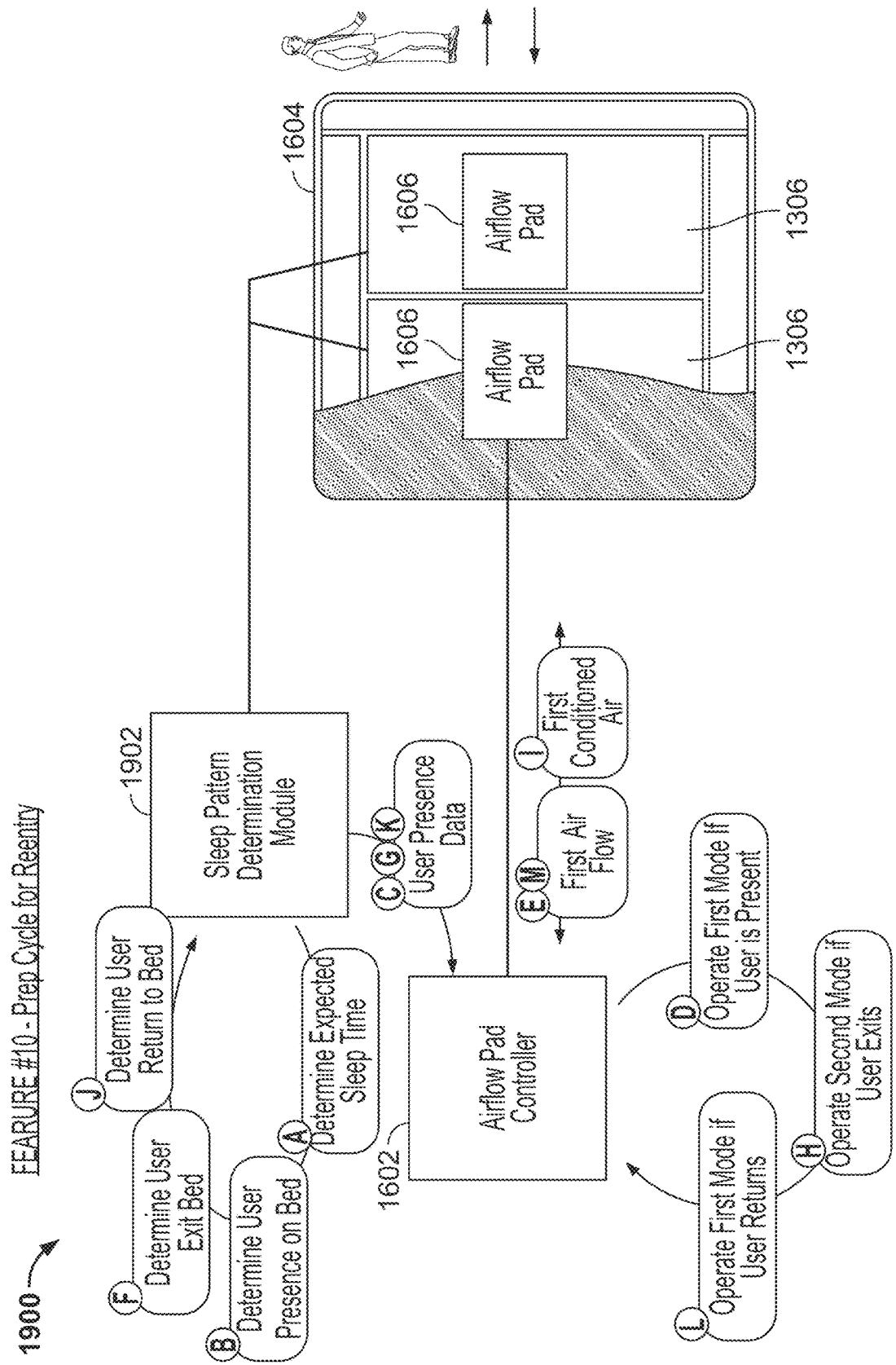
FIG. 46 illustrates an example process for performing a preparation mode of the airflow pad control system.

FIG. 46 illustrates an example process 1900 for performing the preparation mode 1760 of the airflow pad control system 1600. The preparation mode 1760 is a mode in which the airflow pad control system 1600 automatically controls the microclimate of a mattress to desired settings when the user is present on or around the mattress. In addition or alternatively, the preparation mode 1760 can be configured such that the airflow pad control system 1600 prepares the mattress to desired microclimate settings a predetermined time before the user is determined or predicted to use the mattress. In addition or alternatively, in the preparation mode 1760, the airflow pad control system 1600 can prepare the mattress to desired microclimate settings when it is determined the user has left the bed temporarily and is expected to return to the bed soon, such as for sleep breaks due to natural causes (e.g., going to the bathroom) or external disturbance (e.g., taking care of a crying baby or other child in need of care).

In some implementations, the process 1900 include determining user presence on or around the bed. A sleep pattern determination module 1902 is provided for such determination. The sleep pattern determination module 1902 can be implemented by one or more components in the bed system 1100 (FIG. 33). For example, the sleep pattern determination module 1902 can be included at least partially in the air chamber control system 1300. Alternatively or in addition, the server system 1126 can be used to implement at least part of the sleep pattern determination module 1902.

In some implementations, the sleep pattern determination module 1902 can determine an expected sleep time of a user (Step A). An expected sleep time can be automatically determined based on one or more historical and/or sensed factors, such as those retrieved from the bed data 1130, the sleep data 1132, the user account data 1134, and/or the environment data 1136 described in FIG. 33. Alternatively, the expected sleep time can be manually set by the user using, for example, the remote control 1122 or the user computing device 1124. The expected sleep time can be personalized to a particular user of the bed. Alternatively, the expected sleep time can be determined for general users based on statistical analysis.

The sleep pattern determination module 1902 can determine presence of a user on or around the bed (Step B), and transmit user presence data to the airflow pad controller 1602 (Step C). The user presence data can indicate whether a user is present on or around the bed. For example, as described herein, the user presence can be detected by sensing and analyzing the pressure (and a change thereof) within the air chamber 1306 of the mattress 1604.

The airflow pad controller 1602 can operate a first mode of operation if a user is determined to be present on or around the bed based on the user presence data (Step D). According to the first mode of operation, ambient or conditioned air can be supplied to, or drawn from, the mattress 1604 (e.g., the airflow pad 1606) (Step E). For example, where the first mode of operation is the ambient air circulation mode 1762, the airflow pad controller 1602 draws ambient air from the airflow pad 1606 to lower the temperature at the top of the mattress. If the first mode of operation is the cooled air supply mode 1764, the airflow pad controller 1602 operates to cool air and supply the cooled air to the airflow pad 1606, thereby cooling the top of the mattress. If the first mode of operation is the heated air supply mode 1766, the airflow pad controller 1602 operates to heat air and supply the heated air to the airflow pad 1606, thereby warming the top of the mattress.

The sleep pattern determination module 1902 can operate to determine whether the user has exited the bed (Step F), and transmit user presence data to the airflow pad controller 1602 (Step G). The transmitted user presence data can indicate whether a user has left the bed and does not use the bed now. For example, as described herein, the user exit can be detected by sensing and analyzing the pressure (and a change thereof) within the air chamber 1306 of the mattress 1604.

The airflow pad controller 1602 can operate a second mode of operation if the user is determined to have exited the bed based on the user presence data (Step H). According to the second mode of operation, ambient or conditioned air can be supplied to or drawn from, the mattress 1604 (e.g., the airflow pad 1606) (Step I). The second mode of operation is a mode in which the microclimate of the mattress is automatically controlled to desired settings before the user comes back to the bed, so that the user can reenter the bed at the settings that satisfy the user's preference. For example, such desired settings can be microclimate settings that the user has initially set, or that are to be achieved by the first mode of operation.

When the user rests on the mattress, especially for an extended period of time (e.g., for hours), the microclimate (e.g., temperature, humidity, etc.) at the top of the mattress can dynamically change due to the presence and movement of the user on the mattress. For example, a user on the mattress dissipates body heat against the mattress and thus affects the control of the microclimate on the mattress. In some instances, the original microclimate settings (e.g., temperature and/or humidity settings) according to the first mode of operation are not achieved at least temporarily due to the user presence. Therefore, in some implementations, the second mode of operation can be designed to ensure that the first mode of operation is achieved when the user comes back. Alternatively, the second mode of operation can be configured to provide user preferred sensory effects when the user reenters the bed and contacts the mattress, by making the top of the mattress warmer or cooler (and/or drier) depending on the user's preference.

The sleep pattern determination module 1902 can determine whether the user has returned onto or around the bed (Step J), and transmit user presence data to the airflow pad controller 1602 (Step K). The user presence data can indicate whether a user is present on or around the bed again. For example, as described herein, the user presence can be detected by sensing and analyzing the pressure (and a change thereof) within the air chamber 1306 of the mattress 1604.

The airflow pad controller 1602 can resume the first mode of operation if the user is determined to have returned based on the user presence data (Step L). According to the first mode of operation, ambient or conditioned air can be supplied to, or drawn from, the mattress 1604 (e.g., the airflow pad 1606) (Step M).

In an example process of controlling a microclimate of a mattress, the bed system 1100 can operate to determine a time period of expected user sleep and sense whether a user is present on the mattress. In response to sensing presence during the time period of expected user sleep, the bed system can operate to flow air through the mattress in a first operation mode to control microclimate of the mattress while the user is on the mattress. In response to sensing that the user exited the mattress during the time period of expected user sleep, the bed system can operate to flow air through the mattress in a second operation mode that is different than the first operation mode. In response to sensing that the user returned to the mattress during the time period of expected user sleep, the bed system can operate to resume the first operation mode.

In an example process of controlling a microclimate of a mattress, the bed system can sense whether a user is present on the mattress, and determine that a user exited the mattress during a predetermined time period. Upon determining that the user exited the mattress, the bed system can operate to initiate activation of an air controller to draw air from an air layer of the mattress to increase distribution of air through a foam layer above the airflow insert pad and decrease a temperature at the foam layer. Upon determining the user returns onto the mattress, the bed system can operate to deactivate the air controller in the cooling mode. Alternatively, upon determining the user returns the mattress, the bed system can operate to resume or activate the air controller in a mode of operation that was performed before the user exited the mattress. In some implementations, prior to determining the user exited the mattress, the bed system can operate to detect the user is on the mattress during the predetermined time period. The predetermined time period can be a period of time that the user typically spends for sleep. For example, the predetermined time period can range from midnight to 6 AM, by way of example.

Control Based on Sleep Cycle (Feature Group #9)

Figure 47:
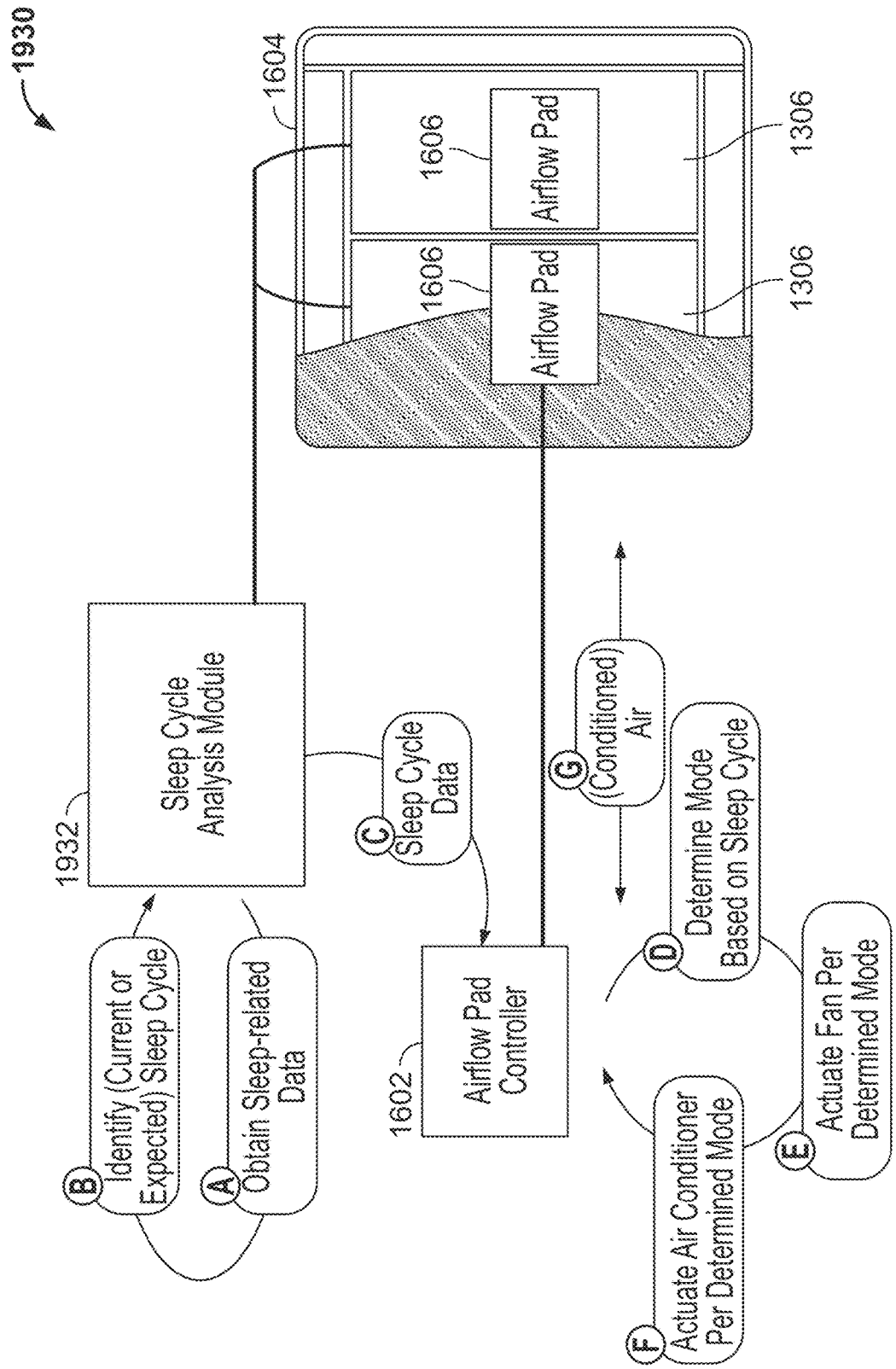
FIG. 47 illustrates an example process for controlling a microclimate of a mattress based on a sleep cycle.

FIG. 47 illustrates an example process 1930 for controlling a microclimate of a mattress based on a sleep cycle. The process can include determining a sleep cycle of the user of the mattress, which can be performed by a sleep cycle analysis module 1932. The sleep cycle analysis module 1932 can be implemented by one or more components in the bed system 1100 (FIG. 33). For example, the sleep cycle analysis module 1932 can be included at least partially in the air chamber control system 1300. Alternatively or in addition, the server system 1126 can be used to implement at least part of sleep cycle analysis module 1932.

In some implementations, the sleep cycle analysis module 1932 obtains sleep-related data (Step A). The sleep-related data can include information identifying a sleep cycle of a user. The sleep-related data can be obtained based at least on other data in the bed system 1100, such as the bed data 1130, the sleep data 1132, and the environment data 1136. In addition or alternatively, the sleep-related data can be collected and/or analyzed using another system configured to monitor the sleep cycle of a user.

The sleep cycle is an oscillation between the slow-wave and REM (paradoxical) phases of sleep. The standard figure given for the average length of the sleep cycle in an adult man may be 90 minutes. During sleep, people usually go through five stages of sleep. Simply put, stages 1-2 are light sleep, stages 3-4 deep sleep, and stage 5 is REM sleep, also referred to as rapid eye movement sleep. The first stage (NREM stage 1 or N1) is light sleep and in this stage, people drift in and out of sleep. The eyes move slowly, muscle activity is slow, and people would be easy to wake up. In the second stage (NREM stage 2 or N2), the body starts preparing for deep sleep. Eye movements and brain waves slow down, the body temperature drops, and the heart rate slows down. Entering the third stage (NREM stage 3 or N3), people are now in deep sleep. Extremely slow brain waves called delta waves are intermixed with smaller, faster brain waves. In stage four (NREM 4 or N4), people stay in deep sleep and the brain almost exclusively produces the slow delta waves, guiding towards the fifth stage. Entering the last stage, stage five, also called REM sleep, provides that the eyes are closed but move rapidly from side-to-side, due to the intense dream and brain activity a sleeper goes through in this stage.

The sleep cycle can be detected using various techniques, which can be included in the bed system 1100, or implemented with a separate system that can communicate with the bed system 1100. Example techniques include electroencephalography that shows the timing of sleep cycles by virtue of the marked distinction in brainwaves manifested during REM and non-REM sleep. Delta wave activity, correlating with slow-wave (deep) sleep, can show regular oscillations throughout a good night's sleep. Secretions of various hormones, including renin, growth hormone, and prolactin, may correlate positively with delta-wave activity, while secretion of thyroid-stimulating hormone correlates inversely. Heart rate variability, well-known to increase during REM, may also correlate inversely with delta-wave oscillations over the ~90-minute cycle. In addition or alternatively, the techniques for determining in which stage of sleep the asleep subject is, electroencephalography may be combined with other devices used for this differentiation. EMG (electromyography) may be used to distinguish between sleep phases: for example, in general, a decrease of muscle tone is characteristic of the transition from wake to sleep, and during REM sleep there is a state of muscles atonia, resulting in an absence of signals in the EMG. In addition or alternatively, EOG (electrooculography) can be used to measure the eyes' movement. For example, REM sleep is characterized by a rapid eye movement pattern and detectable using the EOG. In addition or alternatively, methods based on cardiorespiratry parameters may be used in the analysis of sleep cycle if they are associated the other measurements such as electroencephalography, electrooculography and the electromyography. In addition or alternatively, homeostatic functions (e.g., thermoregulation) may occur normally during non-REM sleep, but not during REM sleep. Thus, during REM sleep, body temperature tends to drift away from its mean level, and during non-REM sleep, to return to normal. Alternation between the stages therefore maintains body temperature within an acceptable range.

The sleep cycle analysis module 1932 can operate to identify a sleep cycle of the user based on the sleep-related data (Step B), and transmit sleep cycle data (including the identified sleep cycle) to the airflow pad controller 1602 (Step C). The sleep-related data can be used along with other data, such as the bed data 1130, the sleep data 1132, and the environment data 1136, to identify a sleep cycle of the user. The sleep cycle analysis module 1932 can identify a current sleep cycle of the user, and further identify an expected sleep cycle of the user at a particular time.

The airflow pad controller 1602 can determine a mode of operation based on the sleep cycle data (Step D), and actuate the fan 1610 according to the determined mode of operation (Step E). In some implementations, the airflow pad controller 1602 can further actuate the air conditioner 1612 to condition air according to the mode of operation (Step F). Ambient or conditioned air can then be supplied to or drawn from the mattress per the determined mode of operation (Step G).

In an example process of controlling a microclimate of a mattress, the bed system 1100 can operate to determine a sleep cycle of a subject on the mattress, and determine a mode from a plurality of modes based on the sleep cycle. As described herein, the plurality of modes can include a cooling mode in which an air controller (e.g., the airflow pad controller) is operated to cause ambient or cooled air to flow from or into an airflow insert pad of the mattress, and a heating mode in which the air controller is operated to cause heated air to flow to the airflow insert pad of the mattress. According to the determined mode, the bed system can control the air controller. In some implementations, the air controller operates in a first mode in response to one or more processors determining that a user is in stage N1, wherein the air controller operates in a second mode in response to the one or more processors determining that the user is in stage N2, wherein the air controller operates in a third mode in response to the one or more processors determining that the user is in stage N3, and wherein the air controller operates in a fourth mode in response to the one or more processors determining that the user is in REM sleep.

Independent Cooling/Heating in Multiple Zones
(Feature Group #11)

Figure 48:
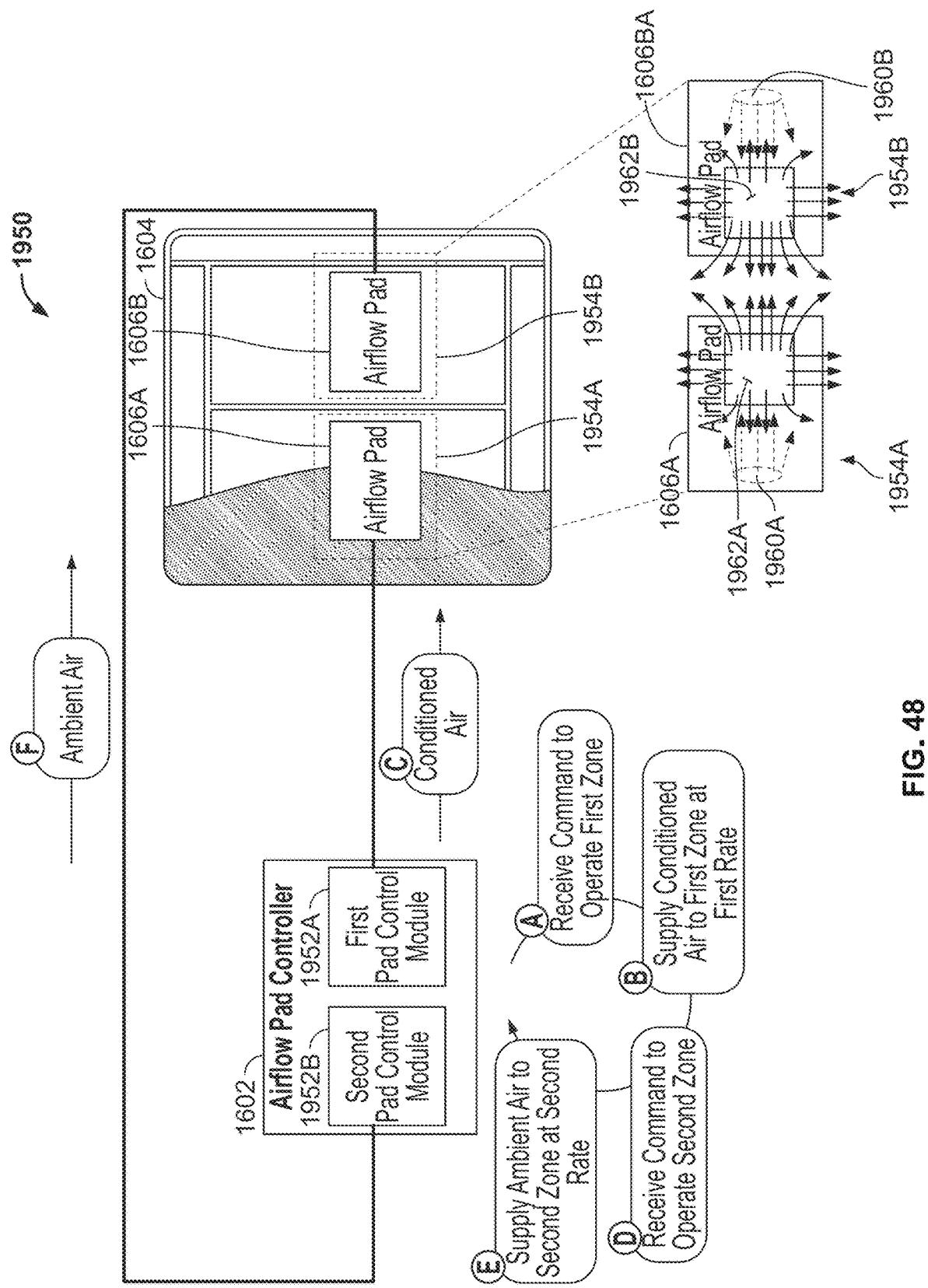
FIG. 48 illustrates an example microclimate control system with multiple climate control zones.

FIG. 48 illustrates an example microclimate control system 1950 with multiple climate control zones. For example, the mattress 1604 has multiple climate control zones 1954, such as a first climate control zone 1954A and a second climate control zone 1954B. Each of the climate control zones 1954 can include an airflow pad 1606. For example, the first climate control zone 1954A and the second climate control zone 1954B include the first airflow pad 1606A and the second airflow pad 1606B, respectively. In other examples, at least one of the climate control zones can include a plurality of airflow pads. The airflow pad controller 1602 can include a plurality of pad control modules for corresponding climate control zones. For example, the airflow pad controller 1602 includes a first pad control module 1952A associated with the first climate control zone 1954A (and the first airflow pad 1606A therein), and a second pad control module 1952B associated with the second climate control zone 1954B (and the second airflow pad 1606B therein).

Multiple climate control zones 1954 can be controlled independently. Alternatively or in addition, at least two of the climate control zones 1954 can be controlled in an interdependent manner. For example, one of the climate control zones can be controlled and/or adjusted based on input parameters for controlling another climate zone (e.g., an adjacent climate control zone) and/or output characteristics resulting from the control of the other climate control zone, so that the operations in both of the climate control zones can be improved or optimized. By way of example, an operation of the first climate control zone 1954A (e.g., suctioning ambient air from the first airflow pad 1606A in the first climate control zone 1954A) can affect (e.g., lower) the temperature at or around the second climate control zone 1954B adjacent the first airflow pad 1606A of the first climate control zone 1954A. Accordingly, a desired climate control of the second climate control zone 1954B can be adjusted to compensate the change in the temperature resulting from the control of the first climate control zone 1954A.

In one example, the airflow pad controller 1602 receives a command to control a microclimate in the first climate control zone 1954A (Step A). For example, the command is generated in response to a user input of activating a first mode of operation on the first climate control zone 1954A, using for example the remote control 1122 or the user computing device 1124. According to the command, the airflow pad controller 1602 can operate the first mode of operation, in which air is conditioned and driven to the first climate control zone 1954A (e.g., to the first airflow pad 1606A) at a first flow rate (Step B), so that the conditioned air can be supplied to the first climate control zone 1954A at the first flow rate (Step C). Depending on the mode of operation, the conditioned air can be cooled air or heated air.

The airflow pad controller 1602 receives a command to control a microclimate in the second climate control zone 1954B (Step D). For example, the command is generated in response to a user input of activating a second mode of operation on the second climate control zone 1954B, using for example the remote control 1122 or the user computing device 1124. According to the command, the airflow pad controller 1602 can operate the second mode of operation, in which ambient air is driven to the second climate control zone 1954B (e.g., to the second airflow pad 1606B) at a second flow rate (Step E), so that the air can be supplied to the second climate control zone 1954B at the second flow rate (Step F). Alternatively, in other examples, the air supplied to the second climate control zone 1954B can be cooled or heated air depending on the second mode of operation.

The flow rates created for multiple climate control zones can be determined to reduce an amount of heat transferred from one climate control zone to another (e.g., adjacent) climate control zone. For example, as illustrated, the air (Air1) supplied to the first airflow pad 1606A through an inlet 1960A is distributed through the first airflow pad 1606A and can exit through an outlet 1962A. Similarly, the air (Air2) supplied to the second airflow pad 1606B through an inlet 1960B is distributed through the second airflow pad 1606B and can exit through an outlet 1962B. The air (Air1) exiting the first airflow pad 1606A can face the air (Air2) exiting the second airflow pad 1606B at an interface region 1964 between the first climate control zone 1954A and the second climate control zone 1954B. The flow rate of the air (Air1) in the first climate control zone 1954A and the flow rate of the air (Air2) in the second climate control zone 1954B can be determined and adjusted to reduce heat transfer between the air (Air1) and the air (Air2) in the interface region 1964, and/or reduce interference of the air (Air1) with the air (Air2), or vice versa, in the interference region 1964.

In an example process of independently controlling multiple climate control zones in a mattress, the bed system can operate to receive a command to supply air to the first climate control zone that is heated. In response to receiving the command, the bed system can command the one or more air controllers to supply heated air to the first climate control zone and to supply ambient air to the second climate control zone. A flow rate of ambient air to the second climate control zone can be selected to reduce an amount of heat transferred from the first climate control zone to the second climate control zone. In some implementations, the bed system can operate to command the one or more air controllers to supply ambient air to the second climate control zone without receiving any user request to supply air to the second climate control zone. Further, in response to sensing a user's presence on the second climate control zone, the bed system can operate to command the one or more controllers to stop supplying ambient air to the second climate control zone. In response to sensing a user's presence on the second climate control zone, the bed system can operate to command the one or more controllers to reduce supply of ambient air to the second climate control zone. In response to sensing a user's presence on the second climate control zone, the bed system can operate to command the one or more controllers to stop supplying heated air to the first climate control zone and to stop supplying ambient air to the second climate control zone. In response to sensing a user's presence on the second climate control zone, the bed system can operate to command the one or more controllers to reduce supply of heated air to the first climate control zone and to reduce supply of ambient air to the second climate control zone. In response to sensing a user's presence on the first climate control zone, the bed system can operate to command the one or more controllers to stop supplying heated air to the first climate control zone and to stop supplying ambient air to the second climate control zone. In response to sensing a user's presence on the first climate control zone, the bed system can command the one or more controllers to reduce supply of heated air to the first climate control zone and to reduce supply of ambient air to the second climate control zone. In some implementations, the flow rate of ambient air to the second climate control zone can be substantially less than a flow rate of heated air to the first climate control zone.

In an example process of independently controlling multiple climate control zones in a mattress, the mattress can have more than two climate control zones, such as first, second, third, and fourth climate control zones. The bed system can include one or more air controllers (e.g., control modules) in fluid communication with each of the first, second, third, and fourth climate control zones and configured to independently supply air to or draw air from each of the first, second, third, and fourth climate control zones. The bed system can operate to command the one or more air controllers to operate in a first mode whereby heated or cooled air is supplied to the first zone while air is simultaneously drawn from the second zone. The bed system can operate to command the one or more air controllers to operate in a second mode whereby heated or cooled air is supplied to the third zone while air is simultaneously drawn from the fourth zone. The bed system can further operate to command the one or more air controllers to operate in a third mode whereby heated air is supplied to the first and third zones while air is simultaneously drawn from the second and fourth zones. The bed system can operate to command the one or more air controllers to operate in a fourth mode whereby heated air is supplied to the first zone, cooled air is supplied to the third zone, and air is simultaneously drawn from the second and fourth zones. In some implementations, the first and second zones can be on a first side of the mattress for supporting a first user, and the third and fourth zones can be on a second side of the mattress for supporting a second user.

In some embodiments, air can be delivered to multiple zones in response to a request to deliver air to only one zone. For example, one or more users may request that heat be supplied to the first climate control zone 1954A but not request that heat be supplied to the second climate control zone 1954B. This could occur, for example, if two users occupy the bed and a first user desires heat be added and the second user does not desire that heat be added. In such a case heat can be supplied to the first climate control zone 1954A. In order to reduce or prevent heat overflow from the first climate control zone 1954A to the second climate control zone 1954B, a small or moderate amount of ambient air can be supplied to the second climate control zone 1954B. Accordingly, the system can supply heated air to the first climate control zone 1954A and ambient air to the second climate control zone 1954B in response to a request to supply heated air to the first climate control zone 1954A even without any request for ambient air to be supplied to the second climate control zone 1954B.

Bed Temperature Control Methodology Using Pressure as an Input (Feature Group #15)

Figure 49:
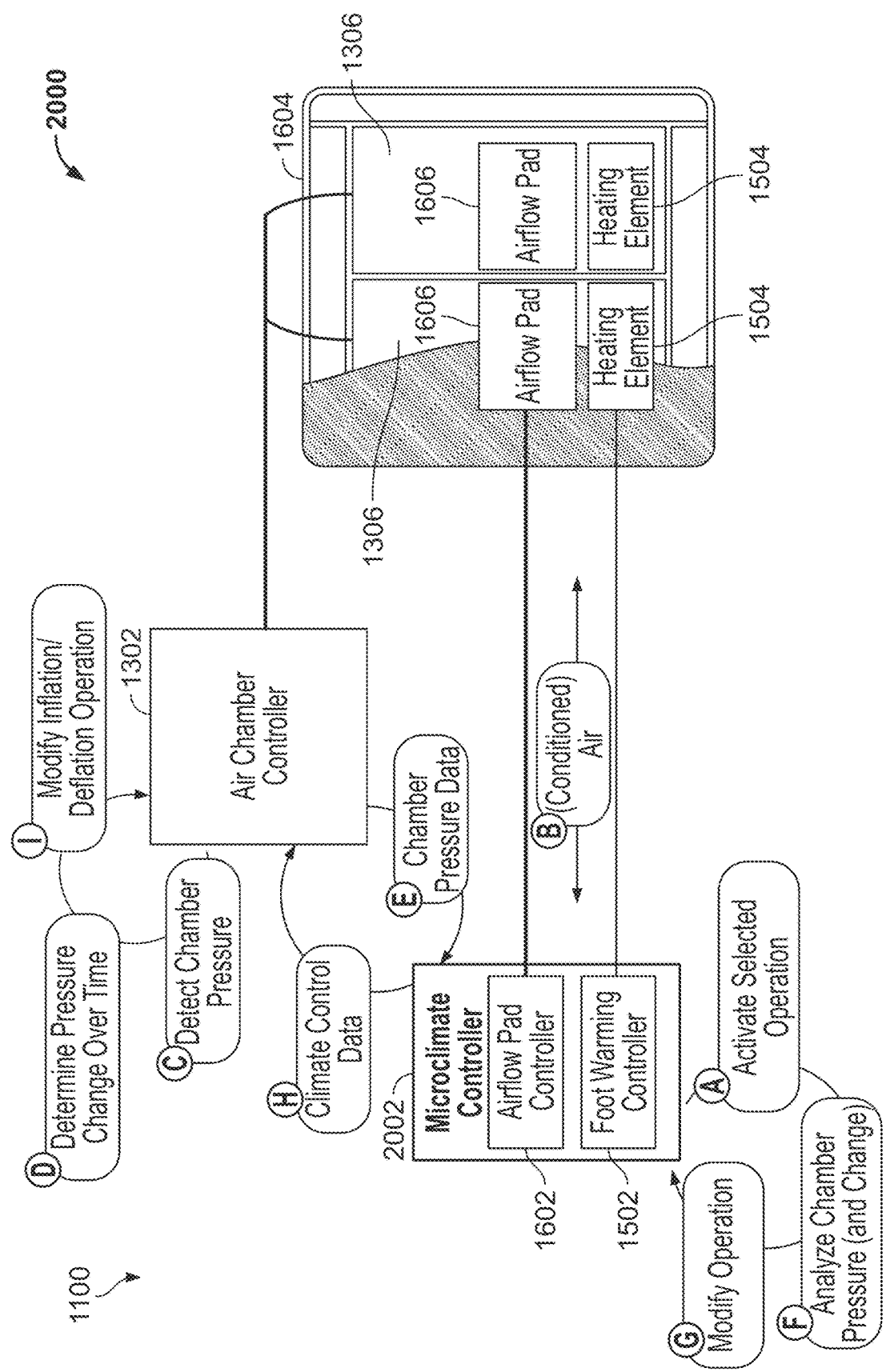
FIG. 49 illustrates an example method of controlling a microclimate of a bed using an air chamber pressure.

FIG. 49 illustrates an example method 2000 of controlling a microclimate of a bed using an air chamber pressure. The method 2000 is configured to limit deviation of an internal pressure of an air mattress, thereby providing consistent comfort while the mattress is operated in heating or cooling mode. For example, when an air mattress is actively controlled in a heating or cooling operation, the pressure inside the mattress air chamber changes. Such pressure change causes a deviation from the air pressure set point that has been manually selected by a user or automatically selected to provide desired comfort to the user. The method 2000 is configured to limit the amount of air pressure change caused by such active heating or cooling operation. The method 2000 can permit for the bed system to limit the amount of energy inputted into the system or removed from the system, thereby reducing or eliminating a deviation from the air pressure set point. The method can allow a better customer experience by minimizing or limiting pressure changes in the air mattress caused by active heating or cooling in the mattress.

The bed system 1100 includes a microclimate controller 2002 configured to control a microclimate of the mattress 1604. For example, the microclimate controller 2002 includes one or both of the foot warming controller 1502 and the airflow pad controller 1602. The microclimate controller 2002 can operate to activate a selected operation (Step A). For example, as described in, for example, FIG. 40, the airflow pad controller 1602 can operate in the cooling mode 1752 (e.g., the ambient air circulation mode 1762 or the cooled air supply mode 1764) to cool the mattress, or in the heating mode 1754 (e.g., the heated air supply mode 1766) to warm the mattress. When the airflow pad controller 1602 operates, ambient or conditioned air is delivered to or drawn from the mattress through the airflow pad 1606 (Step B).

Alternatively or in addition, the foot warming controller 1502 can activate the heating element 1504 to warm the foot section of the mattress.

The air chamber controller 1302 can operate to detect a pressure in the air chamber 1306 of the mattress (Step C). For example, the air chamber controller 1302 inflates the air chamber 1306 to reach a pressure that is set by the user or automatically determined for the user. The air chamber controller 1302 can detect the pressure inside the air chamber 1306 to monitor or ensure the pressure reaches the pressure set point. In addition, the air chamber controller 1302 can operate to determine a change in the air chamber pressure over time (Step D). The air chamber controller 1302 can further calculate a rate of change in pressure based on the determination. The air chamber controller 1302 can transmit chamber pressure data to the microclimate controller 2002 (Step E). The chamber pressure data can include information about the chamber pressure and/or the rate of pressure change as determined in Steps C and D.

The microclimate controller 2002 can analyze the chamber pressure and the change thereof based on the chamber pressure data (Step F). The microclimate controller 2002 can modify the operation based on the analysis (Step G). For example, the heating or cooling operation can be modulated to maintain or achieve the air chamber pressure to the set point or other target point.

In some embodiments, the microclimate controller 2002 can further transmit the climate control data to the air chamber controller 1302 (Step H). The climate control data can include information about the heating or cooling operation that is performed on the mattress by the microclimate controller 2002. For example, the climate control data can include information about the temperature setting(s) made for the airflow pad controller 1602 and/or the foot warming controller 1502, the temperature(s) that are measured at various locations, such as the temperature of air measured at the airflow pad 1606 or the airflow pad controller 1602, and the temperature of the heating element 1504 or near the heating element 1504.

The air chamber controller 1302 can modify the operation for the air chamber 1306 based on the climate control data and/or the chamber pressure data (Step I). For example, the air chamber controller 1302 can change its inflation or deflation operation for the air chamber 1306 to maintain or achieve the air chamber pressure to the set point or other target point while the microclimate control is performed for the mattress.

Figure 50:
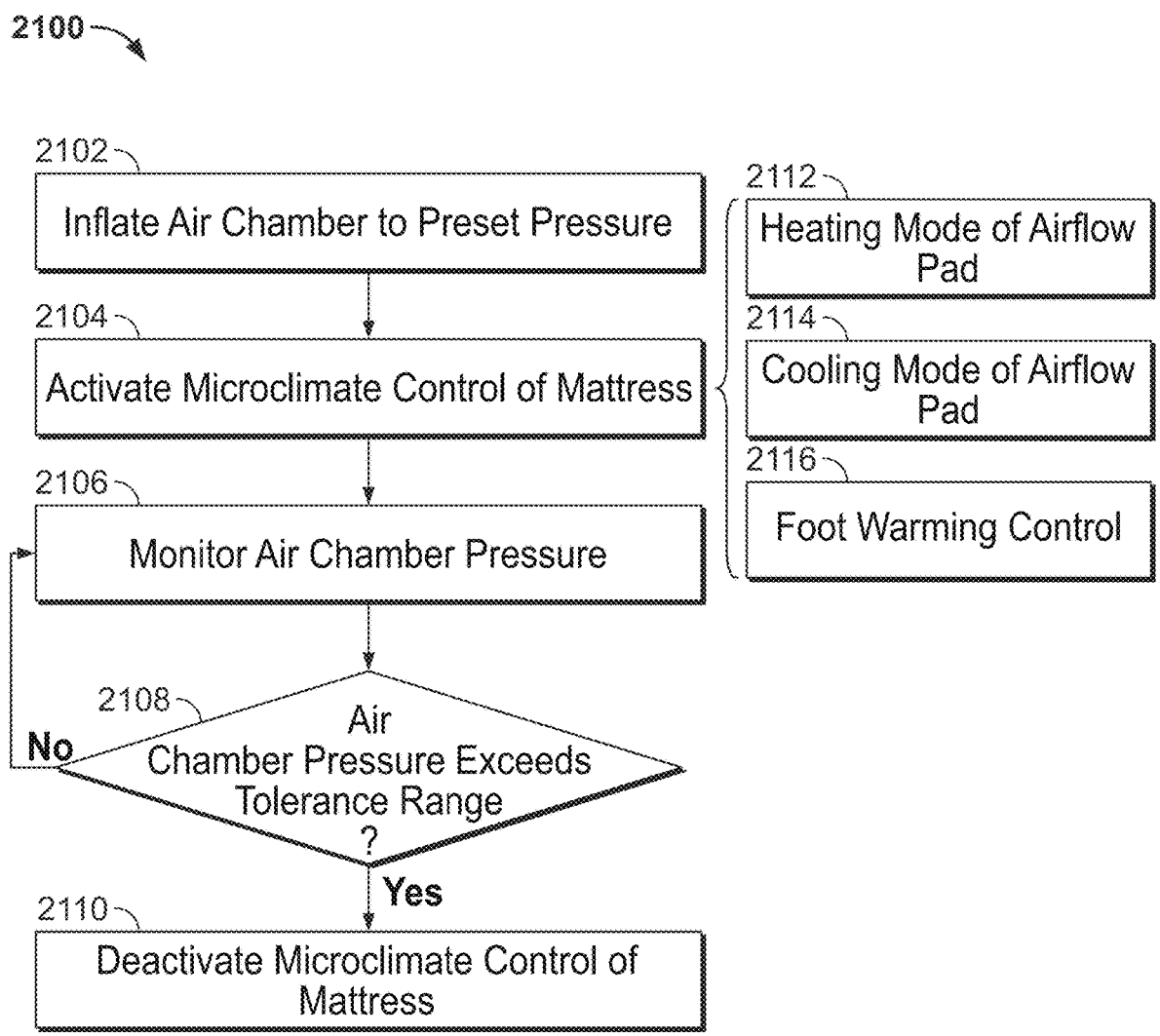
FIG. 50 is a flowchart of an example method for controlling a microclimate of a bed using an air chamber pressure.

FIG. 50 is a flowchart of an example method 2100 for controlling a microclimate of a bed using an air chamber pressure. The method 2100 can be used to modify the operation of the microclimate controller 2002 (as in Step G). For example, the microclimate control can be stopped or temporarily paused if the pressure in the air chamber is determined to hit an air pressure limit that is determined based on a tolerance around the pressure set point or target point. Such a pressure limit can be set with a goal of staying near a user's desired pressure so as to help achieve or preserve user comfort.

The method 2100 is further described with reference to FIG. 49. The method 2100 can begin by inflating the air chamber 1306 to a preset pressure (Block 2102). The method 2100 further includes activating a microclimate control of the mattress (Block 2104). For example, the airflow pad controller 1602 can operate in a heating mode (e.g., the heating mode 1754 in FIG. 40) (Block 2112) where heated air supplied to the mattress through the airflow pad 1606. In another example, the airflow pad controller 1602 can operate in a cooling mode (e.g., the cooling mode 1752 in FIG. 40) (Block 2114) where ambient or cooled air supplied to the mattress through the airflow pad 1606. In addition or alternatively, the foot warming controller 1502 can activate the foot heating element 1504 at a temperature set point (Block 2116).

The method 2100 can further include monitoring a pressure inside the air chamber 1306 (Block 2106), and determine whether the air chamber pressure exceeds a tolerance range (Block 2108). If the air chamber pressure exceeds the tolerance range ("Yes"), the method 2100 includes deactivating the microclimate control of the mattress (Block 2110). Otherwise ("No"), the method 2100 returns to monitoring the air chamber pressure (Block 2106). The tolerance range of pressure can be predetermined with a lower point not greater than the pressure set point or target point, and a higher point not less than the pressure set point or target point.

For example, the cooling operation that is performed on the mattress can lower the air chamber pressure below the set point. In this case, if the detected air chamber pressure becomes lower than a lower point of the tolerance range, the cooling operation can be deactivated at least temporarily so that (e.g., until) the air chamber pressure can be returned to or maintained with the tolerance range. On the other hand, the heating operation that is performed on the mattress can increase the air chamber pressure above the set point. In this case, if the detected air chamber pressure becomes higher than a higher point of the tolerance range, the heating operation can be deactivated at least temporarily so that (e.g., until) the air chamber pressure can be returned to or maintained with the tolerance range.

Figure 51:
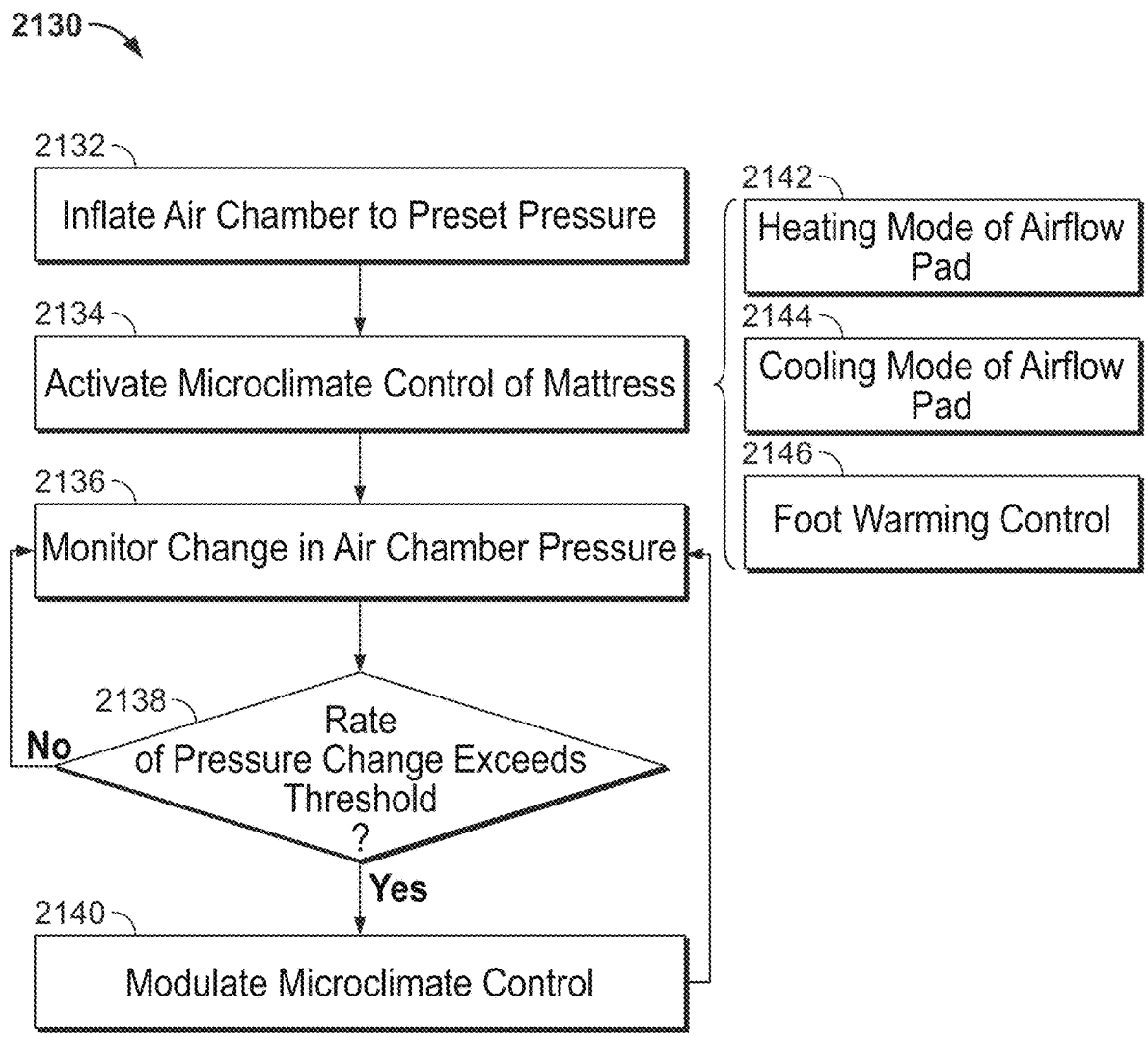
FIG. 51 is a flowchart of an example method for controlling a microclimate of a bed using an air chamber pressure.

FIG. 51 is a flowchart of an example method 2130 for controlling a microclimate of a bed using an air chamber pressure. The method 2130 can be used to modify the operation of the microclimate controller 2002 (as in Step G). For example, the microclimate control of the mattress can be limited or modulated to limit a rate of change of the air chamber pressure below a threshold value.

The method 2130 is further described with reference to FIG. 49. The method 2130 can begin by inflating the air chamber 1306 to a preset pressure (Block 2132). The method 2130 further includes activating a microclimate control of the mattress (Block 2134). For example, the airflow pad controller 1602 can operate in a heating mode (e.g., the heating mode 1754 in FIG. 40) (Block 2142) where heated air supplied to the mattress through the airflow pad 1606. In another example, the airflow pad controller 1602 can operate in a cooling mode (e.g., the cooling mode 1752 in FIG. 40) (Block 2144) where ambient or cooled air supplied to the mattress through the airflow pad 1606. In addition or alternatively, the foot warming controller 1502 can activate the foot heating element 1504 at a temperature set point (Block 2146).

The method 2130 can further include monitoring a change in pressure of the air chamber 1306 (Block 2136), and determine whether the rate of the pressure change exceeds a threshold value (Block 2138). If the air chamber pressure rate exceeds the threshold value ("Yes"), the method 2130 includes modulating the microclimate control of the mattress (Block 2140). Otherwise ("No"), the method 2130 returns to monitoring the air chamber pressure change (Block 2136). The threshold value for the rate of pressure change can be predetermined to ensure that the pressure change in the air chamber does not substantially affect desired comfort to the user based on the air chamber pressure set point.

Figure 52:
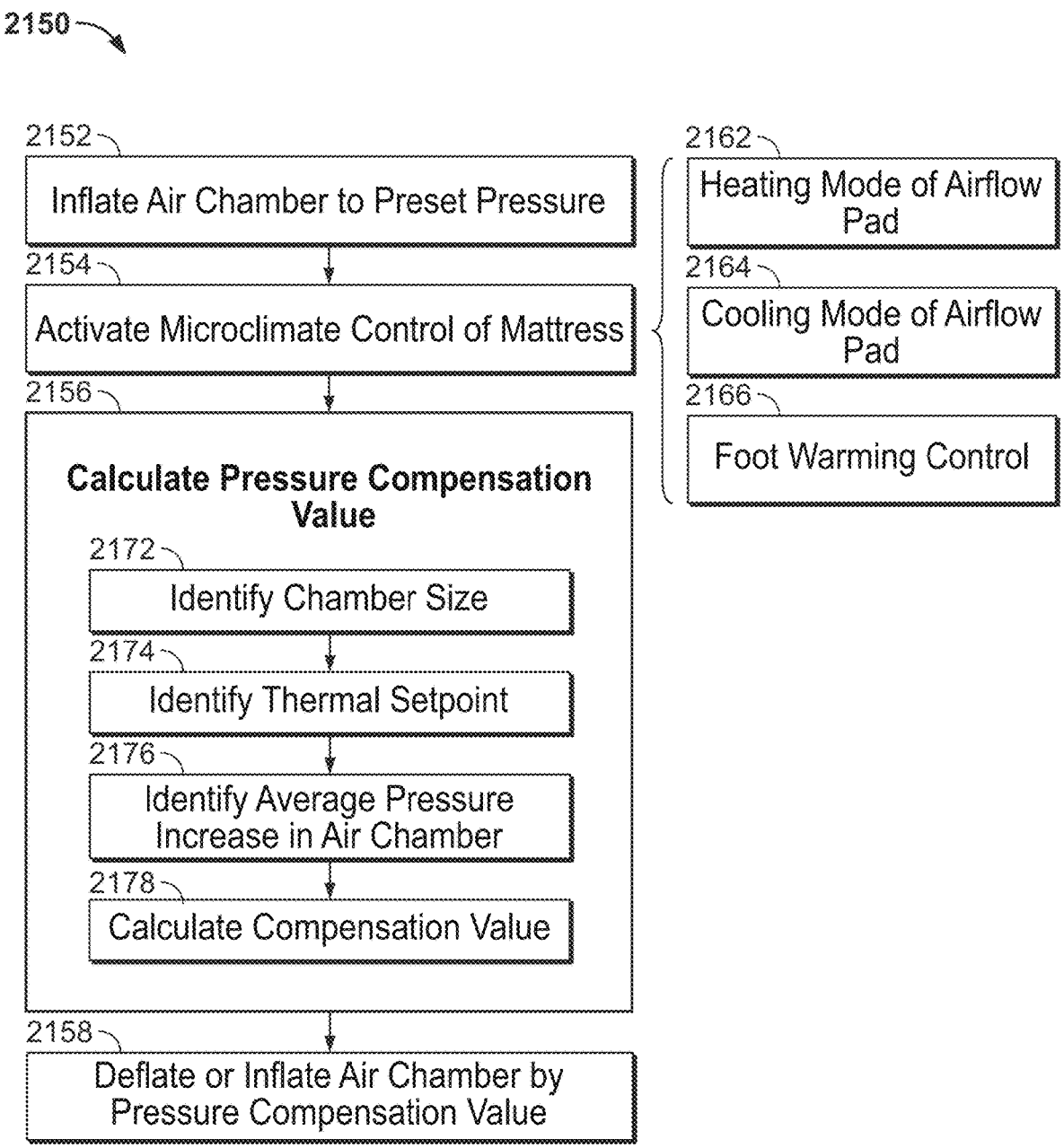
FIG. 52 is a flowchart of an example method for controlling a microclimate of a bed using an air chamber pressure.

FIG. 52 is a flowchart of an example method 2150 for controlling a microclimate of a bed using an air chamber pressure. The method 2150 can be used to modify the operation of the microclimate controller 2002 (as in Step G). In this method, depending on the microclimate control of the mattress, the air chamber can be inflated or deflated to compensate the impact of the microclimate control on the pressure in the air chamber. The method 2150 can be used to overcompensate for a given routine operation prior to the timeframe when the user enters the bed. For example, if the mattress is activated in a heating mode for a period of time (e.g., an hour) before the user enters the bed, the air chamber can be deflated to a pressure much lower than the pressure set point or desired target pressure to compensate for the impact that the heating operation has (or is expected to have) on the air chamber pressure. The degree of compensation can be determined based on one or more factors, such as the size of the air chamber, the thermal set point target, and/or the average pressure increase that the air chamber experiences. The method 2150 permits adjusting the operation (inflation or deflation) of the air mattress only once or in fewer times than multiple adjustments with smaller amounts, while the microclimate control of the mattress is active.

The method 2150 is further described with reference to FIG. 49. The method 2150 can begin by inflating the air chamber 1306 to a preset pressure (Block 2152). The method 2150 further includes activating a microclimate control of the mattress (Block 2154). For example, the airflow pad controller 1602 can operate in a heating mode (e.g., the heating mode 1754 in FIG. 40) (Block 2162) where heated air supplied to the mattress through the airflow pad 1606. In another example, the airflow pad controller 1602 can operate in a cooling mode (e.g., the cooling mode 1752 in FIG. 40) (Block 2164) where ambient or cooled air supplied to the mattress through the airflow pad 1606. In addition or alternatively, the foot warming controller 1502 can activate the foot heating element 1504 at a temperature set point (Block 2166).

The method 2150 can further include calculating a pressure compensation value (Block 2156), and inflate or deflate the air chamber 1306 by the pressure compensation value (Block 2158). In some implementations, the pressure compensation value can be calculated by identifying a size of the air chamber (Block 2172), identifying a thermal set point (Block 2174), identifying an average pressure increase that occurs in the air chamber (Block 2176), and calculating the pressure compensation value based on the size of the air chamber, the thermal set point, and/or the average pressure increase of the air chamber.

In some implementations, the methods described in FIGS. 50-52 can be performed separately. In other implementations, two or all of the methods described in FIGS. 50-52 can be performed in combination for more complex balancing between user comfort and thermal performance tradeoffs.

Human Body Heat Output Compensation Control Scheme for an Actively Heated Meshed Mattress (Feature Group #16)

Figure 53:
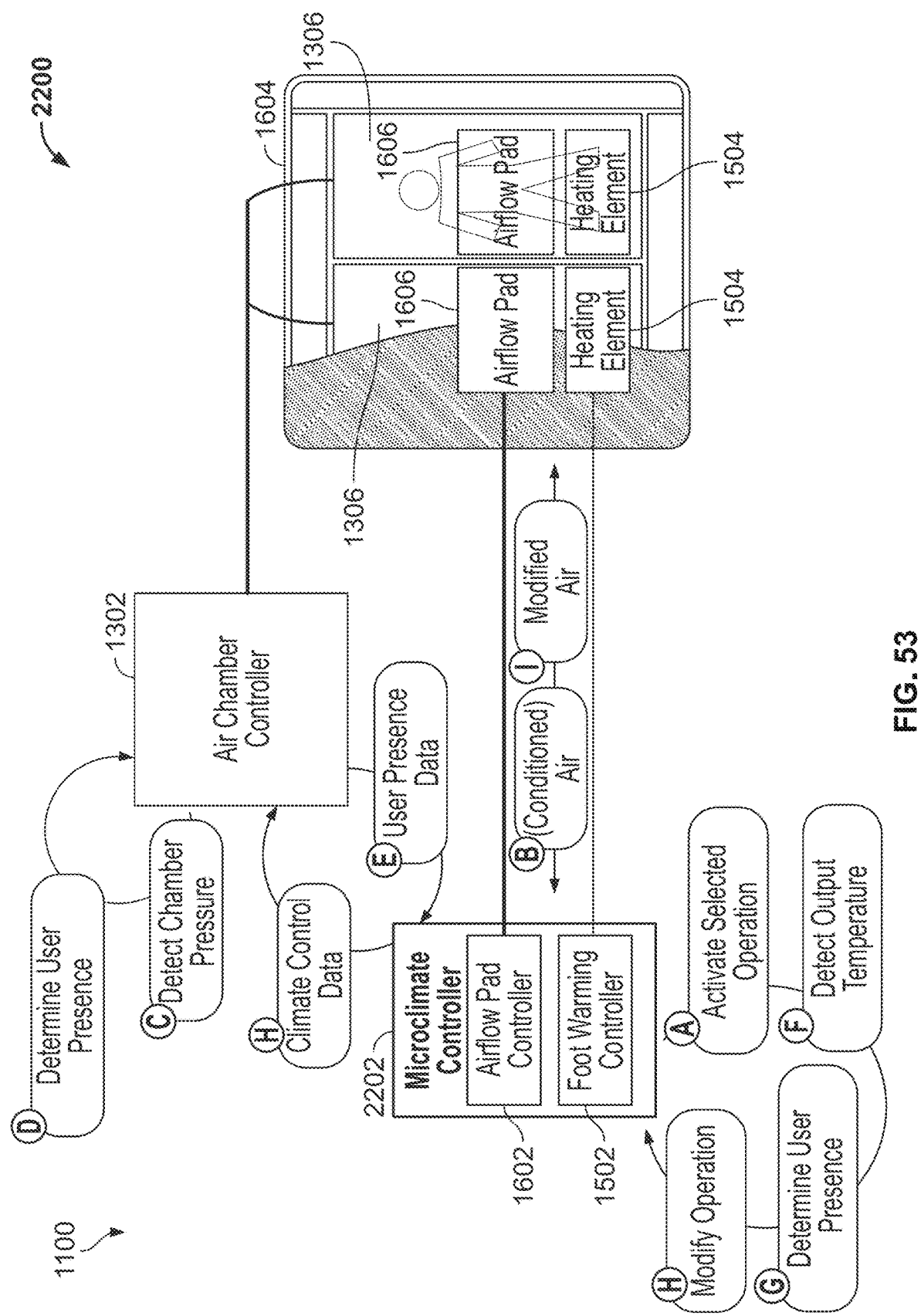
FIG. 53 illustrates an example method of controlling a microclimate of a bed to compensate thermal effects of a user resting on the bed.

FIG. 53 illustrates an example method 2200 of controlling a microclimate of a bed to compensate thermal effects of a user resting on the bed. The method 2200 provides a solution to harness a thermal output from a sleeper's internal body and limit deviation of an internal pressure of an air mattress, thereby providing consistent comfort while the mattress is operated in heating or cooling mode. The method 2200 can be used independently, or along with the method 2000 described in FIGS. 49-52.

For example, a sleeper generates a body heat, and such thermal outputs can heat up an air chamber of the mattress, thereby causing an increase in pressure of the air chamber. The pressure change in the air chamber causes a deviation from a pressure set point that was selected by the sleeper or automatically determined based on one or more factors to provide personal comfort. The thermal output resulting from the sleeper's body heat is added to the thermal input from an active heating or cooling operation with the mattress. For example, the pressure inside the mattress air chamber can be deviated from a set point due to the thermal output from the user's body as well as the thermal output from active heating or cooling operation of the mattress.

The method 2200 can be configured to limit the amount of pressure change in the mattress air chamber that is caused by a total thermal energy influx into the mattress air chamber (e.g., resulting from the user's body heat and the heating or cooling operation). The method 2200 is configured to offset the thermal input to the bed from active heating or cooling systems by the amount of the thermal effect of the user's body resting on the bed, thereby maintaining, or minimizing a deviation from, the set point of air pressure inside the mattress air chamber, and thus ensuring to provide consistent comfort with the bed. In some implementations, the method 2200 can apply an offset value to one or more active heating/cooling engines of the bed (e.g., a microclimate control system such as the foot warming control system 1500 and the airflow pad control system 1600), so that the active bed heating/cooling engines can operate at a point offset from the set point (e.g., temperature set point) that has been selected by the user or automatically determined to provide desired user comfort. In some implementations, such an offset value can be predetermined based on one or more factors, such as user presence, a particular user's body heat dissipation data or prediction, etc. The offset value can be determined to achieve no or limited deviation from the pressure set point of the mattress air chamber. In some implementations, the offsetting operation can be implemented as a single step change (with a single offset value). Alternatively, the offsetting operation can be performed with multiple step changes over time (with a plurality of smaller offset values). Alternatively, the offset operation can be gradually performed with either linear or non-linear gradient.

The bed system 1100 includes a microclimate controller 2202 configured to control a microclimate of the mattress 1604. For example, the microclimate controller 2202 includes one or both of the foot warming controller 1502 and the airflow pad controller 1602. The microclimate controller 2202 can operate to activate a selected operation (Step A). For example, as described in, for example, FIG. 40, the airflow pad controller 1602 can operate in the cooling mode 1752 (e.g., the ambient air circulation mode 1762 or the cooled air supply mode 1764) to cool the mattress, or in the heating mode 1754 (e.g., the heated air supply mode 1766) to warm the mattress. When the airflow pad controller 1602 operates, ambient or conditioned air is delivered to or drawn from the mattress through the airflow pad 1606 (Step B). Alternatively or in addition, the foot warming controller 1502 can activate the heating element 1504 to warm the foot section of the mattress.

The air chamber controller 1302 can operate to detect a pressure in the air chamber 1306 of the mattress (Step C). For example, the air chamber controller 1302 inflates the air chamber 1306 to reach a pressure that is set by the user or automatically determined for the user. The air chamber controller 1302 can detect the pressure inside the air chamber 1306 to monitor or ensure the pressure reaches the pressure set point. The air chamber controller 1302 can determine whether a user is present on the mattress (Step D). In some implementations, the air chamber controller 1302 can detect a change in the air chamber pressure that represents the presence of user on the mattress. Alternatively, other devices than the air chamber controller 1302 can be used to detect the user presence, such as using load cells, image capturing, etc. The air chamber controller 1302 can transmit user presence data to the microclimate controller 2202 (Step E). The user presence data can include information about whether a user is present on the bed.

The microclimate controller 2202 can detect output temperature (Step F). Where the airflow pad is operated, the output temperature can be a temperature of the air being supplied to the bed. Where the foot heating element is operated, the output temperature can be a temperature of the heating element 1504. The microclimate controller 2202 can determine a user presence (Step G). In some implementations, the microclimate controller 2202 can determine such a user presence based on the user presence data.

Upon determining that a user is present on the bed, the microclimate controller 2202 can modify the operation (Step H). For example, the microclimate controller 2202 can operate to achieve a temperature that is offset from the output temperature by an offset value. The offset value can be determined to achieve no deviation of a pressure in the air chamber 1306 from the air pressure set point that was manually selected by a user or automatically determined for the user. Alternatively, the offset value can be determined to limit a deviation of a pressure in the air chamber 1306 from the air pressure set point to a predetermined range. In some examples, the predetermined range can be between about 0.1% and about 10%. Alternatively, the microclimate controller 2202 can operate to achieve a temperature that is offset from a temperature set point (e.g., the set point manually selected by a user or automatically determined for the user) by the offset value. Where the airflow pad is operated, air is supplied or drawn in accordance with the modified operation (Step I).

In some implementations, the microclimate controller 2202 can modify the operation by the offset value in a single step. In alternative implementations, the microclimate controller 2202 can modify the operation by the offset value in multiple steps over time. For example, the offset value can be divided into a plurality of smaller values, and the operation can be modified by each of the smaller values multiple times until all the smaller values are reflected in the operation. In yet alternatively implementations, the microcontroller 2202 can gradually modify the operation until the offset value is reached. For example, the microcontroller 2202 can modify the operation such that the temperature can linearly or non-linearly change to a temperature offset by the offset value.

In addition, in some implementations, the microclimate controller 2202 can consider other factors to modify the operation as described above. For example, the microclimate controller 2202 can use ambient temperature (e.g., a room temperature around the bed) as a compensation factor. By way of example, the microclimate control, as well as the air chamber inflation, can vary depending on the room temperature (e.g., when the room is at 50° F. or when the room is at 70° F.).

The method 2202 can provide a better customer experience by minimizing or limiting pressure changes in the mattress that may be caused by the thermal output from the sleeper's body, in addition to active heating or cooling operations for the mattress. Instead of measuring the sleeper's core body temperature and thus physically interfering with the sleeper, the method 2202 can utilize more accessible, non-interruptive data, such as the discharge temperature (e.g., temperature of output air into the mattress) from the microclimate controller. As described above, the method can detect the discharge temperature and modify the operation to change the discharge temperature to compensate the effect of thermal output from the sleeper's body on the mattress.

Power Monitor (Feature Group #17)

Figure 54:
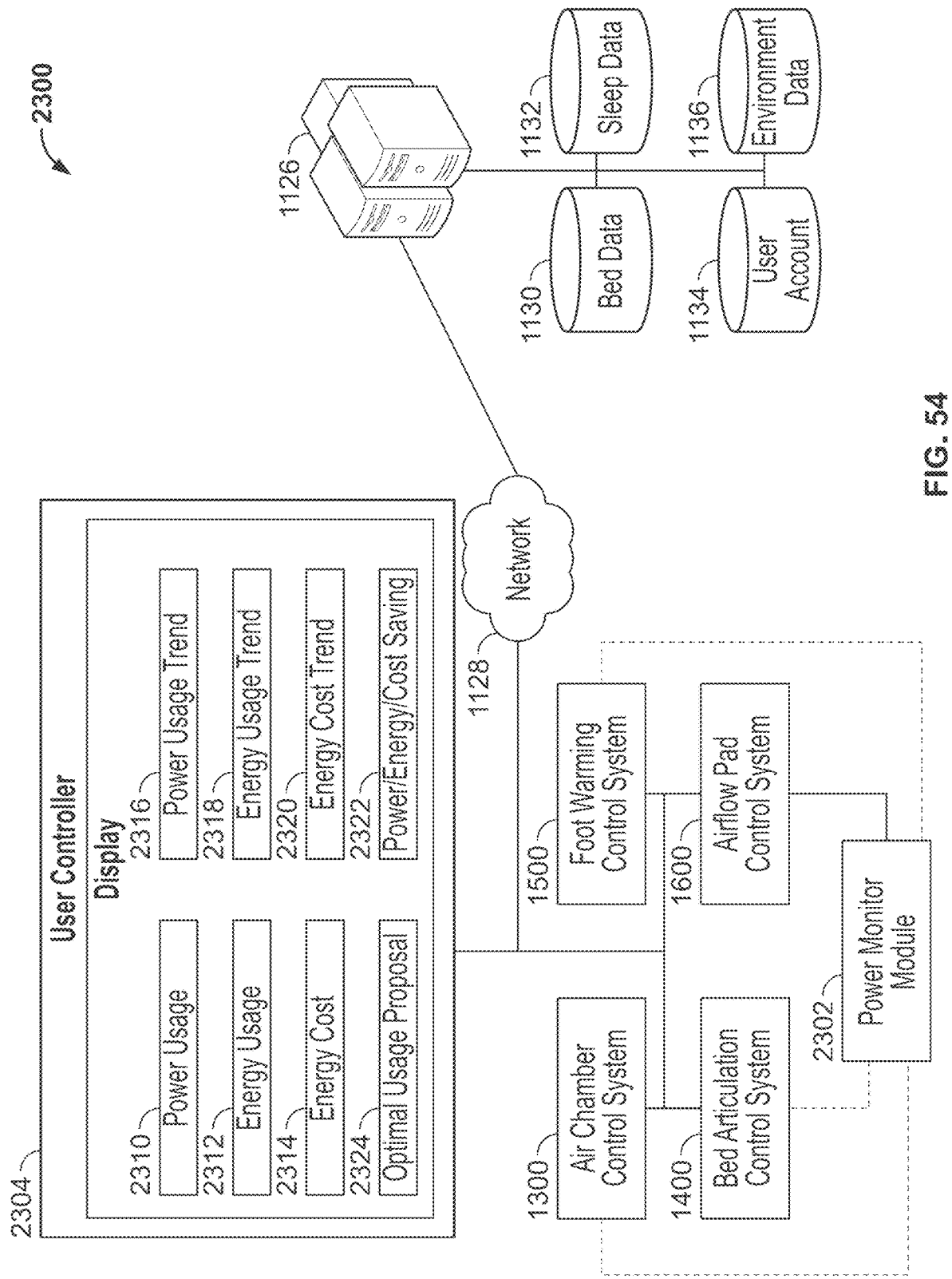
FIG. 54 is a block diagram of an example bed system with an integrated power monitor capability.

FIG. 54 is a block diagram of an example bed system 2300 with an integrated power monitor capability. The bed system 2300 can be configured similar to the bed system 1100 described herein. For example, the bed system 2300 can include the air chamber control system 1300, the bed articulation control system 1400, the foot warming control system 1500, and the airflow pad control system 1600. The bed system 1100 can include the server system 1126 that can communicate with at least one of the systems 1300, 1400, 1500, 1600 via the network 1128. The bed system 1100 can further include a user controller 2304, such as the remote control 1122 and the user computing device 1124, that is configured to enable a user to interact with the bed system 2300. The user controller 2304 can communicate with the server system 1126 over the network 1128.

The bed system 2300 can further include a power monitor module 2302 implemented in the bed system 2300. The power monitor module 2302 can be implemented in various components in the bed system 2300. For example, the power monitor module 2302 can be included at least partially in the air chamber control system 1300. Alternatively, the power monitor module 2302 can be included at least partially in one of the bed articulation control system 1400, the foot warming control system 1500, the airflow pad control system 1600, and the user controller 2304 (e.g., the remote control 1122 and the user computing device 1124). Alternatively, the power monitor module 2302 can be implemented at least partially in two or more of the air chamber control system 1300, the bed articulation control system 1400, the foot warming control system 1500, the airflow pad control system 1600, the user controller 2304 (e.g., the remote control 1122 and the user computing device 1124). In addition or alternatively, the power monitor module 2302 can be at least partially implemented in the server system 1126 and communicate with the other components, such as the air chamber control system 1300, the bed articulation control system 1400, the foot warming control system 1500, the airflow pad control system 1600, and the user controller 2304 (e.g., the remote control 1122, and the user computing device 1124).

The power monitor module 2302 is configured to monitor electrical power or energy consumption of at least one of the components in the bed system 2300. In some implementations, the power monitor module 2302 can monitor power consumption (e.g., in a unit of watt, etc.) of the airflow pad control system 1600. In addition or alternatively, the power monitor module 2302 can monitor energy consumption (e.g., in a unit of kWh, etc.) of the airflow pad control system 1600. For example, the power monitor module 2302 can monitor voltage and/or current used in the airflow pad control system 1600, and calculate the power consumption and/or the energy usage of the airflow pad control system 1600. In addition, the power monitor module 2302 can obtain electricity prices at or during the time of operation, and calculate the energy cost in operating the airflow pad control system 1600. Such energy costs can be obtained from utility companies or other public resources.

The power monitor module 2302 can monitor power or energy consumption, and/or calculate energy costs, of other components of the bed system 2300, such as the air chamber control system 1300, the bed articulation control system 1400, and the foot warming control system 1500.

The information monitored and calculated by the power monitor module 2302 can be outputted to the user in various formats. For example, the information can be presented in the display of the user controller 2304 (e.g., the remote control 1122 and the user computing device 1124). In addition or alternatively, the information can be outputted in other formats, such as audible notifications, etc. In embodiments where the power monitor module 2302 monitors the airflow pad control system 1600, the information can include one or more of power usage 2310 of the airflow pad control system 1600, energy usage 2312 of the airflow pad control system 1600, energy cost 2314 of the airflow pad control system 1600, a power usage trend 2316 of the airflow pad control system 1600, an energy usage trend 2318 of the airflow pad control system 1600, an energy cost trend 2320 of the airflow pad control system 1600, savings in power, energy, and/or energy cost 2322 with the airflow pad control system 1600, and a proposal 2324 of optimal usage of the airflow pad control system 1600. The power usage trend 2316 indicates a history or change of power usage by the airflow pad control system 1600 over time. The energy usage trend 2318 indicates a history or change of energy usage by the airflow pad control system 1600 over time. The energy cost trend 2320 indicates a history or change of energy cost of using the airflow pad control system 1600 over time. The savings in power, energy, and/or energy cost 2322 indicates how much power, energy, and/or energy cost have been saved by the airflow pad control system 1600, in comparison to, for example, using other similar systems, using other heating or cooling systems for the bed, or using no heating or cooling relative to the bed. The optimal usage proposal 2324 shows one or more proposals of using the airflow pad control system 1600 in optimal ways, such as efficiently heating or cooling the bed while saving energy.

In some implementations, the information obtained and calculated by the power monitor module 2302 can be used as additional factors to calculate a sleep quality. For example, the bed system 1100 can calculate a sleep quality score based on various parameters detected in the bed system 1100, such as the user's heart rate, respiratory rate, other vital signs of the user, the amount of time spent in REM sleep, total time in bed, a body temperature, environmental factors (e.g., room light level, room temperature, room humidity, noise level, etc.), and other considerations. In addition, a change of each parameter over a particular period of time (e.g., over the entire sleep overnight, or during a particular period of time overnight, etc.) can be used to calculate the sleep quality score. In addition, the scores of one or more previous sleep quality scores can be used to calculate a sleep quality score for a particular sleep of the user. By way of example, the sleep score can indicate high quality sleep when heart rate is low, when respiratory rate is low, and when tossing when turning movements are infrequent. The sleep quality score can account for the contribution of microclimate controls using, for example, the foot warming control and/or the airflow pad control as described herein. By way of example, the bed system 1100 can generate an actual sleep quality score for a particular sleep or a series of sleeps for which the microclimate control has been activated as desired, and further generate a hypothetical sleep quality score that would have been calculated if the same microclimate control had not been used. The actual sleep quality score and the hypothetical sleep quality score can be presented (e.g., displayed) to the user so that the user can recognize how the microclimate control has contributed to the sleep quality for the user. In addition, the information (e.g., power/energy consumption and cost) obtained by the power monitor module 2302 can be presented together with the actual sleep quality score and the hypothetical sleep quality score so that the user can determine any adjustment of the microclimate control to achieve a different level of sleep quality in view of the power/energy consumption and cost. By way of example, the user can determine to reduce use of the microclimate control to reduce the power/energy cost while sacrificing the sleep quality to some degree. In addition or alternatively, the bed system 1100 can automatically determine an optimal usage of power for controlling the microclimate of the bed, and/or accordingly control the microclimate of the bed using, for example, the foot warming control and the airflow pad control, to achieve a sleep quality score (or a range of sleep quality score) that has been manually selected or automatically determined to be desirable for the user and further to accomplish a power/energy consumption and/or cost that meet the user's needs.

Further, the information obtained and calculated by the power monitor module 2302 can be transmitted to and used by home automation systems for improving energy saving strategies. For example, an home automation system that includes the bed system 1100 can obtain not only the power/energy consumption and/or cost for operating the microclimate control of the bed, but also the power/energy consumption and/or cost for operating other heating/cooling apparatuses (e.g., furnace, air conditioner, space heater, etc.) to determine an optimal combined use of the microclimate control of the bed and the control of other heating/cooling apparatuses to achieve a desired sleep quality score. By way of example, the home automation system or the bed system 1100 can determine an energy cost for operating home heating/cooling apparatuses to achieve a sleep quality score without the microclimate control being used (or with the microclimate control being used in certain manner), and further determine an energy cost for activating the microclimate control (e.g., the foot warming control and/or the airflow pad control) to achieve the same or similar sleep quality score without the home heating/cooling apparatuses being used or with the home heating/cooling apparatuses used at adjusted temperature settings (e.g., at a lower temperature setting for a furnace or space heater). Based on comparison between the two energy costs, the home automation system or the bed system 1100 can determine which is more cost-efficient, and provide the proposal to the user and/or automatically control the microclimate control of the bed and/or the home heating/cooling apparatuses to lower or optimize the energy cost overall. The information obtained and calculated by the power monitor module 2302 can be used in automatic operation of the bed system 2300. By way of example, if the power consumption exceeds a threshold value, the airflow pad control system 1600 can be deactivated for a predetermined period of time, or until the power consumption becomes below the threshold value or another value.

General Computer Diagram

Figure 55:
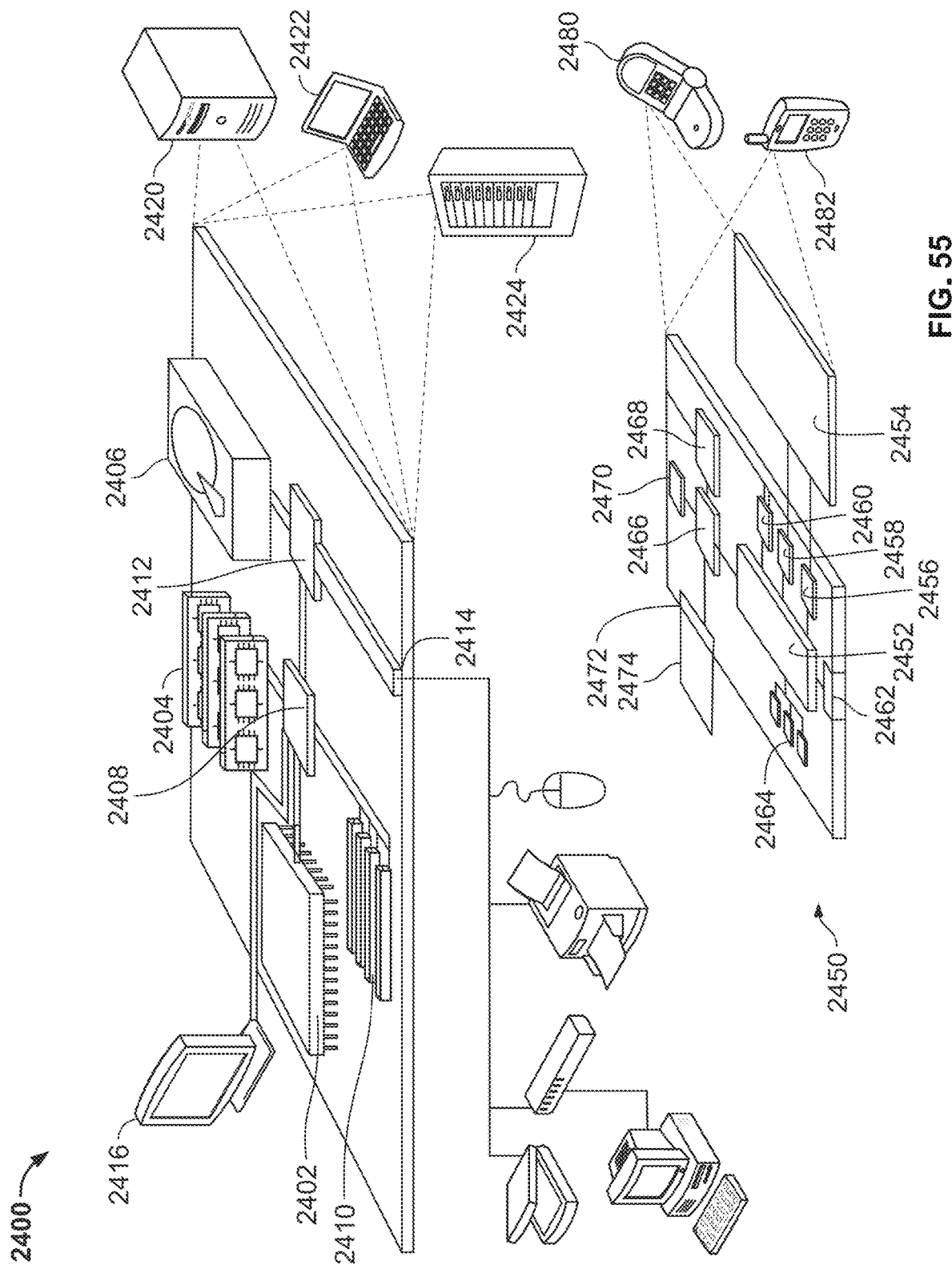
FIG. 55 is a block diagram of computing devices that may be used to implement the systems and methods described in this document.

FIG. 55 is a block diagram of computing devices 2400, 2450 that may be used to implement the systems and methods described in this document, as either a client or as a server or plurality of servers. Computing device 2400 is intended to represent various forms of digital computers, such as laptops, desktops, workstations, personal digital assistants, servers, blade servers, mainframes, and other appropriate computers. Computing device 2450 is intended to represent various forms of mobile devices, such as personal digital assistants, cellular telephones, smartphones, and other similar computing devices. The components shown here, their connections and relationships, and their functions, are meant to be examples only, and are not meant to limit implementations described and/or claimed in this document.

Computing device 2400 includes a processor 2402, memory 2404, a storage device 2406, a high-speed interface 2408 connecting to memory 2404 and high-speed expansion ports 2410, and a low speed interface 2412 connecting to low speed bus 2414 and storage device 2406. Each of the components 2402, 2404, 2406, 2408, 2410, and 2412, are interconnected using various busses, and may be mounted on a common motherboard or in other manners as appropriate. The processor 2402 can process instructions for execution within the computing device 2400, including instructions stored in the memory 2404 or on the storage device 2406 to display graphical information for a GUI on an external input/output device, such as display 2416 coupled to high-speed interface 2408. In other implementations, multiple processors and/or multiple buses may be used, as appropriate, along with multiple memories and types of memory. Also, multiple computing devices 2400 may be connected, with each device providing portions of the necessary operations (e.g., as a server bank, a group of blade servers, or a multi-processor system).

The memory 2404 stores information within the computing device 2400. In one implementation, the memory 2404 is a volatile memory unit or units. In another implementation, the memory 2404 is a non-volatile memory unit or units. The memory 2404 may also be another form of computer-readable medium, such as a magnetic or optical disk.

The storage device 2406 is capable of providing mass storage for the computing device 2400. In one implementation, the storage device 2406 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 2404, the storage device 2406, or memory on processor 2402.

The high-speed controller 2408 manages bandwidth-intensive operations for the computing device 2400, while the low speed controller 2412 manages lower bandwidth-intensive operations. Such allocation of functions is an example only. In one implementation, the high-speed controller 2408 is coupled to memory 2404, display 2416 (e.g., through a graphics processor or accelerator), and to high-speed expansion ports 2410, which may accept various expansion cards (not shown). In the implementation, low-speed controller 2412 is coupled to storage device 2406 and low-speed expansion port 2414. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 2400 may be implemented in a number of different forms, as shown in the figure. For example, it may be implemented as a standard server 2420, or multiple times in a group of such servers. It may also be implemented as part of a rack server system 2424. In addition, it may be implemented in a personal computer such as a laptop computer 2422. Alternatively, components from computing device 2400 may be combined with other components in a mobile device (not shown), such as device 2450. Each of such devices may contain one or more of computing device 2400, 2450, and an entire system may be made up of multiple computing devices 2400, 2450 communicating with each other.

Computing device 2450 includes a processor 2452, memory 2464, an input/output device such as a display 2454, a communication interface 2466, and a transceiver 2468, among other components. The device 2450 may also be provided with a storage device, such as a microdrive or other device, to provide additional storage. Each of the components 2450, 2452, 2464, 2454, 2466, and 2468, are interconnected using various buses, and several of the components may be mounted on a common motherboard or in other manners as appropriate.

The processor 2452 can execute instructions within the computing device 2450, including instructions stored in the memory 2464. The processor may be implemented as a chip set of chips that include separate and multiple analog and digital processors. Additionally, the processor may be implemented using any of a number of architectures. For example, the processor may be a CISC (Complex Instruction Set Computers) processor, a RISC (Reduced Instruction Set Computer) processor, or a MISC (Minimal Instruction Set Computer) processor. The processor may provide, for example, for coordination of the other components of the device 2450, such as control of user interfaces, applications run by device 2450, and wireless communication by device 2450.

Processor 2452 may communicate with a user through control interface 2458 and display interface 2456 coupled to a display 2454. The display 2454 may be, for example, a TFT (Thin-Film-Transistor Liquid Crystal Display) display or an OLED (Organic Light Emitting Diode) display, or other appropriate display technology. The display interface 2456 may comprise appropriate circuitry for driving the display 2454 to present graphical and other information to a user. The control interface 2458 may receive commands from a user and convert them for submission to the processor 2452. In addition, an external interface 2462 may be provide in communication with processor 2452, so as to enable near area communication of device 2450 with other devices. External interface 2462 may provide, for example, for wired communication in some implementations, or for wireless communication in other implementations, and multiple interfaces may also be used.

The memory 2464 stores information within the computing device 2450. The memory 2464 can be implemented as one or more of a computer-readable medium or media, a volatile memory unit or units, or a non-volatile memory unit or units. Expansion memory 2474 may also be provided and connected to device 2450 through expansion interface 2472, which may include, for example, a SIMM (Single In Line Memory Module) card interface. Such expansion memory 2474 may provide extra storage space for device 2450, or may also store applications or other information for device 2450. Specifically, expansion memory 2474 may include instructions to carry out or supplement the processes described above, and may include secure information also. Thus, for example, expansion memory 2474 may be provide as a security module for device 2450, and may be programmed with instructions that permit secure use of device 2450. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 2464, expansion memory 2474, or memory on processor 2452 that may be received, for example, over transceiver 2468 or external interface 2462.

Device 2450 may communicate wirelessly through communication interface 2466, which may include digital signal processing circuitry where necessary. Communication interface 2466 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 2468. In addition, short-range communication may occur, such as using a Bluetooth, Wi-Fi, or other such transceiver (not shown). In addition, GPS (Global Positioning System) receiver module 2470 may provide additional navigation- and location-related wireless data to device 2450, which may be used as appropriate by applications running on device 2450.

Device 2450 may also communicate audibly using audio codec 2460, which may receive spoken information from a user and convert it to usable digital information. Audio codec 2460 may likewise generate audible sound for a user, such as through a speaker, e.g., in a handset of device 2450. Such sound may include sound from voice telephone calls, may include recorded sound (e.g., voice messages, music files, etc.) and may also include sound generated by applications operating on device 2450.

The computing device 2450 may be implemented in a number of different forms, as shown in the figure. For example, it may be implemented as a cellular telephone 2480. It may also be implemented as part of a smartphone 2482, personal digital assistant, or other similar mobile device.

Additionally computing device 2400 or 2450 can include Universal Serial Bus (USB) flash drives. The USB flash drives may store operating systems and other applications. The USB flash drives can include input/output components, such as a wireless transmitter or USB connector that may be inserted into a USB port of another computing device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback) and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), peer-to-peer networks (having ad-hoc or static members), grid computing infrastructures, and the Internet.

The computing system can include clients and servers. A client and server are generally remote from each other and typically interact through a communication network. The relationship of client and server arises by virtue of computer programs running on the respective computers and having a client-server relationship to each other.

Alternative Implementations

Referring to FIGS. 56-60, alternative or additional features and embodiments of the bed system are described. FIGS. 56A-D illustrate an example air duct 2600 that can replace the air duct 404 described herein. Alternatively, one or more features of the air duct 2600 can be used with the air duct 404, or replace corresponding features of the air duct 404. The air duct 2600 can include a funnel plenum 2602, as illustrated in FIG. 56A-B. The funnel plenum provides an internal curved surface configured to provide maximum air flow therethrough. The funnel plenum 2602 can be placed inside the airflow pad 400, as illustrated in FIGS. 56C-D. For example, the airflow pad 400 can include a sleeve 2604 that is integral with the jacket of the airflow pad 400 and configured to surround the air duct 2600. The sleeve 2604 can be configured to reduce air leakage and/or noise from air flow. The funnel plenum 2602 can be placed within the jacket of the air duct 2600 such that the air duct 2600 passes through the sleeve 2604.

FIGS. 57A-B illustrate an example piece 2620 that can be attached to the rail 206 to keep the air duct 2600 (or the air duct 404) securely in place. As described herein, for example, the rail 206 can include a notch 242 (or cutout section) for routing the air duct 2600 (or the air duct 404) therethrough. The piece 2620 can be attached to the rail 206 across the notch 242 to keep the air duct secured and maintain the structural integrity of the mattress rail.

Figure 58C:
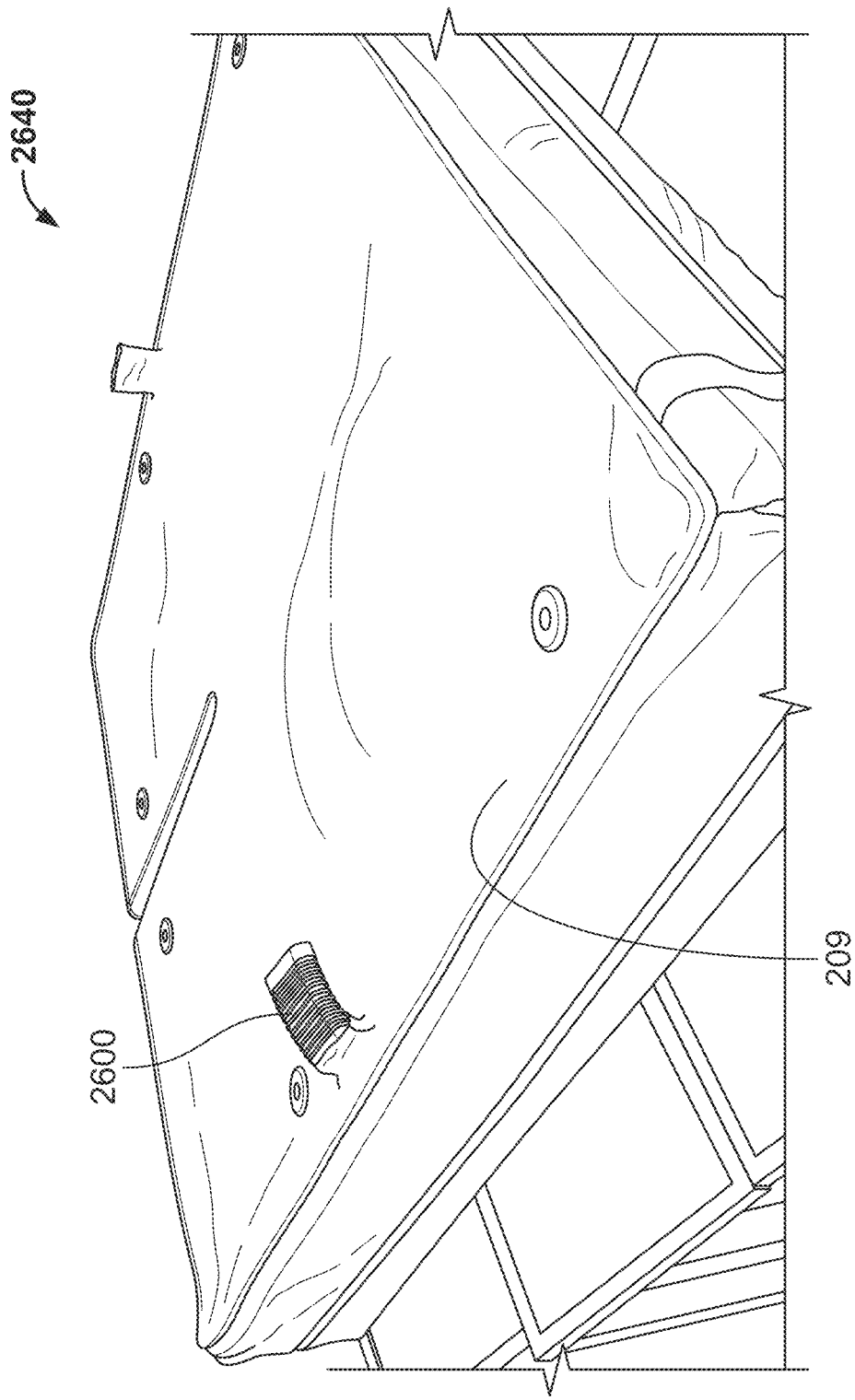

FIGS. 58A-C illustrate an example mattress system 2640. The mattress system 2640 is similar to the mattress system 200 as illustrated in, for example, FIGS. 2 and 3. For example, the mattress system 2640 is similarly configured to the mattress system 200, including the air chambers 222 placed into a tub cavity, the bottom layer 208 placed above the air chambers 222, and the cover 209 closing at least the bottom of the mattress. The cover 209 can include openings at the bottom thereof to route the air duct therethrough.

Figure 59A:
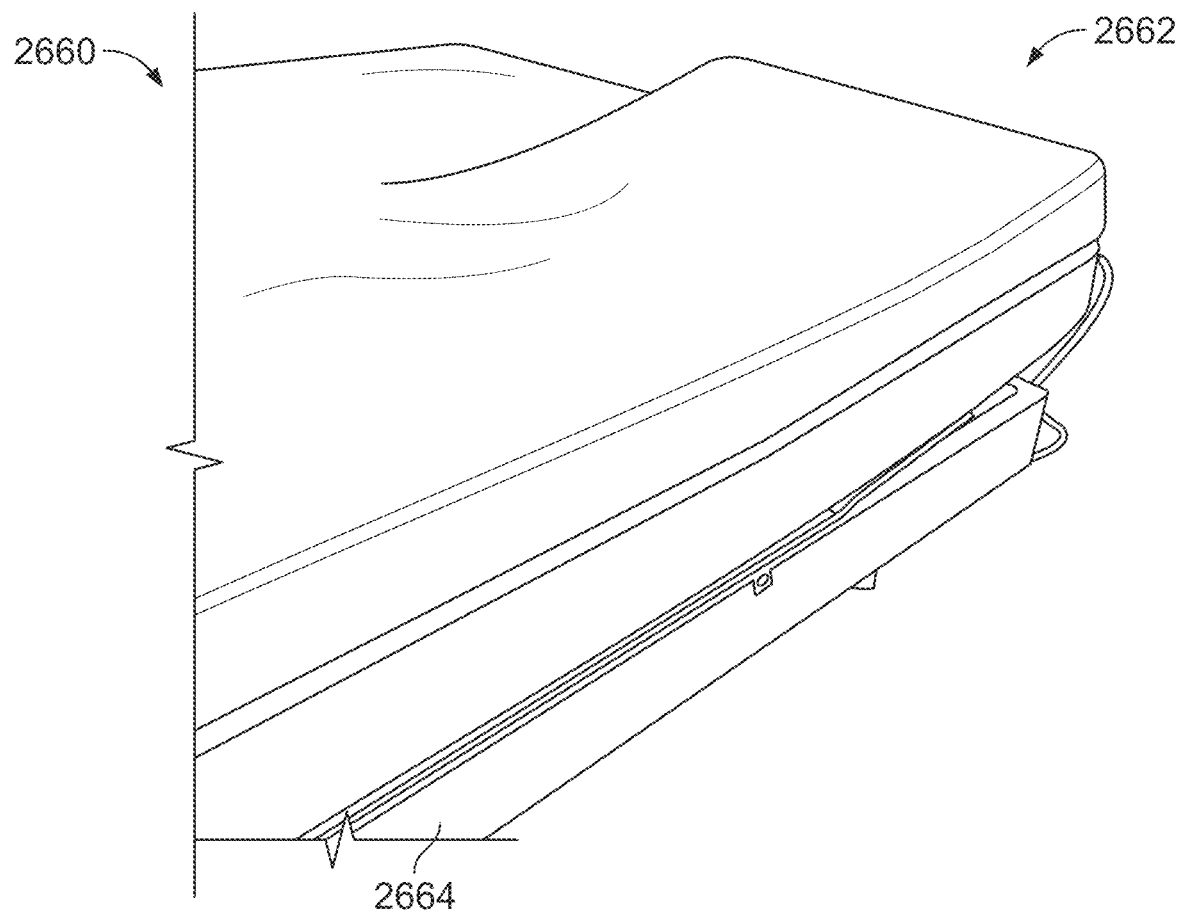
FIGS. 59A-C illustrate an alternative example of air duct connection.
Figure 59B:
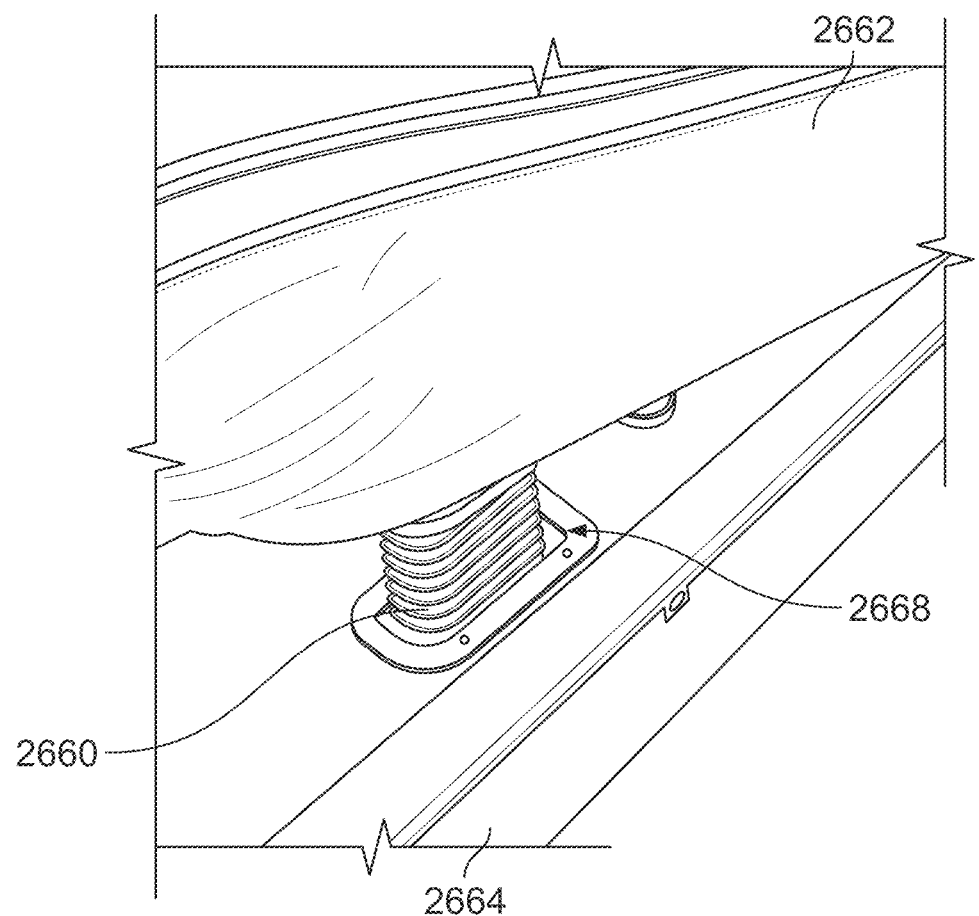
Figure 59C:
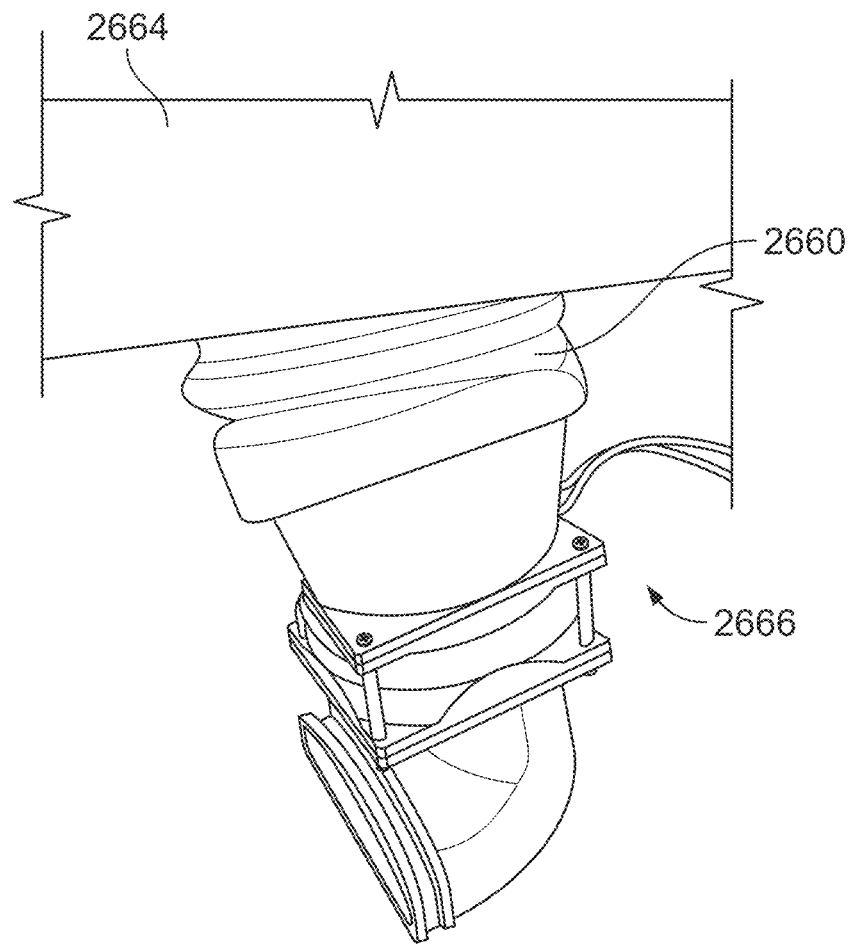

FIGS. 59A-C illustrate an alternative example of air duct connection 2660. In this example, the air duct 2660 extending from a mattress 2662 is routed through an opening 2668 provided in a foundation 2664. The air duct 2660 is fluidly coupled to a fan assembly 2666 mounted at the bottom of the foundation 2664, or hidden behind or inside the foundation 2662.

Figure 60A:
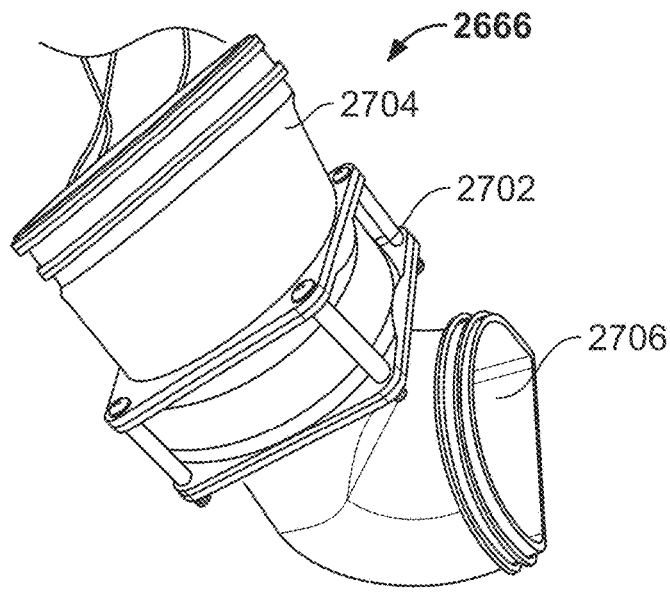
FIGS. 60A-C illustrate an alternative example of fan assembly.
Figure 60B:
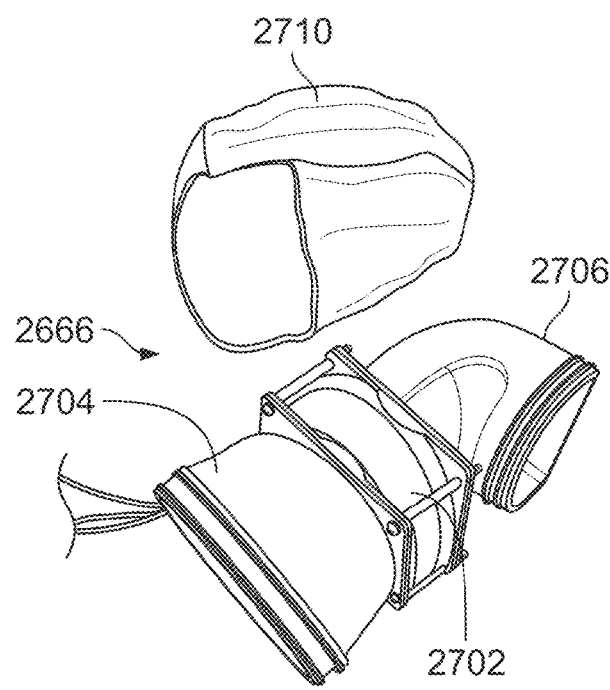
Figure 60C:
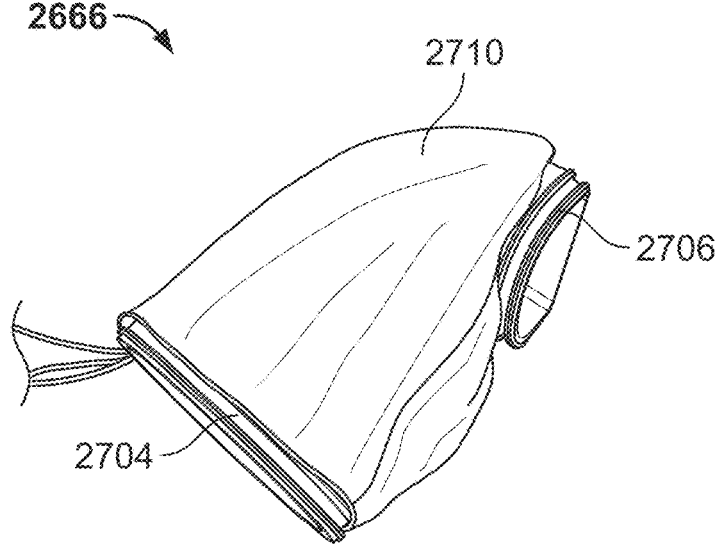

FIGS. 60A-C illustrate an alternative fan assembly 2666. The fan assembly 2666 can replace the air controller 700. Alternatively, one or more features of the fan assembly 2666 can be used with the air controller 700, or replace corresponding features of the air controller 700. The fan assembly 2666 can include a fan 2702, and a first plenum 2704 and a second plenum 2706 connected to opposite sides of the fan 2702. The first plenum 2704 is configured to couple the air duct 2600 extending from the airflow pad, and the second plenum 2706 is configured to be exposed to the surroundings. In some implementations, a sleeve 2710 can be provided to cover at least part of the fan assembly 2666 for preventing air leakage and/or noise resulting from air flow.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Accordingly, various features have been described above in seventeen different feature groups for clarity and organization purposes, however, it will be understood that features from the various feature groups can be beneficially combined together in a common system. For example, materials described in Feature Group #2 can be used in mattresses in a mattress having reinforcement straps as described in Feature Group #3. Accordingly, various embodiments are specifically intended to include features of more than one, and sometimes many, feature groups. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A bed comprising:
 a mattress comprising:
   an inflatable air chamber;
   an air distribution layer positioned above the inflatable air chamber;
   a foam layer positioned above the air distribution layer and proximate a top of the mattress, wherein the foam layer and the air distribution layer are both configured to allow airflow therethrough, and wherein the air distribution layer resists air flow less than the foam layer;
   a first air hose connected to the inflatable air chamber for inflating the inflatable air chamber; and
   a second air hose connected to the air distribution layer for moving air through the air distribution layer, wherein the second air hose extends from a location that is lower than the inflatable air chamber, around a first side of the inflatable air chamber, to the air distribution layer above the inflatable air chamber,
  wherein the mattress further comprises a mattress cover, and wherein the first and second air hoses enter the mattress through a common hole in the mattress cover.

2. The bed of claim 1, wherein the inflatable air chamber comprises a first inflatable air chamber and the air distribution layer comprises first and second air distribution zones, wherein the first inflatable air chamber is positioned under the first air distribution zone, and wherein the mattress further comprising a second inflatable air chamber positioned under the second air distribution zone.

3. The bed of claim 2, wherein the mattress further comprises an insulator positioned between the first air chamber and the second air chamber to reduce heat transfer between the first air chamber and the second air chamber.

4. The bed of claim 2, wherein the mattress further comprises an insulator positioned between the first and second air chambers and also between the first and second air distribution layers to reduce heat transfer between left and right sides of the mattress.

5. The bed of claim 2, and further comprising:
a foundation having a support platform configured for supporting the mattress and including a first foundation opening extending through the support platform and configured to receive the first and second air hoses;
a pump assembly fluidly connected to an end hose end of the first air hose and configured to supply fluid to the inflatable air chamber, wherein the pump assembly is positioned in the foundation; and
an air controller fluidly connected to the second air hose and configured to move air through the air distribution layer, wherein the air controller is positioned in the foundation.

6. The bed of claim 1, wherein the first air hose is at least partially routed adjacent the second air hose.

7. The bed of claim 1, wherein the first air hose is at least partially routed together with the second air hose within the mattress.

8. The bed of claim 1, wherein the air distribution layer includes a layer cover, and wherein the second air hose is fastened to the layer cover to fluidly connect the second air hose with the air distribution layer.

9. The bed of claim 1, and further comprising:
a foundation having a support platform configured for supporting the mattress and including a first foundation opening extending through the support platform and configured to receive the first and second air hoses.

10. The bed of claim 9, further comprising:
a hose connector including a base fixed to a top surface of the foundation, and a rib extending from the base away from the top surface of the foundation, the rib configured to be inserted into the second air hose and maintain a width of at least an end of the second air hose against the first air hose running adjacent the second air hose, when the end of the second air hose is connected to the hose connector.

11. The bed of claim 1, wherein the inflatable air chamber is configured to be inflated and deflated to a selected pressure.

12. A bed comprising:
a mattress comprising:
an inflatable air chamber;
an air distribution layer positioned above the inflatable air chamber;
a foam layer positioned above the air distribution layer and proximate a top of the mattress, wherein the foam layer and the air distribution layer are both configured to allow airflow therethrough, and wherein the air distribution layer resists air flow less than the foam layer;
a first air hose connected to the inflatable air chamber for inflating the inflatable air chamber; and
a second air hose connected to the air distribution layer for moving air through the air distribution layer, wherein the second air hose extends from a location that is lower than the inflatable air chamber, around a first side of the inflatable air chamber, to the air distribution layer above the inflatable air chamber,
wherein the inflatable air chamber comprises a first inflatable air chamber and the air distribution layer comprises first and second air distribution zones, wherein the first inflatable air chamber is positioned under the first air distribution zone, and wherein the mattress further comprising a second inflatable air chamber positioned under the second air distribution zone, and wherein the mattress further comprises:
a third air hose connected to the second inflatable air chamber for inflating the second inflatable air chamber; and
a fourth air hose connected to the second air distribution layer for moving air through the second air distribution layer, wherein the fourth air hose extends from a second location that is lower than the second inflatable air chamber, around a second side of the second inflatable air chamber, to the second air distribution layer above the second inflatable air chamber.

13. The bed of claim 12, wherein the mattress further comprises a mattress cover, and wherein the first and second air hoses enter the mattress through a first common hole in the mattress cover and the third and fourth air hoses enter the mattress through a second common hole in the mattress cover.

14. The bed of claim 12, wherein the mattress further comprises:
a first rail positioned on the first side of the first inflatable air chamber, wherein the first rail defines a first hose passage, and wherein the first and second hoses enter the mattress proximate the first hose passage; and
a second rail positioned on the second side of the second inflatable air chamber, wherein the second rail defines a second hose passage, and wherein the third and fourth hoses enter the mattress proximate the second hose passage.

15. The bed of claim 14, wherein the first rail includes a first notch that defines the first hose passage, and the second rail includes a second notch that defines the second hose passage.

16. The bed of claim 15, wherein the first rail and the second rail extend between a head portion and a foot portion of the mattress,
wherein the first and second inflatable air chambers are positioned between the first rail and the second rail,
wherein the first notch is defined at a middle portion of the first rail between the head portion and the foot portion of the mattress, and
wherein the second notch is defined at a middle portion of the second rail between the head portion and the foot portion of the mattress.

17. The bed of claim 12, wherein the inflatable air chamber is configured to be inflated and deflated to a selected pressure.

* * * * *